(12) United States Patent
Hwang et al.

(10) Patent No.: US 11,534,049 B2
(45) Date of Patent: *Dec. 27, 2022

(54) IMAGE GENERATING DEVICE

(71) Applicant: VPIX Medical Incorporation, Daejeon (KR)

(72) Inventors: Kyungmin Hwang, Daejeon (KR); Ki Hun Jeong, Daejeon (KR)

(73) Assignee: VPIX Medical Incorporation, Daejeon (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/135,699

(22) Filed: Dec. 28, 2020

(65) Prior Publication Data

US 2021/0113061 A1 Apr. 22, 2021

Related U.S. Application Data

(63) Continuation of application No. 16/855,700, filed on Apr. 22, 2020, now Pat. No. 10,908,412.

(Continued)

(30) Foreign Application Priority Data

Sep. 11, 2019 (KR) ........................ 10-2019-0112711

(51) Int. Cl.
*A61B 1/00* (2006.01)
*A61B 1/04* (2006.01)
(Continued)

(52) U.S. Cl.
CPC .......... *A61B 1/00009* (2013.01); *A61B 1/043* (2013.01); *A61B 1/0661* (2013.01);
(Continued)

(58) Field of Classification Search
CPC .............. G02B 26/103; G02B 21/0036; G02B 21/0028; G02B 21/008; H04N 5/232122;
(Continued)

(56) References Cited

U.S. PATENT DOCUMENTS 9,936,865 B2 * 4/2018 Choi ..................... G02B 26/103
10,908,412 B2 * 2/2021 Hwang .............. A61B 1/00009
(Continued)

FOREIGN PATENT DOCUMENTS

KR 10-2015-0052672 A 5/2015
KR 10-2014-0003276 A 7/2015
(Continued)

OTHER PUBLICATIONS

International Search Report of PCT/KR2020/001141, dated May 8, 2020.
(Continued)

*Primary Examiner* — John Bedtelyon
(74) *Attorney, Agent, or Firm* — K&L Gates LLP

(57) ABSTRACT

An optical device may include an optical fiber having a fixed end and a free end; a first actuator positioned at a actuator position between the fixed end and the free end and configured to apply a first force on the actuator position of the optical fiber such that a movement of the free end of the optical fiber in a first direction is caused, wherein the first direction is orthogonal to a longitudinal axis of the optical fiber; and a deformable rod disposed adjacent to the optical fiber, and having a first end and a second end, wherein the first end is connected to a first rod position of the optical fiber and the second end is connected to a second rod position of the optical fiber.

11 Claims, 73 Drawing Sheets

Related U.S. Application Data

(60) Provisional application No. 62/842,365, filed on May 2, 2019.

(51) Int. Cl.
*A61B 1/06* (2006.01)
*A61B 1/07* (2006.01)
*G02B 21/00* (2006.01)
*G02B 26/10* (2006.01)
*H04N 5/232* (2006.01)
*H04N 5/235* (2006.01)
*H04N 5/225* (2006.01)

(52) U.S. Cl.
CPC .............. *A61B 1/07* (2013.01); *G02B 21/008* (2013.01); *G02B 21/0028* (2013.01); *G02B 26/103* (2013.01); *H04N 5/2354* (2013.01); *H04N 5/232122* (2018.08); *G02B 21/0036* (2013.01); *H04N 2005/2255* (2013.01)

(58) Field of Classification Search
CPC .... H04N 2005/2255; A61B 1/07; A61B 1/043
See application file for complete search history.

(56) References Cited

U.S. PATENT DOCUMENTS

| | | |
|---|---|---|
| 2012/0310098 A1 | 12/2012 | Popovic |
| 2013/0242069 A1 | 9/2013 | Kobayashi |
| 2014/0232993 A1 | 8/2014 | Kim et al. |
| 2016/0051131 A1 | 2/2016 | Jeong et al. |
| 2017/0071455 A1 | 3/2017 | Shimamoto |
| 2017/0224340 A1 | 8/2017 | Weir et al. |
| 2018/0374229 A1 | 12/2018 | Kumar |
| 2020/0069165 A1 | 3/2020 | Thomson et al. |

FOREIGN PATENT DOCUMENTS

| | | |
|---|---|---|
| KR | 10-2015-0107024 A | 9/2015 |
| WO | 2020/087015 A1 | 4/2020 |

OTHER PUBLICATIONS

Written Opinion of PCT/KR2020/001141, dated May 8, 2020.
Office Action of U.S. Appl. No. 16/855,700, dated Jun. 26, 2020.
Notice of Allowance of U.S. Appl. No. 16/855,700, dated Oct. 15, 2020.
Notice of Allowance of U.S. Appl. No. 16/855,847, dated Oct. 29, 2020.
Office Action of KR Patent Application No. 10-2019-0150825, dated Feb. 22, 2021.
Hwang Kyungmin et al. "Frequency selection rule for high definition and high frame rate Lissajous scanning", Scientific Reports, vol. 7.14075, 2017 pp. 1~8.
International Search Report issued in PCT Patent Application No. PCT/KR2020/001141 dated May 8, 2020.
Office Action issued in U.S. Appl. No. 16/855,847 dated Jul. 21, 2020.
Grant of Patent in KR Patent Application No. 10-2019-0112711, dated Aug. 5, 2021.
Grant of Patent in KR Patent Application No. 10-2019-0150827, dated Sep. 6, 2021.
Examination Report in Australian Patent Application No. 2020266362, dated Apr. 27, 2022.

* cited by examiner

FIG. 50
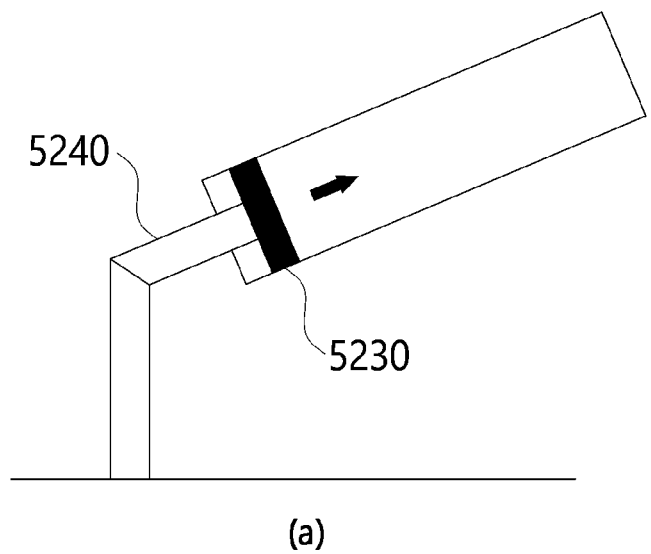
(a)
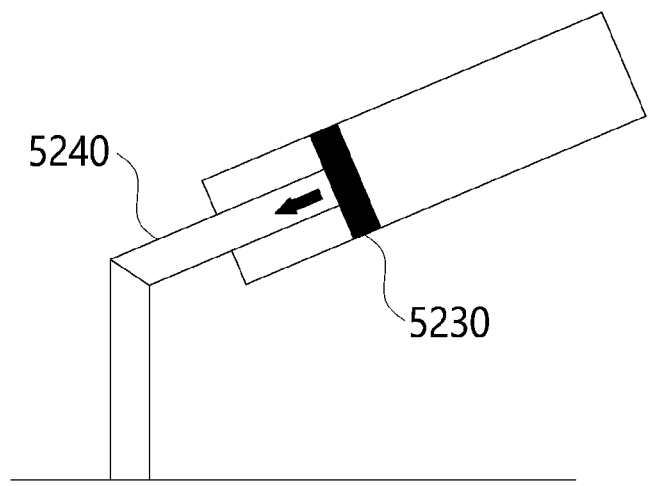
(b)

FIG. 52

| A POSITION CORRESPONDING TO FIRST SIGNAL | FIRST-FIRST POSITION | ... | FIRST-(N-1)$^{TH}$ POSITION | FIRST-N$^{TH}$ POSITION |
|---|---|---|---|---|
| A POSITION CORRESPONDING TO SCOND SIGNAL | SECOND-FIRST POSITION | ... | SECOND-(N-1)$^{TH}$ POSITION | SECOND-N$^{TH}$ POSITION |
| ACQUISITION SIGNAL VALUE | FIRST OBTAINED VALUE | ... | (N-1)$^{TH}$ OBTAINED VALUE | N$^{TH}$ OBTAINED VALUE |

| A POSITION CORRESPONDING TO FIRST SIGNAL | X1 | X2 | ... | X1 | ... | X2 | X3 |
|---|---|---|---|---|---|---|---|
| A POSITION CORRESPONDING TO SCOND SIGNAL | Y1 | Y2 | ... | Y1 | ... | Y2 | Y3 |
| ACQUISITION SIGNAL VALUE | I1 | I2 | ... | I1 | ... | I2 | I3 |

(b)

| A POSITION CORRESPONDING TO FIRST SIGNAL | X2 | X1 | ... | X2 | ... | X3 | X1 |
|---|---|---|---|---|---|---|---|
| A POSITION CORRESPONDING TO SCOND SIGNAL | Y2 | Y1 | ... | Y2 | ... | Y3 | Y1 |
| ACQUISITION SIGNAL VALUE | I1 | I2 | ... | I1 | ... | I2 | I3 |

IMAGE GENERATING DEVICE

CROSS-REFERENCE TO RELATED APPLICATION

This application claims priority to and the benefit of U.S. Provisional Application No. 62/842,365, filed on May 2, 2019, Korean Patent Application No. 10-2019-0112711, filed on Sep. 11, 2019, the disclosure of which is incorporated herein by reference in its entirety.

BACKGROUND

1. Field

Embodiments relate to an image generating device for observing the inside of an object in real-time and an image generation method using the same.

2. Discussion of Related Art

Optical devices are for emitting light to an object to observe the inside and outside of the object and are widely used in various medical fields, biological research, and industrial fields.

In particular, endoscopes, which are being widely used in the medical field, have the advantage of observing and diagnosing pathological conditions in real-time by being inserted into human bodies in a non-invasive manner. However, typical endoscopes can observe only surfaces of living bodies and thus have a disadvantage in that it is necessary to detach and check a part of biological tissue using a separate optical device, a chemical biopsy, and the like in order to observe the inside and characteristics of cells.

The disclosure of this section is to provide background information relating to the invention. Applicant does not admit that any information contained in this section constitutes prior art.

SUMMARY

One aspect of the invention provides endomicroscopes developed for observing the characteristics of living bodies in real-time, and also miniaturized while providing high-resolution images in order to observe pathological conditions through a minimal incision in real-time.

The following embodiments are directed to providing a high-resolution image by emitting a preset scanning pattern to an object.

Also, the following embodiments are directed to providing a high-resolution image by changing the phase of the scanning pattern in real-time.

Also, the following embodiments are directed to making an input signal for driving an optical fiber in the scanning pattern correspond to an output signal by which the optical fiber is actually driven by attaching a structure.

Also, the following embodiments are directed to preventing breakage of the structure by separating the structure from an end of the optical fiber when the optical fiber is driven.

Also, the following embodiments are directed to adjusting an aspect ratio of an output image by adjusting the voltage level of an optical fiber input signal.

Also, the following embodiments are directed to calibrating the phase of an image for the first time when a probe is mounted on a mounting stand.

Also, the following embodiments are directed to calibrating the phase of an output image by using the difference between light intensity values obtained at one pixel position.

Also, the following embodiments are directed to providing a method of discovering a phase for calibrating an output image by using a predetermined phase change period.

According to an embodiment, an optical device, comprising: an optical fiber having a fixed end and a free end; a first actuator positioned at a actuator position between the fixed end and the free end and configured to apply a first force on the actuator position of the optical fiber such that a movement of the free end of the optical fiber in a first direction is caused, wherein the first direction is orthogonal to a longitudinal axis of the optical fiber; and a deformable rod disposed adjacent to the optical fiber, and having a first end and a second end, wherein the first end is connected to a first rod position of the optical fiber and the second end is connected to a second rod position of the optical fiber, wherein the first rod position and the second rod position of the optical fiber are positioned between the actuator position and the free end, wherein the deformable rod is substantially parallel to the optical fiber from the first rod position of the optical fiber to the second rod position of the optical fiber, and wherein, in the cross section perpendicular to the longitudinal axis of the optical fiber, the deformable rod is arranged such that an angle between a virtual line connected from the first end of the deformable rod to the first rod position of the optical fiber and the first direction is within a predetermined angle, whereby the movement of the optical fiber in a second direction perpendicular to the first direction is limited when the free end of the optical fiber moves in the first direction as the first actuator applies the first force on the actuator position of the optical fiber, can be provided.

According to another embodiment, an optical device comprising: an optical fiber having a fixed end and a free end, and configured to irradiate a predetermined scanning pattern; a first actuator positioned at a actuator position between the fixed end and the free end and configured to apply a first force on the actuator position of the optical fiber such that a movement of the free end of the optical fiber in a first direction is caused; a second actuator configured to apply a second force on the actuator position of the optical fiber such that a movement of the free end of the optical fiber in a second direction is caused, wherein the first direction is orthogonal to a longitudinal axis of the optical fiber, and the second direction is perpendicular to the first direction; a deformable rod having a first end and a second end, and disposed in the first direction or the second direction adjacent to the optical fiber, wherein the first end is fixed to a first rod position of the optical fiber and the second end is fixed to a second rod position of the optical fiber, wherein the first rod position and the second rod position of the optical fiber are positioned between the actuator position and the free end; and a controller configured to apply a first driving frequency to the first actuator and a second driving frequency to the second actuator; wherein an aspect ratio of the scanning pattern irradiated by the optical fiber is associated with the attachment direction of the deformable rod, and wherein the controller adjusts the aspect ratio of the scanning pattern by applying a first voltage to the first actuator and a second voltage to the second actuator, can be provided.

According to another embodiment, an image generating device comprising an irradiation unit configured to irradiate light to an object, a light receiving unit configured to receive the returned light from the object and obtain a signal based on the returned light, and a controller configured to generate an image based on the signal obtained from the light receiving unit, the device comprising: an optical fiber having a fixed end and a free end; a first actuator positioned at a actuator position between the fixed end and the free end and configured to apply a first force on the actuator position of the optical fiber such that a movement of the free end of the optical fiber in a first direction is caused; a second actuator configured to apply a second force on the actuator position of the optical fiber such that a movement of the free end of the optical fiber in a second direction is caused, wherein the first direction is orthogonal to a longitudinal axis of the optical fiber, and the second direction is perpendicular to the first direction; a deformable rod having a first end and a second end, and disposed in the first direction or the second direction adjacent to the optical fiber, wherein the first end is fixed to a first rod position of the optical fiber and the second end is fixed to a second rod position of the optical fiber, wherein the first rod position and the second rod position of the optical fiber are positioned between the actuator position and the free end, wherein an aspect ratio of the generated image is associated with the attachment direction of the deformable rod, and wherein the controller adjusts the aspect ratio of the generated image by applying a first voltage to the first actuator and a second voltage to the second actuator, may be provided.

According to another embodiment, an optical device, comprising: an optical fiber having a fixed end and a free end; a first actuator positioned at a actuator position between the fixed end and the free end and configured to apply a first force on the actuator position of the optical fiber such that a movement of the free end of the optical fiber in a first direction is caused; a second actuator configured to apply a second force on the actuator position of the optical fiber such that a movement of the free end of the optical fiber in a second direction, wherein the first direction is orthogonal to a longitudinal axis of the optical fiber, and the second direction is perpendicular to the first direction; a mass having a preselected size, and disposed between the fixed end and the free end of the optical fiber; and a housing receiving the optical fiber, the first actuator and the second actuator, wherein the optical fiber vibrates inside the housing by the first force and the second force, and a maximum movement range of the optical fiber depends on the location of the mass, wherein the mass is located away from the free end of the optical fiber by a buffer distance to prevent the mass from colliding with an inner wall of the housing and being damaged when the optical fiber vibrates, and wherein the buffer distance is set based on at least one of the size of the mass, an inner diameter of the housing, and the maximum movement range of the optical fiber, and wherein the buffer distance is determined at least one of the following is less than ½ of an inner diameter of the housing: the maximum movement range of the optical fiber from the center of the inner diameter and a maximum movement range of the mass from the center of the inner diameter, may be provided.

According to another embodiment, an image generating device for obtaining an image of an object, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set based on the first signal, the second signal and the light receiving signal, wherein the control module configured to obtain a second data set based on the first data set by adjusting at least one of the first phase component of the first signal and the second phase component of the second signal, wherein the control module configured to select from the first data set and the second data set based on predetermined criteria, and wherein the image of the object is generated based on the selected data set, can be provided.

According to another embodiment, an image generating method for obtaining an image of an object, comprising: generating a first signal having a first frequency component and a first phase component for a first axis direction, and a second signal having a second frequency component and a second phase component in a second axis direction through a control module; obtaining light receiving signal based on returned light from the object, through a light receiving unit; obtaining a first data set based on the first signal, the second signal and the light receiving signal, obtaining a second data set based on the first data set by adjusting at least one of the first phase component of the first signal and the second phase component of the second signal, selecting from the first data set and the second data set based on predetermined criteria, and generating the image of the object based on the selected data set, can be provided.

According to another embodiment, an image generating device for obtaining an image of an object, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set based on the first signal, the second signal and the light receiving signal, wherein the control module configured to obtain a second data set based on the first data set by adjusting at least one of the first phase component of the first signal and the second phase component of the second signal using a first amount of phase adjustment, wherein the control module configured to select from the first data set and the second data set based on predetermined criterion, wherein the control module configured to obtain a third data set based on the second data set by adjusting phase component of at least one of signals used for obtaining the second data set using the first amount of phase adjustment, when the second data set is selected among the first data set and the second data set, wherein the control module configured to select from the second data set and the third data set based on the predetermined criterion, and wherein the control module configured to generate the image of the object based on the second data set, when the second data set is selected among the second data set and the third data set, can be provided.

According to another embodiment, an image generating device for obtaining an image of an object, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set using the first signal, the second signal and the light receiving signal, wherein the control module adjusts a phase component of at least one of the first signal or the second signal by a first amount of phase adjustment by plurality of times, wherein the control module configured to obtain a plurality of data sets using each of the signal adjusted by the plurality of times and a light receiving signal adjusted by the plurality of times, wherein the control module configured to obtain a data set using at least one of the signal and the light receiving signal, when each time at least one of the signal is adjusted by the first amount of phase adjustment, wherein the control module configured to obtain a nth data set using at least one of the signal which the phase component is adjusted by the first amount of phase adjustment n times and the light receiving signal, when at least one of the signal is adjusted by the first amount of phase adjustment n times, wherein the control module adjusts a phase component of at least one of the first signal or the second signal by the first amount of phase adjustment by (n+1) times, when the nth data set is more corresponding to the predetermined criterion than a (n−1)th data set obtained previously than the nth data set, wherein the (n−1)th data set is obtained when the phase component of at least one of the first signal and the second signal is adjusted by the first amount of phase adjustment (n−1) times, wherein the control module configured to obtain a (n+1)th data set using at least one of the signal which the phase component is adjusted by the first amount of phase adjustment by (n+1) times and the light receiving signal, and wherein the control module producing the image based on at least one of the signal which the phase component is adjusted by the first amount of phase adjustment (n−1) times, when the (n−1)th data set is more corresponding to the predetermined criterion than the nth data set, can be provided.

According to another embodiment, an image generating device for obtaining an image of an object, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first phase adjusted signal which is a sum of a n times of a first amount of phase adjustment and the first phase component of the first signal, wherein the control module configured to obtain a second phase adjusted signal which is a sum of a m times of a first amount of phase adjustment and the second phase component of the second signal, wherein the n and m are different integer and larger than 1, and wherein the control module configured to generate the image using a first data set obtained based on the first phase adjusted signal, when the first data set obtained based on the first phase adjusted signal and the second signal is more corresponding to a predetermined criterion than a second data set obtained based on the second phase adjusted signal and the second signal, can be provided.

According to another embodiment, an image generating device for obtaining an image of an object, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to generate and output a first image using the first signal and the second signal at a first point of time, wherein at least one of the first signal and the second signal is adjusted during a predetermined time period after the first point of time, wherein the control module generates and outputs a second image using at least one of the phase adjusted signal at a second point of time after the predetermined time period, wherein a difference between the phase of the first signal at the first point of time and the phase of the first signal at the second point of time and a difference between the phase of the second signal at the first point of time and the phase of the second signal at the second point of time are different by substantially an integer multiple of a first amount of phase adjustment, and wherein the first amount of phase adjustment is determined based on the first frequency component and the second frequency component, can be provided. According to another embodiment, an image generating method for obtaining an image of an object, comprising: generating a first signal having a first frequency component and a first phase component for a first axis direction, and a second signal having a second frequency component and a second phase component in a second axis direction through a control module; obtaining light receiving signal based on returned light from the object, through a light receiving unit; obtaining a first data set based on the first signal, the second signal and the light receiving signal; obtaining a second data set based on the first data set by adjusting at least one of the first phase component of the first signal and the second phase component of the second signal using a first amount of phase adjustment; selecting from the first data set and the second data set based on predetermined criterion; obtaining a third data set based on the second data set by adjusting phase component of at least one of signals used for obtaining the second data set using the first amount of phase adjustment, when the second data set is selected among the first data set and the second data set; selecting from the second data set and the third data set based on the predetermined criterion; generating the image of the object based on the second data set, when the second data set is selected among the second data set and the third data set, can be provided.

According to another embodiment, a light irradiating unit, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set based on the first signal, the second signal and the light receiving signal, wherein the control module configured to obtain a second data set based on the first data set by adjusting at least one of the first phase component of the first signal and the second phase component of the second signal using a first amount of phase adjustment, wherein the control module configured to select from the first data set and the second data set based on predetermined criterion, wherein the control module configured to obtain a third data set based on the second data set by adjusting phase component of at least one of signals used for obtaining the second data set using the first amount of phase adjustment, when the second data set is selected among the first data set and the second data set, wherein the control module configured to select from the second data set and the third data set based on the predetermined criterion, and wherein the control module configured to generate the image of the object based on the second data set, when the second data set is selected among the second data set and the third data set, can be provided.

According to another embodiment, an optical device for emitting light to an object, comprising: a control module configured to generate actuating signals; and an emission unit configured to receive the actuating signals and emit light to the object based on the actuating signals; wherein when the emission unit receives a first actuating signal having a first actuating frequency and a first phase and a second actuating signal having a second actuating frequency and a second phase among the actuating signals, the emission unit emits the light with a first scanning pattern based on the first actuating signal and the second actuating signal, wherein when the emission unit receives a third actuating signal having the third actuating frequency and a third phase and a fourth actuating signal having a fourth actuating frequency and a fourth phase among the actuating signals, the emission unit emits the light with a second scanning pattern based on the third actuating signal and the fourth actuating signal, wherein the first phase and the second phase have different by a first phase difference, wherein the third phase and the fourth phase have different by a second phase difference, and wherein the control module configured to generate the actuating signals by setting difference between the first phase difference and the second phase difference being n times of a predetermined phase, can be provided.

According to another embodiment, an light emitting method by an optical device for emitting light to an object, wherein the optical device comprising a control module configured to generate actuating signals and an emission unit configured to receive the actuating signals and emit light to the object based on the actuating signals, the light emitting method comprising: receiving a first actuating signal having a first actuating frequency and a first phase and a second actuating signal having a second actuating frequency and a second phase among the actuating signals, the emission unit emits the light with a first scanning pattern based on the first actuating signal and the second actuating signal, through the emission unit; and receiving a third actuating signal having the third actuating frequency and a third phase and a fourth actuating signal having a fourth actuating frequency and a fourth phase among the actuating signals, the emission unit emits the light with a second scanning pattern based on the third actuating signal and the fourth actuating signal, through the emission unit; wherein the first phase and the second phase have different by a first phase difference, wherein the third phase and the fourth phase have different by a second phase difference, wherein the control module configured to generate the actuating signals by setting difference between the first phase difference and the second phase difference being n times of a predetermined phase, can be provided.

According to another embodiment, a mounting device for mounting an image generating device comprising a probe, emitting light to an object from an one end of the probe and receiving light returning from the object at the one end of the probe, the mounting device comprising: a housing configured to hold at least part of the image generating device, wherein the at least part of the image generating device includes the one end of the probe; and a reference image providing unit configured to provide at least one of a reference image such that the image generating device performs a phase adjustment of an actuating signal related to positions of the emitted light on the object from the one end of the probe when the housing holds the at least part of the image generating device; wherein the reference image providing unit adjusts a position of the reference image for corresponding a distance between the one end of the probe and the reference image to a focal length of the probe, can be provided.

According to another embodiment, a mounting device for mounting an image generating device comprising a probe, emitting light to an object from an one end of the probe and receiving light returning from the object at the one end of the probe, comprising: a housing configured to hold at least a part of the image generating device, wherein at least the part of the image generating device includes the one end of the probe; and a reference image providing unit configured to provide a plurality of a reference image for performing a phase adjustment of an actuating signal which determines a position of light emission on the object from the one end, when the housing holds at least of the part of the image generating device; wherein the reference image providing unit comprises a plurality of layers including each of the plurality of reference image for corresponding a distance between the one end of the probe and the reference image to a focal length of the probe, can be provided.

According to another embodiment, an image generating device for obtaining an image of an object, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module performs a first phase adjustment at least one of the first signal and the second signal using a light receiving signal based on light returning from a reference image, when light is emitted from the emitting unit to the reference image arranged in a mounting device, at a state of the emitting unit mounted in the mounting device, wherein the mounting device has the reference image inside, wherein the control module repeatedly performs a second phase adjustment periodically using the light receiving signal based on light returning from the reference image, when light is emitted from the emitting unit to the reference image arranged in a mounting device, at a state of the emitting unit not mounted in the mounting device, wherein the second phase adjustment is performed based on a phase at least one of the first signal and the second signal adjusted by the first phase adjustment, can be provided.

According to another embodiment, a phase adjusting method by an image generating device for obtaining an image of an object, wherein the image generating device comprising a control module configured to generate a first signal having a first frequency component and a first phase component for a first axis direction, and a second signal having a second frequency component and a second phase component in a second axis direction; an emitting unit configured to emit light to the object using the first signal and the second signal and a light receiving unit configured to obtain light receiving signal by returning light from the object, based on the light emitted by the emitting unit, the phase adjusting method comprising: performing a first phase adjustment at least one of the first signal and the second signal using a light receiving signal based on light returning from a reference image, when light is emitted from the emitting unit to the reference image arranged in a mounting device, at a state of the emitting unit mounted in the mounting device, wherein the mounting device has the reference image inside, through the control module; and repeatedly performing a second phase adjustment periodically using the light receiving signal based on light returning from the reference image, when light is emitted from the emitting unit to the reference image arranged in a mounting device, at a state of the emitting unit not mounted in the mounting device, through the control module; wherein the second phase adjustment is performed based on a phase at least one of the first signal and the second signal adjusted by the first phase adjustment, can be provided.

BRIEF DESCRIPTION OF THE DRAWINGS

The above and other aspects, features and advantages of the present invention will become more apparent to those of ordinary skill in the art by describing exemplary embodiments thereof in detail with reference to the accompanying drawings, in which:

FIG. 50 shows a diagram representing that a reference pattern part disposed below a mounting device is moved upward through an adjustment part according to an embodiment (a), and a diagram representing that a reference pattern part disposed below a mounting device is moved downward through an adjustment part according to an embodiment (b);

FIG. 52 is a table showing a scheme in which signals obtained by a control module are stored according to an embodiment;

FIG. 53 shows a table representing a scheme in which obtained signals are stored when there is no phase delay according to an embodiment (a), and a table representing a scheme in which obtained signals are stored when there is a phase delay according to an embodiment (b);

DETAILED DESCRIPTION OF EXEMPLARY EMBODIMENTS

Figure 1:
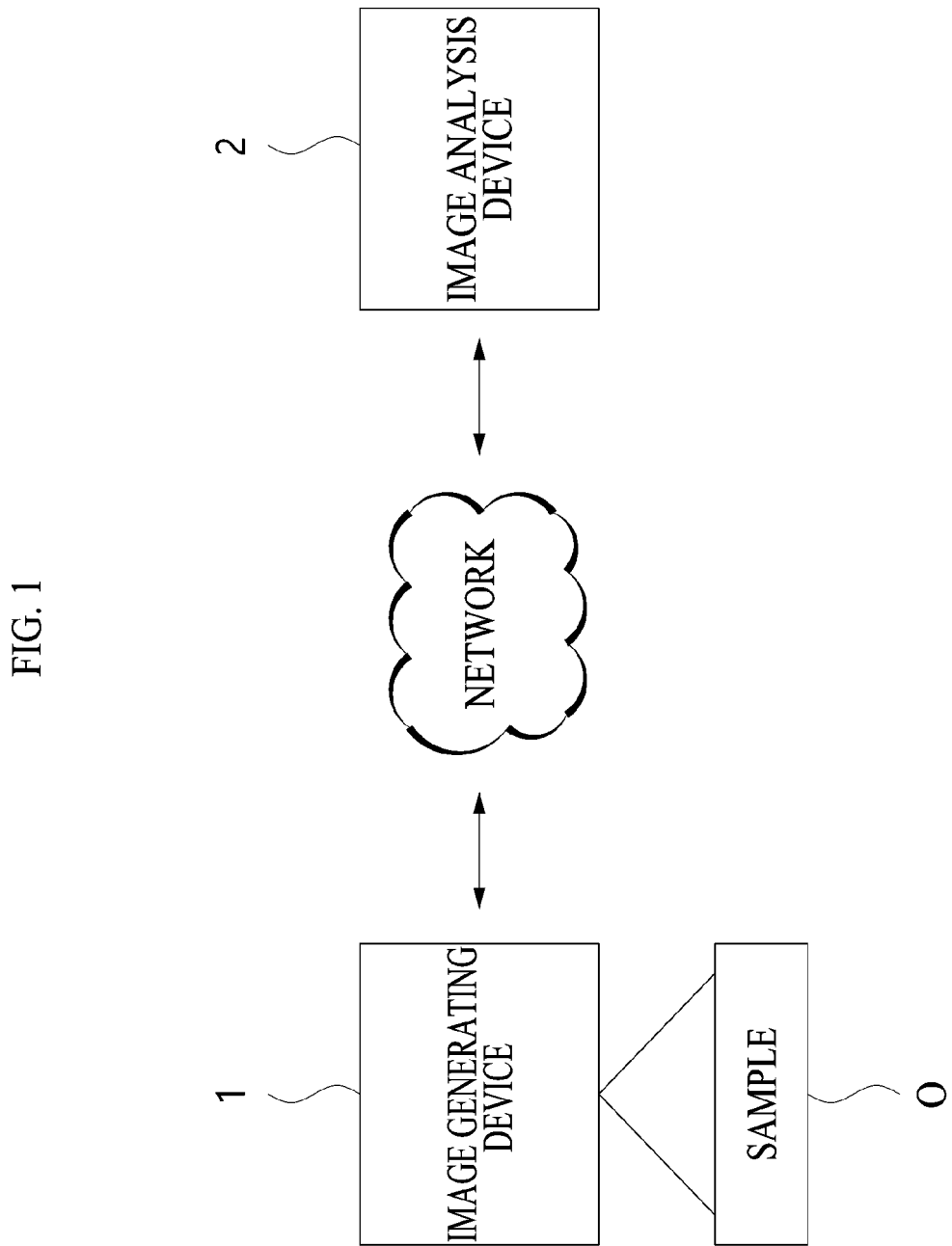
FIG. 1 is a diagram for exemplarily describing an environment in which an image generating device is used according to an embodiment of the present invention.

The above aspects, features, and advantages of the present invention will become more apparent from the following detailed description taken in conjunction with the accompanying drawings. Since the present invention may be variously modified and have several exemplary embodiments, specific embodiments will be shown in the accompanying drawings and described in detail.

In the drawings, the thickness of layers and regions is exaggerated for clarity. Also, when it is mentioned that an element or layer is "on" another element or layer, the element or layer may be formed directly on another element or layer, or a third element or layer may be interposed therebetween. Like reference numerals refer to like elements throughout the specification. Further, like reference numerals will be used to designate like elements having similar functions throughout the drawings within the scope of the present invention.

Detailed descriptions about well-known functions or configurations associated with the present invention will be ruled out in order not to unnecessarily obscure subject matters of the present invention. It should also be noted that, although ordinal numbers (such as first and second) are used in the following description, they are used only to distinguish similar elements.

The suffixes "module" and "unit" for elements used in the following description are given or used interchangeably only for facilitation of preparing this specification, and thus they are not assigned a specific meaning or function.

According to an embodiment, there may be provided an optical device including an optical fiber having a fixed end and a free end; a first actuator positioned at a actuator position between the fixed end and the free end and configured to apply a first force on the actuator position of the optical fiber such that a movement of the free end of the optical fiber in a first direction is caused, wherein the first direction is orthogonal to a longitudinal axis of the optical fiber; and a deformable rod disposed adjacent to the optical fiber, and having a first end and a second end, wherein the first end is connected to a first rod position of the optical fiber and the second end is connected to a second rod position of the optical fiber, wherein the first rod position and the second rod position of the optical fiber are positioned between the actuator position and the free end, wherein the deformable rod is substantially parallel to the optical fiber from the first rod position of the optical fiber to the second rod position of the optical fiber, and wherein, in the cross section perpendicular to the longitudinal axis of the optical fiber, the deformable rod is arranged such that an angle between a virtual line connected from the first end of the deformable rod to the first rod position of the optical fiber and the first direction is within a predetermined angle, whereby the movement of the optical fiber in a second direction perpendicular to the first direction is limited when the free end of the optical fiber moves in the first direction as the first actuator applies the first force on the actuator position of the optical fiber. Also, the optical device may further include a second actuator configured to apply a second force on the actuator position of the optical fiber, wherein the second actuator induce the free end of the optical moves in the second direction.

Also, the optical fiber may vibrate by the first force applied from the first actuator and the second force applied from the second actuator and moves corresponding to a Lissagjous pattern in accordance with a predetermined condition.

Also, the optical fiber may have a first rigidity and the deformable rod has a second rigidity.

Also, the deformable rod may change the rigidity of the optical fiber for at least one of the first direction and the second direction when the optical fiber moves in accordance with the first force and the second force.

Also, the optical fiber may drive different resonant frequencies with respect to the first direction and the second direction.

Also, a length of the deformable rod may be shorter than a length of the optical fiber.

Also, the first end of the deformable rod may be fixed to the first rod position of the optical fiber by a first connector and the second end of the deformable rod is fixed to the second rod position of the optical fiber by a second connector.

Also, the first connector and the second connector may move as the optical fiber vibrates.

Also, the optical device may further include a controller configured to apply a first driving frequency to the first actuator and a second driving frequency to the second actuator.

Also, a difference between the first driving frequency and the second driving may be more than a predetermined range.

Also, the predetermined angle may be below +a ° and −b ° about the first direction.

Also, the a ° and b ° may have different values.

Also, an absolute value of a minus b (|a−b|) may be below 10 about the first direction.

Also, an absolute value of a minus b (|a−b|) may be below 5 about the first direction.

According to another aspect, there may be provided an optical device including an optical fiber having a fixed end and a free end, and configured to irradiate a predetermined scanning pattern; a first actuator positioned at a actuator position between the fixed end and the free end and configured to apply a first force on the actuator position of the optical fiber such that a movement of the free end of the optical fiber in a first direction is caused; a second actuator configured to apply a second force on the actuator position of the optical fiber such that a movement of the free end of the optical fiber in a second direction is caused, wherein the first direction is orthogonal to a longitudinal axis of the optical fiber, and the second direction is perpendicular to the first direction; a deformable rod having a first end and a second end, and disposed in the first direction or the second direction adjacent to the optical fiber, wherein the first end is fixed to a first rod position of the optical fiber and the second end is fixed to a second rod position of the optical fiber, wherein the first rod position and the second rod position of the optical fiber are positioned between the actuator position and the free end; and a controller configured to apply a first driving frequency to the first actuator and a second driving frequency to the second actuator; wherein an aspect ratio of the scanning pattern irradiated by the optical fiber is associated with the attachment direction of the deformable rod, and wherein the controller adjusts the aspect ratio of the scanning pattern by applying a first voltage to the first actuator and a second voltage to the second actuator.

Also, the first driving frequency and the second driving frequency may be different.

Also, the controller may apply the same voltage to the first actuator and the second actuator so that the optical fiber irradiates the scanning pattern having a different aspect ratio with respect to the first direction and the second direction.

Also, the aspect ratio of the first direction may be greater than the second direction when the deformable rod is fixed on the first direction.

Also, the aspect ratio of the second direction may be greater than the first direction when the deformable rod is fixed on the second direction.

Also, the controller may apply a voltage greater than the second actuator to the first actuator to irradiate the scanning pattern having a one-to-one ratio with respect to the first direction and the second direction.

Also, the controller may control the optical fiber so as to move corresponding a Lissajous pattern in accordance with a predetermined condition.

Also, a difference between the first driving frequency and the second driving may be more than a predetermined range.

Also, the first end of the deformable rod may be fixed to the first rod position of the optical fiber by a first connector and the second end of the deformable rod is fixed to the second rod position of the optical fiber by a second connector.

Also, the first connector and the second connector may move together as the optical fiber vibrates.

Also, in the cross section perpendicular to the longitudinal axis of the optical fiber, the deformable rod may be arranged such that an angle between a virtual line connected from the first end of the deformable rod to the first rod position of the optical fiber and the first direction is within a predetermined angle.

Also, the predetermined angle may be below +a ° and −b ° about the first direction.

Also, the a ° and b ° may have different values.

Also, an absolute value of a minus b (|a−b|) may be below 10 about the first direction.

Also, an absolute value of a minus b (|a−b|) may be below 5 about the first direction.

Also, the optical fiber has a first rigidity and the deformable rod may have a second rigidity.

Also, the deformable rod may change the rigidity of at least one of the first direction and the second direction of the optical fiber when the optical fiber moves in accordance with the first force and the second force.

According to another aspect, there may be provided an image generating device including an irradiation unit configured to irradiate light to an object, a light receiving unit configured to receive the returned light from the object and obtain a signal based on the returned light, and a controller configured to generate an image based on the signal obtained from the light receiving unit, the device comprising: an optical fiber having a fixed end and a free end; a first actuator positioned at a actuator position between the fixed end and the free end and configured to apply a first force on the actuator position of the optical fiber such that a movement of the free end of the optical fiber in a first direction is caused; a second actuator configured to apply a second force on the actuator position of the optical fiber such that a movement of the free end of the optical fiber in a second direction is caused, wherein the first direction is orthogonal to a longitudinal axis of the optical fiber, and the second direction is perpendicular to the first direction; a deformable rod having a first end and a second end, and disposed in the first direction or the second direction adjacent to the optical fiber, wherein the first end is fixed to a first rod position of the optical fiber and the second end is fixed to a second rod position of the optical fiber, wherein the first rod position and the second rod position of the optical fiber are positioned between the actuator position and the free end, wherein an aspect ratio of the generated image is associated with the attachment direction of the deformable rod, and wherein the controller adjusts the aspect ratio of the generated image by applying a first voltage to the first actuator and a second voltage to the second actuator. According to another aspect, there may be provided an optical device including an optical fiber having a fixed end and a free end; a first actuator positioned at a actuator position between the fixed end and the free end and configured to apply a first force on the actuator position of the optical fiber such that a movement of the free end of the optical fiber in a first direction is caused; a second actuator configured to apply a second force on the actuator position of the optical fiber such that a movement of the free end of the optical fiber in a second direction, wherein the first direction is orthogonal to a longitudinal axis of the optical fiber, and the second direction is perpendicular to the first direction; a mass having a preselected size, and disposed between the fixed end and the free end of the optical fiber; and a housing receiving the optical fiber, the first actuator and the second actuator, wherein the optical fiber vibrates inside the housing by the first force and the second force, and a maximum movement range of the optical fiber depends on the location of the mass, wherein the mass is located away from the free end of the optical fiber by a buffer distance to prevent the mass from colliding with an inner wall of the housing and being damaged when the optical fiber vibrates, and wherein the buffer distance is set based on at least one of the size of the mass, an inner diameter of the housing, and the maximum movement range of the optical fiber, and wherein the buffer distance is determined at least one of the following is less than ½ of an inner diameter of the housing: the maximum movement range of the optical fiber from the center of the inner diameter and a maximum movement range of the mass from the center of the inner diameter.

Also, the buffer distance may be at least equal to or greater than a length of the mass.

Also, the optical device may further include a deformable rod disposed adjacent to the optical fiber, and having a first end and a second end, wherein the first end is fixed to a first rod position of the optical fiber and the second end is fixed to a second rod position of the optical fiber, wherein the first rod position and the second rod position of the optical fiber are positioned between the actuator position and the free end, wherein the deformable rod is substantially parallel to the optical fiber from the first rod position of the optical fiber to the second rod position of the optical fiber.

Also, in the cross section perpendicular to the longitudinal axis of the optical fiber, the deformable rod may be arranged such that an angle between a virtual line connected from the first end of the deformable rod to the first rod position of the optical fiber and the first direction is within a predetermined angle.

Also, the optical fiber may vibrate by the first force applied from the first actuator and the second force applied from the second actuator and move corresponding to a Lissagjous pattern in accordance with a predetermined condition.

Also, the first end of the deformable rod may be fixed to the first rod position of the optical fiber by a first connector and the second end of the deformable rod is fixed to the second rod position of the optical fiber by a second connector.

Also, the optical device may further include a controller configured to apply a first driving frequency to the first actuator and a second driving frequency to the second actuator.

Also, a difference between the first driving frequency and the second driving may be more than a predetermined range.

Also, the size of the mass may be preselected so that the optical fiber is resonantly driven with a predetermined amplitude with respect to the first direction and the second direction.

Also, the mass may be attached to the second rod position to fix the second end of the deformable rod on the optical fiber.

Also, the second rod position may be determined such that the optical fiber has a different resonant frequency with respect to the first direction and the second direction.

According to another aspect, there may be provided an image generating device for obtaining an image of an object, including a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set based on the first signal, the second signal and the light receiving signal, wherein the control module configured to obtain a second data set based on the first data set by adjusting at least one of the first phase component of the first signal and the second phase component of the second signal, wherein the control module configured to select from the first data set and the second data set based on predetermined criteria, and wherein the image of the object is generated based on the selected data set. Also, the light receiving signal may include a light intensity corresponding to a plurality of pixel positions determined by the first signal and the second signal.

Also, the light intensity corresponding to at least one of the pixel positions may be plural, and the control module may be configured to select a data set among the first data set and the second data set based on a difference among the plurality of light intensities corresponding to each of the pixel positions in the first data set and the second data set.

Also, the control module may select the data set among the first data set and the second data set for obtaining the image of the object, and the selected data set may have the smallest sum of the difference among the plurality of light intensities corresponding to each of pixel positions.

Also, the difference among the plurality of light intensities may comprise a variance among the plurality of light intensities.

Also, the difference among the plurality of light intensities may be a standard deviation among the plurality of light intensities.

Also, at least one of the light intensities corresponding to a first pixel position in the second data set may be different from at least one of the light intensities corresponding to the first pixel position in the first data set.

Also, the first data set may be generated using the first signal, the second signal and the light receiving signal, and the second data set may be generated using a phase-adjusted first signal, the second signal and the light receiving signal when the first phase component of the first signal is adjusted.

Also, the first data set may be generated using the first signal, the second signal and the light receiving signal, and the second data set may be generated using the first signal, a phase-adjusted second signal and the light receiving signal when the second phase component of the second signal is adjusted.

Also, the first data set may be generated using a signal that at least one phase components of the first signal and the second signal is adjusted and the light receiving signal, and the second data set may be generated using a signal that at least one phase components of the first signal and the second signal is adjusted and the light receiving signal.

Also, the light intensity of the light receiving signal corresponding to the plurality of pixel positions of the second data set may be shifted from the first data set.

Also, the first axis direction may be perpendicular to the second axis direction, and the first axis direction may represent x-axis of a rectangular coordinate system and the second axis direction may represent y-axis of the rectangular coordinate system.

Also, the first phase component of the first signal may be adjusted, wherein the first signal which phase not adjusted may be applied to the emitting unit, and the phase-adjusted first signal may be used for generating the phase-adjusted data set.

Also, the emitting unit may emit the light in a predetermined pattern as the first signal and the second signal are applied.

Also, the control module may determine the adjusted phase component which is corresponding to the image generated by using the phase-adjusted data set as a final adjustment phase for adjusting at least one of the first signal and the second signal.

According to another aspect, there may be provided an image generating method for obtaining an image of an object, including: generating a first signal having a first frequency component and a first phase component for a first axis direction, and a second signal having a second frequency component and a second phase component in a second axis direction through a control module; obtaining light receiving signal based on returned light from the object, through a light receiving unit; obtaining a first data set based on the first signal, the second signal and the light receiving signal, obtaining a second data set based on the first data set by adjusting at least one of the first phase component of the first signal and the second phase component of the second signal, selecting from the first data set and the second data set based on predetermined criteria, and generating the image of the object based on the selected data set.

According to another aspect, there may be provided a non-transitory computer-readable recording medium having recorded thereon one or more programs comprising commands for executing the image generating method.

According to another aspect, there may be provided an image generating device for obtaining an image of an object including a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set based on the first signal, the second signal and the light receiving signal, wherein the control module configured to obtain a second data set based on the first data set by adjusting at least one of the first phase component of the first signal and the second phase component of the second signal using a first amount of phase adjustment, wherein the control module configured to select from the first data set and the second data set based on predetermined criterion, wherein the control module configured to obtain a third data set based on the second data set by adjusting phase component of at least one of signals used for obtaining the second data set using the first amount of phase adjustment, when the second data set is selected among the first data set and the second data set, wherein the control module configured to select from the second data set and the third data set based on the predetermined criterion, and wherein the control module configured to generate the image of the object based on the second data set, when the second data set is selected among the second data set and the third data set.

Also, the first amount of phase adjustment may be set to correspond a fill factor according to signals corresponding to the first data set and a fill factor according to signals corresponding to the second data set, wherein the fill factors represents a degree of inclusion of a light emission region from the image generating device in a predetermined plurality regions.

Also, the control module may be configured to obtain at least one of a candidate phase based on phase component of signals corresponding to the second data set for generating the image of the object, wherein the control module may be configured to obtain at least one of a candidate data set corresponding to at least one of the candidate phase, wherein the control module may be configured to select a first candidate data set mostly corresponding to the predetermined criterion among the at least one of the candidate data set, and wherein the control module configured to generate the image of the object based on the first candidate data set.

Also, the control module may be configured to obtain a fourth data set based on the second data set by adjusting at least one of signals used for obtaining the second data set using a second amount of phase adjustment, wherein the control module may be configured to select from the second data set and the fourth data set based on the predetermined criterion, wherein the control module may be configured to obtain a fifth data set based on the fourth data set by adjusting at least one of signals used for obtaining the fourth data set using the second amount of phase adjustment, when the fourth data set is selected among the second data set and the fourth data set, wherein the control module may be configured to select from the fourth data set and the fifth data set based on the predetermined criterion, and wherein the control module may be configured to generate the image of the object based on the fourth data set, when the second data set is selected among the fourth data set and the fifth data set.

Also, the signals corresponding to the first data set may include a signal substantially 90 degree changed from a first phase angle component of the first signal and a signal substantially 90 degree changed from a second phase angle component of the second signal, wherein the first phase angle component is based on the first frequency component and the first phase component, and the second phase angle component is based on the second frequency component and the second phase component.

Also, the control module may compare the first frequency component and the second frequency component, wherein the control module may be configured to adjust a phase component of signal having the first frequency component among the signals corresponding to the first data set by the first amount of phase adjustment, when the first frequency component is smaller than the second frequency component, and wherein the control module may be configured to adjust a phase component of signal having the second frequency component among the signals corresponding to the first data set by the first amount of phase adjustment, when the second frequency component is smaller than the first frequency component.

Also, first data set may include a first pixel position and a second pixel position, wherein the light receiving signal includes light intensities corresponding to of the first pixel position and light intensities corresponding to the second pixel position, wherein the second data set may include a third pixel position and a fourth pixel position, wherein the light receiving signal may include light intensities corresponding to the third pixel position and light intensities corresponding to the fourth pixel position, wherein the control module may be configured to obtain a first sum representing a sum of a difference value of the light intensities corresponding to the first pixel position and a difference value of the light intensities corresponding to the second pixel position, wherein the control module may be configured to obtain a second sum representing a sum of a difference value of the light intensities corresponding to the third pixel position and a difference value of the light intensities corresponding to the fourth pixel position, and wherein the control module may be configured to determine the second data set is more corresponding to the predetermined criterion than the first data set, when the second sum is smaller than the first sum.

Also, the difference value of the light intensities corresponding to the pixel positions may be a standard deviation of the light intensities corresponding to the pixel positions.

Also, the control module may be configured to obtain a difference value among the phase component of the signals corresponding to the second data set, wherein the control module may be configured to adjust at least one of phase component among the first signal and the second signal using the difference value among the phase component and a predetermined phase adjustment value, and wherein the emitting unit may be configured to emit light to the object by receiving the signal at least one of the phase component among the first signal and the second signal using the difference value among the phase component and the predetermined phase adjustment value.

Also, the predetermined phase adjustment value may be determined based on substantially half of an odd multiple of the first amount of phase adjustment and the first amount of phase adjustment, when the first frequency component and the second frequency component are odd, and wherein the predetermined phase adjustment value may be determined based on substantially half of an even multiple of the first amount of phase adjustment and the first amount of phase adjustment, when one of the first frequency component and the second frequency component is even.

According to another aspect, there may be provided an image generating device for obtaining an image of an object, including a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set using the first signal, the second signal and the light receiving signal, wherein the control module adjusts a phase component of at least one of the first signal or the second signal by a first amount of phase adjustment by plurality of times, wherein the control module configured to obtain a plurality of data sets using each of the signal adjusted by the plurality of times and a light receiving signal adjusted by the plurality of times, wherein the control module configured to obtain a data set using at least one of the signal and the light receiving signal, when each time at least one of the signal is adjusted by the first amount of phase adjustment, wherein the control module configured to obtain a nth data set using at least one of the signal which the phase component is adjusted by the first amount of phase adjustment n times and the light receiving signal, when at least one of the signal is adjusted by the first amount of phase adjustment n times, wherein the control module adjusts a phase component of at least one of the first signal or the second signal by the first amount of phase adjustment by (n+1) times, when the nth data set is more corresponding to the predetermined criterion than a (n−1)th data set obtained previously than the nth data set, wherein the (n−1)th data set is obtained when the phase component of at least one of the first signal and the second signal is adjusted by the first amount of phase adjustment (n−1) times, wherein the control module configured to obtain a (n+1)th data set using at least one of the signal which the phase component is adjusted by the first amount of phase adjustment by (n+1) times and the light receiving signal, and wherein the control module producing the image based on at least one of the signal which the phase component is adjusted by the first amount of phase adjustment (n−1) times, when the (n−1)th data set is more corresponding to the predetermined criterion than the nth data set.

Also, at least one of the signal adjusted by the first amount of phase adjustment may be the first signal having the first frequency component and the first phase component, wherein the control module may be configured to obtain a mth data set using a second signal which the phase component is adjusted by the first amount of phase adjustment m times and the light receiving signal, when the second phase component of the second signal is adjusted by the first amount of phase adjustment by m times, wherein the m is an integer larger than 2, wherein the control module may adjust a phase component of at least one of the first signal or the second signal by the first amount of phase adjustment (m+1) times, when the mth data set is more corresponding to the predetermined criterion than a (m−1)th data set obtained previously than the mth data set, wherein the (m−1)th data set may be obtained when the phase component of the second signal is adjusted by the first amount of phase adjustment (m−1) times, wherein the control module may be configured to obtain a (m+1)th data set using at least one of the signal which the phase component is adjusted by the first amount of phase adjustment (m+1) times and the light receiving signal, wherein the control module producing the image based on the second signal which the phase component may be adjusted by the first amount of phase adjustment (m−1) times, when the (m−1)th data set is more corresponding to the predetermined criterion than the mth data set.

Also, the data set of any one of the obtained data sets may include a plurality of first pixel position and a plurality of second pixel position, wherein the light receiving signal of the any one of the data set may include light intensities corresponding to the first pixel position and light intensities corresponding to the second pixel position, wherein the other data set which excepts the any one of the data set among the obtained data sets may include a third pixel position and a fourth pixel position, wherein the light receiving signal may include light intensities corresponding to the third pixel position and light intensities corresponding to the fourth pixel position, wherein the control module may be configured to obtain a first sum representing a sum of a difference value of the light intensities corresponding to the first pixel position and a difference value of the light intensities corresponding to the second pixel position, wherein the control module may be configured to obtain a second sum representing a sum of a difference value of the light intensities corresponding to the third pixel position and a difference value of the light intensities corresponding to the fourth pixel position, and wherein the control module determines the second data set may be more corresponding to the predetermined criterion than the first data set, when the second sum is smaller than the first sum.

Also, the difference value of the light intensities corresponding to the pixel position is a standard deviation of the light intensities corresponding to the pixel position.

According to another aspect, there may be provided an image generating device for obtaining an image of an object, including a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first phase adjusted signal which is a sum of a n times of a first amount of phase adjustment and the first phase component of the first signal, wherein the control module configured to obtain a second phase adjusted signal which is a sum of a m times of a first amount of phase adjustment and the second phase component of the second signal, wherein the n and m are different integer and larger than 1, and wherein the control module configured to generate the image using a first data set obtained based on the first phase adjusted signal, when the first data set obtained based on the first phase adjusted signal and the second signal is more corresponding to a predetermined criterion than a second data set obtained based on the second phase adjusted signal and the second signal.

Also, the data set of any one of the obtained data sets may include a first pixel position and a second pixel position, wherein the light receiving signal of the any one of the data set includes light intensities corresponding to the first pixel position and light intensities corresponding to the second pixel position, wherein the other data set which excepts the any one of the data set among the obtained data sets may include a third pixel position and a fourth pixel position, wherein the light receiving signal may include light intensities corresponding to the third pixel position and light intensities corresponding to the fourth pixel position, wherein the control module may be configured to obtain a first sum representing a sum of a difference value of the light intensities corresponding to the first pixel position and a difference value of the light intensities corresponding to the second pixel position, wherein the control module may be configured to obtain a second sum representing a sum of a difference value of the light intensities corresponding to the third pixel position and a difference value of the light intensities corresponding to the fourth pixel position, and wherein the control module may determine the second data set is more corresponding to the predetermined criterion than the first data set, when the second sum is smaller than the first sum.

Also, the difference value of the light intensities corresponding to the pixel position is a standard deviation of the light intensities corresponding to the pixel position.

According to another aspect, there may be provided an image generating device for obtaining an image of an object, including a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to generate and output a first image using the first signal and the second signal at a first point of time, wherein at least one of the first signal and the second signal is adjusted during a predetermined time period after the first point of time, wherein the control module generates and outputs a second image using at least one of the phase adjusted signal at a second point of time after the predetermined time period, wherein a difference between the phase of the first signal at the first point of time and the phase of the first signal at the second point of time and a difference between the phase of the second signal at the first point of time and the phase of the second signal at the second point of time are different by substantially an integer multiple of a first amount of phase adjustment, and wherein the first amount of phase adjustment is determined based on the first frequency component and the second frequency component.

According to another aspect, there may be provided an image generating method for obtaining an image of an object, including generating a first signal having a first frequency component and a first phase component for a first axis direction, and a second signal having a second frequency component and a second phase component in a second axis direction through a control module; obtaining light receiving signal based on returned light from the object, through a light receiving unit; obtaining a first data set based on the first signal, the second signal and the light receiving signal; obtaining a second data set based on the first data set by adjusting at least one of the first phase component of the first signal and the second phase component of the second signal using a first amount of phase adjustment; selecting from the first data set and the second data set based on predetermined criterion; obtaining a third data set based on the second data set by adjusting phase component of at least one of signals used for obtaining the second data set using the first amount of phase adjustment, when the second data set is selected among the first data set and the second data set; selecting from the second data set and the third data set based on the predetermined criterion;

and generating the image of the object based on the second data set, when the second data set is selected among the second data set and the third data set.

According to another aspect, there may be provided a non-transitory computer-readable recording medium having recorded thereon one or more programs comprising commands for executing the image generating method.

According to another aspect, there may be provided a light irradiating unit, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module configured to obtain a first data set based on the first signal, the second signal and the light receiving signal, wherein the control module configured to obtain a second data set based on the first data set by adjusting at least one of the first phase component of the first signal and the second phase component of the second signal using a first amount of phase adjustment, wherein the control module configured to select from the first data set and the second data set based on predetermined criterion, wherein the control module configured to obtain a third data set based on the second data set by adjusting phase component of at least one of signals used for obtaining the second data set using the first amount of phase adjustment, when the second data set is selected among the first data set and the second data set, wherein the control module configured to select from the second data set and the third data set based on the predetermined criterion, and wherein the control module configured to generate the image of the object based on the second data set, when the second data set is selected among the second data set and the third data set.

According to another aspect, there may be provided an optical device for emitting light to an object, comprising: a control module configured to generate actuating signals; and an emission unit configured to receive the actuating signals and emit light to the object based on the actuating signals; wherein when the emission unit receives a first actuating signal having a first actuating frequency and a first phase and a second actuating signal having a second actuating frequency and a second phase among the actuating signals, the emission unit emits the light with a first scanning pattern based on the first actuating signal and the second actuating signal, wherein when the emission unit receives a third actuating signal having the third actuating frequency and a third phase and a fourth actuating signal having a fourth actuating frequency and a fourth phase among the actuating signals, the emission unit emits the light with a second scanning pattern based on the third actuating signal and the fourth actuating signal, wherein the first phase and the second phase have different by a first phase difference, wherein the third phase and the fourth phase have different by a second phase difference, and wherein the control module configured to generate the actuating signals by setting difference between the first phase difference and the second phase difference being n times of a predetermined phase.

Also, the optical device may further include a light receiving unit configured to receive light returning from the object and generate light receiving signal, for obtaining light returning from the object and obtaining an image of the object using the obtained light; wherein the control module is configured to obtain a first data set using light returned from the object with the first scanning pattern, wherein the control module is configured to obtain a second data set using light returned from the object with the second scanning pattern, and wherein the control module is configured to obtain a third data set using the first data set and the second data set and generates the image of the object based on the third data set.

Also, a plurality of regions may be defined from the third data set, and wherein a first fill factor representing a degree of inclusion of the plurality of regions from the third data set in a predetermined total regions of the image of the object may be larger than a predetermined criterion.

Also, the first fill factor is 100%.

Also, the predetermined phase may be based on the first actuating frequency or the second actuating frequency and a predetermined total regions when light is emitted from the optical device, when the phase difference between the first phase and the second phase and the phase difference between the third phase and the fourth phase are differed by n times of a predetermined phase.

Also, the predetermined phase is determined by a first formula $$a = \frac{1}{2\pi f_x} \sin^{-1}\left(\frac{2}{\text{pixel}}\right) \qquad \text{[The first Formula]}$$

where a indicates the predetermined phase, $f_x$ indicates the first driving frequency, and pixel indicates the number of predetermined regions.

Also, the predetermined phase may be determined by a second Formula $$a = \frac{1}{2\pi f_y} \sin^{-1}\left(\frac{2}{\text{pixel}}\right) \qquad \text{[The second Formula]}$$

where a indicates the predetermined phase, $f_y$ indicates the second driving frequency, and pixel indicates the number of predetermined regions.

Also, the n may be obtained based on the first actuating frequency or the second actuating frequency, a greatest common denominator of the first actuating frequency and the second actuating frequency and a predetermined total regions, when the phase difference between the first phase and the second phase and the phase difference between the third phase and the fourth phase, by n times of a predetermined phase.

Also, n may be determined by a third Formula $$n = \frac{GCD * \pi}{f_x * \sin^{-1}\left(\frac{2}{\text{pixel}}\right)} \qquad \text{[The third Formula]}$$

where GCD indicates the greatest common divisor between the first driving frequency and the second driving frequency, $f_x$ indicates the first driving frequency, and pixel indicates the number of predetermined regions.

Also, n may be determined by a forth Formula $$n = \frac{GCD * \pi}{f_y * \sin^{-1}\left(\frac{2}{\text{pixel}}\right)} \qquad \text{[The fourth Formula]}$$

where GCD indicates the greatest common divisor between the first driving frequency and the second driving frequency, $f_y$ indicates the second driving frequency, and pixel indicates the number of predetermined regions.

According to another aspect, there may be provided an light emitting method by an optical device for emitting light to an object, wherein the optical device comprising a control module configured to generate actuating signals and an emission unit configured to receive the actuating signals and emit light to the object based on the actuating signals, the light emitting method comprising: receiving a first actuating signal having a first actuating frequency and a first phase and a second actuating signal having a second actuating frequency and a second phase among the actuating signals, the emission unit emits the light with a first scanning pattern based on the first actuating signal and the second actuating signal, through the emission unit; and receiving a third actuating signal having the third actuating frequency and a third phase and a fourth actuating signal having a fourth actuating frequency and a fourth phase among the actuating signals, the emission unit emits the light with a second scanning pattern based on the third actuating signal and the fourth actuating signal, through the emission unit; wherein the first phase and the second phase have different by a first phase difference, wherein the third phase and the fourth phase have different by a second phase difference, wherein the control module configured to generate the actuating signals by setting difference between the first phase difference and the second phase difference being n times of a predetermined phase. According to another aspect, there may be provided a non-transitory computer-readable recording medium having recorded thereon one or more programs comprising commands for executing the light emitting method.

According to another aspect, there may be provided a mounting device for mounting an image generating device including a probe, emitting light to an object from an one end of the probe and receiving light returning from the object at the one end of the probe, the mounting device comprising: a housing configured to hold at least part of the image generating device, wherein the at least part of the image generating device includes the one end of the probe; and a reference image providing unit configured to provide at least one of a reference image such that the image generating device performs a phase adjustment of an actuating signal related to positions of the emitted light on the object from the one end of the probe when the housing holds the at least part of the image generating device; wherein the reference image providing unit adjusts a position of the reference image for corresponding a distance between the one end of the probe and the reference image to a focal length of the probe.

According to another aspect, there may be provided a mounting device for mounting an image generating device comprising a probe, emitting light to an object from an one end of the probe and receiving light returning from the object at the one end of the probe, including a housing configured to hold at least a part of the image generating device, wherein at least the part of the image generating device includes the one end of the probe; and a reference image providing unit configured to provide a plurality of a reference image for performing a phase adjustment of an actuating signal which determines a position of light emission on the object from the one end, when the housing holds at least of the part of the image generating device; wherein the reference image providing unit comprises a plurality of layers including each of the plurality of reference image for corresponding a distance between the one end of the probe and the reference image to a focal length of the probe.

Also, the mounting device may further include an adjusting unit configured to adjust the position of the reference image for corresponding the distance between the one end of the probe and the reference image to the focal length of the probe.

Also, the reference image may be configured to use a reflective material for using a reflected signal when the image generating device emits light.

Also, the reference image providing unit may further include a cartridge configured to provide a fluorescent material to the reference image.

Also, the cartridge may comprise at least one of fluorescent materials which fluoresce signal having an wavelength of 405 nm, 488 nm, 630 nm and 785 nm.

Also, the mounting device may further include a fixing unit configured to fix the probe into the mounting device in predetermined angle.

Also, at least one layer of the reference image providing unit provides the reference image in a transparent material.

Also, the reference image may have a circular pattern.

According to another aspect, there may be provided an Image generating device for obtaining an image of an object, comprising: a control module configured to generate a first signal having a first frequency component and a first phase component for a first axis direction, and a second signal having a second frequency component and a second phase component for a second axis direction; an emitting unit configured to emit light to the object using the first signal and the second signal; and a light receiving unit configured to obtain light receiving signal based on returned light from the object; wherein the control module performs a first phase adjustment at least one of the first signal and the second signal using a light receiving signal based on light returning from a reference image, when light is emitted from the emitting unit to the reference image arranged in a mounting device, at a state of the emitting unit mounted in the mounting device, wherein the mounting device has the reference image inside, wherein the control module repeatedly performs a second phase adjustment periodically using the light receiving signal based on light returning from the reference image, when light is emitted from the emitting unit to the reference image arranged in a mounting device, at a state of the emitting unit not mounted in the mounting device, wherein the second phase adjustment is performed based on a phase at least one of the first signal and the second signal adjusted by the first phase adjustment.

Also, the first phase adjustment may be the phase adjustment for corresponding an image obtained through the control module to the reference image by comparing the image obtained by the control module and the reference image, wherein the image obtained by the control module is based on the light receiving signal obtained from the reference image.

Also, the control module may be configured to obtain a first data set based on the first signal, the second signal and the light receiving signal, wherein the control module configured to obtain a second data set based on the first data set by adjusting at least one of the first phase component of the first signal and the second phase component of the second signal wherein the control module configured to select from the first data set and the second data set based on predetermined criterion, wherein the image of the object is generated based on the selected data set. wherein the first data set and the second data set includes a plurality of pixel positions, wherein the first data set and the second data set include light intensities corresponding to the plurality of pixel positions, wherein the predetermined criterion is determined by a difference between the light intensities corresponding to each of at least part of the plurality of pixel positions.

Also, the image generating device may be configured to adjust at least one of the first signal and the second signal based on the first phase adjustment, wherein the emitting unit is actuated until the second phase adjustment performed.

According to another aspect, there may be provided a phase adjusting method by an image generating device for obtaining an image of an object, wherein the image generating device comprising a control module configured to generate a first signal having a first frequency component and a first phase component for a first axis direction, and a second signal having a second frequency component and a second phase component in a second axis direction; an emitting unit configured to emit light to the object using the first signal and the second signal and a light receiving unit configured to obtain light receiving signal by returning light from the object, based on the light emitted by the emitting unit, the phase adjusting method including: performing a first phase adjustment at least one of the first signal and the second signal using a light receiving signal based on light returning from a reference image, when light is emitted from the emitting unit to the reference image arranged in a mounting device, at a state of the emitting unit mounted in the mounting device, wherein the mounting device has the reference image inside, through the control module; and repeatedly performing a second phase adjustment periodically using the light receiving signal based on light returning from the reference image, when light is emitted from the emitting unit to the reference image arranged in a mounting device, at a state of the emitting unit not mounted in the mounting device, through the control module; wherein the second phase adjustment is performed based on a phase at least one of the first signal and the second signal adjusted by the first phase adjustment.

According to another aspect, there may be provided a non-transitory computer-readable recording medium having recorded thereon one or more programs comprising commands for executing the phase adjusting method.

1 Image Generating Device

In the following embodiment, the term "image generating device" may refer to an optical device for acquiring and providing at least one of a reflected image RI, a fluorescence image FI, and a transmitted image TI of an object in real-time.

As an example, the image generating device may include various kinds of endomicroscopes for directly observing or diagnosing pathological conditions of living bodies.

An endomicroscope is an optical microscope that is based on laser light such as a confocal type, two-photon type, and OCT type.

In general, a confocal microscope uses a pinhole to block out-of-focus light and focus only light having passed through the pinhole onto an objective lens to perform imaging on a pixel basis.

As one microscope using this confocal principle, there is a confocal laser scanning microscope (CLSM), which applies laser light to a sample, generates light of a certain wavelength, receives only in-focus light, converts the light into a digital signal, and observes the digital signal.

Unlike typical optical microscopes, a confocal laser scanning microscope (CLSM) may focus a laser beam onto a sample and may generate an image using fluorescent light, reflected light, and transmitted light emitted from the sample.

For example, a fluorescence image may be observed by using autofluorescence emitted from a specific material included in a sample or by injecting a fluorescent material into a sample.

Also, when a confocal laser scanning microscope is used, it is possible to obtain an image having outstanding sharpness and high resolution because scattered light originating from other parts of the sample is blocked.

As another example, an image generating device may include a laser microscanner for precisely observing or diagnosing an object in real-time.

Laser microscanners are typically classified into a micro electric mechanical system (MEMS) scanner using a semiconductor processing method and an optical fiber scanner using an optical fiber.

Also, laser microscanners may be classified into a side-viewing type, a circumferential-viewing type, and a forward-viewing type.

An MEMS scanner includes a lens scanner and a mirror scanner for reflecting laser light and usually performs side imaging.

An MEMS scanner requires an additional device for re-bending a beam bent by a mirror in order to perform forward imaging, and thus is difficult to compactly package.

On the contrary, an optical fiber scanner is driven using an actuator such as a piezoelectric element and thus can be simply and compactly packaged compared to an MEMS mirror scanner.

Also, an optical fiber scanner is driven at a resonant frequency of an optical fiber and thus implements a wide field of view (FOV) at a relatively low voltage.

The above-described image generating devices may be utilized in various fields for acquiring a fluorescence image, a reflected image, a transmitted image, and the like of an object in the form of a two-dimensional (2D) or three-dimensional (3D) image.

For example, the image generating devices may be used to observe and diagnose a picture of an object in real-time in fields such as biological research, disease diagnosis, and endoscopic surgery.

Also, for example, the image generating device may be used to measure the remaining life of a metal structure under inspection on the basis of cracks, holes, and the degree of creep of a metal installation.

Also, for example, the image generating device may be applied even to a light detection and ranging (LiDAR) device for generating 3D stereo information by reflecting and scanning a laser beam in a distributed fashion and measuring an optical return distance.

1.1 Usage Environment

FIG. 1 is a diagram for exemplarily describing an environment in which an image generating device is used according to an embodiment of the present invention.

Referring to FIG. 1, an image generating device 1 according to an embodiment of the present invention may scan an object O to generate an image in real-time.

For example, the image generating device 1 may be a miniaturized optical fiber scanner for monitoring pathological conditions of living tissue in a laboratory or an operating room in real-time.

Also, an image analysis device 2 may be a device for performing a pathological diagnosis in real-time by using an image generated by the image generating device 1.

For example, the image analysis device 2 may be an electronic device assigned to a medical technician capable of performing a pathological diagnosis. Alternatively, for example, the image analysis device 2 may be provided in the form of a module inside an electronic device assigned to a medical technician capable of performing a pathological diagnosis.

Also, the image generating device 1 and the image analysis device 2 may be connected to each other over a network N.

The network N may include various wired or wireless networks, and the image generating device 1 and the image analysis device 2 may transmit and receive various kinds of information over the network N.

For example, the image generating device 1 may transmit an image generated in the image generating device 1 to the image analysis device 2 over the network N in real-time.

In an embodiment, when the image analysis device 2 is provided in the form of a module in an electronic device assigned to a medical technician, the image analysis device 2 may be a program and a software application for performing a pathological diagnosis on the basis of an image transmitted from the image generating device 1 in real-time.

For example, a medical technician may diagnose a cancer and determine a surgical site on the basis of a biometric image displayed on the electronic device.

Also, for example, a medical technician may enter information related to cancer diagnosis and surgical site determination through an application running on the electronic device.

Alternatively, for example, the image analysis device 2 may automatically diagnose a cancer and determine a surgical site on the basis of a prestored image analysis program.

In this case, a machine learning algorithm in which criteria for cancer diagnosis, surgical site determination, and the like are prestored may be stored in the image analysis device 2.

Also, for example, the image analysis device 2 may merge or map information related to cancer diagnosis or surgical site determination to an image received from the image generating device 1 and may transmit the merging or mapping result to the image generating device 1 or another electronic device (not shown).

The aforementioned embodiment illustrates an environment in which the image generating device 1 is used in order to aid in understanding, and the scope of the present invention is not limited to the above-described embodiment.

1.2 Configuration of Image Generating Device

Schematic elements of an image generating device according to an embodiment of the present invention will be described in detail below with reference to FIGS. 2 to 5.

Figure 2:
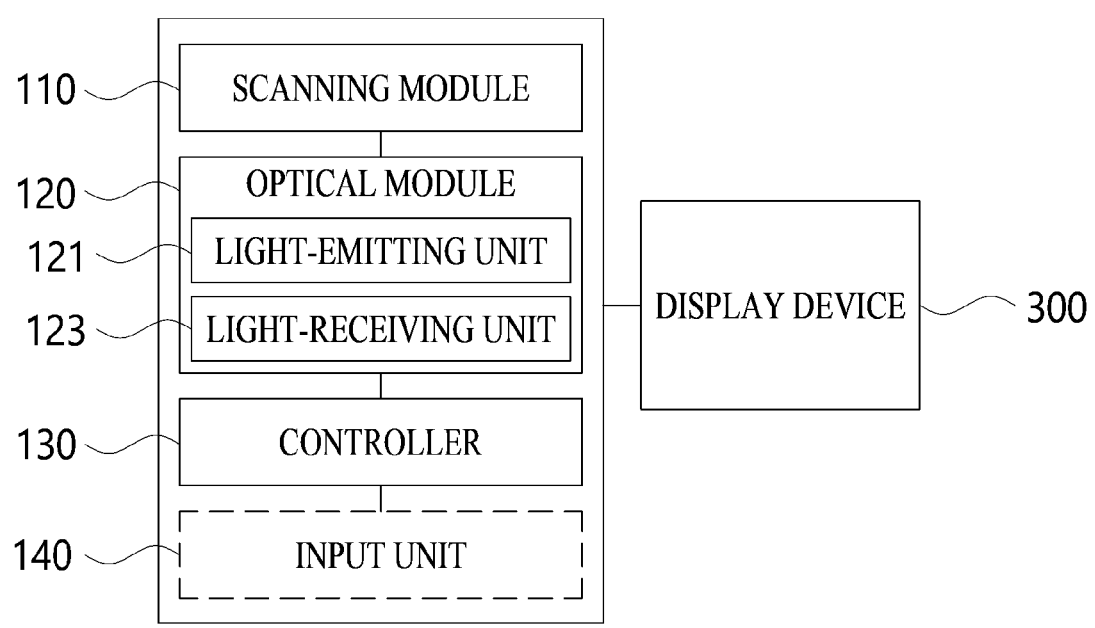
FIG. 2 is a block diagram for exemplarily describing a configuration of an image generating device according to an embodiment of the present invention.

FIG. 2 is a block diagram for exemplarily describing a configuration of an image generating device according to an embodiment of the present invention.

Referring to FIG. 2, an image generating device 1 according to an embodiment of the present invention may include a scanning module 110, a controller 130, and an optical module 120.

The scanning module 110 may emit light to the object while the scanning module 110 is spaced a predetermined distance apart from or is in contact with an object. Accordingly, the scanning module 110 may measure the inside of the object within a preset distance from the surface of the object.

For example, the preset distance may be changed by adjusting a focal length of the lens module, which will be described below, and may range from 0 um to 250 um.

Also, the scanning module 110 may be a stationary device or a handheld optical device.

For example, when the scanning module 110 is of a handheld type, the scanning module may be implemented in the form of an endoscope, a pen, or the like.

Figure 3:
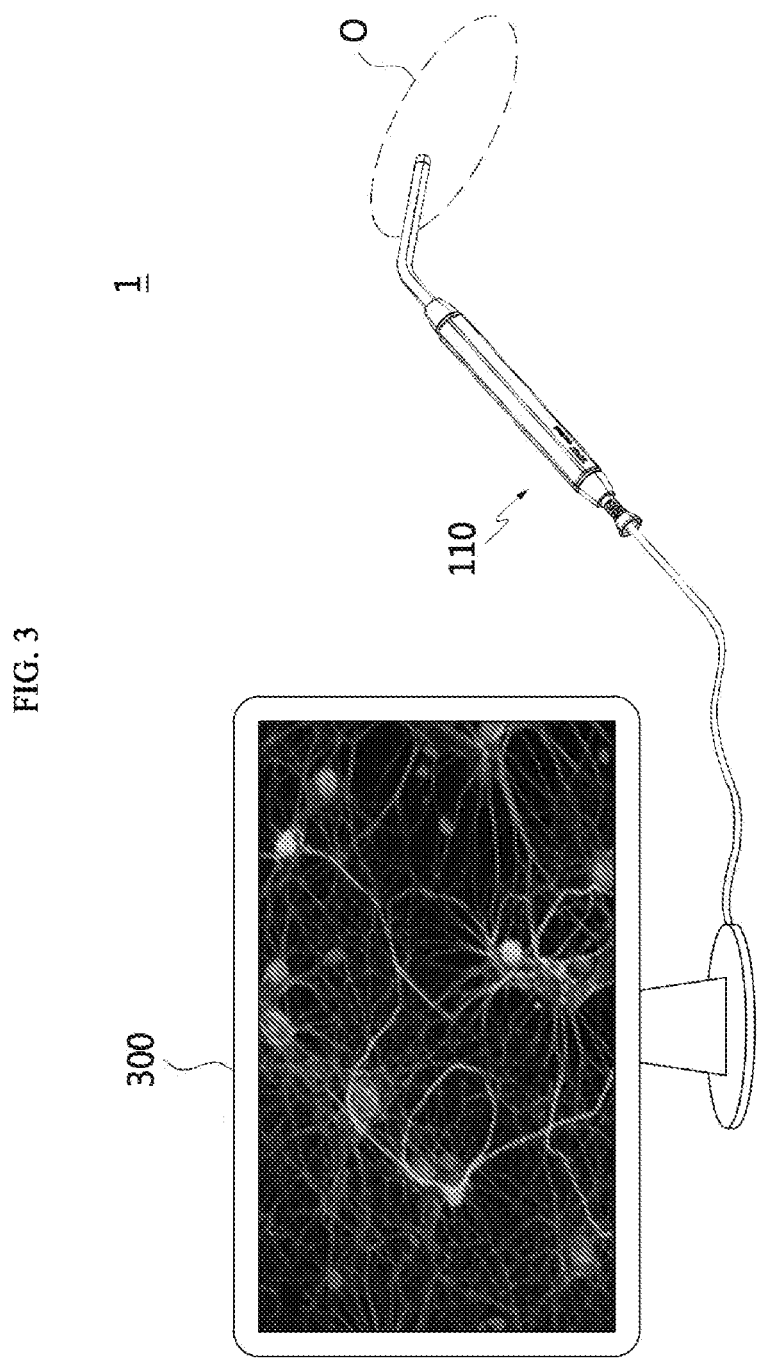
FIG. 3 is a diagram illustratively showing the form of a scanning module according to an embodiment of the present invention.

Referring to FIG. 3, according to an embodiment, the scanning module 110 may be a pen-type optical device.

For example, a user may bring the optical device into direct contact with an object to be observed or a perimeter of the object, and the scanning module 110 may measure the inside of the object up to a preset distance from the surface of the object.

In an embodiment, the scanning module 110 may be an endoscopic microscope which is used in hospitals. For example, a medical technician may bring the scanning module 110 into contact with a patient's skin surface, and the scanning module 110 may measure the state of epidermis cells at a depth of 50 um from the contact surface.

For example, a medical technician may bring the scanning module 110 into contact with a patient's body part while the body part is cut open to diagnose a cancer or determine a surgical site, and the scanning module 110 may measure living internal tissue at a depth of 70 um from the contact surface.

In this case, a fluorescent dye may be pre-injected in the form of a parenteral injection in order to effectively check the pathological state of the living internal tissue. In this case, the scanning module 110 may emit light to the object, and the optical module 120, which will be described below, may detect a fluorescent signal returning from the object.

Meanwhile, the scanning module 110 may perform a scanning operation according to a driving signal applied from the controller 130, which will be described below. The principle of the scanning operation performed by the scanning module 110 will be described in detail with reference to exemplary embodiments below.

The controller 130 may be configured to control the overall scanning operation of the scanning module 110 such that the scanning module 110 performs scanning according to a present scanning pattern.

The controller 130 may apply a preset driving signal to the scanning module 110.

The preset driving signal may include a frequency, a voltage, a phase, and the like.

For example, the controller 130 may adjust the frequency, voltage, phase, and the like in order to change the range of light emission performed by the scanning module 110.

Alternatively, the controller 130 may control the scanning module 110 to perform the scanning operation on the basis of a driving signal entered by a user.

The preset scanning pattern may vary, and the controller 130 may apply a driving signal corresponding to the preset scanning pattern to the scanning module 110.

Figure 4:
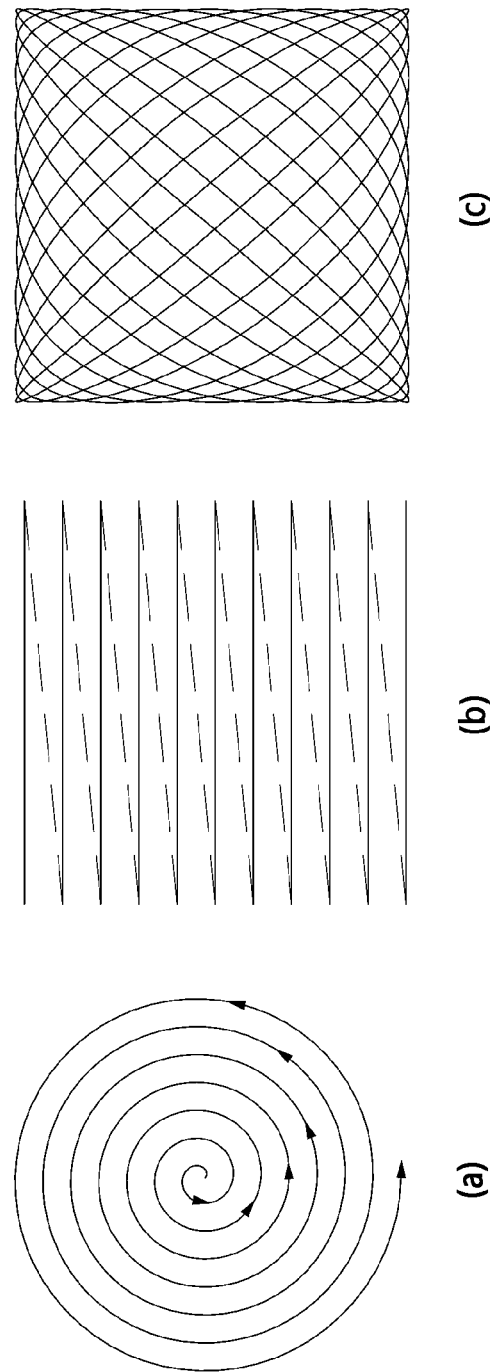
FIG. 4 is a diagram schematically showing various scanning patterns according to an embodiment of the present invention.

For example, as shown in FIG. 4, the scanning pattern may include spiral scanning, raster scanning, Lissajous scanning, and the like.

Referring to the image (a) of FIG. 4, the spiral scanning is a scanning method that draws a part of a spiral shape and has a lateral axis and a longitudinal axis which are implemented using the same frequency.

In the case of the spiral scanning, laser light intensity is high at the center, and thus a lot of signal loss and noise may be caused. For example, at the center, photo bleaching or photo damage may occur.

Referring to the image (b) of FIG. 4, the raster scanning is a scanning method performed sequentially in the horizontal direction and has a lateral axis and a longitudinal axis between which there is a large frequency difference.

In the case of the raster scanning, a relatively high voltage is required for a slow axis, and this may cause a reduction in frame rate.

Referring to the image (c) of FIG. 4, the Lissajous scanning is a pattern generated by an intersection of two sinusoidal curves perpendicular to each other and has a lateral axis and a longitudinal axis implemented using different frequencies.

In the case of the Lissajous scanning, fast scanning may be implemented at a high frame rate. For example, the frame rate may be at least 10 Hz.

The optical module 120 is an optical system that applies light to the scanning module 110 and detects a returning signal through the scanning module 110.

According to embodiments of the present invention, the optical module 120 may be a confocal microscope system, and the optical module 120 may be separated from the scanning module 110 and provided as a separate device.

The optical module 120 may include at least a light-emitting unit 121 and a light-receiving unit 123.

The light-emitting unit 121 may be a laser device that emits a laser signal of a preset wavelength.

In this case, the laser device may be selected depending on which one of a reflected image, a fluorescence image, and a transmitted image of the object is to be observed.

For example, a laser device used in the embodiments of the present invention may emit a laser signal in the near-infrared region.

As an example, for fluorescent imaging, the laser signal may have a wavelength of 405 nm, 488 nm, 785 nm, or the like depending on a used fluorescent dye.

For example, the fluorescent dye may be used to distinguish pathological features of cells, blood vessels, and tissues in a living body, and ICG, FNa, 5-ALA, or other medically approved dyes may be applied as the fluorescent dye.

Also, the light-emitting unit 121 may apply a laser source appropriate for the scanning module 110 on the basis of a signal input from an optical module control device (not shown).

In an embodiment, the optical module control device may control the gain of an image, the power of a laser signal emitted from the light-emitting unit 121, and the like.

For example, when the image generating device 1 according to an embodiment of the present invention is a medical optical device, the power of the laser signal may be set to 1 mW or less.

In another embodiment, the optical module control device may be provided as a portion of the controller 130, which has been described above. In this case, the controller 130 may control the gain of an image, the power of a laser signal emitted from the light-emitting unit 121, and the like.

Also, the light-receiving unit 123 may be configured to detect a signal returning from the object in response to light emitted from the light-emitting unit 121 through the scanning module 110.

In this case, the signal detected by the light-receiving unit 123 may be transferred to the controller 130, which has been described above, and an image processing module 200, which will be described below.

For example, the controller 130 or the image processing module 200 may reconstruct an image of the object on the basis of the signal transferred from the light-receiving unit 123. The image processing operation performed by the image processing module 200 will be described in detail in the following relevant sections.

Optionally, the image generating device 1 may further include an input unit 140.

For example, the input unit 140 may be an input means for selecting the operation mode of the image generating device 1.

As an example, the operation mode may include at least a first mode and a second mode which are preset.

For example, the first mode may be a low-resolution mode or a discovery mode.

Alternatively, for example, the second mode may be a high-resolution mode or a zoom-in mode.

Therefore, a user may select the first mode or the second mode depending on the purpose of use and view an image of appropriate resolution through a display device 300.

Also, for example, the input unit 140 may be an input means for selecting the working distance of the scanning unit 1100.

As an example, the working distance may include a first distance, a second distance, a third distance, and the like which are preset, and an input means corresponding to a preset working distance may be additionally provided. The working distance may correspond to a focal distance of a lens module, which will be described below.

For example, according to the selected working distance, the controller 130 may perform the scanning operation of the scanning unit 1100 and perform a calibration operation on an image generated by the scanning unit 1100.

Meanwhile, in addition to the above-described embodiments, input means corresponding to various functions for controlling the operation of the image generating device 1 may be additionally provided.

Figure 5:
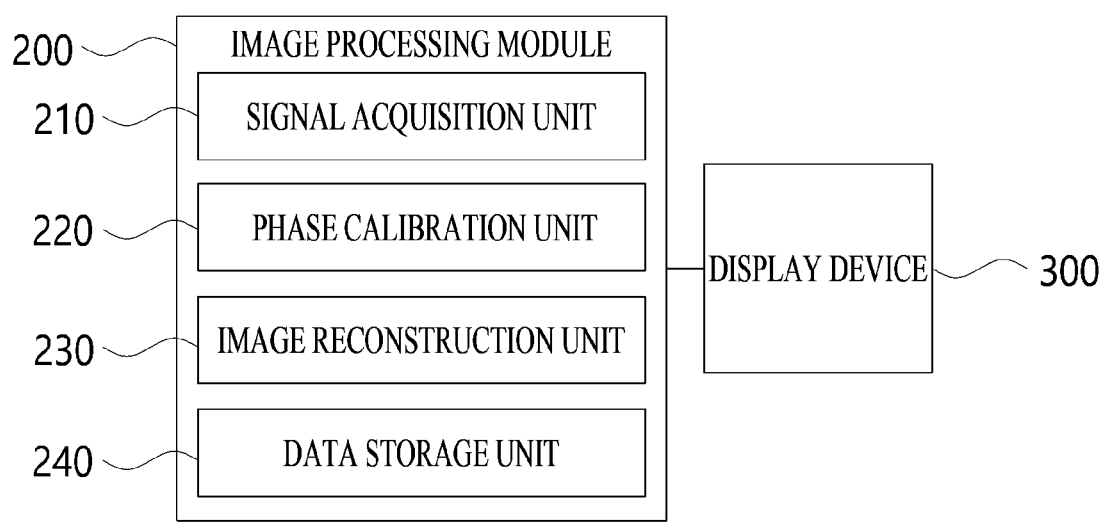
FIG. 5 is a block diagram for exemplarily describing a configuration of an image processing module 200 according to an embodiment of the present invention.

FIG. 5 is a block diagram for exemplarily describing a configuration of the image processing module 200 according to an embodiment of the present invention.

As described above with reference to FIG. 3, the image processing module 200 is configured to reconstruct an image of the object on the basis of a signal transferred from the light-receiving unit 123.

Referring to FIG. 5, the image processing module 200 may include a signal acquisition unit 210, a phase calibration unit 220, an image reconstruction unit 230, and a data storage unit 240.

The signal acquisition unit 210 may be configured to obtain a signal detected by the light-receiving unit 123.

The signal obtained by the signal acquisition unit 210 is a signal returning through the scanning module after light is emitted to the object through the scanning module 110 and may be defined as a scanning unit output signal.

For example, the signal acquisition unit 210 may additionally perform an operation of converting an analog signal transferred from the light-receiving unit 123 into a digital signal.

In this case, an analog-to-digital (A/D) conversion module (not shown) may be additionally provided for converting a signal received by the signal acquisition unit 210 into a digital signal.

The phase calibration unit 220 is configured to correct a phase difference occurring when a driving signal applied from the controller 130 to the scanning module 110 is transferred to the scanning module 110.

For example, in the case of an optical fiber probe driven using a force due to mechanical deformation of a piezoelectric element, a phase difference with time may occur when the driving signal applied to the piezoelectric element is transferred to the optical fiber.

For example, the scanning unit driving signal for actually driving the optical fiber may be different from the driving signal applied to the piezoelectric element. Accordingly, the scanning unit output signal detected by the light-receiving unit 123 and the driving signal applied to the piezoelectric element are caused to be different.

Therefore, during the image reconstruction process performed by the image processing module 200, image distortion may occur by a predetermined phase difference occurring due to the difference between the scanning unit output signal and the driving signal applied to the piezoelectric element. In this case, the phase difference may be changed in real-time and may vary with a change in position of the scanning module 110.

In other words, in order to provide a real-time image, it may be necessary for the image generating device 1 according to an embodiment of the present invention to reconstruct the image of the object in consideration of the phase difference varying in real-time.

As an example, a detector (not shown) for detecting the scanning unit driving signal for actually driving the scanning module 110 may be additionally installed inside the scanning module 110. In this case, a phase difference due to the difference between the scanning unit driving signal and the driving signal applied to the scanning module 110 may be calculated. Accordingly, the image processing module 200 according to an embodiment of the present invention may reconstruct the image in consideration of the calculated phase difference.

As another example, when the optical device according to an embodiment of the present invention is provided in the form of an optical microprobe, there may not be enough space inside the probe to install the detector.

In this case, an algorithm for correcting the phase difference may be prestored in the phase calibration unit 220. The cause of the phase difference and the phase calibration operation performed by the phase calibration unit 220 will be described in detail in the following related sections.

The image reconstruction unit 230 may be configured to reconstruct the image of the object in consideration of a result of the phase calibration performed by the phase calibration unit 220.

In this case, various kinds of image processing algorithms, machine-learning algorisms, and the like may be additionally provided to the image reconstruction unit 230.

For example, the image reconstruction unit 230 may additionally provide functions for improving image quality such as noise removal, calibration, image division, image merge, and the like for a generated image.

Also, for example, the image reconstruction unit 230 may additionally provide a function of detecting a pathological feature in a generated image and displaying the detected pathological feature.

Also, for example, the image reconstruction unit 230 may detect a pathological feature in a generated image and then additionally and automatically perform a cancer diagnosis and a surgical site determination.

The data storage unit 240 may be a memory for storing various types of data and may include one or more memories.

For example, an algorithm, a program, and the like related to various kinds of functions provided by the image processing module 200 may be stored in the data storage unit 240.

As an example, a phase calibration algorithm, various image processing algorithms for processing various kinds of image processing, a machine learning algorithm, and the like may be stored in the data storage unit 240.

Also, for example, the data storage unit 240 may store image data obtained from the image generating device 1, image data reconstructed by the image reconstruction unit 230, and the like.

Also, for example, an algorithm, a program, and the like related to various kinds of functions provided by the image processing module 200 may be stored in the data storage unit 240.

As an example, a phase calibration algorithm, various image processing algorithms for processing various kinds of image processing, a machine learning algorithm, and the like may be stored in the data storage unit 240.

In conclusion, the image processing module 200 according to an embodiment of the present invention may reconstruct a digital image of the object on the basis of the signal transferred from image generating device 1, and the image reconstructed by the image processing module 200 may be output through the display device 300 in real-time.

Also, as described above with reference to FIG. 1, the image reconstructed by the image processing module 200 may be transmitted to the image analysis device 2 in real-time. Accordingly, a medical technician may perform a pathological feature determination and diagnosis such as a cancer diagnosis and a surgical site determination on the basis of the reconstructed image.

For convenience of description in the present specification, it is assumed that the image processing module 200 is provided as a separate element in the image generating device 1, but the functions performed by the image processing module 200 may be provided as a portion of the controller 130.

Alternatively, the image processing module 200 may be provided as a separate device or a portion of another electronic device.

Alternatively, some of the functions performed by the image processing module 200 may be provided by the controller 130, and the other functions may be provided by a separate device.

1.3 Configuration of Scanning Module

Internal elements of the scanning module 110 will be described in detail below with reference to FIGS. 6 to 10.

Also, for convenience of description, the following description assumes that a handheld optical fiber probe is used to implement Lissajous scanning for an object as a main embodiment.

Figure 6:
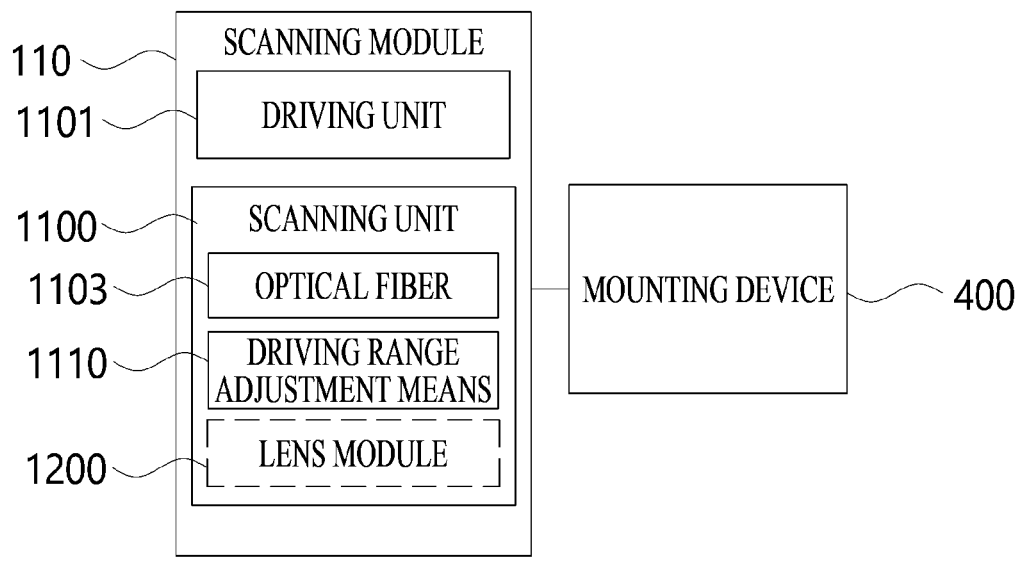
FIG. 6 is a block diagram for exemplarily describing an internal configuration of a scanning module 110 according to an embodiment of the present invention.
Figure 7:
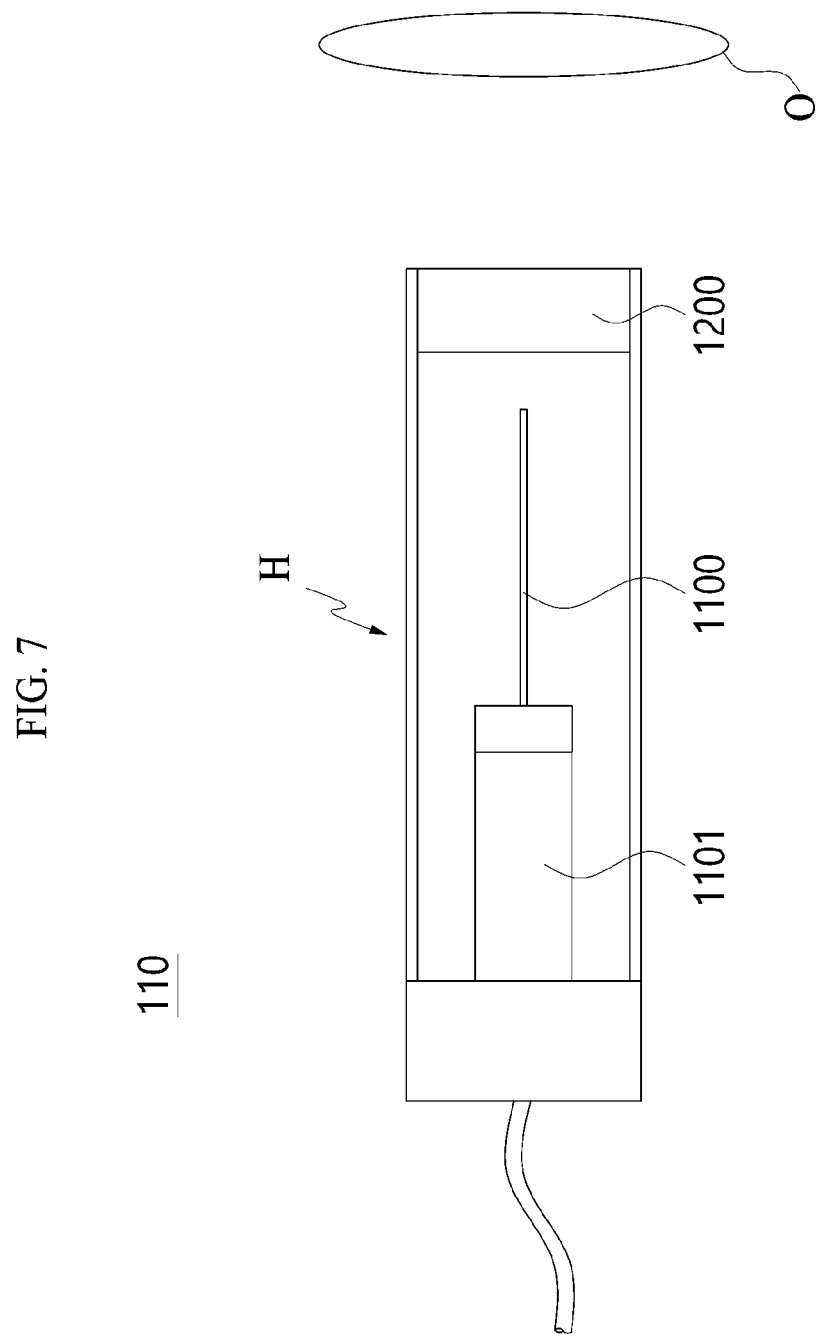
FIG. 7 is a sectional view for exemplarily describing an internal configuration of the scanning module 110 according to an embodiment of the present invention.

FIG. 6 is a block diagram for exemplarily describing an internal configuration of the scanning module 110 according to an embodiment of the present invention. FIG. 7 is a sectional view for exemplarily describing an internal configuration of the scanning module 110 according to an embodiment of the present invention.

Referring to FIGS. 6 and 7, the scanning module 110 according to an embodiment of the present invention may include a driving unit 1101, a scanning unit 1100, and a lens module 1200.

For example, as shown in FIG. 7, the driving unit 1101, the scanning unit 1100, and the lens module 1200 of the scanning module 110 according to an embodiment of the present invention may be accommodated in a housing H. In this case, the scanning unit 1100 may scan an object O according to a preset scanning pattern by a force applied from the driving unit 1101.

The housing H may have various sizes and shapes to provide a minimal space where the scanning unit 1100 can be driven in the housing H.

For example, the housing H may be cylindrical, and the inner diameter R of the cylindrical housing H may be designed in consideration of a maximum driving range of at least one of a first axis and a second axis of the scanning unit 1100.

Elements of the scanning module 110 accommodated in the housing H will be described in detail below.

The driving unit 1101 may be an actuator that provides a driving force so that the scanning unit 1100 performs a scanning operation according to a preset scanning pattern.

For example, the driving unit 1101 may be an actuator that is driven on the basis of any one of a piezoelectric element, an electrostatic element, an electromagnetic element, an electro-thermal element, a coil, and a micromotor.

An actuator based on a piezoelectric element is easy to package for front imaging and has high durability compared to actuators based on an electromagnetic element, an electro-thermal element, a coil, a micromotor, and the like.

A piezoelectric element is an element made of a material that generates mechanical energy when electrical energy is applied or that generates electrical energy when mechanical energy is applied.

For example, when an electrical signal is applied to a PZT-based piezoelectric material, the piezoelectric material may be deformed, and the scanning unit 1100 may be vibrated by a force transferred from the piezoelectric material.

Also, the piezoelectric element may be processed into various shapes such as triangles, quadrangles, polygons, cubes, cylinders, and other solid figures.

For example, the driving unit 1101 may use a piezoelectric element having a cylindrical structure as the actuator.

In this case, the piezoelectric element may have two facing piezoelectric electrodes driven in the first axis and the second axis.

For example, the driving unit 1101 may include a pair of first actuating units 1101a driven in the first axis and a pair of second actuating units 1101b driven in the second axis orthogonal to the first axis.

In this case, the first axis is a vertical axis, and the second axis is a horizontal axis orthogonal to the first axis.

In an embodiment, the controller 130 may apply driving signals to the first and second driving units 1101, and the first and second driving units 1101 may transfer a force generated according to the applied driving signals to the scanning unit 1100.

The scanning unit 1100 may include an optical fiber 1103, a driving range adjustment means 1110, and a lens module 1200.

The optical fiber 1103 may be used as a light transfer path through which the light transferred from the light-emitting unit 121 is emitted to the object.

Also, one end or the fixed end of the optical fiber 1103 may be coupled to the driving unit 1101.

Also, the other end of the optical fiber 1103 may be a free end vibrated by a force applied from the driving unit 1101.

In this case, the driving unit 1101 may apply a force to an actuator position P0 placed between the fixed end and the free end of the optical fiber 1103. For example, the actuator position P0 may be a position on which a force generated when the piezoelectric material is deformed by a driving signal applied to the driving unit 1101 acts.

Accordingly, the free end of the optical fiber 1103 may perform a scanning operation according to a preset scanning pattern by a force applied from the driving unit 1101.

In an embodiment, the optical fiber 1103 may be a single optical fiber having a cylindrical shape and may be surrounded by the piezoelectric element of the cylindrical structure.

In this case, the optical fiber may receive a first force from the first actuating unit 1101a and vibrate in the first direction and may receive a second force from the second actuating unit 1101b and vibrate in the second direction.

Also, the free end of the optical fiber 1103 may receive the force caused by the deformation of the first actuating unit 1101a and the second actuating unit 1101b and then may vibrate and emit light along a trajectory of the optical fiber 1103. For example, the controller 130 may apply the first driving signal and the second driving signal to the first actuating unit 1101a and the second actuating unit 1101b, respectively. The first actuating unit 1101a and the second actuating unit 1101b may transfer a first force caused by applying the first driving signal and transfer a second force caused by applying the second driving signal to the optical fiber to drive the free end of the optical fiber.

For example, the first driving signal is a first resonant frequency for resonantly driving the optical fiber in the first direction, and the second driving signal is a second resonant frequency for resonantly driving the optical fiber in the second direction.

In general, when an object is driven using a resonant frequency, the object tends to oscillate indefinitely, and thus it is possible to obtain a larger swing even if the same voltage is applied.

In an embodiment, when the free end of the optical fiber 1103 is set to draw a Lissajous pattern, the optical fiber 1103 may be designed to have different resonant frequencies with respect to the first axis and the second axis. A method of setting the first resonant frequency and the second resonant frequency will be described in detail in the following related sections.

Accordingly, when the driving unit 1101 is driven using the resonant frequency of the optical fiber 1103, it is possible to implement large fields of view (FOVs) using even small voltages. Also, for example, the first resonant frequency and the second resonant frequency applied to the driving unit 1101 may be determined depending on the length of the optical fiber 1103, stiffnesses with respect to the first axis and the second axis of the optical fiber, etc.

Meanwhile, the driving unit 1101 and one end of the optical fiber 1103 may be coupled to each other such that the optical fiber 1103 can be accurately disposed at the center of the driving unit 1101.

For example, when the optical fiber is surrounded by the driving unit 1101 having the cylindrical structure, at least a portion of the optical fiber 1103 may be inserted into the driving unit 1101 and aligned with the center of the driving unit 1101.

That is, by the optical fiber 1103 being aligned with the center of the piezoelectric element of the cylindrical structure, the axis of a force acting when the driving unit 1101 is moved by a driving signal applied from the controller 130 may match the axis of a force acting when the optical fiber 1103 is vibrated. A method of coupling the optical fiber and the driving unit will be described in detail in the following relevant sections.

The driving range adjustment means 1110 may be a structure for adjusting a scanning pattern that is drawn by the optical fiber 1103 so that the optical fiber 1103 can be vibrated according to the preset scanning pattern.

As described above, in order for the optical fiber 1103 to draw a Lissajous scanning pattern, the optical fiber 1103 may have different driving frequencies with respect to the first axis and the second axis.

This is because when the optical fiber 1103 is vibrated at the same resonant frequency with respect to the first axis and the second axis, the optical fiber 1103 draws a circular scanning pattern.

In general, the resonant frequency fr of the optical fiber 1103 may be determined by Formula 1 below:

$$f_r = 1/2\pi \sqrt{(k/m)} \qquad \text{[Formula 1]}$$

where k is the elastic modulus of a material, and m is the mass.

That is, referring to FIG. 1, the resonant frequency fr of the optical fiber 1103 may vary depending on the elastic modulus k of the optical fiber. The elastic modulus k of the optical fiber may be determined depending on the stiffness of the optical fiber. When the single optical fiber 1103 having a cylindrical shape is applied, the optical fiber 1103 may have the same stiffness with respect to the first axis and the second axis, and thus the first resonant frequency with respect to the first axis of the optical fiber 1103 may be the same as the second resonant frequency with respect to the second axis.

Accordingly, a structure having a predetermined elasticity may be attached to any one of the first axis and the second axis so that the stiffness of the optical fiber 1103 varies depending on the first axis and the second axis.

Also, for example, it may be necessary to design the structure so that the difference between the first resonant frequency and the second resonant frequency of the optical fiber 1103 deviates from a preset range. This is because when the difference between the first resonant frequency and the second resonant frequency does not deviate from the preset range, the Lissajous scanning pattern drawn by the optical fiber 1103 may be distorted.

In an embodiment, the driving range adjustment means 1110 may be attached to the optical fiber 1103 in any one of a first axis direction and a second axis direction in which the optical fiber 1103 vibrates such that the optical fiber 1103 has a structure asymmetrical with respect to the first axis and the second axis.

In another embodiment, the driving range adjustment means 1110 may be attached to the optical fiber 1103 in both of the first axis direction and the second axis direction such that the optical fiber 1103 has a structure asymmetrical with respect to the first axis and the second axis.

Accordingly, the optical fiber 1103 may vibrate at different driving frequencies with respect to the first direction and the second direction and thus emit a Lissajous pattern that meets a predetermined criterion.

Also, for example, the driving range adjustment means 1110 may include one or more of a mass, a deformable structure, and the like which are attached to any position on a z-axis or in the longitudinal direction of the optical fiber 1103.

In this case, the driving range in which the optical fiber 1103 vibrates may be adjusted according to the length, size, shape, attachment position, attachment angle, and the like of the mass and the deformable structure attached to the optical fiber 1103. A detailed structure of the driving range adjustment means 1110 will be described in detail through the following related embodiments.

1.4 Optical Module

A laser beam emitted from the optical module 120 through the optical fiber 1103 may be directly emitted to an object through a distal end of the optical fiber 1103.

In this case, when light is radiated from the distal end of the optical fiber 1103, it is difficult to generate an image of the object.

Optionally, a lens module 1200 for collecting light radiated from the distal end of the optical fiber 1103 may be disposed at the distal end of the optical fiber 1103.

Alternatively, the distal end of the optical fiber 1103 may be processed such that light emitted through the optical fiber 1103 can be collected. For example, the distal end of the optical fiber 1103 may be processed into a spherical shape. Accordingly, the laser beam collected at the distal end of the optical fiber 1103 may be directly emitted to the object.

Alternatively, by processing the distal end of the optical fiber 1103 and further installing the lens module 1200 at the distal end of the optical fiber 1103, it is possible to improve a numerical aperture (NA) at an output stage.

Figure 8:
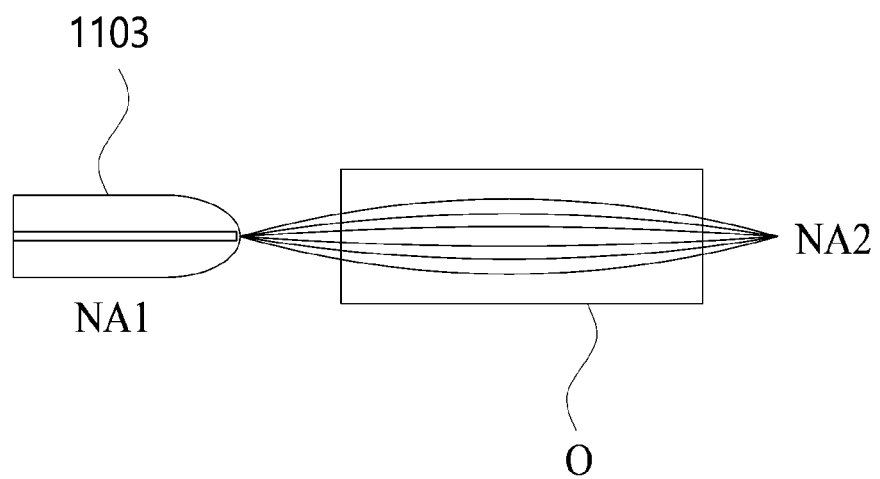
FIG. 8 is a diagram illustratively showing a beam that is output when an optical fiber is processed into a conical or hemispherical shape according to another embodiment of the present invention.

FIG. 8 is a diagram illustratively showing a beam that is output when the optical fiber 1103 is processed into a spherical shape according to another embodiment of the present invention.

In general, resolution increases as an NA increases at an output stage, and also resolution increases and an FOA decreases as the magnification of a lens decreases.

Accordingly, since the magnification of a lens is fixed, it may be advantageous to use an optical fiber 1103 having a large NA.

In order to increase the NA of the optical fiber 1103, an end of the optical fiber 1103 may be processed. For example, the end of the optical fiber 1103 may be processed into a conical shape.

For example, the end of the optical fiber may be processed into the spherical shape by polishing a side surface of the optical fiber 1103 in a conical shape and polishing the end to be round.

In this case, NA1 of the optical fiber increases, and thus NA2 increases at the output stage. Accordingly, an image with high resolution and no FOA loss may be obtained.

1.5 Lens Module

Figure 9:
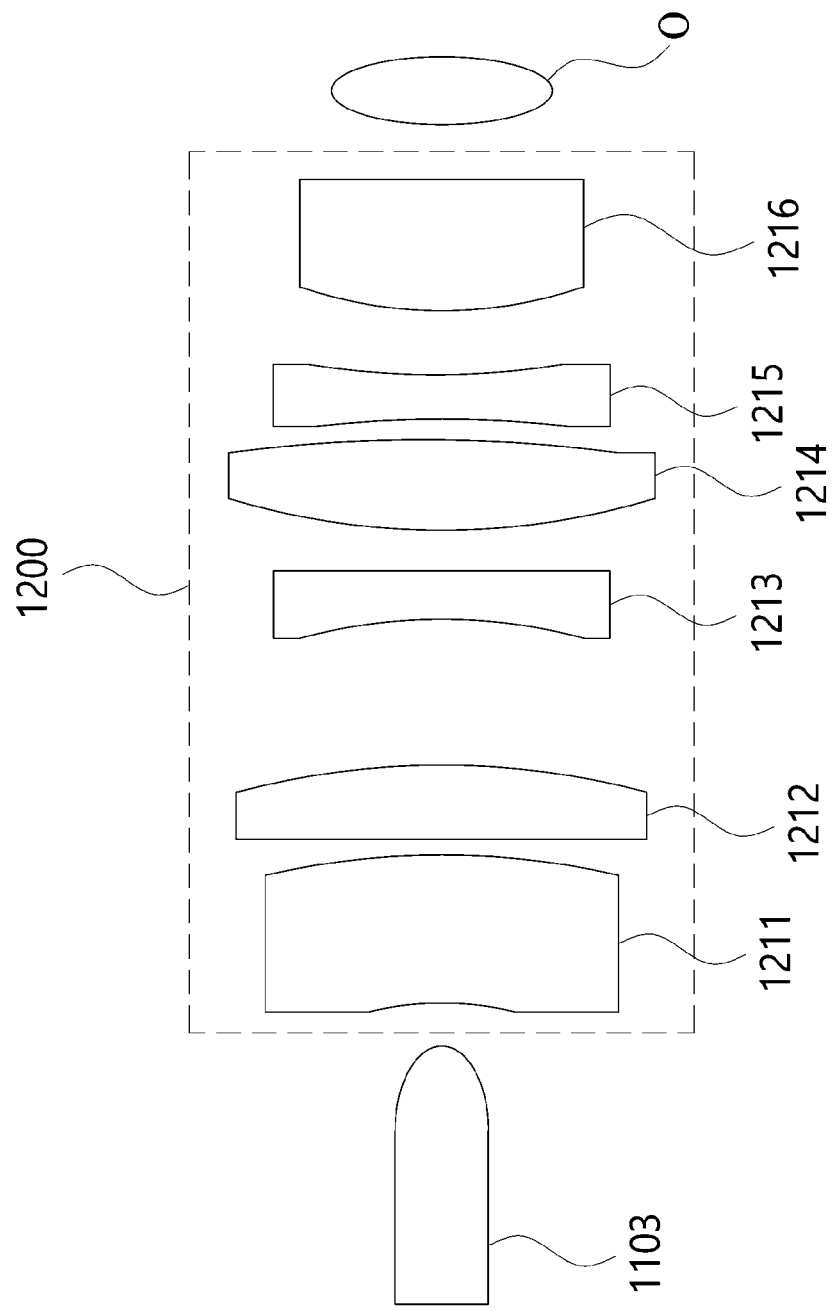
FIGS. 9 and 10 are diagrams for exemplarily describing a configuration of a lens module according to an embodiment of the present invention.
Figure 10:
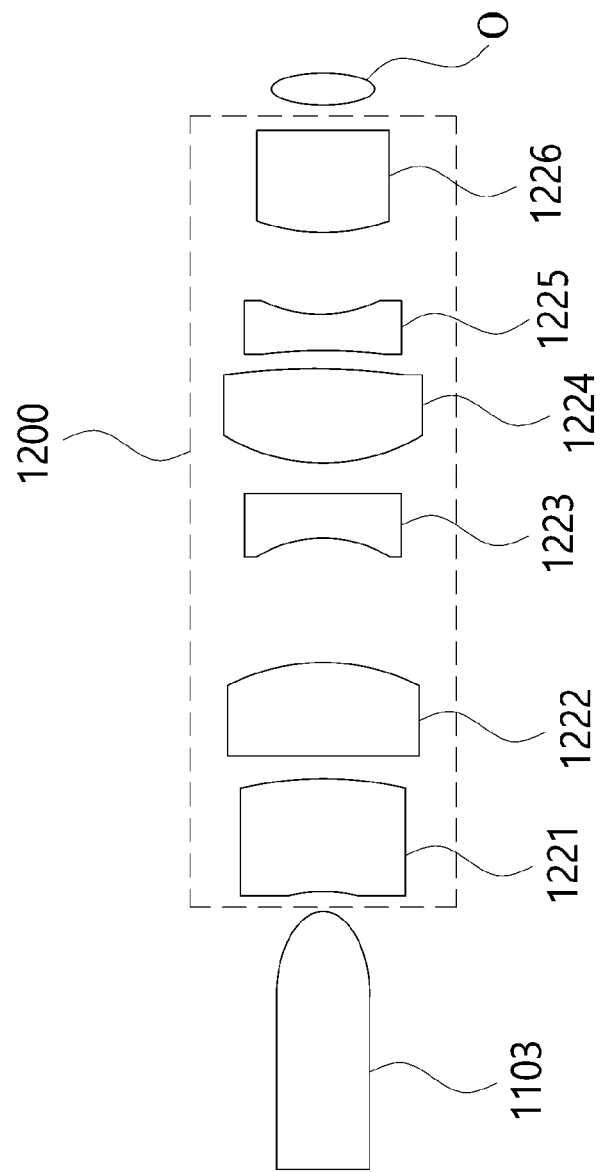

FIGS. 9 and 10 are diagrams for exemplarily describing a configuration of the lens module 1200 according to an embodiment of the present invention.

As described above, the scanning unit 1100 according to an embodiment of the present invention may further include the lens module 1200 for collecting light radiated from the distal end of the optical fiber 1103. The lens module 1200 according to an embodiment of the present invention may be designed in consideration of processability of the lens module and distortion correction for high-resolution implementation.

Also, the lens module 1200 may be designed in an appropriate size in consideration of the miniaturization of the scanning module 110.

Also, the lens module 1200 may include at least five lenses, and at least one of the lenses may be formed as an aspherical lens.

For example, as shown in FIGS. 9 and 10, the lens module 1200 according to an embodiment of the present invention may include first lenses 1211 and 1221, second lenses 1212 and 1222, third lenses 1213 and 1223, fourth lenses 1214 and 1224, fifth lenses 1215 and 1225, and sixth lenses 1216 and 1226.

Also, for example, the resolution and magnification may be optimized according to a thickness and a ratio between a thickness and a diameter of each lens.

Also, for example, all of the first lenses 1211 and 1221, the second lenses 1212 and 1222, the third lenses 1213 and 1223, the fourth lenses 1214 and 1224, the fifth lenses 1215 and 1225, and the sixth lenses 1216 and 1228 may be aspherical lenses.

The first lenses 1211 and 1221 are convergent lenses that collect light entering the optical fiber 1103 and that make the light enter parallel to an optical axis thereof. The first lenses 1211 and 1221 can reduce peripheral optical efficiency losses by making the light enter parallel to the optical axis.

The second lenses 1212 and 1222 and the third lenses 1213 and 1223 are lenses for spherical aberration correction, and the fourth lenses 1214 and 1224 and the fifth lenses 1215 and 1225 are lenses for spherical aberration correction and chromatic aberration correction.

For example, the fourth lenses 1214 and 1224 and the fifth lenses 1215 and 1225 may be coupled to each other in a symmetrical form in order to increase the effect of the chromatic aberration correction.

Also, the sixth lenses 1216 and 1226 may be focusing lenses for finally focusing the light onto the object.

Also, a separate mounting device 5200 may be further provided to store the scanning module 110 according to an embodiment of the present invention.

For example, the mounting device 5200 may have a space provided therein to stably accommodate the scanning module 110.

Also, for example, the mounting device 5200 may further have a module for performing an initial calibration operation while the scanning module 110 is mounted. The calibration operation performed through the mounting device 5200 will be described in detail in the following relevant sections.

2 Design Conditions of Scanning Unit

Design conditions of the scanning unit 1100 according to embodiments of the present invention will be described in detail below with reference to FIGS. 11 to 29.

As described above, the scanning unit 1100 according to embodiments of the present invention may be designed to emit light according to a Lissajous pattern.

For example, depending on preset conditions, an additional structure such as a mass and a deformable rod may be attached to the optical fiber 1103 to perform a Lissajous pattern. The design of an additional structure for adjusting the driving range of the optical fiber 1103 so that the optical fiber 1103 draws a Lissajous figure meeting a preset condition will be described in detail below.

2.1 Mass

The overall rate and driving range of an optical fiber scanner may be determined by the length and weight of the optical fiber 1103.

Accordingly, upon designing the scanning unit 1100 according to an embodiment of the present invention, first, the length and weight of the optical fiber 1103 may be determined to draw a scanning pattern meeting a preset condition.

Figure 11:
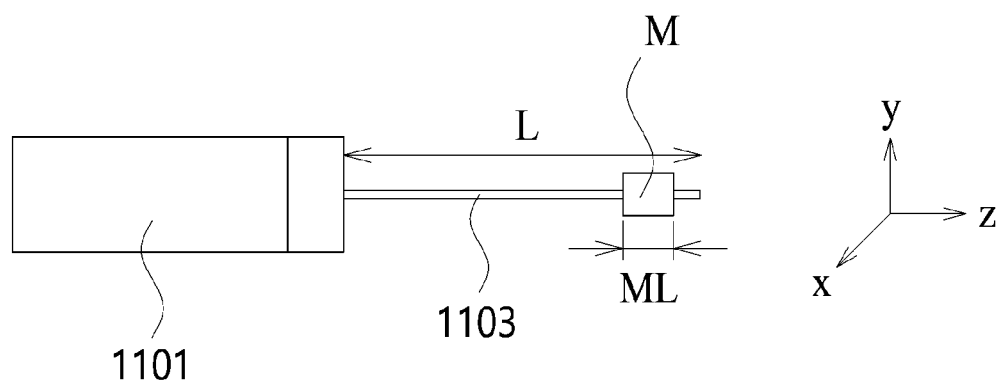
FIG. 11 is a diagram for exemplarily describing a structure of a scanning unit according to an embodiment of the present invention.

Referring to FIG. 11, the scanning unit 1100 according to an embodiment of the present invention may have a mass M attached to a distal end of the optical fiber 1103.

For example, as shown in FIG. 11, in order to increase Q-factor of the optical fiber 1103 and increase the driving range, a mass M having a preset weight may be attached to the distal end of the optical fiber 1103.

In this case, the mass M may have a weight larger than the weight m of the optical fiber 1103. However, the following description will be based on the length of the mass M because the mass M is a micrometer-scale microstructure and thus has a very small mass.

For example, when the mass M is attached to the distal end of the optical fiber 1103 as shown in FIG. 11, the effective mass of the optical fiber 1103 may be increased, and thus the driving rate of the scanning unit 1100 may be decreased. However, along with the increase in the effective mass of the optical fiber 1103, the maximum amplitude at which the optical fiber 1103 vibrates may be increased.

Also, for example, the mass M may be a microstructure produced in silicon microprocessing and may have various shapes such as a hexahedron, a sphere, and other processable shapes.

In an embodiment, the length L of the optical fiber and the length ML of the mass may be determined according to a target frequency for implementing a high scanning rate.

For example, both of the first resonant frequency of the first axis direction and the second resonant frequency of the second axis direction may be selected to be higher than or equal to 1 kHz.

In this case, the first axis and the second axis are different from each other on an xyz-space. When the longitudinal direction of the optical fiber 1103 indicates a z-axis, the first axis may be a y-axis, and the second axis may be an x-axis orthogonal to the first axis. For convenience of description, the first axis is the y-axis and the second axis is the x-axis as an example in the following description.

Figure 12:
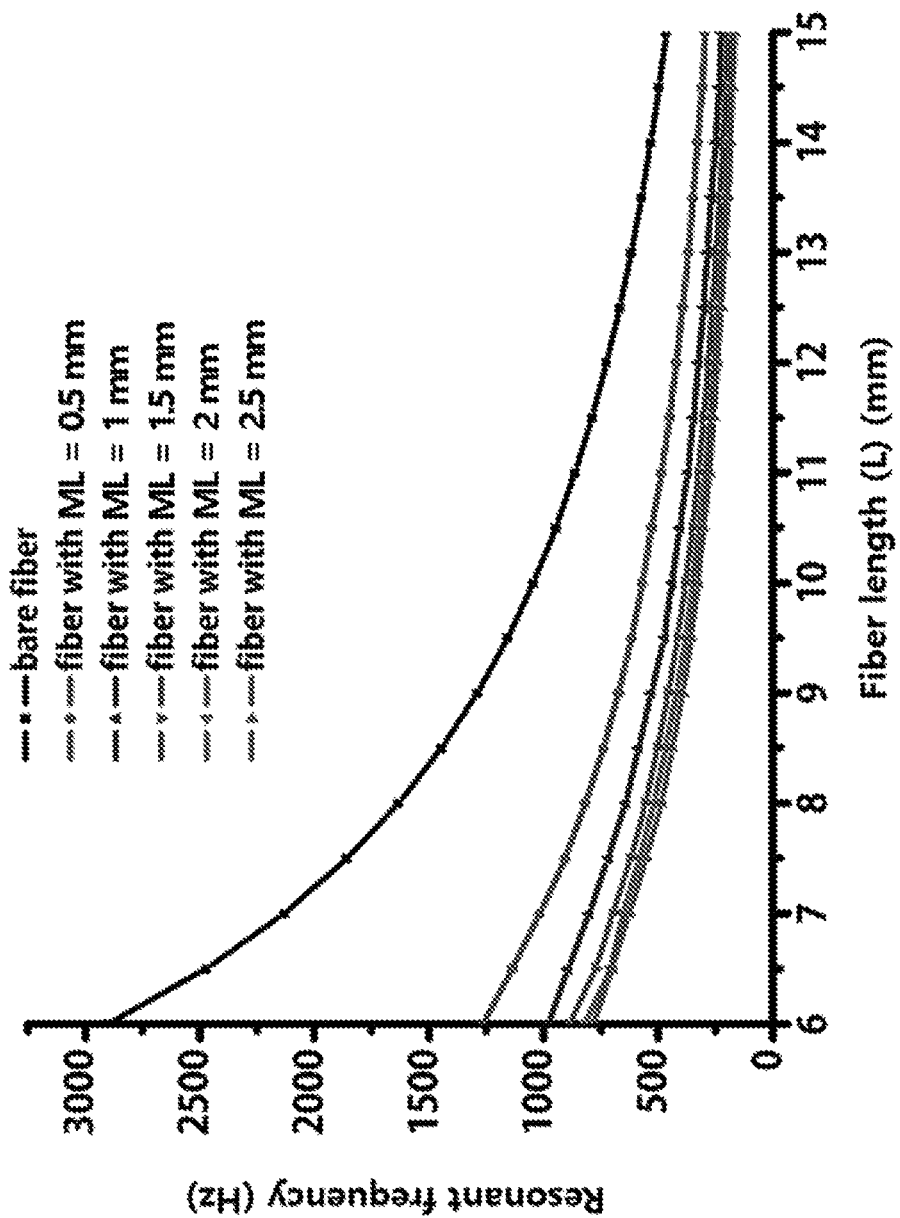
FIG. 12 is a graph for exemplarily describing design conditions of the scanning unit according to an embodiment of the present invention.

FIG. 12 is a graph for illustratively showing a change in resonant frequency according to the length L of the optical fiber 1103 and the length ML of the mass in the scanning unit 1100 according to an embodiment of the present invention.

For example, as shown in FIG. 12, it can be seen that the resonant frequency increases as the length L of the optical fiber 1103 decreases and that the resonant frequency decreases as the length ML of the mass increases.

Accordingly, the length L of the optical fiber 1103 and the length ML of the mass may be selected appropriately depending on the target frequency.

For example, referring to FIG. 12, when the target frequency is 1 kHz or higher, one of a set of the length ML (=0.5 mm) of the mass M and the length L (<=7 mm) of the optical fiber 1103 and a set of the length ML (=1 mm) of the mass M and the length L (<=6 mm) of the optical fiber 1103 may be selected.

In this case, in order to appropriately select the length L of the optical fiber 1103 and the length ML of the mass according to the target frequency, scanning amplitude may be further considered upon resonant driving.

The design conditions of the scanning unit 1100 are exemplary, and the scanning unit 1100 may be designed in various ways in order to implement scanning patterns corresponding to other preset conditions.

2.2 Buffer Distance

The maximum amplitude at which the optical fiber 1103 is driven may increase as the mass M is attached closer to the free end of the optical fiber 1103.

Accordingly, by further attaching the mass M to the distal end of the optical fiber 1103, the FOV of an image obtained due to the vibration of the optical fiber 1103 may be expanded.

Figure 13:
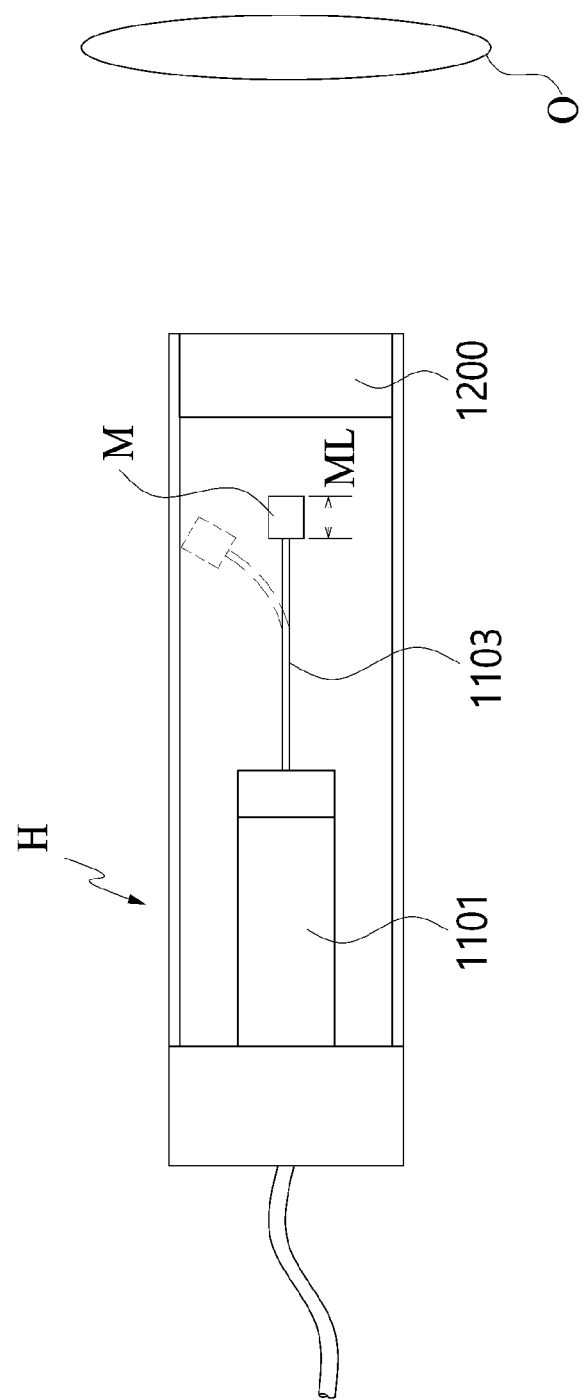
FIGS. 13 and 14 are diagrams for exemplarily describing an attachment position of a mass M according to an embodiment of the present invention.

However, referring to FIG. 13, the mass M may be attached to the distal end of the optical fiber 1103. In this case, when the optical fiber 1103 is vibrated by a force applied from the driving unit 1101, the mass M attached to the distal end of the optical fiber 1103 may collide with an inner wall of the housing H. Also, in this case, the mass M is more likely to be broken by frequent collisions with the inner wall of the housing H, and thus the performance and durability of the scanning module 110 are degraded.

Furthermore, when the lens module 1200 is further installed as shown in FIG. 13, the mass M may collide with the lens module 1200, and the lens module 1200 may be damaged. When the lens module 1200 is damaged, the quality of the image reconstructed by the controller 130 may be degraded.

Accordingly, it may be necessary to adjust the attachment position of the mass M so that the mass M does not directly collide with the lens module 1200 and/or the inner wall of the housing H.

Figure 14:
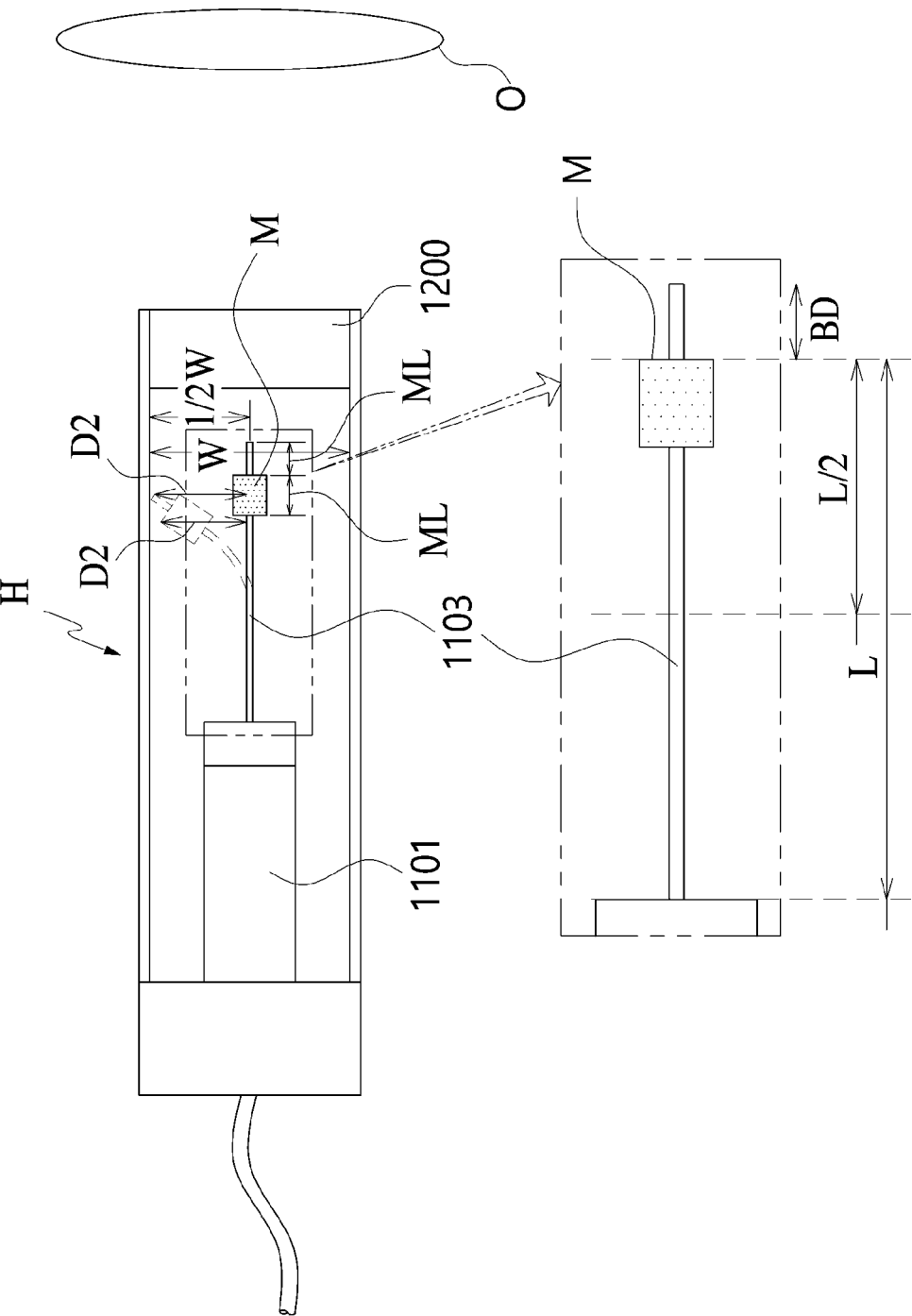

FIG. 14 is a diagram for exemplarily describing the attachment position of the mass M according to an embodiment of the present invention.

For convenience of description, an attachment distance for preventing the mass M from being broken along with a collision with the inner wall of the housing H is defined as a buffer distance.

Relatively, the optical fiber 1103 may be resonantly driven by a force applied from the driving unit 1101. In this case, when an end of the optical fiber 1103 having a smaller weight and a smaller area in contact with the inner wall than the mass M is brought into contact with the inner wall of the housing H, the optical fiber 1103 may have a low possibility of being damaged by a collision with the inner wall of the housing H.

Accordingly, in the case of the scanning unit 1100 according to an embodiment of the present invention, it is possible to prevent damage due to a collision between the mass M and the inner wall of the housing H by attaching the mass M to the optical fiber 1103 while being spaced a predetermined distance from the distal end of the optical fiber 1103.

For example, the mass M may be attached between the fixed end and the free end of the optical fiber 1103.

In this case, the attachment position of the mass M may be determined in consideration of one or more factors for implementing a scanning pattern according to a preset condition, for example, the resonant frequency, the scanning rate, the driving range adjustment for the optical fiber 1103, and the like. For example, preferably, the mass M may be attached adjacent to the free end of the optical fiber 1103 with respect to the half point of the total length L of the optical fiber in order to improve the scanning rate and expand the FOV.

Also, for example, referring to FIG. 14, in order to improve the scanning rate, expand the FOV, and minimize breakage of the mass M due to a collision with the inner wall of the housing H, the mass M may be attached between the half point of the total length L of the optical fiber and the shortest end of the optical fiber.

That is, the buffer distance BD may be defined as Formula 2 below:

$$\frac{L}{2} < BD < L.$$ [Formula 2]

In this case, as shown in FIG. 14, it is possible to minimize a collision of the mass M with the inner wall of the housing H when the optical fiber 1103 vibrates.

As an example, the buffer distance BD may be determined in further consideration of the length ML of the mass M.

For example, when the buffer distance BD is at least greater than or equal to the length ML of the mass M, it is possible to prevent the mass M from colliding with the inner surface of the housing H.

As another example, the buffer distance BD may be set on the basis of the inner diameter W of the housing H and the maximum driving ranges of the optical fiber 1103 and the mass M. This is to miniaturize the housing H and to prevent damage to the optical fiber 1103 and the mass M.

For example, referring to FIG. 14, it is assumed that when the optical fiber 1103 vibrates within the housing H, the maximum driving range in which the optical fiber 1103 is vibrable is D1 from the center point of the inner diameter of the housing H, and the maximum driving range in which the mass M is vibrable is D2 from the center point of the inner diameter of the housing H. Here, D1 and D2 may be defined as follows:

$D1 < \frac{1}{2}W$, and $D2 < \frac{1}{2}W.$

In this case, D2 may indicate the highest point when the mass M moves to the maximum driving range in which the optical fiber 1103 moves in the housing H so that the mass M does not collide with the inner wall of the housing H. Also, for example, the buffer distance BD may be determined in consideration of all of the length ML of the mass, the maximum driving ranges in which the optical fiber and the mass are vibrable in the first axis, and the inner diameter of the housing H.

Accordingly, in the case of the scanning module 110 according to an embodiment of the present invention, it is possible to provide an optical device with enhanced product performance and durability by minimizing breakage of elements packaged in the scanning module 110 while miniaturizing the packaging of the scanning module 110.

2.3 Driving Range Adjustment Means

As described above, the driving range adjustment means 1110 may be further attached to the optical fiber 1103 according to an embodiment of the present application to perform Lissajous scanning corresponding to a preset condition.

As described above, in order to implement a Lissajous pattern, the resonant frequency of the optical fiber 1103 may need to have different values for the first axis and the second axis.

Also, as shown in the image (c) of FIG. 4, in order to implement the Lissajous scanning corresponding to the preset condition, the difference between the resonant frequencies for the first axis and the second axis may need to deviate from the preset range. In this case, when the difference between the resonant frequencies for the first axis and the second axis is not out of the preset range, the Lissajous pattern emitted from the optical fiber 1103 may be distorted.

For example, the difference between the first resonant frequency fy for the first axis of the optical fiber 1103 and the second resonant frequency fx for the second axis of the optical fiber 1103 needs to be at least greater than or equal to the full-width half-maximum (FWHM) of the resonant frequency fr of the optical fiber 1103.

Figure 15:
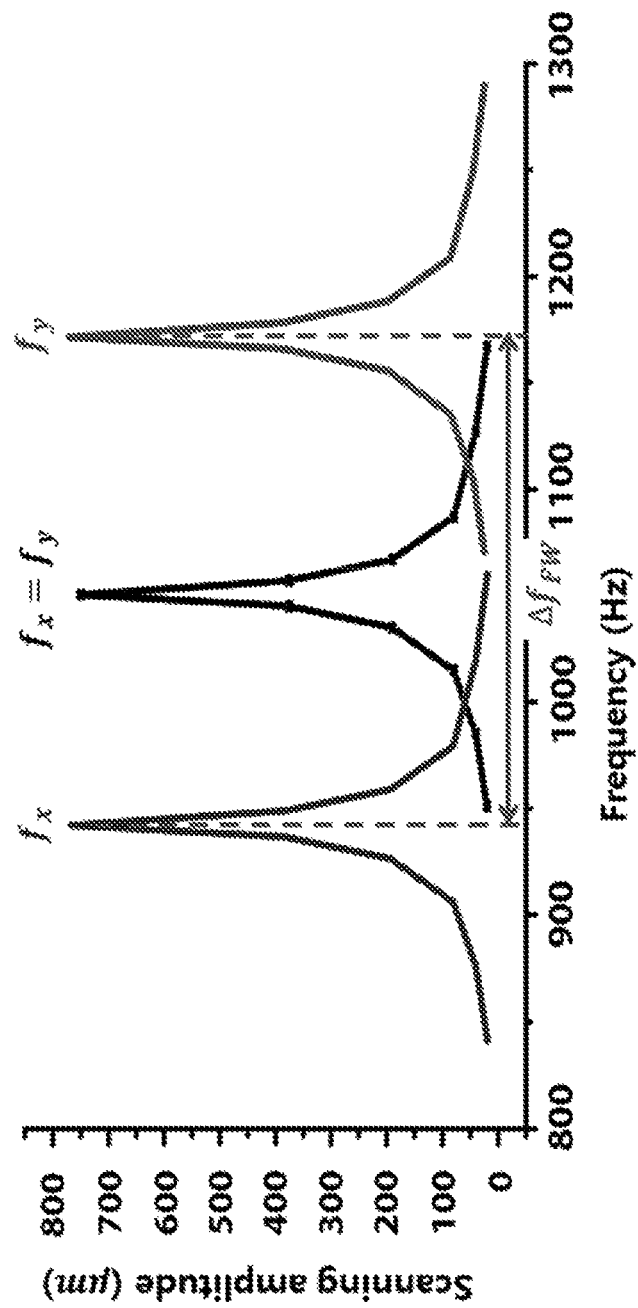
FIG. 15 is a graph for describing frequency separation according to an embodiment of the present invention.

Alternatively, as shown in FIG. 15, the first resonant frequency fy and the second resonant frequency fx of the optical fiber 1103 may be separated by more than the full width (FW) of the resonant fr of the optical fiber 1103.

Referring to FIG. 15, the difference between the first resonant frequency fy and the second resonant frequency fx may be the FW of the resonant frequency fr, which is 200 Hz.

Accordingly, as described above, the optical fiber 1103 may be designed to have different stiffnesses k with respect to the first axis and the second axis by installing an elastic structure such that the optical fiber 1103 has different resonant frequencies with respect to the first axis and the second axis.

In detail, the optical fiber 1103 may become an asymmetric structure with respect to the first axis and the second axis by attaching a deformable rod to any one of the first axis and the second axis of the optical fiber 1103. This is because the resonant frequencies of the optical fiber 1103 in the first axis and the second axis may vary depending on the stiffnesses in the first axis and the second axis.

However, the ratio of the stiffness of the first axis to the stiffness of the second axis of the optical fiber 1103 ($k_y/k_x$) may be designed not to exceed one. Since the driving range (displacement) of the scanner varies depending on the stiffness of each axis, the FOV of the image reconstructed by the controller 130 may not be properly secured when the stiffness ratio of each axis is increased.

Figure 16:
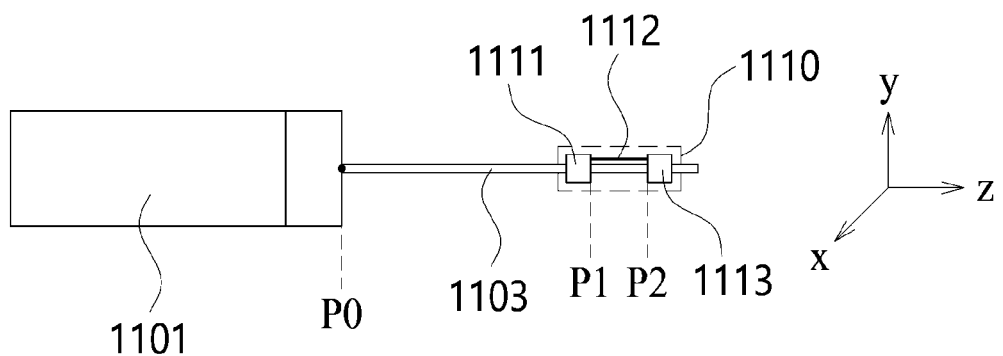
FIGS. 16 to 18 are diagrams for exemplarily describing a structure of a driving range adjustment means according to an embodiment of the present invention.

FIG. 16 is a diagram for exemplarily describing a structure of the driving range adjustment means 1110 according to an embodiment of the present invention.

Referring to FIG. 16, the driving range adjustment means 1110 may include a first connector 1111, a deformable rod 1112, and a second connector 1113.

As described above, the driving range adjustment means 1110 may be designed such that the optical fiber 1103 has an asymmetric structure with respect to the first axis and the second axis. In the asymmetric structure, the difference in resonant frequency between the first axis and the second axis of the optical fiber 1103 is out of a preset range. Accordingly, the optical fiber 1103 may emit a Lissajous pattern with no coupling. The coupling of the Lissajous pattern emitted by the optical fiber 1103 will be described in detail in the following related sections.

For convenience of description, the following description assumes that the controller 130 applies a first driving frequency to a first actuating unit 1101a and applies a second driving frequency to a second actuating unit 1101b.

Also, the first actuating unit 1101a and the second actuating unit 1101b are PZT material-based piezoelectric elements as an example in the following description. For example, the controller 130 may apply the first driving frequency and the second driving frequency to the first actuating unit 1101a and the second actuating unit 1101b, and the first actuating unit 1101a and the second actuating unit 1101b may be mechanically deformed.

In this case, a force generated due to the mechanical deformation of the first actuating unit 1101a and the second actuating unit 1101b may be transferred to the first axis and the second axis of the optical fiber 1103, and the optical fiber 1103 may be vibrated in the first axis and the second axis by the force transferred from the first actuating unit 1101a and the second actuating unit 1101b.

Also, the first driving frequency applied to the first actuating unit 1101a may cause the optical fiber 1103 to vibrate along the first axis, and the second driving frequency applied to the second actuating unit 1101b may cause the optical fiber 1103 to vibrate along the second axis. The deformable rod 1112 may be an elastic structure to be attached to at least one of the first axis and the second axis of the optical fiber 1103 in order to change the stiffness of the optical fiber 1103 with respect to at least one of the first axis and the second axis.

For example, the optical fiber 1103 may be resonantly driven due to a first force applied from the first actuating unit 1101a and a second force applied from the second actuating unit 1101b, and the deformable rod 1112 may change the stiffness of at least one of the first axis and the second axis of the optical fiber 1103 when the optical fiber 1103 is resonantly driven.

In this case, the optical fiber 1103 may have a first stiffness, and the deformable rod 1112 may have a second stiffness. In this case, the second stiffness may be greater than or equal to the first stiffness.

In an embodiment, the deformable rod 1112 may be attached onto the first axis of the optical fiber 1103 in order to amplify the vibration of the optical fiber 1103 in the first axis direction.

In this case, since the stiffness of at least one of the first axis and the second axis of the optical fiber 1103 changes, the optical fiber 1103 may be an asymmetric structure with respect to the first axis and the second axis. Accordingly, a difference in resonant frequency with respect to the first axis and the second axis of the optical fiber 1103 occurs.

In this case, the deformable rod 1112 may be formed of a material with a predetermined elastic force in order to amplify the vibration along the first axis or the second axis of the optical fiber 1103.

Also, the deformable rod 1112 may have various shapes. For example, as shown in FIG. 16, the deformable rod 1112 may have the shape of a rectangular bar or wire.

Also, the deformable rod 1112 may be disposed adjacent to the optical fiber 1103 in the longitudinal length of the optical fiber 1103, i.e., in the z-axis direction and may be spaced a predetermined distance from the optical fiber 1103.

Also, the deformable rod 1112 may have a first end and a second end.

For example, referring to FIG. 16, the first end of the deformable rod 1112 may be fixed at a first rod position P1 on the optical fiber 1103, and the second end may be fixed at a second rod position P2 on the optical fiber 1103.

In this case, the first rod position P1 and the second rod position P2 may be between the actuator position P0 and the free end of the optical fiber 1103.

Here, the actuator position P0 may be a position to which a force for vibrating the optical fiber is transferred according to the driving signals applied to the first actuating unit 1101a and the second actuating unit 1101b.

For example, the actuator position P0 may be between the fixed end and the free end of the optical fiber 1103.

In this case, the first actuating unit 1101a may be configured to apply a first force to the actuator position P0 and may induce the free end of the optical fiber 1103 to be resonantly driven in a first direction.

Also, the second actuating unit 1101b may be configured to apply a second force to the actuator position P0 and may induce the free end of the optical fiber 1103 to be resonantly driven in the first direction.

Meanwhile, one or more deformable rods 1112 may be installed such that the resonant frequencies for the first axis and the second axis are separated beyond a predetermined range to emit a Lissajous pattern corresponding to a preset condition while having different resonant frequencies with respect to the first axis and the second axis.

Also, referring to FIG. 16, the first connector 1111 and the second connector 1113 may be fixers or microstructures for supporting the deformable rod 1112.

For example, the first connector 1111 and the second connector 1113 may be silicon microstructures and may be produced by silicon wafer microprocessing.

Alternatively, for example, the first connector 1111 and the second connector 1113 may be adhesive agents which fix the deformable rod 1112 on the optical fiber 1103 while being spaced a predetermined distance from the optical fiber 1103.

Also, for example, the first connector 1111 and the second connector 1113 may be attached to the z-axis of the optical fiber 1103.

In this case, the deformable rod 1112 may be positioned between the first connector 1111 and the second connector 1113, and the first end and the second end of the deformable rod 1112 may be connected to each other by the first connector 1111 and the second connector 1113.

Also, for example, the first connector 1111 and the second connector 1113 may be fixers that are fixed at the optical fiber 1103. In this case, a predetermined groove may be formed in the first connector 1111 and the second connector 1113 such that the first connector 1111 and the second connector 1113 are stably fixed on the optical fiber 1103.

Also, the first connector 1111 and the second connector 1113 may be designed in various shapes as long as the first connector 1111 and the second connector 1113 are fixed on the optical fiber 1103 to support the deformable rod 1112.

In an embodiment, the first connector 1111 and the second connector 1113 that support the deformable rod 1112 and the first end and the second end of the deformable rod 1112 may move along with the vibration of the optical fiber 1103.

In this case, the deformable rod 1112 may amplify the vibration of the optical fiber 1103 in the first axis direction when the optical fiber 1103 vibrates in the first axis direction according to the first force applied from the first actuating unit 1101a to the actuator position P0.

Alternatively, the deformable rod 1112 may amplify the vibration of the optical fiber 1103 in the second axis direction when the optical fiber 1103 vibrates in the second axis direction according to the second force applied from the second actuating unit 1101b to the actuator position P0.

Accordingly, the optical fiber 1103 may have different resonant frequencies for the first axis and the second axis.

However, the vibration in the second axis direction may be amplified by a portion of the force applied in the first axis direction being transferred to the second axis direction of the optical fiber 1103. Also, the vibration in the first axis direction may be amplified by a portion of the force applied in the second axis direction being transferred to the first axis direction of the optical fiber 1103.

In this case, when the attachment position and direction of the deformable rod 1112 are appropriately designed, a portion of a force applied to any one axis may affect the other axis, and thus it is possible to decrease amplification of the vibration in the other axis. This will be described in detail in the following related sections.

2.4 Deformable Rod Attachment Position

As described above, by attaching the deformable rod 1112 to any one of the first axis and the second axis along which the optical fiber 1103 is driven when the scanning unit 1100 according to an embodiment of the present invention is designed, the optical fiber 1103 may have different resonant frequencies with respect to the first axis and the second axis.

A method of determining the attachment position of the deformable rod 1112 such that the difference between the resonance frequencies of the first axis and the second axis of the optical fiber 1103 is out of a preset range will be described in detail below.

Figure 17:
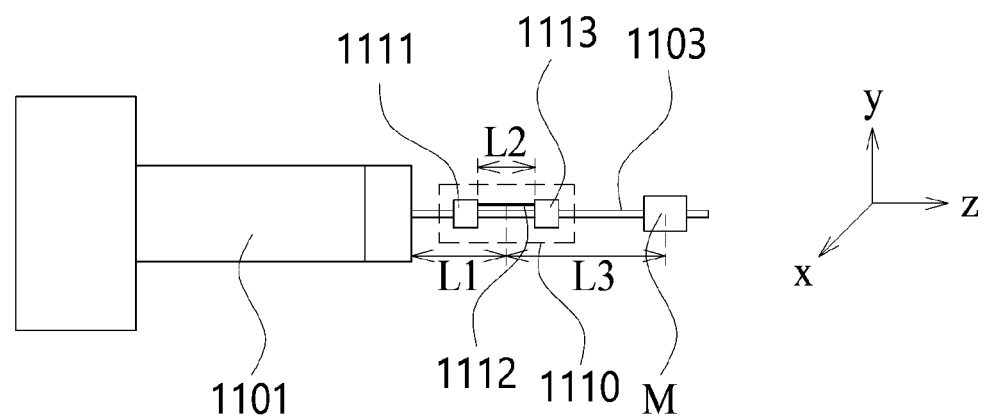

FIG. 17 is a diagram for describing the attachment position of the deformable rod for designing the difference between the resonant frequencies of the first axis and the second axis of the optical fiber 1103 as deviating from a preset range in an embodiment of the present invention.

That is, since the difference in resonant frequency between the first axis and the second axis of the optical fiber 1103 may vary depending on the attachment position of the deformable rod 1112, it may be necessary to adjust the installation position L1 and length L2 of the deformable rod 1112.

For example, the installation position L1 of the deformable rod 1112 may be determined based on the distance from the fixed end of the optical fiber 1103 to the half point of the total length L2 of the deformable rod 1112.

For example, as shown in FIG. 17, the deformable rod 1112 may be disposed alongside and spaced a predetermined distance from the optical fiber 1103 and may be installed at a position spaced L1 apart from one end of the optical fiber 1103.

Also, for example, the deformable rod 1112 may be installed and spaced a predetermined distance L3 apart from the mass M installed at a distal end of the optical fiber 1103.

In this case, the first connector 1111 and the second connector 1113 may be designed to have a much smaller mass than the mass M. Alternatively, the first connector 1111 and the second connector 1113 may be designed to have a mass greater than or equal to that of the mass M.

Figure 18:
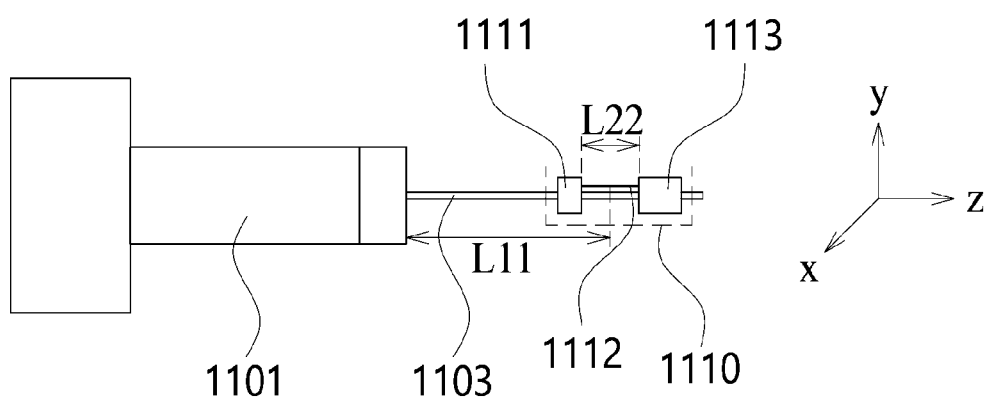

FIG. 18 is a diagram for exemplarily describing the structure of a driving range adjustment means 1110 according to another embodiment of the present invention.

Referring to FIG. 18, the driving range adjustment means 1110 according to another embodiment of the present invention may include a first connector 1111, a deformable rod 1112, and a second connector 1113, and the mass M described with reference to FIG. 17 may also function as the second connector 1113.

In other words, for a scanning unit 1100 according to another embodiment of the present invention, the deformable rod 1112 may be supported by the first connector 1111 and the mass M.

Accordingly, the installation position L1 and the length L2 of the deformable rod 1112 according to another embodiment of the present invention may differ from those when a separate mass M is installed.

This is because the mass M needs to be installed at an appropriate position to perform a function for adjusting the driving speed of the scanning unit 1100 and also to function as an auxiliary member for supporting the deformable rod 1112.

For example, referring to FIG. 18, the deformable rod 1112 according to another embodiment of the present invention may be installed at location L11 spaced a predetermined distance from one end of the optical fiber 1103. As described above with reference to FIG. 14, the buffer distance from the inner wall of the housing may be additionally considered.

Also, by attaching an additional structure to the optical fiber 1103 as described above, distortion may still occur in a scanning pattern emitted by the optical fiber 1103 depending on the attachment direction of the deformable rod 1112 even when the optical fiber 1103 is designed to have different resonant frequencies with respect to the first axis and the second axis.

This is because when the optical fiber 1103 vibrates in the first direction due to the first force applied from the first actuating unit 1101a, the vibration is amplified not only in the first direction but also in the second direction.

Alternatively, this is because when the optical fiber 1103 vibrates in the second direction due to the second force applied from the second actuating unit 1101b, the vibration is amplified not only in the second direction but also in the first direction.

A phenomenon in which a force transferred in one axial direction affects the other axial direction and amplifies the vibration in the other axial direction is defined below as cross-coupling.

2.5 Cross-Coupling

The cross-coupling and the attachment direction of the deformable rod for removing the cross-coupling will be described in detail below.

Figure 19:
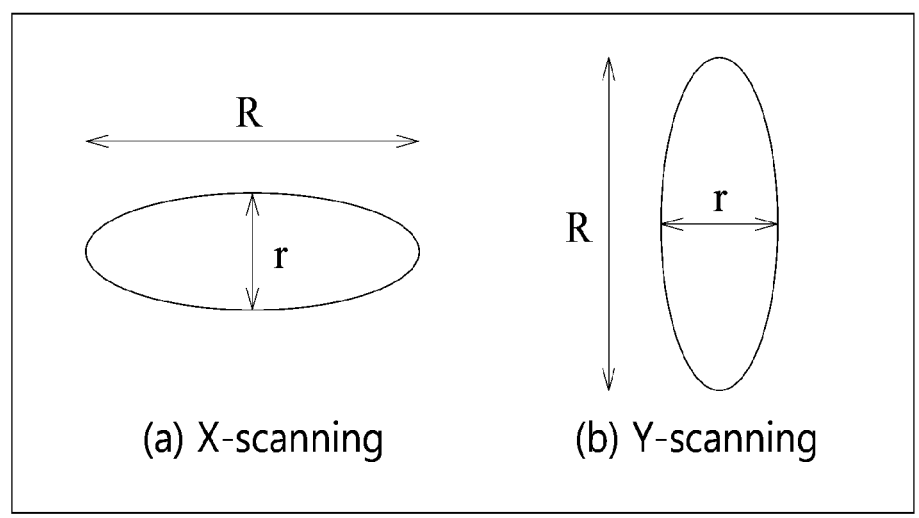
FIG. 19 is a diagram for exemplarily describing cross-coupling according to an embodiment of the present invention.

FIG. 19 is a diagram for exemplarily describing illustrating cross-coupling according to an embodiment of the present invention.

For example, when the controller 130 applies a first driving signal to the first actuating unit 1101a, a portion of a force that should have been transferred to only the first axis of the optical fiber 1103 may be transferred to the second axis, and cross-coupling corresponding to the transferred force may occur along the second axis.

In this case, as shown in the image (b) of FIG. 19, mechanical coupling or a coupled Lissajous pattern may be generated in the second axis direction.

Alternatively, for example, when the controller 130 applies a second driving signal to the second actuating unit 1101b, a portion of a force that should have been transferred to only the second axis of the optical fiber 1103 may be transferred to the first axis, and cross-coupling corresponding to the transferred force may occur along the first axis.

In this case, as shown in the image (a) of FIG. 19, mechanical coupling or a coupled Lissajous pattern may be generated in the first direction.

For convenience of description, the mechanical coupling or the coupled Lissajous pattern is defined as a coupling error.

Here, the coupling error may be generated by various causes.

For example, when the optical fiber 1103 is vibrated by a force transferred from the PZT-device-based driving unit 1101 to the actuator position P0 on the optical fiber 1103, the vibration may occur when the force axes (x-axis and y-axis) of the optical fiber 1103 do not match the resonant driving axes (x'-axis and y'-axis) in which the optical fiber 1103 is actually driven.

Alternatively, for example, since the driving unit 1101 is not perfectly circular, the center of the inner diameter does not match the center of the outer diameter. Thus, it may not be possible to drive the driving unit 1101 such that the force axes (x-axis and y-axis) of the optical fiber 1103 match the resonant driving axes (x'-axis and y'-axis) in which the optical fiber 1103 actually vibrates.

In this case, by adjusting the attachment position and/or direction of the deformable rod 1112 installed at the optical fiber 1103, the force axes (x-axis and y-axis) transferred to the optical fiber 1103 may be adjusted to match the resonant driving axes (x'-axis and y'-axis) of the optical fiber 1103. This is because the resonant driving axis of the optical fiber 1103 may vary depending on the attachment position and/or direction of the deformable rod 1112.

However, even if the force axes of the optical fiber 1103 and the resonant driving axes do not match perfectly, a predetermined error may be allowed when an image reconstructed on the basis of the scanning pattern emitted from the optical fiber 1103 has a quality more than or equal to a preset level.

2.6 Attachment Range of Deformable Rod

An attachment range determination method for the deformable rod 1112 to minimize the coupling error will be described in detail below.

As described above, while being supported by the first connector 1111 and the second connector 1113, the deformable rod 1112 may change the stiffness of at least one of the first axis and the second axis of the optical fiber 1103 such that the optical fiber 1103 has different resonant frequencies with respect to the first axis and the second axis.

As described above, the deformable rod 1112 may have a first end fixed at the first rod position on the optical fiber 1103 and a second end fixed at the second rod position on the optical fiber 1103.

Thus, the deformable rod 1112 may function to amplify the vibration in the first axis or in the second axis while being supported by the first connector 1111 and the second connector 1113.

Figure 20:
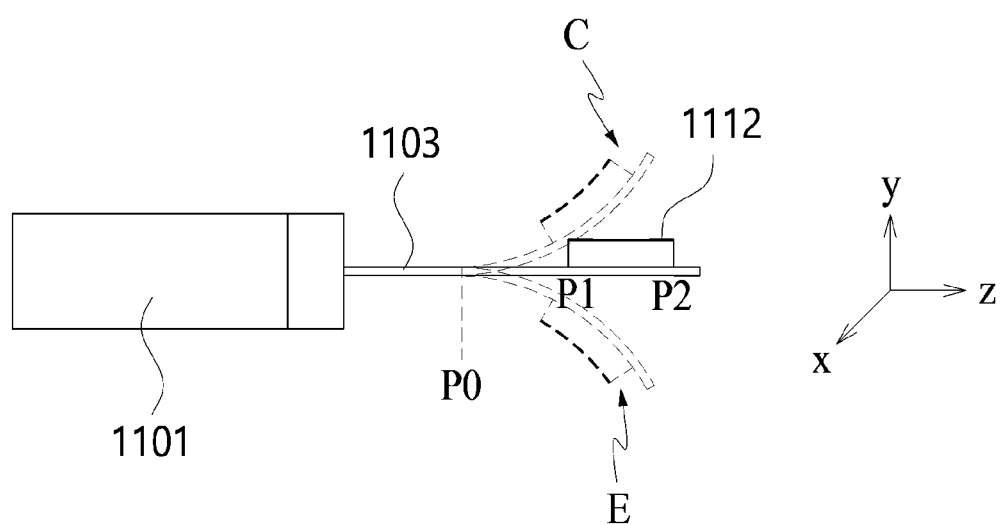
FIG. 20 is a diagram for exemplarily describing a vibration principle of an optical fiber according to another embodiment of the present invention.

That is, referring to FIG. 20, when the deformable rod 1112 vibrates according to a force applied to the optical fiber 1103, compression C and expansion E may amplify the vibration of the optical fiber 1103.

The compression C and expansion E of the deformable rod 1112 may occur both in the first axis direction and in the second axis direction depending on the attachment direction of the deformable rod 1112.

For example, when the deformable rod 1112 is disposed parallel to the optical fiber 1103, the compression C and expansion E of the deformable rod 1112 may occur only in the first axis direction.

Figure 21:
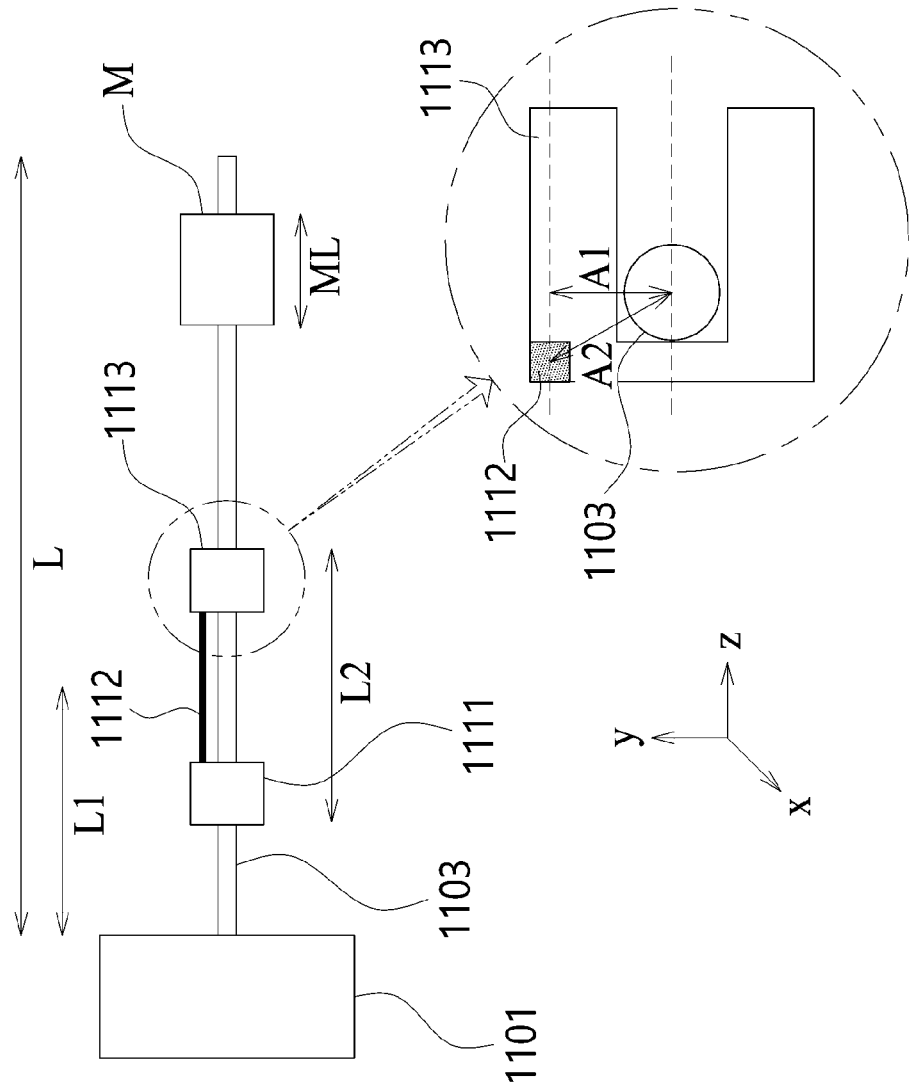
FIGS. 21 and 22 are diagrams for describing an attachment position of a deformable rod according to embodiments of the present invention.
Figure 22:
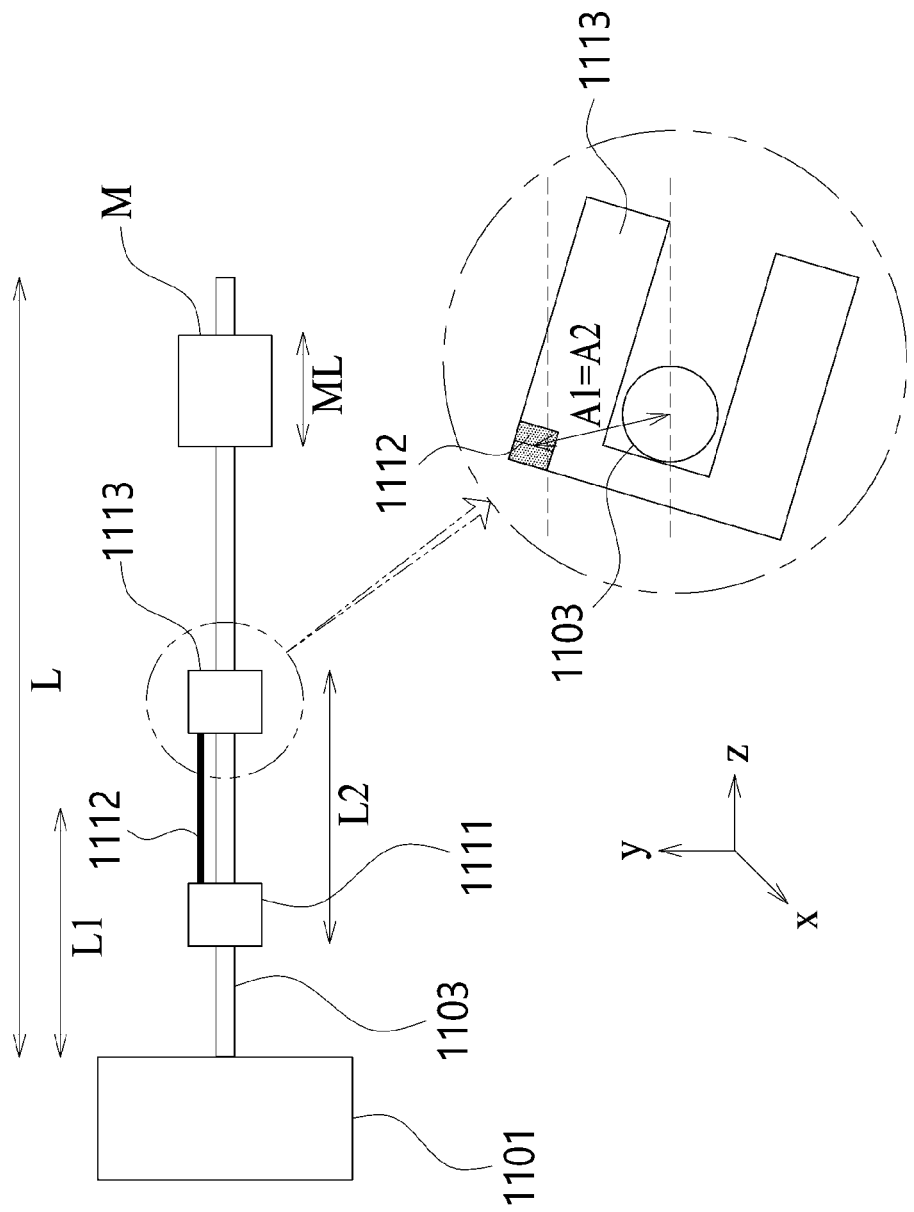

FIGS. 21 and 22 are sectional views for describing an attachment position of a deformable rod according to embodiments of the present invention.

For example, on a cross-sectional surface perpendicular to the z-axis direction or the longitudinal direction of the optical fiber 1103, the attachment position of the deformable rod may be determined such that a virtual line A2 connected from the second end of the deformable rod 1112 to the second rod position on the second optical fiber matches a first axis A1. This is because a resonant driving axis along which the optical fiber 1103 is actually driven is determined by a virtual line A2 connected from the second end of the deformable rod 1112 to the second rod position on the second optical fiber.

For convenience of description, the deformable rod 1112 is positioned in the first axis direction of the optical fiber 1103 as an example in the following description.

Figure 23:
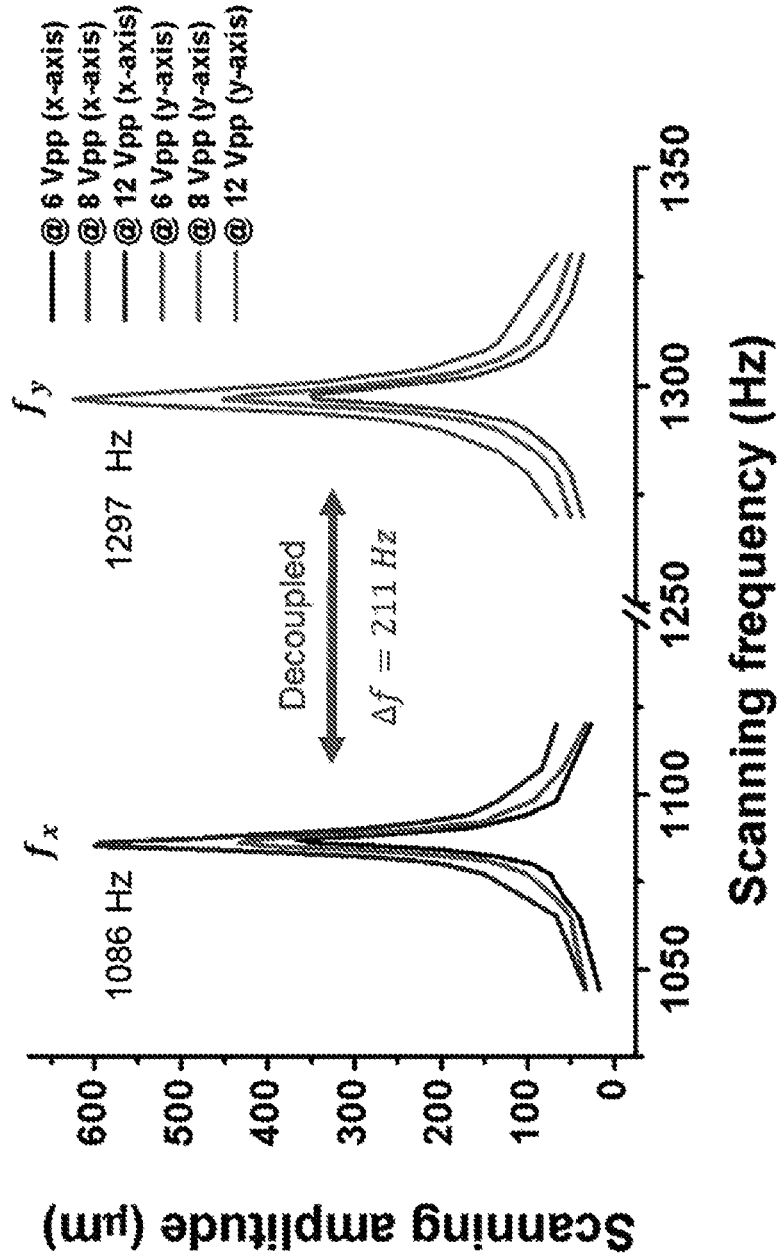
FIG. 23 is a graph for describing frequency separation according to an embodiment of the present invention.

For example, when the attachment position of the deformable rod 1112 is determined such that the force axis (the first axis) of the optical fiber 1103 matches the resonant driving axis along which the optical fiber 1103 is actually driven, the resonant frequencies with respect to the first axis and the second axis of the optical fiber 1103 may be separated beyond a preset range as shown in the FIG. 23.

Referring to FIG. 21, it can be seen that the force axis A1 of the optical fiber 1103 does not match the resonant driving axis A2 in which the optical fiber 1103 is actually driven.

In this case, when the controller 130 applies a first driving signal to the first actuating unit 1101a, the vibration of the optical fiber 1103 induced by the first force applied from the first actuating unit 1101a to the actuator position on the optical fiber 1103 may be amplified not only in the first axis direction but also in the second axis, and thus a predetermined coupling error r may occur as shown in the image (b) of FIG. 19.

Alternatively, when the controller 130 applies a second driving signal to the second actuating unit 1101b, the vibration of the optical fiber 1103 induced by the second force applied from the second actuating unit 1101b to the actuator position on the optical fiber 1103 may be amplified not only in the second axis direction but also in the first axis direction, and thus a predetermined coupling error r may occur as shown in the image (a) of FIG. 19.

On the contrary, referring to FIG. 22, it can be seen that the force axis A1 of the optical fiber 1103 matches the resonant driving axis A2.

Figure 24:
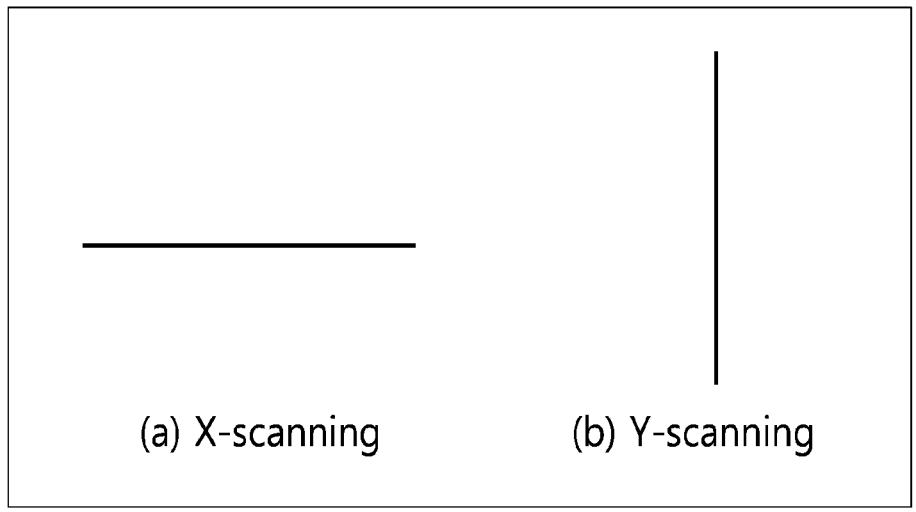
FIG. 24 is a diagram for exemplarily describing Lissajous scanning according to an embodiment of the present invention.

In this case, as shown in FIG. 24, a Lissajous pattern with no coupling may be generated.

The attachment position of the deformable rod 1112 for allowing a predetermined coupling error will be described below with reference to FIGS. 24 to 27.

As described above, on the cross-sectional surface perpendicular to the z-axis direction or the longitudinal direction of the optical fiber 1103, the attachment position of the deformable rod may be determined on the basis of an angle θ between the first direction A1 and the virtual line A2 connected from the second end of the deformable rod 1112 to the second rod position on the second optical fiber.

In an embodiment, the attachment position P1 of the deformable rod 1112 may be determined to be away from the optical fiber 1103 on the virtual line A2.

For example, the deformable rod 1112 may be spaced a predetermined distance from the optical fiber 1103.

Alternatively, for example, the deformable rod 1112 may be installed substantially parallel to the optical fiber 1103.

Alternatively, the deformable rod 1112 may be disposed alongside the optical fiber 1103.

Alternatively, the deformable rod 1112 may be disposed to at least partially overlap the optical fiber 1103.

For convenience of description, the following description assumes that a predetermined coupling error r occurs in the second direction of the optical fiber 1103 when the first actuating unit 1101a is resonantly driven. Under the assumption, an attachment angle range of the deformable rod 1112 to minimize the coupling error will be described.

Figure 25:
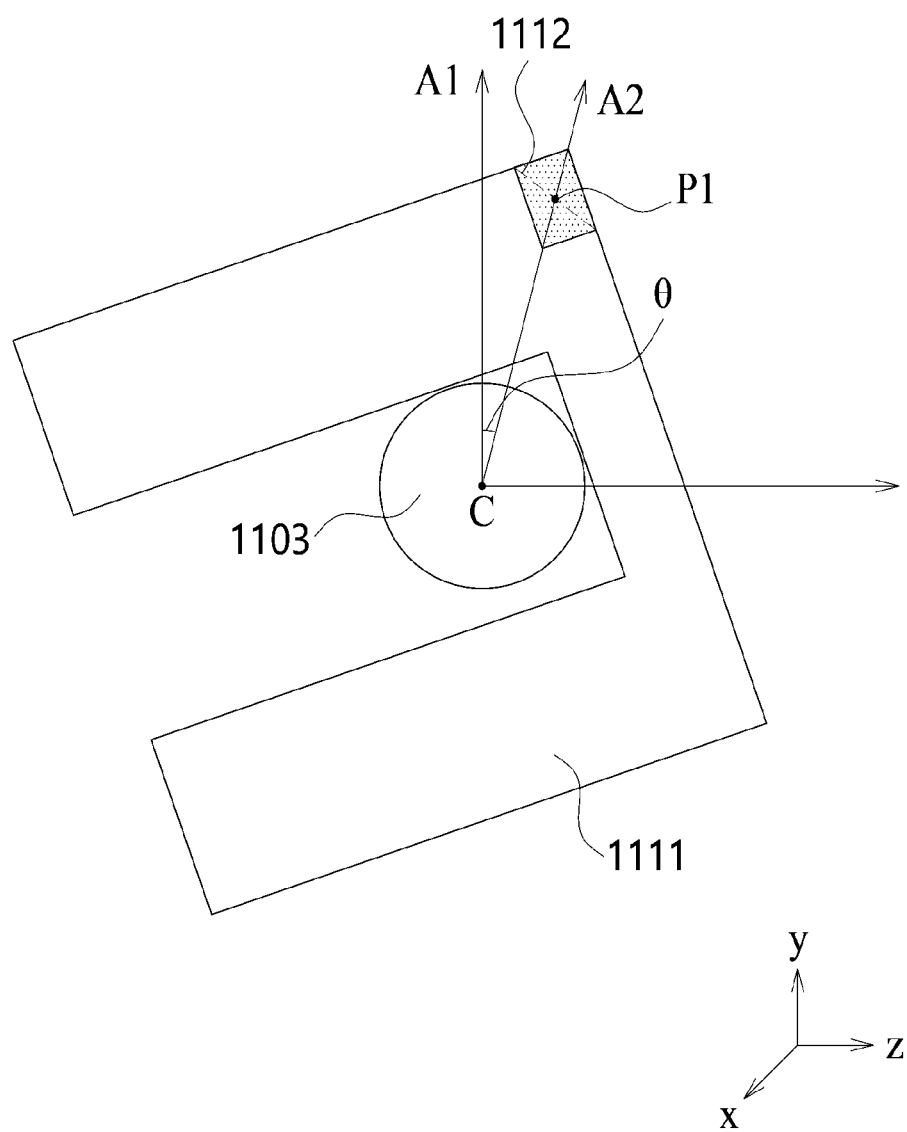
FIG. 25 is a diagram for exemplarily describing an attachment angle range of a deformable rod according to an embodiment of the present invention.

For example, as shown in FIG. 25, the angle θ between the first axis direction A1 and the virtual line A2 connected from the attachment position P1 of the deformable rod 1112 to the second rod position on the optical fiber may range from −b to +a with respect to the first axis direction A1, that is, may range within a total of 10 degrees. In this case, a and b may have different values.

Alternatively, for example, the angle θ between the first axis direction A1 and the virtual line A2 connected from the attachment position P1 of the deformable rod 1112 to the second rod position on the optical fiber may range from −b to +a with respect to the first axis direction A1, that is, may range within a total of 5 degrees. In this case, a and b may have different values.

In this case, the attachment angle range θ may be a value calculated according to a preset criterion.

The preset criterion may have an allowable coupling error r that is reflected to maintain, at a certain level or more, the resolution of an image reconstructed on the basis of the scanning pattern emitted by the optical fiber 1103.

As an example, when a first driving signal is applied to the first actuating unit 1101a, the attachment angle range θ may be calculated in consideration of efficiency a of a force generated in the second axis direction of the optical fiber 1103 due to the first force applied from the first actuating unit 1101a to the actuator position of the optical fiber 1103 and also efficiency b of a driving range in the second axis direction of the optical fiber 1103.

For example, when a force equal to Fy is applied from the first actuating unit 1101a to the actuator position of the optical fiber 1103 in the first axis direction (the y-axis), a predetermined force may be transferred to the second axis (the x-axis), and thus the vibration may be amplified in the second axis direction.

$$Y = F_y \cos θ.$$ [Formula 3]

$$X' = F_y \sin θ.$$ [Formula 4]

Here, Formula 3 indicates a force Y transferred to the y-axis, and Formula 4 indicates a force X' transferred to the x-axis.

In this case, the efficiency a of the force generated in the x-axis direction in order to form a driving range equal to FOVx may be defined as follows:

$$a = \frac{F_y \sin θ}{F_x \cos θ}.$$

In this case, the driving range r in the x-axis direction may be defined as follows:

$$r = \frac{F_y \sin θ}{F_x \cos θ} * FOV_x * b.$$

FIG. 25 is a graph for illustratively showing an x-axis direction driving range that is induced by a force transferred from the first actuating unit 1101a while in the scanning module 110 according to an embodiment of the present invention, and the deformable rod 1112 is installed alongside and on the optical fiber 1103 and the resonant frequencies of the x-axis and the y-axis are separated by A.

$$FOV_x = pixels * resolution.$$

Here, when the number of pixels is 256 and the resolution is 1 um, the x-axis direction driving range r may be defined as follows:

$$r = \frac{F_y}{F_x} \tan θ * 256 * b.$$

In an embodiment, the second-axis (x-axis) direction driving range r may be allowed within at least ½ of a preset system resolution.

For example, when the second-axis (x-axis) direction driving range r is determined within ½ of one pixel, pixels can be distinguished from each other, and thus it is possible to maintain the resolution of the reconstructed image at a preset level.

In this case, when the second-axis (x-axis) direction driving range r is within ½ of the preset system resolution, the attachment angle range θ of the deformable rod 1112 is as follows:

$$\therefore θ \leq \tan^{-1}\left\{\frac{0.5}{256 \cdot b} \frac{F_x}{F_y}\right\}.$$

Here, θ may be defined as the attachment angle range of the deformable rod 1112 that allows a predetermined driving range r or coupling error r in the x-axis direction upon resonant driving in the y-axis direction.

That is, the attachment angle range of the deformable rod 1112 may be calculated in consideration of at least one of a system resolution, the total number of pixels, the maximum driving range of the first axis or the second axis, and the efficiency of a force transferred in the first axis or the second axis.

Figure 26:
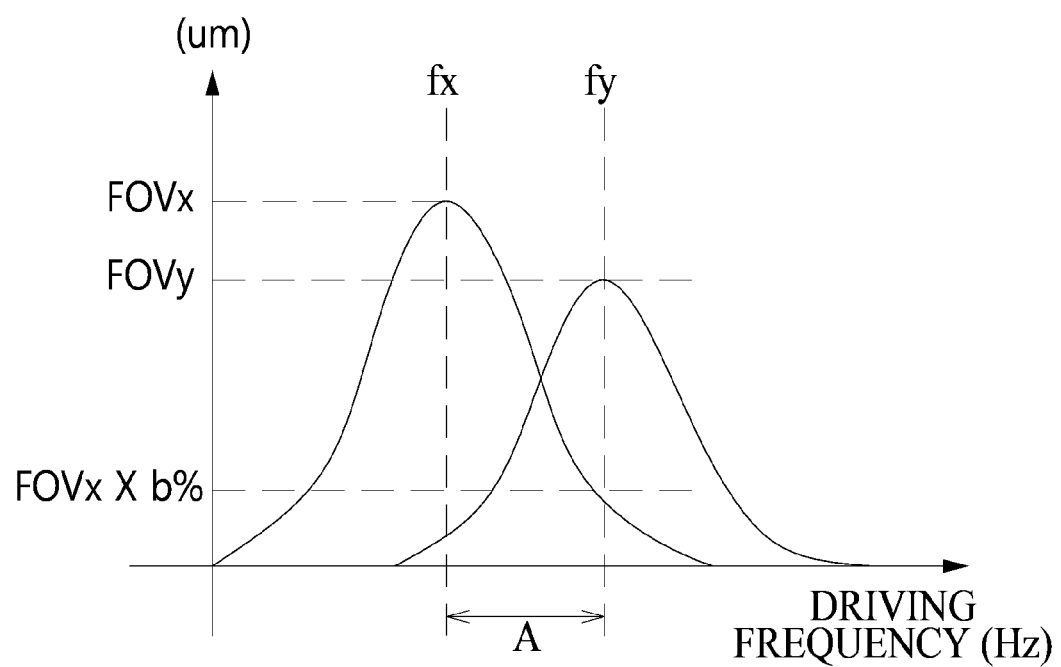
FIG. 26 is a diagram for exemplarily describing a coupling error according to an embodiment of the present invention.

Also, FIG. 26 is a graph for exemplarily describing an attachment angle of the deformable rod 1112 according to the driving range efficiency b in the second axis (x-axis direction) when Fx is equal to Fy.

Referring to FIG. 26, when it is assumed that the efficiency b of the second-axis (x-axis) direction driving range is between 1% and 20%, an attachment angle to allow a predetermined coupling error may range up to 10 degrees.

In an embodiment, when a first-axis direction driving signal is applied to the first actuating unit 1101*a*, the attachment position or the attachment angle of the deformable rod 1112 may be determined such that the driving range of the optical fiber 1103 induced in the second axis direction is less than 10% of the maximum driving range induced in the first axis direction.

In an embodiment, when the efficiency of the driving range in the second axis direction is less than 3%, the attachment angle range of the deformable rod 1112 may be less than 4 degrees (θ≤4)

In conclusion, in embodiments of the present invention, it is possible to allow the coupling error r within a range in which the quality of the reconstructed image may be maintained at a certain level or more.

Accordingly, by appropriately attaching the deformable rod 1112 according to an embodiment of the present invention onto the optical fiber 1103 in the allowable coupling error r, when the optical fiber 1103 vibrates in one axis direction by a force applied from the first actuating unit 1101*a* or the second actuating unit 1101*b*, vibration in another axis direction may be prevented.

2.7 Frequency Characteristics

FIGS. 27 to 30 are diagrams showing frequency characteristics according to an attachment direction of the deformable rod 1112.

For convenience of description, the following description assumes that at least one deformable rod 1112 is installed a predetermined distance apart from the optical fiber 1103 and is attached within the attachment angle range so that the resonant frequencies for the first axis and the second axis of the optical fiber are sufficiently separated.

As described above, when the deformable rod 1112 is attached to any one of the first axis and the second axis of the optical fiber 1103, the elastic modulus k of the axis to which the deformable rod 1112 is attached may increase. This is because it is assumed that the stiffness of the optical fiber 1103 of the axis to which the deformable rod 1112 is attached increases when the k-value influence of the deformable rod 1112 is greater than that of the mass M.

Accordingly, as the stiffness of the axis to which the deformable rod 1112 is attached increases, the value of the driving frequency of the axis to which the deformable rod 1112 is attached may increase.

Figure 27:
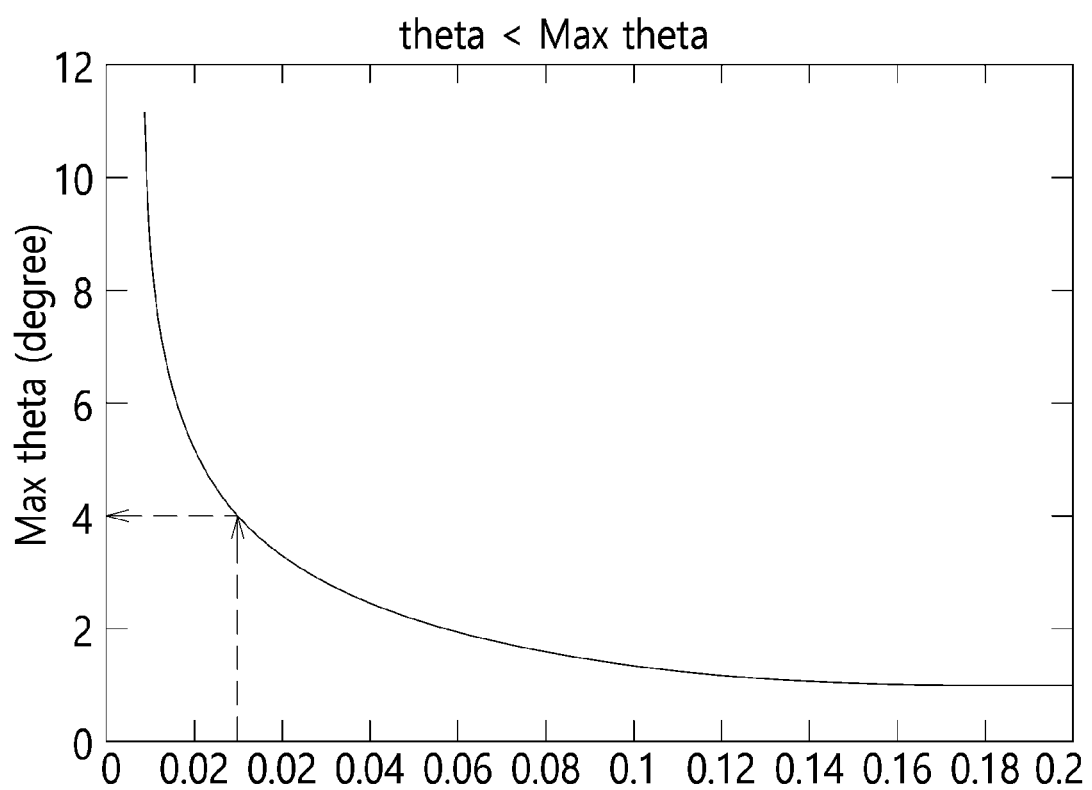
FIG. 27 is a graph for exemplarily describing an attachment angle range of a deformable rod according to an embodiment of the present invention.

For example, referring to FIG. 27, when the deformable rod 1112 is attached to the side fy, the graph may show fx<fr<fy.

Figure 28:
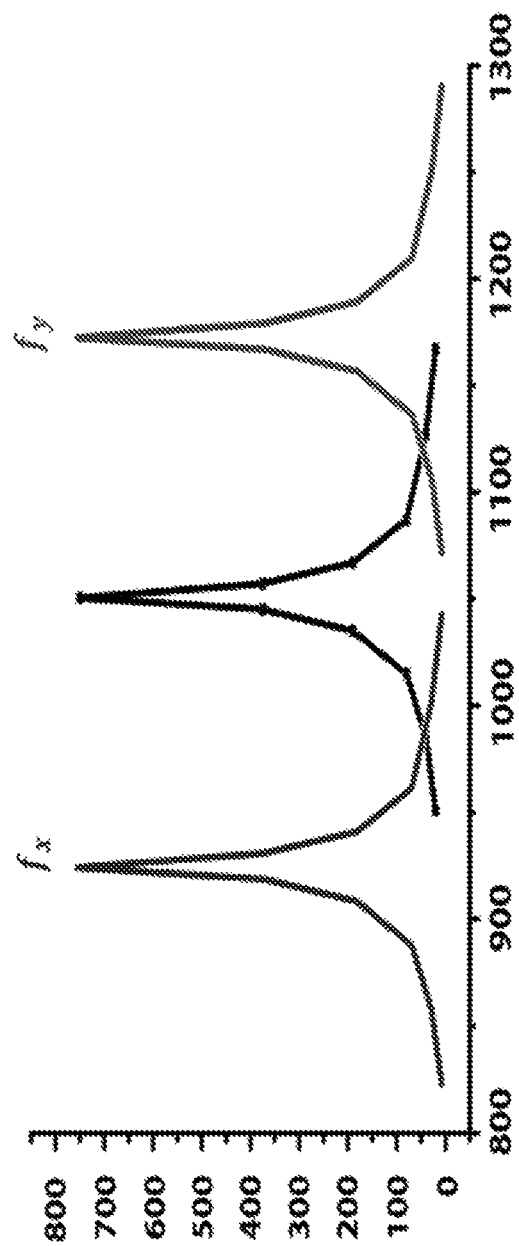
FIGS. 28 to 30 are diagrams showing frequency characteristics according to an attachment direction of the above-described deformable rod.
Figure 29:
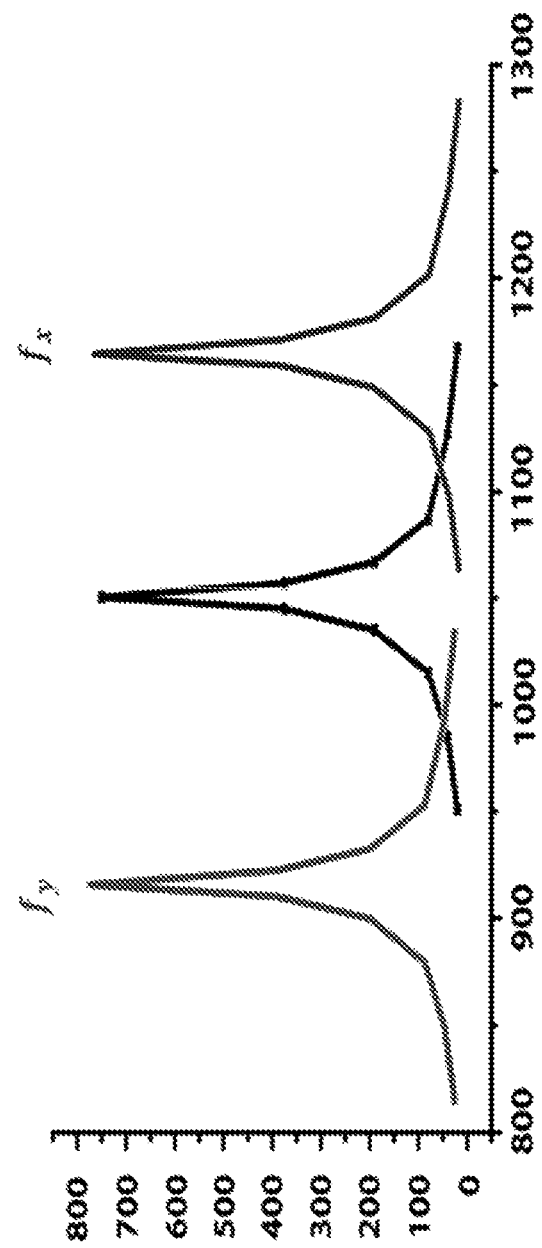
Figure 30:
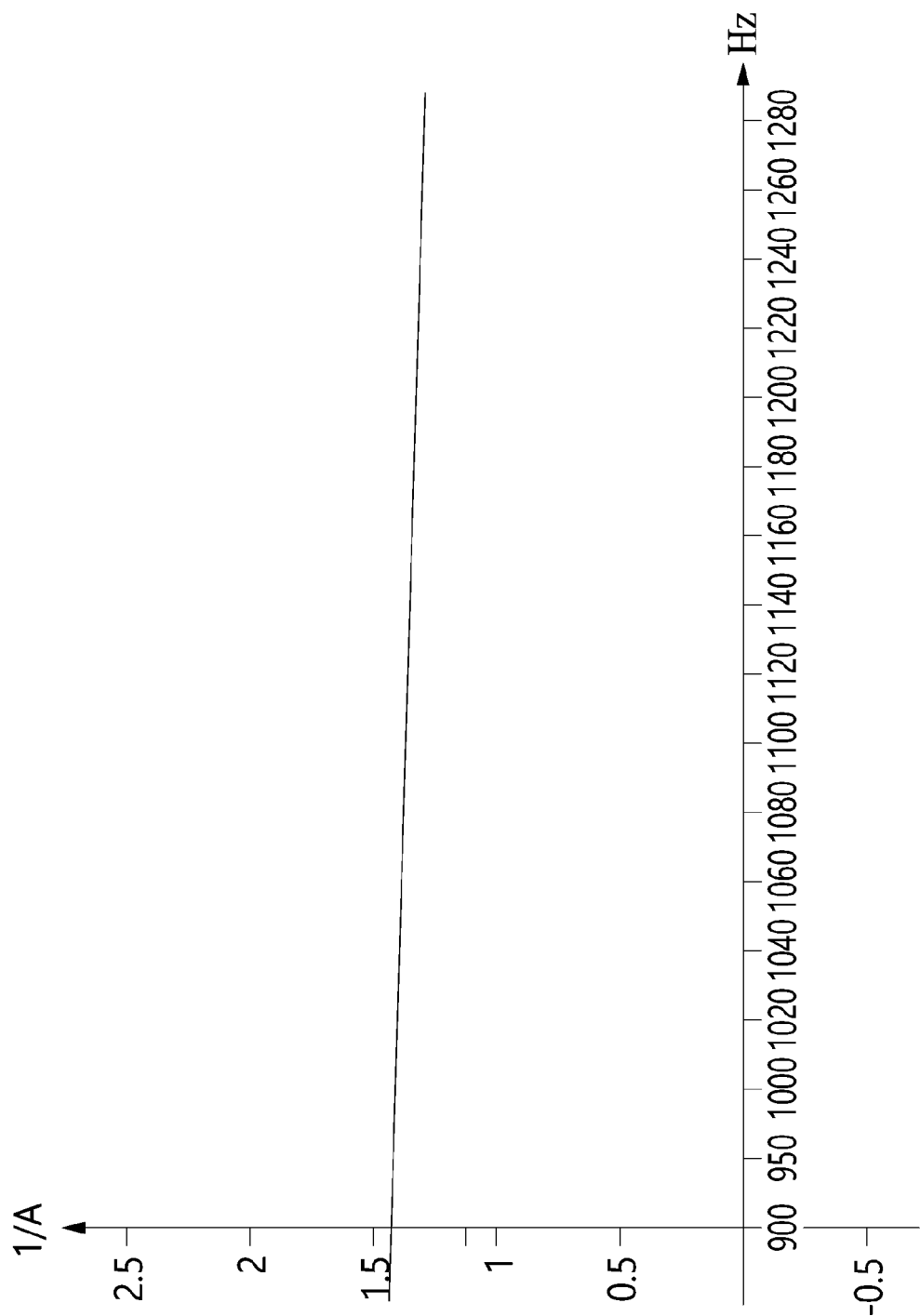

On the other hand, referring to FIG. 28, when the deformable rod 1112 is attached to the side fx, the graph may show fy<fr<fx.

In this case, the maximum driving ranges in which the optical fiber 1103 vibrates in the x-axis and the y-axis may vary depending on the difference in driving frequency between the x-axis and the y-axis. That is, the vibration amplitude of the optical fiber 1103 varies.

Accordingly, the aspect ratio of the x-axis to the y-axis of the scanning pattern emitted by the optical fiber 1103 may vary.

In this case, in the image generating device 1 according to an embodiment of the present invention, the image aspect ratio of the x-axis to the y-axis, which is output from the image generating device 1, may not be 1:1.

As an example, an aspect ratio that is output when the deformable rod 1112 is attached to the y-axis direction, when the resonant frequency of the x-axis is 1100 Hz, and when the resonant frequency of the y-axis is 1300 Hz may be calculated as follows:

$$F=kx.$$

First, it can be seen that when the same force F is given in the above formula, the spring constant K is inversely proportional to the amplitude x of the optical fiber 1103. Accordingly, the reciprocal $k_y/k_x$ of the proportion of the value k for each axis may be assumed as an aspect ratio A.

This is expressed using the following formula:

$$f_x = \frac{1}{2\pi}\sqrt{\frac{k_x}{m}}$$

$$f_y = \frac{1}{2\pi}\sqrt{\frac{k_y}{m}}$$

where $k_x$ is a spring constant for the x-axis, $k_y$ is a spring constant for the y-axis, and m is a mass.

$$\sqrt{\frac{k_x}{k_y}} = \frac{f_x}{f_y}, \frac{k_x}{k_y} = \frac{f_x^2}{f_y^2}$$

$$\Delta f = f_y - f_x (\text{if } f_y > f_x) \geq \frac{FW}{2} \approx 200 \text{ (hz)}$$

$$f_x^2 = A f_y^2$$

Here, since Fx=1100, $$\frac{1}{A} = \frac{k_y}{k_x} \approx 1.4.$$

Accordingly, referring to the graph shown in FIG. 28, when the deformable rod 1112 is attached to the y-axis direction, when the resonant frequency of the x-axis is 1100 Hz, and when the resonant frequency of the y-axis is 1300 Hz, the aspect ratio of the scanning pattern emitted by the optical fiber 1103 (FOVy:FOVx) is approximately 1:1.4.

In an embodiment, the attachment direction of the deformable rod 1112 may be determined in consideration of a preset aspect ratio.

In another embodiment, the controller 130 may adjust the aspect ratio of an image output through a display device by means of voltage control.

Alternatively, the controller 130 may adjust the aspect ratio of the scanning pattern emitted by the optical fiber 1103 by adjusting a voltage applied to the first actuating unit 1101*a* and the second actuating unit 1101*b*.

For example, when the deformable rod 1112 is attached to the y-axis direction, when the resonant frequency of the x-axis is 1100 Hz, and when the resonant frequency of the y-axis is 1300 Hz, the controller 130 may adjust the image aspect ratio to be 1:1 by applying a higher voltage to the y-axis than to the x-axis.

Alternatively, for example, the controller 130 may apply the same voltage to the first actuating unit 1101a and the second actuating unit 1101b such that the output image has different aspect ratios with respect to the x-axis and the y-axis.

Alternatively, for example, the controller 130 may correct the aspect ratio of an output image by applying a first voltage to the first actuating unit 1101a and applying a second voltage to the second actuating unit 1101b.

Alternatively, for example, the controller 130 may correct an image on the basis of aspect ratio information entered by a user.

Figure 31:
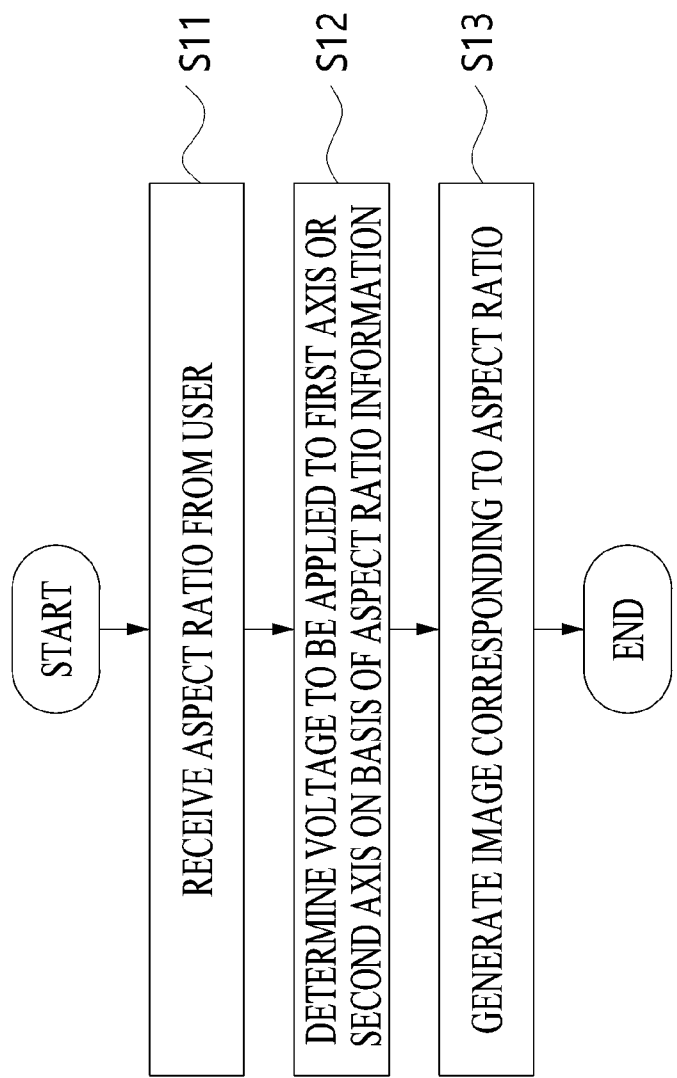
FIG. 31 is a flowchart for exemplarily describing an aspect ratio correction method according to an embodiment of the present invention.

FIG. 31 is a flowchart for exemplarily describing an aspect ratio correction method according to an embodiment of the present invention.

Referring to FIG. 31, the aspect ratio correction method according to an embodiment of the present invention may include receiving aspect ratio information from a user (S11), determining voltages to be applied to a first axis and a second axis on the basis of the aspect ratio information received from the user (S12), generating an image corresponding to an aspect ratio (S13), and the like.

As an example, the following description assumes that in the case of the scanning unit 1100 according to an embodiment of the present invention, the deformable rod 1112 is attached in the y-axis direction of the optical fiber 1103, the resonant frequency of the x-axis is set to 1100 Hz, and the resonant frequency of the y-axis is set to 1300 Hz so that a force transferred to any one axis of the optical fiber 1103 does not maximize the vibration in another axis.

In this case, as calculated through the above formula, the system aspect ratio may be set such that FOVy:FOVx=1:1.4.

First, the controller 130 may receive aspect ratio information from a user (S11).

For example, the user may enter a request corresponding to a change in aspect ratio through the input unit in order to observe an image corresponding to a desired aspect ratio. For example, a plurality of modes may be preset for the image generating device 1 according to an embodiment of the present invention in order to convert a generated image into an image corresponding to a predetermined ratio.

In this case, the controller 130 may acquire the aspect ratio information received through the input unit and additionally check preset system resolution information.

Also, the controller 130 may determine voltages to be applied to the first axis and the second axis on the basis of the aspect ratio information received from the user.

For example, when the aspect ratio information received from the user in operation S11 is a:b, the controller 130 may generate an image corresponding to the aspect ratio information by applying a first voltage to the x-axis and applying a second voltage to the y-axis.

Alternatively, for example, when the aspect ratio information received from the user in operation S11 is 1:1, the controller 130 may perform control such that a higher voltage is applied to the y-axis than to the x-axis.

Also, the controller 130 may generate an image corresponding to the aspect ratio (S13).

For example, the controller 130 may convert an image into an image corresponding to an aspect ratio desired by a user on the basis of the aspect ratio information received in operation S11 and voltage information determined in operation S12 and may provide the image corresponding to the desired aspect ratio.

Accordingly, according to a Lissajous scanning scheme according to an embodiment of the present invention, an attachment position of a deformable rod 1112 that is additionally attached to the optical fiber 1103 may be determined according to a preset image aspect ratio.

In other words, the controller 130 may correct an image to an image having a ratio desired by a user and provide the image having the desired ratio by adjusting the first driving signal for the first axis and the second driving signal for the second axis which are to be applied to the driving unit 1101.

3 Packaging

Figure 32:
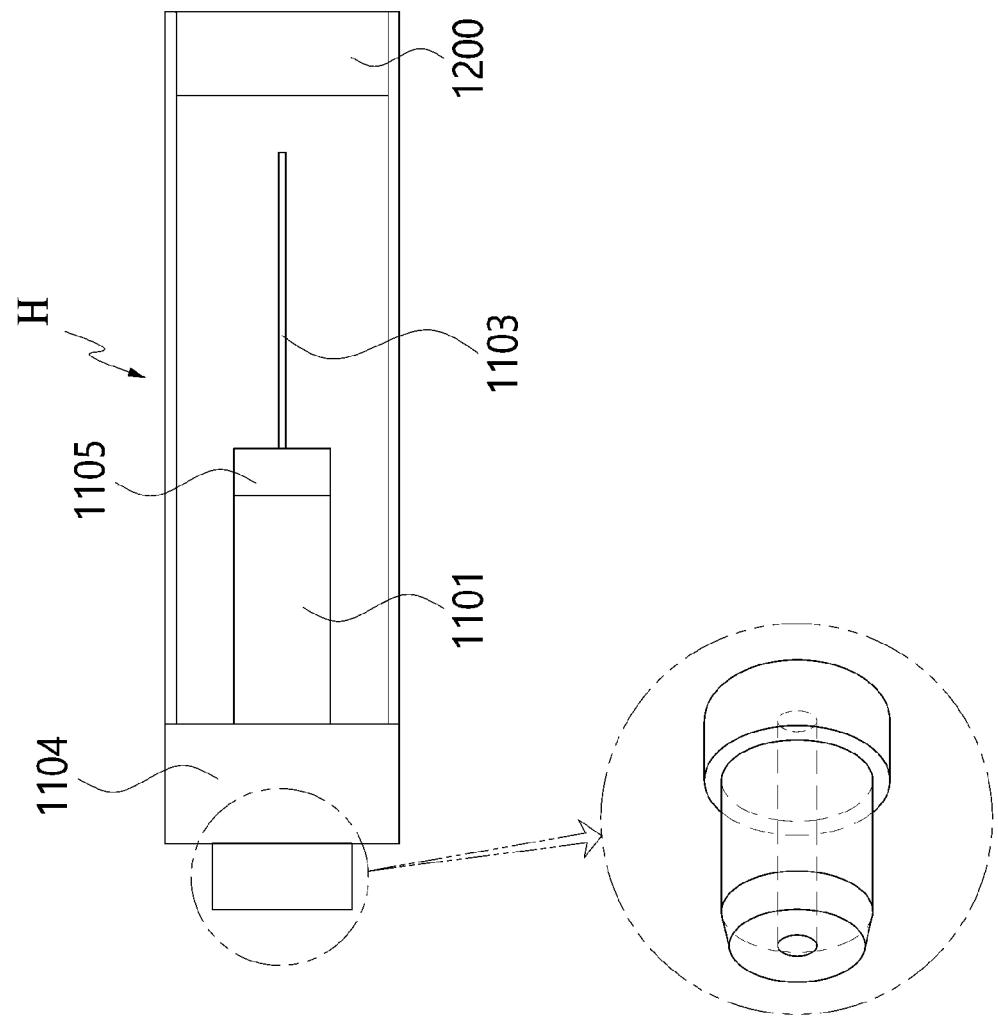
FIGS. 32 to 34 are diagrams for exemplarily describing a coupling structure for accommodating elements inside a housing of the scanning module 110 according to embodiments of the present invention.
Figure 33:
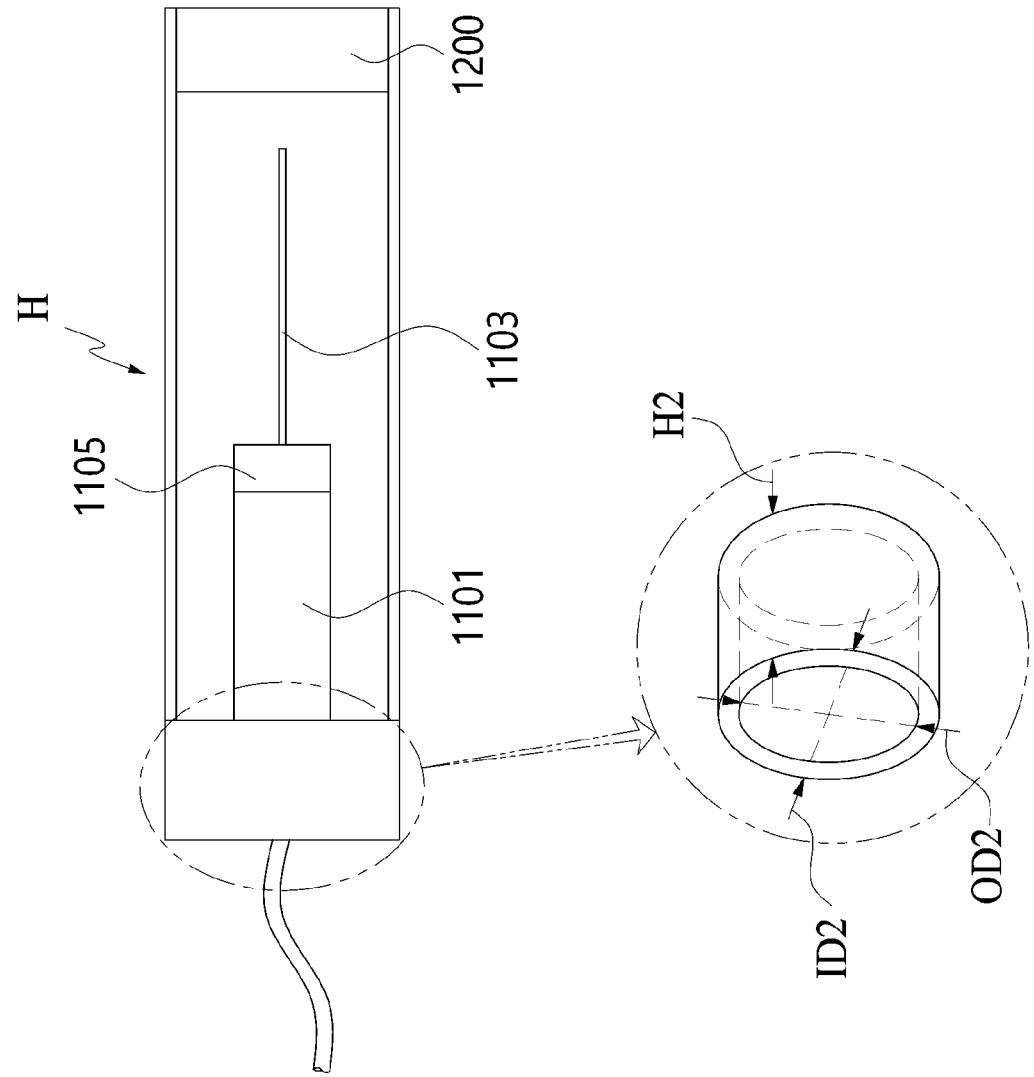
Figure 34:
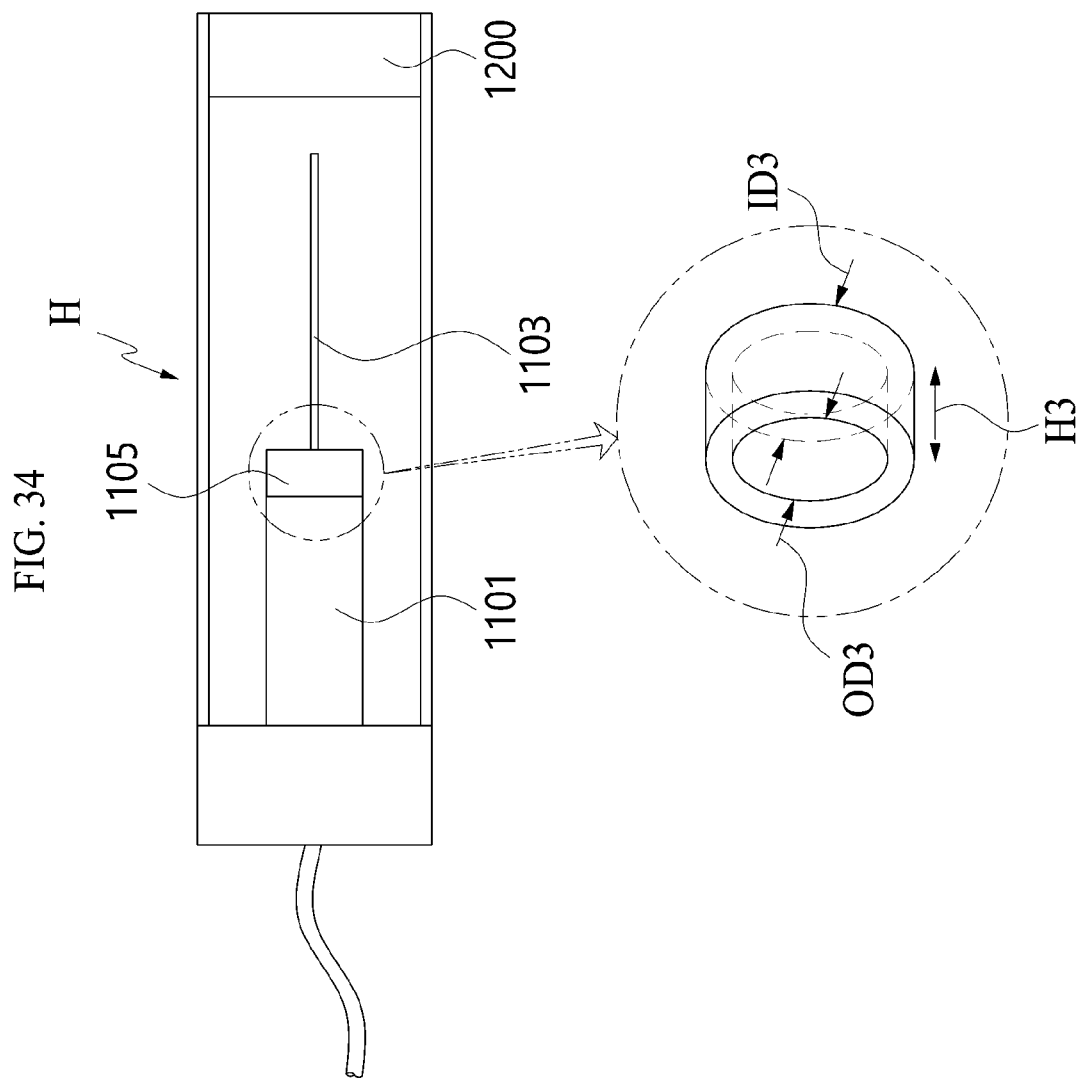

FIGS. 32 to 34 are diagrams for exemplarily describing a coupling structure for accommodating elements inside a housing of the scanning module 110 according to embodiments of the present invention.

As described above, the scanning module 110 according to embodiments of the present invention may be provided in the form of a handheld optical fiber probe. In this case, various types of fixing elements may be provided for compactly and firmly packaging elements in the probe.

The structure and the coupling method of a fixing element for packaging the driving unit 1101 and the optical fiber 1103 in the housing H will be described in detail below.

Also, for example, the following description assumes that the driving unit 1101 is a PZT material-based piezoelectric element and that a piezoelectric element having a cylindrical structure is applied.

First, referring to FIG. 32, a first fixing element 1104 for matching the center of the driving unit 1101 to the center of the optical fiber 1103 may be provided for the optical fiber probe according to embodiments of the present invention.

For example, as shown in FIG. 32, the first fixing element 1104 may have the shape of a cylindrical ring.

Also, for example, the first fixing element 1104 may be formed of a non-conductive material because four electrodes of the driving unit may need to be insulated from each other.

Also, for example, the outer diameter OD1 of the first fixing element 1104 may be designed to be a predetermined size larger or smaller than the inner diameter ID1 of the driving unit 1101. As an example, the inner diameter ID1 of the driving unit 1101 is about 0.9 mm, and the outer diameter OD1 of the first fixing element 1104 may be about 0.904 mm.

Also, for example, the inner diameter ID of the first fixing element 1104 is designed to be a predetermined size larger than the outer diameter OD1 of the optical fiber 1103, and thus it is possible to facilitate the assembly of the optical fiber 1103 and the driving unit 1101.

For example, the optical fiber 1103 may pass through the first fixing element 1104 and then be aligned such that the center of the optical fiber 1103 is positioned at the center of the driving unit 1101.

Also, referring to FIG. 33, a second fixing element 1107 for supporting one end of the housing H may be further provided for the optical fiber probe according to embodiments of the present invention.

For example, the outer diameter OD2 of the second fixing element 1107 may be designed in consideration of the inner diameter of the tube of the housing H, and the inner diameter ID2 of the second fixing element 1107 may be considered in consideration of the outer diameter of the driving unit 1101.

Referring to FIG. 34, a third fixing element 1105 for fixing one end of the optical fiber 1103 to the PZT element may be provided for the optical fiber probe according to embodiments of the present invention.

For example, in the case of the optical fiber probe, the PZT element may be aligned with the center of the optical fiber 1103 by the third fixing element 1105.

For example, the inner diameter ID3 of the third fixing element 1105 may be designed in consideration of the outer diameter OD3 of the optical fiber 1103.

Also, for example, the outer diameter OD3 of the third fixing element 1105 may be determined in consideration of the inner diameter D3 of the driving unit 1101.

In this case, the third fixing element 1105 may be inserted from the front end of the optical fiber, which has passed through the first fixing element 1104 and the driving unit 1101, up to the inside of the driving unit 1101.

Accordingly, the optical fiber 1103 and the driving unit 1101 of the optical fiber probe according to an embodiment of the present invention may remain aligned and coupled to each other by the third fixing element 1105.

In this case, an adhesive may be used for the optical fiber 1103 to maintain the coupling force with the driving unit 1101. For example, ultraviolet (UV)-curable or heat-curable epoxy may be used as the adhesive.

In this case, it may be preferable to symmetrically use a minimal amount of adhesive because an error may occur in the length of the optical fiber 1103 depending on the amount of adhesive.

Also, according to still another embodiment of the present invention, one or more modules for maintaining the internal temperature of the probe at a constant level may be disposed inside the housing of the optical fiber probe.

That is, at least one temperature sensor or temperature adjustment means may be disposed inside the scanning module 110 according to still another embodiment of the present invention.

For example, in the case of an optical fiber probe used in hospitals in order to diagnose diseases, an actual operational difference may occur depending on the usage environment such as operating room temperature and/or living body temperature.

As an example, the resonant frequency of the optical fiber may change when the internal temperature of the housing of the optical fiber probe changes.

The temperature adjustment means may include at least one of a heater and a cooler.

Figure 35:
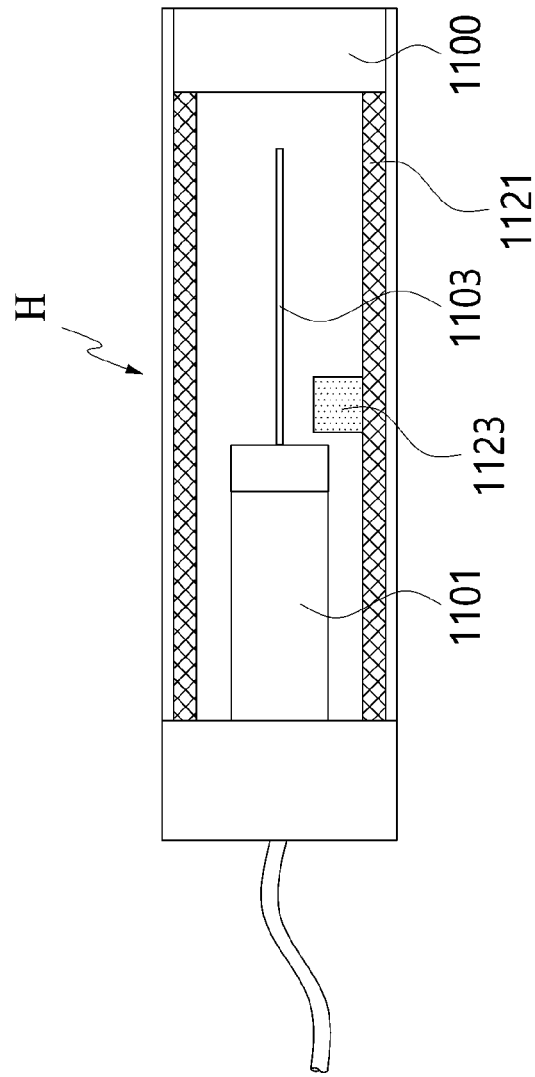
FIG. 35 is a diagram for exemplarily describing an internal structure of a scanning module according to another embodiment of the present invention.

Referring to FIG. 35, a heater 1121 and a temperature sensor 1123 may be disposed inside the scanning module 110 according to still another embodiment of the present invention.

For example, as shown in FIG. 35, the heater 1121 may be installed along the inner wall of the housing H.

Also, as shown in FIG. 35, at least one temperature sensor 1123 may be disposed inside the housing H.

In this case, the controller 130 may be set to control the operation of the heater 1121 when it is determined that the temperature detected by the temperature sensor 1123 does not meet a preset criterion.

As an example, the controller 130 may control the operation of the heater 1121 to heat the inside of the scanning module 110 for a predetermined time by means of the heater 1121 when it is determined that the temperature detected by the temperature sensor 1123 is lower than the preset criterion.

On the other hand, the controller 130 may turn off the heater 1121 when it is determined that the temperature detected by the temperature sensor 1123 is higher than a preset criterion.

Meanwhile, the scanning module 110 according to still another embodiment of the present invention may allow the internal temperature condition of the optical fiber probe to be kept constant by a packaging method using a heat-insulating material in addition to the above-described temperature adjustment means.

Accordingly, by controlling the internal temperature of the housing H to be kept constant by means of the scanning module 110 according to still another embodiment of the present invention, the driving condition of the scanning module 110 may be kept constant.

4 Other Embodiments

With the scanning module 110 according to another embodiment of the present invention, by installing a magnet M inside the housing H, it is possible to ascertain the actual movement of the optical fiber 1103.

For example, when the mass M attached to the distal end of the optical fiber 1103 is a magnet, the magnet may be used to detect a position corresponding to the vibration of the optical fiber 1103.

In this case, the magnet may ascertain a position where the optical fiber 1103 that performs Lissajous scanning is actually moved by using a force transferred from the driving unit 1101.

Accordingly, with the scanning module 110 according to another embodiment of the present invention, it is possible to directly calculate a phase difference that occurs while a driving signal applied from the controller 130 to the scanning module 110 is being transferred to the scanning module 110.

Figure 36:
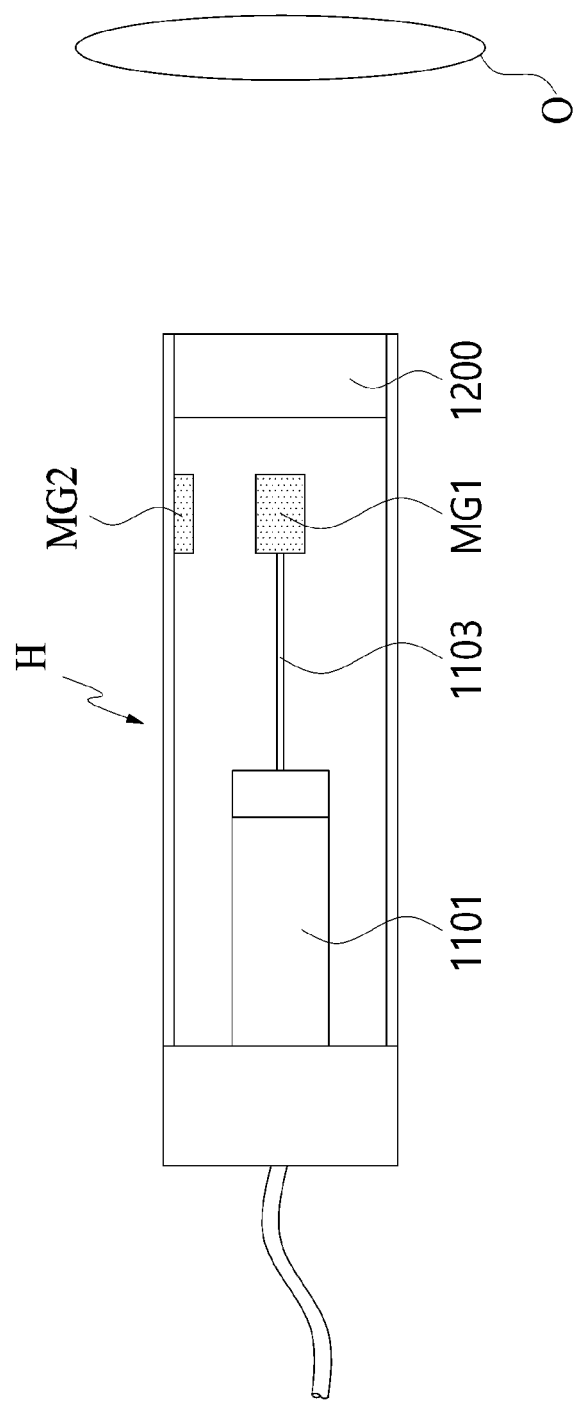
FIG. 36 is a diagram for exemplarily describing an internal structure of a scanning module according to still another embodiment of the present invention.

Referring to FIG. 36, at least a first magnet MG1 and a second magnet MG2 may be disposed inside the scanning module 110 according to another embodiment of the present invention.

For example, the first magnet MG1 may be the mass M attached to the distal end of the optical fiber 1103.

Also, for example, the second magnet MG2 may be configured to detect position information for the first axis and the second axis of the optical fiber 1103.

Alternatively, for example, a magnet for detecting position information for each of the first axis and the second axis of the optical fiber 1103 may be separately disposed.

5 Phase Calibration in Image Generating Device

As described above, the image generating device is a device configured to emit light and generate an image using returning light. For example, when light is output from the light-emitting unit 121, the light may be emitted to an object O through the scanning module 110. The light reflected, scattered, refracted, and diffracted from the object O may return to the image generating device and may be obtained by the light-receiving unit 123. In this case, the controller 130 may obtain light-receiving information indicating information regarding received light.

Here, the controller 130 may control the light-emitting unit 121 to output light and may control the driving unit 1101 of the scanning module 110 to emit light to the object in a predetermined pattern.

In this case, a signal for controlling the driving unit 1101 may include an alternating current signal, which may be a signal having a frequency component and a phase component to be applied to the driving unit 1101. Also, the signal for controlling the driving unit 1101 may have at least one signal to be applied to the scanning module in each orthogonal axis direction.

5.1 Cause of Phase Delay

The controller 130 may apply a driving signal to the driving unit 1101 to operate the driving unit 1101. Also, the driving unit 1101 may output a signal for controlling the scanning unit 1100 (hereinafter referred to as a scanning unit driving signal) and may drive the scanning unit 1100 according to the output of the scanning unit driving signal. Also, the driven scanning unit 1100 may emit light on the basis of an output signal for emitting light according to a predetermined pattern (hereinafter referred to as a scanning unit output signal).

The driving signal, the scanning unit driving signal, and the scanning unit output signal may be electrical signals, but the present invention is not limited thereto. The signals may include a signal indicating a movement corresponding to the input of the signal. For example, when a driving signal is input to the driving unit 1101, the driving or movement of the driving unit 1101 corresponding to the driving signal may be expressed as a scanning unit driving signal. Also, when a scanning unit driving signal is input to the scanning unit 1100, the driving or movement of the scanning unit 1100 corresponding to the scanning unit driving signal may be expressed as a scanning unit output signal. Also, the driving signal, the scanning unit driving signal, and the scanning unit output signal may include signals having various waveforms (e.g., a sinusoidal waveform).

Also, the driving signal, the scanning unit driving signal, and the scanning unit output signal may be the same signal. Alternatively, the driving signal, the scanning unit driving signal, and the scanning unit output signal may be signals with different phases.

Figure 38:
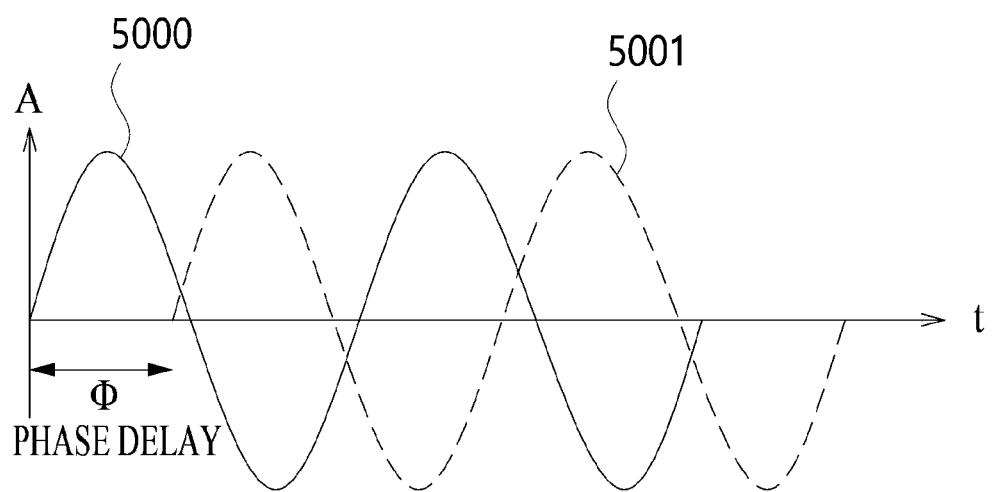
FIG. 38 is a diagram showing the waveform of a signal before a phase delay and the waveform of a signal after a phase delay.

FIG. 38 is a diagram comparatively showing the waveform of a signal before phase delay and the waveform of a signal after phase delay.

Referring to FIG. 38, the x-axis indicates time, and the y-axis indicates amplitude in the graph of FIG. 38. A pre-phase-delay signal 5000 and a post-phase-delay signal 5001 may indicate signals having the same amplitude and the same waveform. However, the present invention is not limited thereto. The pre-phase-delay signal 5000 and the post-phase-delay signal 5001 may have different amplitudes or waveforms. Alternatively, even in the pre-phase-delay signal 5000 or the post-phase-delay signal 5001, the same amplitude or waveform may not always appear over time.

Also, the post-phase-delay signal 5001 may represent a signal with a delayed phase compared to the pre-phase-delay signal 5000, and the pre-phase-delay signal 5000 and the post-phase-delay signal 5001 may have different phases. In FIG. 38, the phase difference between the pre-phase-delay signal 5000 and the post-phase-delay signal 5001 is shown as being constant at every time point. However, the present invention is not limited thereto, and the phase difference between the pre-phase-delay signal 5000 and the post-phase-delay signal 5001 may differ at every time point.

Also, the pre-phase-delay signal 5000 and the post-phase-delay signal 5001 may be applied to all of the above-described driving signals, scanning unit driving signal, and scanning output signal.

According to an embodiment, the driving signal and the scanning unit driving signal may have different phases. For example, when the driving unit 1101 is driven by receiving a driving signal, energy including heat or sound may be emitted from the driving unit 1101, and thus the phase of the driving signal and the phase of the scanning unit driving signal may differ from each other. Alternatively, when the driving unit 1101 is driven by receiving a driving signal, the structure (or shape) of the driving unit 1101 may be deformed, and thus the phase of the driving signal and the phase of the scanning unit driving signal may differ from each other. Here, the deformation of the structure of the driving unit 1101 may mean that the structure of the driving unit 1101 is changed by being driven when a driving signal is input. For example, the change of the structure of the driving unit 1101 may include extension or contraction of the driving unit 1101 along with the driving of the driving unit 1101. However, the present invention is not limited thereto, and the structure of the driving unit 1101 may be changed due to an external cause in addition to the input of the driving signal.

According to another embodiment, the scanning unit driving signal and the scanning unit output signal may have different phases. For example, when the scanning unit 1100 is driven by receiving a scanning unit driving signal, energy including heat or sound may be emitted from the scanning unit 1100, and thus the phase of the scanning unit driving signal and the phase of the scanning unit output signal may differ from each other. Alternatively, when the scanning unit 1100 is driven by receiving a scanning unit driving signal, the structure (or shape) of the scanning unit 1100 may be deformed, and thus the phase of the scanning unit driving signal and the phase of the scanning unit output signal may differ from each other. Here, the deformation of the structure of the scanning unit 1100 may mean that the structure of the scanning unit 1100 is changed by being driven when a scanning unit driving signal is input. For example, the change of the structure of the scanning unit 1100 may include extension or contraction of the scanning unit 1100 along with the driving of the scanning unit 1100. However, the present invention is not limited thereto, and the structure of the driving unit 1101 may be changed due to an external cause in addition to the input of the scanning unit driving signal.

5.2 Method of Finding Phase Delay and Method of Calibrating Phase

According to an embodiment for finding a phase delay, a reference image may be predetermined, and the reference image may be used to determine a phase delay. As an example, the predetermined reference image may be a circular pattern, but the present invention is not limited thereto. Thus, by comparing an image obtained by the controller 130 to the reference image, the degree of the phase delay may be ascertained.

Figure 39:
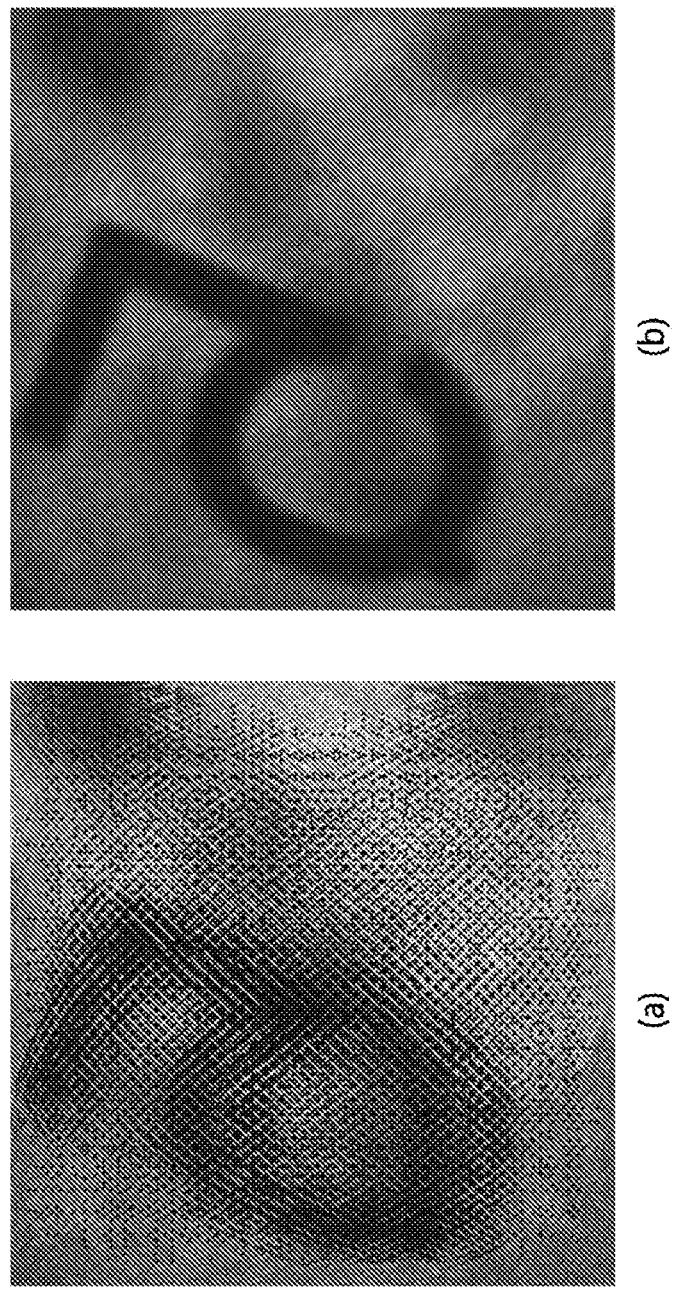
FIG. 39 shows a diagram representing a phase-delayed low-resolution image (a), and a diagram representing a phase-corrected high-resolution image (b)

Referring to FIG. 39, the image shown in (a) indicates a phase-delayed low-resolution image, and the image shown in (b) indicates a phase-calibrated image of which a delayed phase is calibrated, which is a high-resolution image.

The controller 130 may allow the phase of a post-phase-delay signal to be calibrated in order to obtain the image shown in (b) of FIG. 39 instead of the image shown in (a) of FIG. 39.

According to an embodiment, the controller 130 may obtain a phase-calibrated image of which a delayed phase is calibrated by using a phase adjusted through the input unit 140.

As an example, the input unit 140 may adjust a frequency component or a phase component of a signal used for the controller 130 to control the driving unit 1101 or may adjust both of the frequency component and the phase component. However, the present invention is not limited thereto.

In detail, the phase of the driving signal may be adjusted through the input unit 140. When the phase of the driving signal is adjusted, the controller 130 may obtain a high-resolution image of which a phase is calibrated by adjusting the phase component instead of the low-resolution image caused by the post-phase-delay signal.

According to another embodiment, instead of obtaining a phase through the input unit 140, the controller 130 may obtain a phase-calibrated image of which a delayed phase is calibrated by automatically adjusting the phase. In this case, the phase of the driving signal is not controlled using the input unit 140, but the controller 130 may automatically calibrate the phase component of the driving signal. In detail, when the controller 130 automatically calibrates the phase component of the signal for controlling the driving unit 1101, an algorithm may be used to calibrate the phase component. The phase calibration using the algorithm will be described below.

6 Initial Phase Calibration

The image generating device may need to initially calibrate a phase in order to calibrate the phase using an algorithm. However, the present invention is not limited thereto, and even when the phase is calibrated through the input unit 140, it may be necessary to initially calibrate the phase. For example, when the phase is calibrated using the algorithm, an initial image of which a phase is not calibrated may have a large delay in phase. Also, when a phase is initially calibrated, a phase value to be adjusted by the controller 130 may be small. Accordingly, it is possible to reduce the time for performing the phase calibration, and it is also possible to more accurately calibrate the phase.

In detail, when the phase is initially calibrated, the range of the phase to be adjusted through the input unit 140 may be reduced. Also, when the phase is calibrated using the algorithm, the amount of calculation required for even the phase value to be calibrated through the initial phase calibration can be reduced.

For convenience of description, the initial phase calibration may be defined as a phase calibration method other than the phase calibration using the following algorithm. For example, the initial phase calibration may include a phase calibration using the mounting device 5200, a phase calibration using a cut-off filter, and a phase calibration using a micropattern forming unit 5100, which will be described below. In addition, various phase calibration methods may be included in the initial phase calibration.

According to an embodiment, when an object O is scanned, the phase calibration may be performed through the input unit 140 after the initial phase calibration, or the phase calibration may be performed using the following algorithm.

Also, according to another embodiment, after the phase calibration using the algorithm is performed, the initial phase calibration may be performed. Then, the phase calibration using the algorithm may be performed again. It will be appreciated that the present invention is not limited thereto, and the initial phase calibration and the phase calibration using the algorithm may be performed at the same time.

Also, according to another embodiment, an image may be obtained by performing only the initial phase calibration without performing the phase calibration using the algorithm.

A device and method for the initial phase calibration will be described below.

6.1 Phase Calibration Using Lens Module 1200

The initial phase may be calibrated using the lens module 1200 that may be positioned at one end of the scanning unit 1100. For example, by providing a pattern onto the lens module 1200 positioned at one end of the scanning unit 1100, the initial phase may be calibrated using the pattern as the reference image. Alternatively, by providing a filter capable of being mounted on the lens module 1200 and on one end of the scanning unit 1100, the initial phase may be calibrated using the filter.

6.1.1 Phase Calibration Using Micropattern Forming Unit 5100

Figure 40:
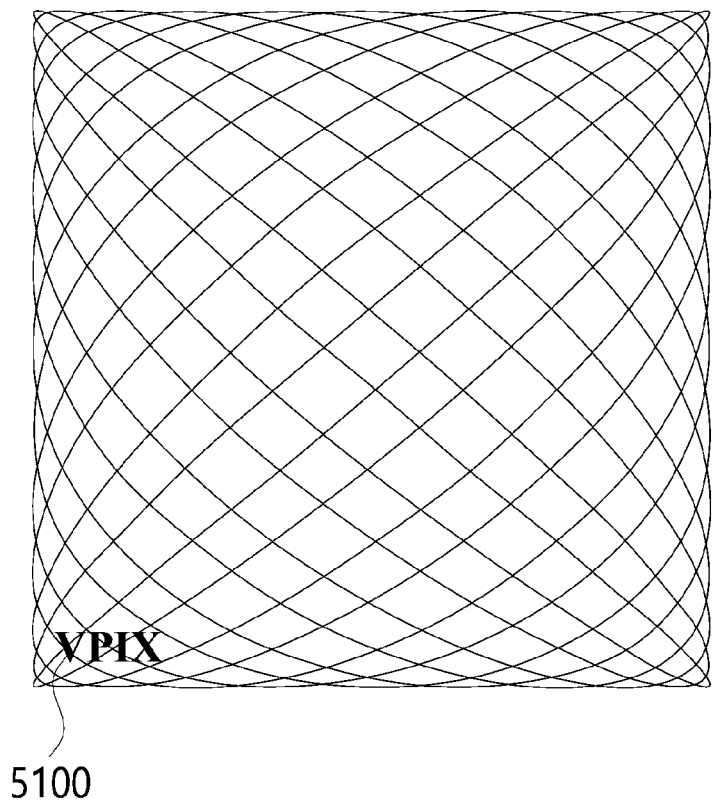
FIG. 40 is a diagram showing a micropattern that appears in a light pattern in which light is emitted.

FIG. 40 is a diagram showing a micropattern forming unit 5100 that exhibits on a path of light emitted in a predetermined pattern (hereinafter referred to as a light pattern) when one element of the scanning module 110 including the lens module 1200 is patterned.

FIG. 40 shows a pattern in which light is emitted in the case of a Lissajous pattern. However, the present invention is not limited thereto, and the pattern in which light is emitted may include various types of scanning patterns including a spiral pattern or a raster pattern. Also, the micropattern forming unit 5100 shown in FIG. 40 is represented by characters. However, the present invention is not limited thereto, and the micropattern forming unit 5100 may include a shape or the like which may be used as the reference image.

Referring to FIG. 40, the light pattern may be formed in a square region. However, the present invention is not limited thereto, and the light pattern may be formed in areas of various shapes. The light pattern may be emitted toward the object O when the scanning unit 1100 is driven, and the micropattern forming unit 5100 may not change according to the light pattern.

Here, when the scanning module 110 is scanning the object O, a micropattern, which is an image corresponding to the micropattern forming unit 5100, may appear on an image obtained by the controller 130.

Also, the micropattern forming unit may be disposed at various positions in the scanning module 110. In detail, the micropattern forming unit may be positioned on the lens module 1200. However, the present invention is not limited thereto, and the micropattern forming unit may be positioned on the scanning unit 1100. Alternatively, the micropattern forming unit may be predetermined on a separate structure, and the structure may be coupled to one end of the scanning module 110 and used to calibrate the initial phase. For convenience of description, the following description assumes that the micropattern forming unit 5100 is positioned on the lens module 1200.

According to an embodiment, the micropattern forming unit 5100 present on the lens module 1200 may be present at a position through which the light pattern has passed. When the scanning module 110 is being scanned, a certain micropattern may be provided regardless of the shape of the object O. Thus, by using the micropattern as the reference image, the initial phase calibration may be performed such that the micropattern of the image obtained by the controller 130 can coincide with the micropattern appearing in the original micropattern forming unit 5100.

Here, the micropattern of the obtained image that coincides with the micropattern appearing in the micropattern forming unit 5100 may mean that when the controller 130 obtains light-receiving information on the basis of the light returning from the object O, information of a pixel of a portion of the image obtained by the controller 130 where the micropattern is expected to appear corresponds to information of a pixel corresponding to the micropattern provided by the micropattern forming unit 5100 at a certain level or more.

However, in order for the controller 130 to obtain an image corresponding to the micropattern forming unit 5100 at a position through which the light pattern has passed when light is emitted from the scanning unit 1100, the micropattern forming unit 5100 may be made of a material capable of absorbing or reflecting the emitted light or capable of exhibiting fluorescence due to the emitted light.

In detail, when the micropattern forming unit 5100 is made of a material capable of absorbing light emitted from the scanning unit 1100, the micropattern forming unit 5100 may absorb the emitted light, and no light may return from the micropattern forming unit 5100 due to the absorption of the light. Here, the absorption of light by the micropattern forming unit 5100 may mean that the micropattern forming unit 5100 absorbs a specific wavelength band of light and thus the light cannot return from the micropattern forming unit 5100. Accordingly, when the controller 130 generates an image using a specific wavelength of light, the specific wavelength is absorbed, and a wavelength corresponding to the shape of the micropattern of the micropattern forming unit 5100 cannot be obtained. Thus, light and shade may occur in the portion of the obtained image corresponding to the micropattern. Accordingly, the portion of the obtained image corresponding to the micropattern is obtained, and thus phase calibration may be performed such that the portion of the obtained image corresponding to the micropattern can coincide with the micropattern of the micropattern forming unit 5100.

Alternatively, when the micropattern forming unit 5100 is made of a material capable of reflecting light emitted from the scanning unit 1100, the micropattern forming unit 5100 may reflect the emitted light, and all of the emitted light may return from the micropattern forming unit 5100. Here, the reflection of light by the micropattern forming unit 5100 may mean that a specific wavelength band of light is reflected and thus light of the same wavelength as that of the light that has been emitted from the micropattern forming unit 5100 is returning. Accordingly, when the controller 130 generates an image using a specific wavelength of light, the wavelength corresponding to the micropattern forming unit 5100 obtained by the controller 130 may not be the specific wavelength for generating the image. Thus, light and shade may occur in a portion of the obtained image corresponding to the micropattern of the micropattern forming unit 5100. Accordingly, the portion of the obtained image corresponding to the micropattern is obtained, and thus phase calibration may be performed such that the portion of the obtained image corresponding to the micropattern can coincide with the micropattern of the micropattern forming unit 5100.

Alternatively, when the micropattern forming unit is made of a material capable of exhibiting fluorescence using emitted light, light returning from the micropattern forming unit 5100 may be fluorescent light. Here, the exhibition of fluorescent light by the micropattern forming unit 5100 may mean that the micropattern forming unit 5100 absorbs the emitted light and generates light having a wavelength different from that of the absorbed light such that light of a specific wavelength is returning from the micropattern forming unit 5100. Also, a material capable of emitting light having a wavelength of 405 nm, 488 nm, or 785 nm may be used as the fluorescent material used in the micropattern forming unit 5100. Thus, when the controller 130 generates an image using light having a specific wavelength due to the fluorescent material, the light of the wavelength corresponding to the micropattern forming unit 5100 may be obtained. Thus, light and shade may occur in the portion of the obtained image corresponding to the micropattern. Accordingly, the portion of the obtained image corresponding to the micropattern shape is obtained, and thus phase calibration may be performed such that the portion of the obtained image corresponding to the micropattern can coincide with the micropattern of the micropattern forming unit 5100.

Here, the phase calibration may mean that the controller 130 obtains an image in which the micropattern appears and performs calibration such that the obtained image in which the micropattern appears corresponds to the shape of the micropattern of the micropattern forming unit 5100 at a predetermined level or more. In detail, the micropattern shape of the micropattern forming unit 5100 may be obtained by the controller 130, and thus the controller 130 may compare a micropattern included in an image obtained by driving the scanning unit 1100 to the micropattern shape pre-obtained by the controller 130 to obtain the corresponding degree. In this case, when the comparison result obtained by the controller 130 is less than or equal to the predetermined level, the comparison may be performed again after the phase of the driving signal is changed. Also, when the comparison result obtained by the controller 130 is greater than or equal to the predetermined level, the controller 130 may obtain an image of the object O by using the changed driving signal as a phase value to be calibrated. In this case, the phase of the driving signal may be changed using the input unit 140 on the controller 130. However, the present invention is not limited thereto, and the phase may be automatically calibrated using the algorithm.

However, the phase calibration using the micropattern is not limited to the initial phase calibration and can be performed while the object O is being scanned.

6.1.2 Phase Calibration Using Cut-Off Filter

Figure 41:
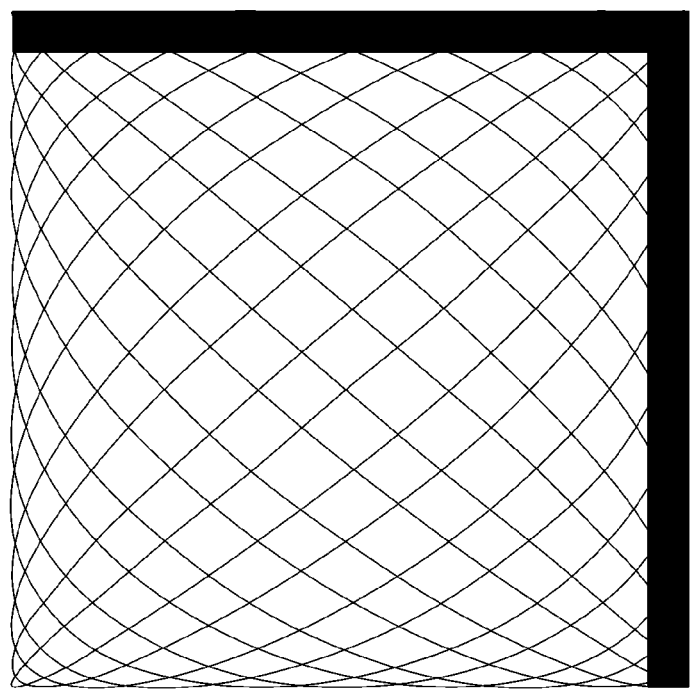
FIG. 41 is a diagram showing light and shade corresponding to a cut-off filter and appearing in a light pattern in which light is emitted.

FIG. 41 is a diagram showing that a corner of a light pattern on an element of the scanning module 110 including the lens module 1200 is cut off. Here, the cut-off may mean that a portion of the corner of the light pattern is formed of a material capable of absorbing or reflecting the light or exhibiting fluorescence due to the light and the image of the object O may not be obtained at the portion of the corner.

Also, the cut-off filter may be positioned on the lens module 1200. However, the present invention is not limited thereto, and the cut-off filter may be positioned on the scanning unit 1100. Alternatively, the cut-off filter may be present on a separate structure, and the structure may be coupled to one end of the scanning module 110 and used to calibrate the initial phase. For convenience of description, the following description assumes that the cut-off filter is positioned on the lens module 1200.

Also, as shown in FIG. 41, the cut-off filter is present on the corner of the optical device. Thus, when light is emitted from the scanning unit 1100, the cut-off filter may absorb or reflect light or exhibit fluorescence at a portion where the density of the emitted light is increased. Therefore, it is possible to prevent photo bleaching in which a fluorescent material in the object O may be damaged when the intensity of the emitted light is increased or photo damaging in which the object O itself may be damaged due to a high light intensity.

According to an embodiment, when the cut-off filter is made of a material capable of absorbing or reflecting light, the light-receiving unit 123 of an image generating module for generating an image using a specific wavelength of light may not obtain light-receiving information. In detail, the light absorbed or reflected at the cut-off corner does not reach the light-receiving unit 123 and does not generate light-receiving information. Thus, a pixel value corresponding to the corner portion does not appear in the image obtained by the controller 130, and the corner portion may be displayed as an unused area.

Alternatively, when the cut-off filter is made of a fluorescent material, the light returning from the object O may be composed of a specific wavelength that can be obtained by the light-receiving unit 123. Accordingly, the light-receiving unit 123 may obtain fluorescence at the cut-off corner as the light-receiving information, and thus a pixel value corresponding to the corner portion may be obtained from the image obtained by the controller 130 in the form of an unused area.

Figure 42:
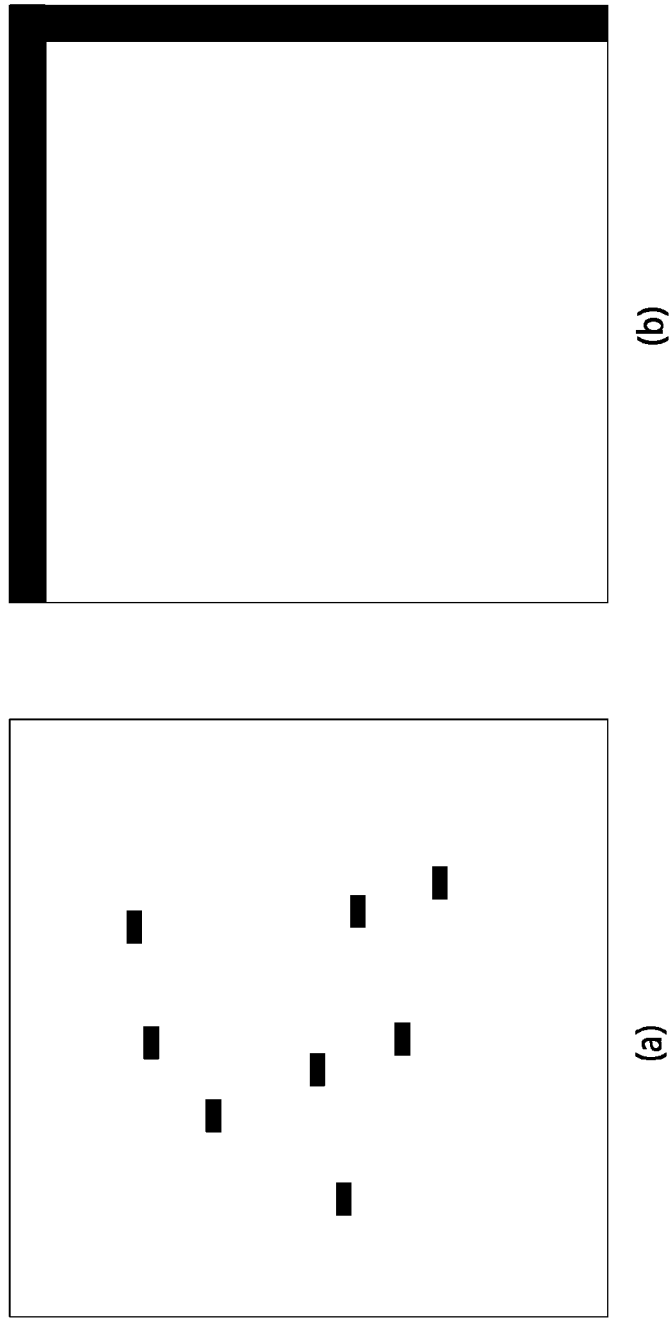
FIG. 42 shows a diagram representing that a non-used region occurs in an obtained image when a phase is delayed (a), and a diagram representing that a non-used region occurs at a corner in an obtained image when a phase is corrected (b)

The image (a) of FIG. 42 is a diagram showing an unused area corresponding to the cut-off filter in an image obtained when the phase of a scanning unit driving signal or a scanning unit output signal is delayed. The image (b) of FIG. 42 is a diagram showing an unused area corresponding to the cut-off filter in an image obtained when the phase of a scanning unit driving signal or a scanning unit output signal is calibrated.

In detail, when the phase of the scanning unit driving signal or the scanning unit output signal is delayed compared to the phase of the driving signal, an unused area corresponding to the cut-off may be generated not in a place where the cut-off portion is originally present as shown in the image (a) of FIG. 42 but in any space of the obtained image. Thus, when the unused area corresponding to the cut-off is generated not at the corner of the obtained image but in any space of the obtained image after the obtained image is checked, the phase of the scanning unit driving signal or the scanning unit output signal may be delayed.

According to an embodiment, information regarding the unused area in the image obtained by the controller 130 according to the cut-off filter may be obtained by the controller 130. Also, when the scanning is performed using the scanning module 110, the degree to which the unused area is present on the corner of the obtained image may be obtained by the controller 130. When the degree to which the unused area is present on the corner, which is obtained by the controller 130, is less than or equal to a certain level, the degree to which the unused area is present on the corner may be re-obtained by the controller 130 after the phase of the driving signal is changed. In this case, when the degree to which the unused area is present on the corner, which is obtained by the controller 130, is greater than or equal to a certain level, the controller 130 may obtain the image of the object O using the adjusted phase of the driving signal as the phase value to be calibrated. Here, the phase of the driving signal may be changed using the input unit 140 on the controller 130. However, the present invention is not limited thereto, and the phase may be automatically calibrated using the algorithm.

According to another embodiment, the phase of the driving signal of the phase-delayed image as shown in (a) of FIG. 42 may be calibrated using the input unit 140. In detail, when the image shown in (a) of FIG. 42 is obtained by the controller 130, the phase of the driving signal may be adjusted using the input unit 140. By adjusting the phase of the driving signal, the unused area generated in any space may be moved, and the unused area may be generated on the corner of the obtained image. Therefore, the phase-calibrated image as shown in (b) of FIG. 42 may be obtained by the controller 130.

According to another embodiment, the phase of the driving signal of the phase-delayed image as shown in (a) of FIG. 42 may be calibrated using an algorithm for phase calibration, which will be described below.

6.2 Phase Calibration Using Mounting Device 5200 of Scanning Module 110

As described above, the scanning module 110 may scan the object O, and the controller 130 may obtain an image corresponding to the scanning.

Here, the mounting device 5200 does not perform scanning on the object O. When the scanning module 110 is not used, the mounting device 5200 may be used to mount the scanning module 110. Also, the phase of the driving signal may be calibrated by the mounting device 5200 on which the scanning module 110 is mounted.

According to an embodiment, a reference image may be provided to the mounting device 5200 of the scanning module 110, and the phase calibration may be performed on the basis of the reference image. In detail, when the phases of the scanning unit driving signal and the scanning unit output signal are delayed, the phase of the driving signal may be calibrated such that the image obtained by the controller 130 can coincide with the reference image.

Here, the phase of the driving signal may be calibrated using the input unit 140 on the controller 130 or using algorithm-based phase calibration.

6.2.1 Structure of Mounting Device 5200 of Scanning Module 110

Figure 43:
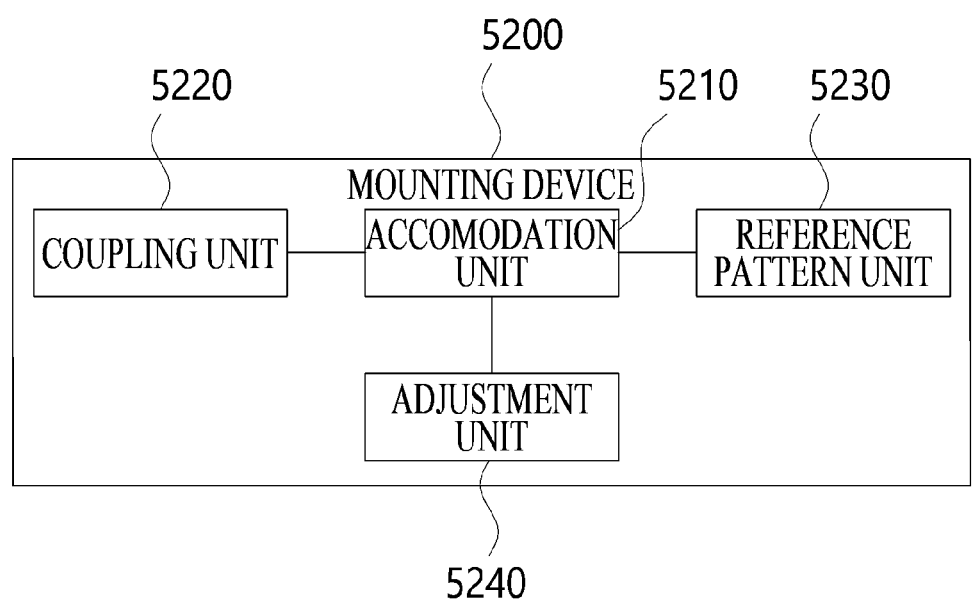
FIG. 43 is a block diagram showing a mounting device according to an embodiment.

Referring to FIG. 43, the mounting device 5200 may include an accommodation unit 5210, a coupling unit 5220, a reference pattern unit 5230, or an adjustment unit 5240. Here, the accommodation unit 5210 of the mounting device 5200 of the scanning module 110 may accommodate the scanning module 110. For example, the accommodation unit 5210 may include a housing for accommodating the scanning module 110. Also, the coupling unit 5220 of the mounting device 5200 of the scanning module 110 may couple the scanning module 110 accommodated in the accommodation unit 5210 to the accommodation unit 5210 so that the scanning module 110 accommodated in the accommodation unit 5210 is prevented from falling out of the accommodation unit 5210 or so that the scanning module 110 is fixed at a specific position of the accommodation unit 5210. Also, the reference pattern unit 5230 of the mounting device 5200 of the scanning module 110 may provide a reference image so that the controller 130 can calibrate the phase of the driving signal while the scanning module 110 is mounted on the mounting device 5200. Also, when the lens module 1200 on the scanning module 110 is not focused, the adjustment unit 5240 of the mounting device 5200 of the scanning module 110 may provide an element for performing focusing at the mounting device 5200 while the scanning module 110 is mounted on the mounting device 5200 of the scanning module 110. The accommodation unit 5210, the coupling unit 5220, the reference pattern unit 5230, and the adjustment unit 5240 will be described in detail below.

6.2.1.1 Accommodation Unit 5210 of Mounting Device 5200

Figure 44:
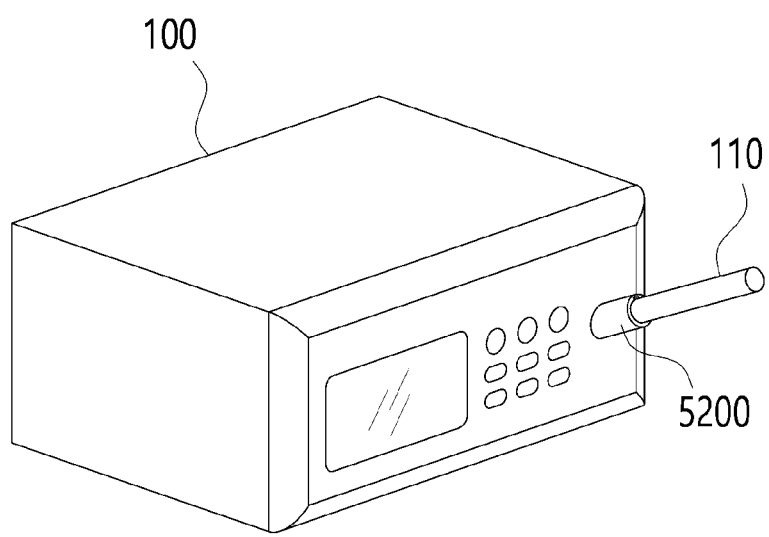
FIG. 44 is a diagram showing that a scanning module is accommodated in an image generating device according to an embodiment.

FIG. 44 is a diagram showing that the scanning module 110 is accommodated in the image generating device.

According to an embodiment, as shown in FIG. 44, the accommodation unit 5210 of the mounting device 5200 on which the scanning module 110 can be mounted may be provided to the image generating device. In detail, the scanning module 110 may be mounted on the accommodation unit 5210 of the mounting device 5200 present on the image generating device of FIG. 44. Also, there is no limitation on the position on the image generating device shown in FIG. 44.

According to another embodiment, the accommodation unit 5210 of the mounting device 5200 on which the scanning module 110 can be mounted may be present at a position physically different from that of the image generating device. In this case, the accommodation unit 5210 of the mounting device 5200 present at a position different from that of the image generating device may be pre-connected to the image generating device, and thus the mounting device 5200 may be controlled through the controller 130 of the image generating device.

Also, the accommodation unit 5210 may accommodate the entirety of the scanning module 110. However, the present invention is no limited thereof, and the accommodation unit 5210 may accommodate only a portion of an element for emitting light included in the scanning module 110 so that the phase delay of the driving signal, the scanning unit driving signal, or the scanning unit output signal can be calibrated.

6.2.1.2 Coupling Unit 5220 of Mounting Device 5200

Figure 45:
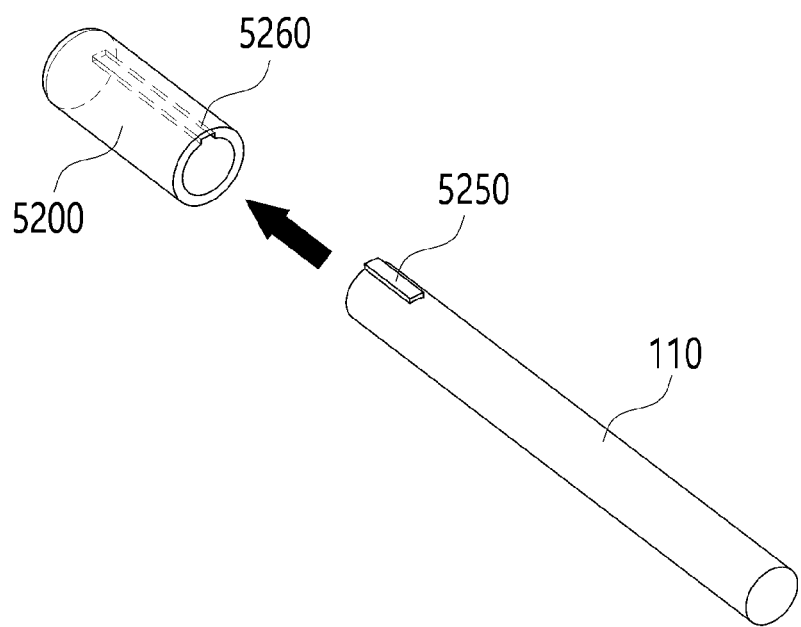
FIG. 45 is a diagram for describing that a scanning module is mounted on a mounting device according to an embodiment.
Figure 46:
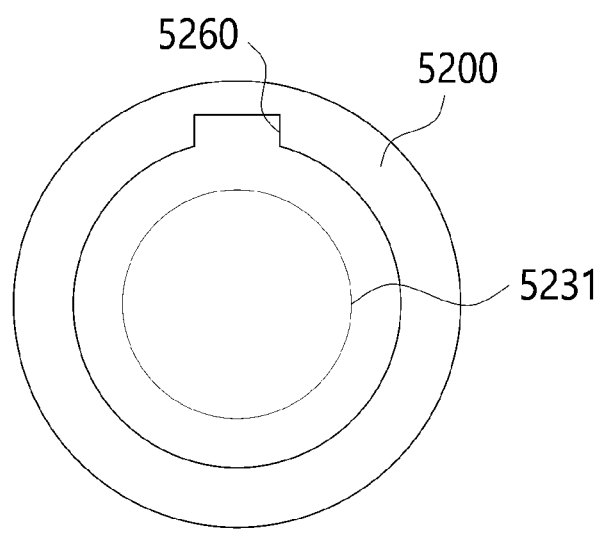
FIG. 46 is a sectional view showing an accommodation part of a mounting device according to an embodiment when viewed from the top.

FIG. 45 is a diagram showing that the scanning module 110 is mounted on the mounting device 5200. Also, FIG. 46 is a diagram showing the accommodation unit 5210 of the mounting device 5200 when viewed from the entrance thereof.

According to an embodiment, a coupling member 5250 may be provided on the scanning module 110 as shown in FIG. 45. Here, the coupling member may be coupled to the coupling unit 5220 of the mounting device 5200, and thus the scanning module 110 may be coupled to the mounting device 5200 at a certain angle.

In detail, the coupling unit 5220 of the mounting device 5200 and the coupling member may be formed in the same shape so that the scanning module 110 and the mounting device 5200 can be coupled to each other, or the coupling unit 5220 may be present in the shape including the shape of the coupling member. For example, when the coupling member has a quadrangular shape, the coupling unit 5220 of the mounting device 5200 may have a quadrangular shape capable of accommodating the quadrangular shape of the coupling member or may have a shape that circumscribes the quadrangular shape of the coupling member. However, the present invention is not limited thereto, and the coupling unit 5220 of the mounting device 5200 may have a shape in which the coupling unit 5220 of the mounting device 5200 is coupled to the coupling member, including the shape of the coupling member. Also, the coupling member of the scanning module 110 and the coupling unit 5220 of the mounting device 5200 may be various members with a coupling force so as to couple the coupling member and the coupling unit 5220 to each other. For example, the coupling member of the scanning module 110 and the coupling unit 5220 of the mounting device 5200 may be provided as magnetic members. Since there is a magnetic force between the coupling member and the coupling unit 5220, the scanning module 110 may be coupled to a specific position of the accommodation unit 5210 when the scanning module 110 is coupled to the accommodation unit 5210 of the mounting device 5200. Also, since there is a magnetic force, the coupling member and the coupling unit 5220 may be automatically coupled to each other at the specific position.

6.2.1.3 Reference Pattern Unit 5230 of Mounting Device 5200

The reference pattern unit 5230 may be provided to the mounting device 5200 such that the initial phase calibration can be performed by the controller 130. Here, the reference pattern unit 5230 may be provided in a space of the mounting device 5200. However, for convenience of description, the following description assumes that the reference pattern unit 5230 is provided on a lower end portion of the mounting device 5200. Here, when the scanning module 110 is mounted on the mounting device 5200, the lower end portion of the mounting device 5200 may be the bottom surface of the accommodation unit 5210 that is present on an extension line in a direction in which light is emitted by the scanning module 110.

Figure 47:
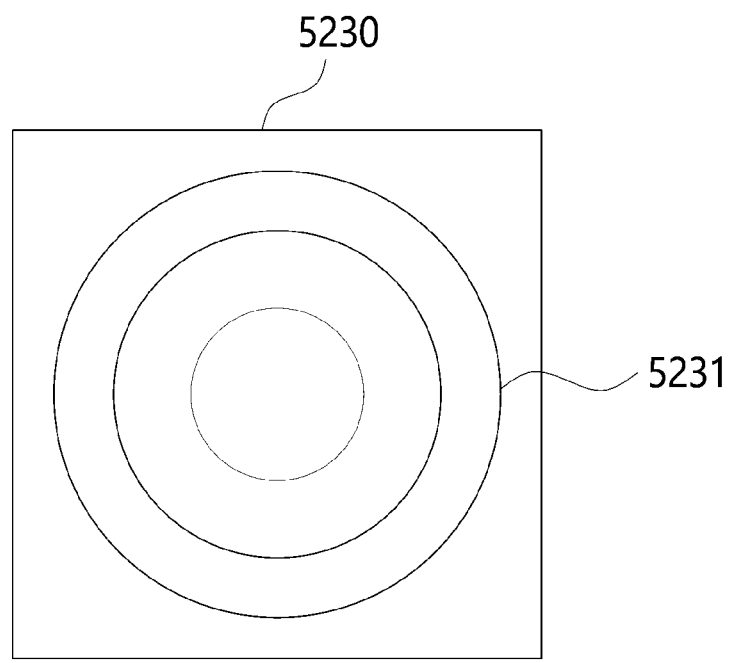
FIG. 47 is a top view showing a reference pattern part according to an embodiment.

FIG. 47 is a diagram of the reference pattern unit 5230 when viewed from the top. In detail, when the scanning module 110 is mounted on the mounting device 5200, the scanning module 110 may emit light toward the reference image 5231 of the reference pattern unit 5230 provided on the lower end of the mounting device 5200 and may obtain an image using returning light. Here, when the phase of the scanning unit driving signal or the scanning unit output signal is delayed, the obtained image may be a phase-delayed image. In this case, the controller 130 may calibrate the phase of the driving signal, the phase of the scanning unit driving signal, or the scanning unit output signal such that the obtained image can coincide with the reference image 5231.

Referring to FIG. 47, the reference image 5231 may be one or more circular patterns in order to always provide a certain image irrespective of an angle at which the scanning module 110 is mounted on the mounting device 5200. However, the present invention is not limited thereto, and the reference image may be a predetermined reference image 5231. In detail, when the coupling unit 5220 and the coupling member are not present, the scanning module 110 may not be mounted at a predetermined position when the scanning module 110 is mounted on the mounting device 5200. Accordingly, even when the scanning module 110 is not mounted at a predetermined position, the reference image 5231 may be a circular pattern so that the initial phase calibration can be performed.

According to an embodiment, the reference image 5231 may be made of a material capable of absorbing light emitted by the scanning unit 1100. In detail, when the reference image 5231 is made of a material capable of absorbing light emitted by the scanning unit 1100, the reference image 5231 may absorb the emitted light, and no light may return from the reference image 5231. Here, the absorption of light by the reference image 5231 may mean that the reference image 5231 absorbs a specific wavelength band of light and thus the light cannot return from the reference image 5231. Accordingly, when the controller 130 generates an image using a specific wavelength of light, a wavelength corresponding to the reference image 5231 cannot be obtained. Thus, light and shade may occur in the portion of the obtained image corresponding to the reference image 5231. Therefore, the portion of the obtained image corresponding to the reference image 5231 may be obtained, and thus the phase of the obtained image may be calibrated.

According to another embodiment, the reference image 5231 may be made of a material capable of reflecting light emitted by the scanning unit 1100. In detail, when the reference image 5231 is made of a material capable of reflecting light emitted by the scanning unit 1100, the reference image 5231 may reflect the emitted light, and all of the emitted light may return from the reference image 5231. Here, the reflection of light by the reference image 5231 may mean that the reference image 5231 reflects a specific wavelength band of light and light having the same wavelength as that of the light having been emitted returns from the reference image 5231. Accordingly, when the controller 130 generates an image using a specific wavelength of light, a wavelength corresponding to the reference image 5231 may not be a specific wavelength. Thus, light and shade may occur in the portion of the obtained image corresponding to the reference image 5231. Therefore, the portion of the obtained image corresponding to the reference image 5231 may be obtained, and thus the phase of the obtained image may be calibrated.

According to another embodiment, the reference image 5231 may be made of a material capable of exhibiting fluorescence. In detail, when the reference image 5231 is made of a material capable of exhibiting fluorescence using emitted light, light returning from the reference image 5231 may be fluorescent light. Here, the exhibition of fluorescent light by the reference image 5231 may mean that the reference image 5231 absorbs the emitted light and generates light having a wavelength different from that of the absorbed light such that light of a specific wavelength returns from the reference image 5231. Accordingly, when the controller 130 generates an image using a specific wavelength caused by a fluorescent material, a wavelength corresponding to the reference image 5231 cannot be obtained. Thus, light and shade may occur in the portion of the obtained image corresponding to the reference image 5231. Therefore, the portion of the obtained image corresponding to the reference image 5231 may be obtained, and thus the phase of the obtained image may be calibrated.

Here, the phase calibration may mean that the controller 130 obtains an image in which the reference image 5231 appears and performs calibration such that the image in which the reference image 5231 appears and the reference image 5231 which is present on the mounting device 5200 correspond to each other at a predetermined level or more. In detail, the reference image 5231 of the mounting device 5200 may be obtained by the controller 130, and thus the controller 130 may compare a reference image 5231 included in an image obtained by driving the scanning unit 1100 to the reference image 5231 pre-obtained by the controller 130 to obtain the corresponding degree. In this case, when the comparison result obtained by the controller 130 is less than or equal to the predetermined level, the comparison may be performed again after the phase of the driving signal is changed. Also, when the comparison result obtained by the controller 130 is greater than or equal to the predetermined level, the controller 130 may obtain an image of the object O by using the changed driving signal as a phase value to be calibrated. In this case, the phase of the driving signal may be changed using the input unit 140 on the controller 130. However, the present invention is not limited thereto, and the phase may be automatically calibrated using the algorithm.

6.2.1.3.1 Structure of Reference Pattern Unit 5230

In order to provide a reference image 5231 matching the focal length of the lens module 1200 on the scanning module 110, the reference pattern unit 5230 may be provided with a structure matching the focal length.

Figure 48:
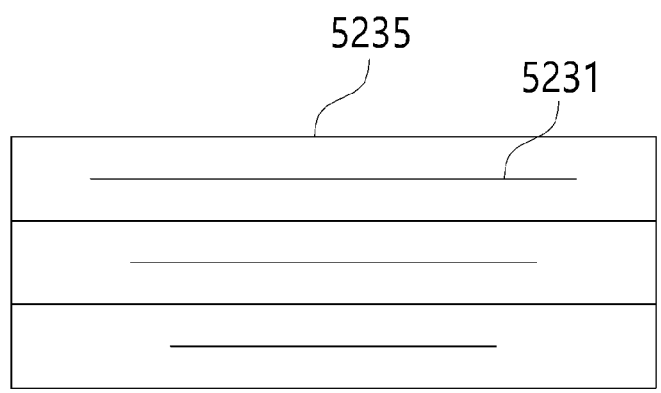
FIG. 48 is a side view showing a reference image existing on a reference pattern part according to an embodiment.

FIG. 48 is a diagram showing that the reference image 5231 on the reference pattern unit 5230 is present in a transparent structure.

According to an embodiment, referring to FIG. 48, an image may be present in an optical transmission structure 5235 in order to provide the reference image 5231 to match the focal length of the lens module 1200. In detail, the optical transmission structure 5235 may be made of glass or transparent plastic. However, the present invention is not limited thereto, and any material capable of transmitting light may be used as the material of the optical transmission structure 5235. Also, here, the reference image 5231 present in the optical transmission structure 5235 may be provided to match the focal length of the lens module 1200, and the size of the reference image 5231 may decrease as the focal length increases. However, the present invention is not limited thereto, and the size of the reference image 5231 may increase as the focal length increases or may be constant. When the optical transmission structure 5235 is shown from the upper side in which light is emitted, the reference image 5231 varying by depth may be provided as shown in FIG. 47.

Figure 49:
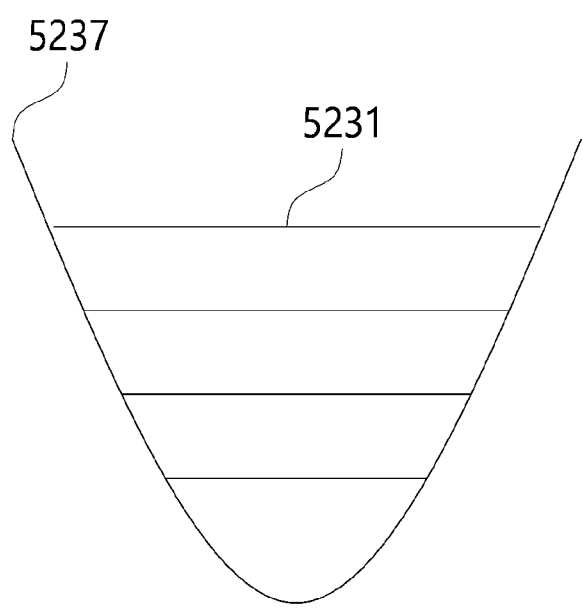
FIG. 49 is a side view showing a reference pattern part existing in a concave structure shape according to an embodiment.

According to another embodiment, referring to FIG. 49, the reference image 5231 may be present in a concave structure 5237 in order to provide the reference image 5231 to match the focal length of the lens module 1200. In detail, as the depth of the concave structure 5237 increases, the size of the reference image 5231 provided in the concave structure 5237 may decrease. Thus, a smaller reference image 5231 may be provided as the focal length becomes deeper. Here, the reference image 5231 may be drawn around the concave structure 5237, and the reference image 5251 drawn around the concave structure 5237 is smaller in size as the depth increases in the concave structure 5237. When the concave structure 5237 is shown from the upper side in which light is emitted, the reference image 5231 having a size varying by depth may be provided as shown in FIG. 47.

6.2.1.3.2 Case in which Reference Image 5231 is Made of Fluorescent Material The controller 130 may obtain an image using light of a specific wavelength. Thus, when the reference image 5231 is provided using a fluorescent material, the controller 130 may obtain light-receiving information corresponding to the reference image 5231.

According to an embodiment, when the reference image 5231 is made of a fluorescent material, the fluorescent material may include IcG, 5-ALA, or Fna. However, the present invention is not limited thereto, and any material capable of exhibiting fluorescence due to light emission may be used. However, when a fluorescent material is used for the reference image 5231, fluorescence may not be exhibited due to the continued use of the fluorescent material. Thus, it may be necessary to supplement the fluorescent material.

Here, in order to supplement the fluorescent material to be used for the reference image 5231, a cartridge that can additionally provide a fluorescent material may be provided. The cartridge may be inserted into or removed from a lower end of the mounting device 5200. However, the present invention is not limited thereto, and the cartridge may be present on an upper portion or side surface of the mounting device 5200 or outside the mounting device 5200 to provide the fluorescent material to the reference image 5231. For convenience of description, the following description assumes that the cartridge is present on the lower end portion of the mounting device 5200.

In detail, the cartridge may be a structure including a fluorescent material therein, and the fluorescent material may be provided for the reference image 5231 to obtain a fluorescence image caused by the fluorescent material of the reference image 5231 when light is emitted to the scanning module 110. Also, when the reference image 5231 does not exhibit fluorescence due to light emission (e.g., including that the fluorescent material is degraded by photo bleaching caused by light emission), a cartridge that is provided at the lower end of the mounting device 5200 may be removed therefrom, and a new cartridge containing a fluorescent material capable of exhibiting fluorescence may be inserted to the lower end portion of the mounting device 5200. However, the present invention is not limited thereto, and the cartridge may have a structure provided outside the mounting device 5200 to continuously supply the fluorescent material to the reference image 5231.

6.2.1.4 Adjustment Unit 5240 of Mounting Device 5200

The mounting device 5200 may include an adjustment unit 5240 in order to provide the reference image 5231 matching the focal length of the lens module 1200 of the scanning module 110. Here, the adjustment unit 5240 may control the position of the reference pattern unit 5230 to be moved close to or far away from the lens module 1200 of the scanning module 110 in order to provide the reference pattern unit 5230 in which the reference image 5231 is provided to match the focal length.

In this case, when the reference image 5231 is present at a position not matching the focal length of the lens module 1200 of the scanning module 110, the image obtained by the controller 130 may not match the reference image 5231. Thus, the adjustment unit 5240 may be necessary to adjust the reference pattern unit 5230 in which the reference image 5231 is present according to the focal length of the lens module 1200.

The image (a) of FIG. 50 is a diagram showing that the reference pattern unit 5230 is adjusted toward the entrance of the mounting device 5200 so that the reference pattern unit 5230 is coupled to the adjustment unit 5240 at the lower end portion of the mounting device 5200 to adjust the focal length in order to provide the reference image 5231 matching the focal length of the lens module 1200. The image (b) of FIG. 50 is a diagram showing that the reference pattern unit 5230 present at the lower end of the mounting device 5200 is moved toward the lower end portion of the mounting device 5200 in order to provide the reference image 5231 matching the focal length of the lens module 1200.

According to an embodiment, the adjustment unit 5240 may be present in order to adjust the distance of the reference pattern unit 5230 present at the lower end portion of the mounting device 5200. In detail, the adjustment unit 5240 may be present on the lower end of the mounting unit. However, the present invention is not limited thereto, and the adjustment unit 5240 may be present outside the mounting device 5200 to adjust the position of the reference pattern unit 5230. Although not shown, an adjustment module may be included in the adjustment unit 5240, and the adjustment module may be controlled by a user. According to the user's control, the adjustment module may adjust the reference image 5231 to match the focal length of the lens module 1200. Here, the provision of the reference image 5231 to match the focal length of the lens module 1200 may mean that the controller 130 compares an obtained image to the reference image 5231 and then moves the position of the reference pattern unit 5230 such that the obtained image can coincide with the reference image 5231 well.

According to another embodiment, the adjustment unit 5240 may automatically adjust the position of the reference pattern unit 5230 such that the reference image 5231 present on the reference pattern unit 5230 can be provided to match the focal length of the lens module 1200. In detail, the adjustment unit 5240 present at the lower end portion of the mounting device 5200 may be provided with an electrical or mechanical motor, and the motor may adjust the position of the reference pattern unit 5230 such that the reference pattern unit 5230 can coincide with the focal length of the lens module 1200. Here, in order to adjust the position of the reference pattern unit 5230 such that the reference pattern unit 5230 can coincide with the focal length of the lens module 1200, a controller for controlling the reference pattern unit 5230 may be present on the mounting device 5200 although not shown. Also, the mounting device 5200 may include a communication unit for communicating with the image generating device, and the communication unit may communicate with the controller 130 of the image generating device in a wired or wireless communication manner. Although not shown, a communication unit of the controller 130 of the image generating device may obtain information regarding the position of the reference pattern unit 5230 from the controller of the mounting device 5200 and may compare an image obtained by the scanning module 110 emitting light to the reference image 5231. Also, when the comparison result between the obtained image and the reference image 5231 is that no image matching the focal length of the lens module 1200 is obtained, the controller 130 of the image generating device may adjust the adjustment unit 5240 of the mounting device 5200 through the communication unit, and the position of the reference pattern unit 5230 may be moved by the adjustment unit 5240 to coincide with the focal length of the lens module 1200.

6.3 Initial Phase Calibration Method by Mounting Device 5200

Figure 51:
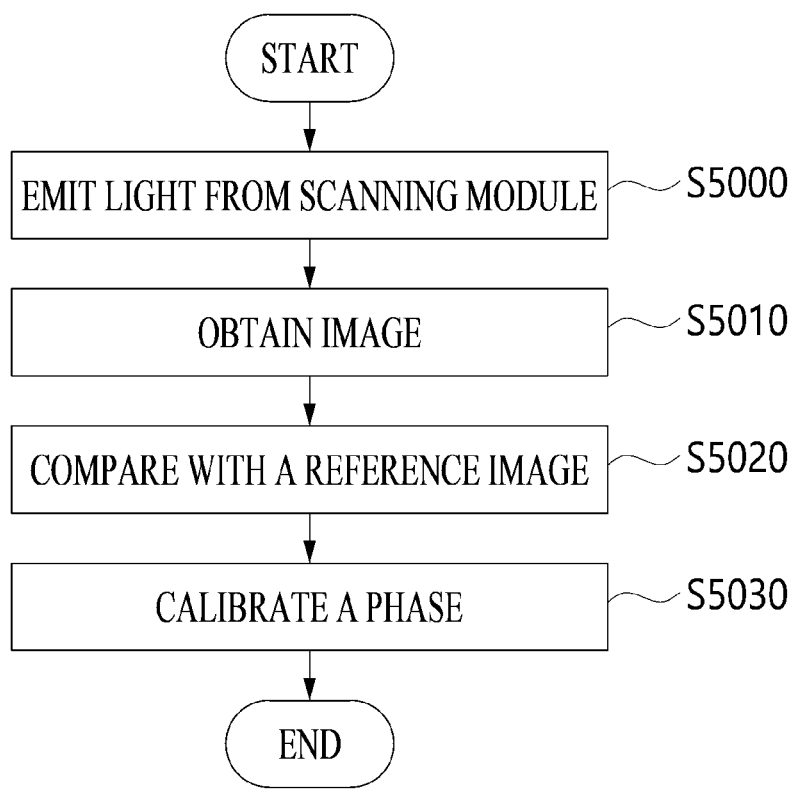
FIG. 51 is a flowchart showing that a phase is corrected using a reference image existing in a mounting device according to an embodiment.

FIG. 51 is a diagram for describing an initial phase calibration method using the reference image 5231 present in the mounting device 5200.

Referring to FIG. 51, the initial phase calibration method may be performed by the controller 130. Also, the initial phase calibration method may include emitting light from the scanning module 110 to the reference pattern unit 5230 (S5000), obtaining an image using light returning from the reference pattern unit 5230 (S5010), comparing the obtained image to the reference image 5231 (S5020), and calibrating the phase of a driving signal on the basis of a result of the comparison (S5030).

When light is emitted from the scanning module 110 to the reference pattern unit 5230 (S5000), the controller 130 may apply a driving signal to the driving unit 1101. Also, the driving unit 1101 receives the driving signal and applies, to the scanning unit 1100, a scanning unit driving signal for driving the scanning unit 1100. When the scanning unit driving signal is received, the scanning unit 1100 may emit light to an object O according to the scanning unit driving signal.

In this case, when phase calibration is not performed, a phase delay may occur between the driving signal and the scanning unit driving signal or the scanning unit output signal. Thus, before the scanning module 110 is separated from the mounting device 5200 to scan the object O, the phase delay may need to be calibrated. Therefore, for convenience of description, the calibration of the phase delay will be described as the initial phase calibration.

Here, when the initial phase calibration is not performed, the scanning of the object O is performed. When the phase calibration using the algorithm is performed, the calibration may be made with a phase other than an actual delayed phase value between the driving signal and the scanning unit output signal. Thus, when the initial phase calibration is performed while the scanning module 110 is not used, the time for discovering a phase to be calibrated during the scanning may be shortened, and also the controller 130 may directly obtain an image of the object O.

When the controller 130 obtains the image (S5010) and the controller 130 compares the obtained image to the reference image 5231 (S5020), the scanning module 110 may emit light toward the reference pattern unit 5230 while the scanning module 110 is mounted on the mounting device 5200. In detail, when light is emitted toward the reference pattern unit 5230 while the scanning module 110 is mounted, the light may continue to be emitted toward the reference pattern unit 5230 while the scanning module 110 is mounted. However, the present invention is not limited thereto, and the light may be emitted every predetermined period, and the initial phase calibration may be performed. Also, when the degree to which a calibrated image obtained by the controller 130 according to the initial phase calibration coincides with the reference image 5231 is less than or equal to a predetermined level, light may continue to be emitted such that an image calibrated at the predetermined level or more can coincide with the reference image 5231. Also, when light is emitted every predetermined period to perform the initial phase calibration, any time may be set every predetermined period. However, the present invention is not limited thereto, and the initial phase calibration may continue to be performed while the scanning module 110 is driven. In detail, when the image generating device is operating, the scanning module 110 may also be operating. Here, when the image generating device is not operating, the scanning module 110 may also stop operating. Thus, the phase delay value when the scanning module 110 starts to operate again may not be the same as the phase delay value of the scanning unit output signal before the scanning module 110 stops operating. Accordingly, performing the initial phase calibration by emitting light every predetermined period may be possible until the scanning module 110 stops operating when the scanning module 110 continues to operate as the image generating device is operated.

Here, the image obtained by the controller 130 coinciding with the reference image 5231 may mean that when light-receiving information based on light returning from the object O is obtained by the controller 130, information of a pixel of a portion of the image obtained by the controller 130 where the reference image 5231 is predicted to appear corresponds to information of a pixel corresponding to the reference image 5231 at a certain level or more.

Thus, when the phase of the driving signal, the scanning unit driving signal, or the scanning unit output signal is initially delayed, the image obtained by the controller 130 using the light that is emitted from the scanning module 110 and that returns from the reference pattern unit 5230 may not coincide with the reference image 5231. Thus, the initial phase calibration may be performed so that the image of the reference pattern unit 5230 and the image obtained by the controller 130 can coincide with each other.

When the phase of the driving signal is calibrated (S5030), the phase of the driving signal may be calibrated using the phase value as found above to be calibrated. For example, when the reference image 5231 does not coincide with the image obtained by the controller 130, the phase of the driving signal, the scanning unit driving signal, or the scanning unit output signal may be adjusted such that the image obtained by the controller 130 can coincide with the reference image 5231 using the input unit 140 of the controller 130 in order to perform the initial phase calibration method.

According to another embodiment, when the reference image 5231 does not coincide with the image obtained by the controller 130, the delayed phase of the driving signal, the scanning unit driving signal, or the scanning unit output signal may be calibrated by the controller 130 using the algorithm in order to perform the initial phase calibration. The phase calibration using the algorithm will be described below.

7 Phase Calibration Using Standard Deviation

The phase of the driving signal and the phase of the scanning unit driving signal or the scanning unit output signal may be different from each other when the controller 130 applies the driving signal to the driving unit 1101. Also, as described with reference to FIG. 38, the pre-phase-delay signal 5000 may be the driving signal, and the post-phase-delay signal 5001 may be the scanning unit driving signal or the scanning unit output signal.

In detail, light emitted by the scanning unit 1100 according to the scanning unit output signal may return from the object O due to an interaction between the light and the object O, including reflection, scattering, refraction, and diffraction, and the light-receiving unit 123 may obtain the light-receiving information by using the returning light. The controller 130 may obtain an image using the light-receiving information.

In this case, when an image is generated using the driving signal and the light-receiving information obtained by the controller 130, an image having a clear resolution may not be obtained due to a phase delay between the driving signal and the scanning unit output signal. Thus, when the phase delay of the driving signal is calibrated using light-receiving information obtained during scanning, real-time phase calibration may be possible, and the controller 130 may obtain a clear resolution image. A method of obtaining and calibrating a phase delay using the light-receiving information in order to calibrate the phase of the driving signal according to the phase delay value will be described below.

7.1 Image Acquisition Scheme of Controller 130

FIG. 52 is a diagram showing information to be stored in order for the controller 130 to obtain an image using the driving signal and the obtained light-receiving information. Here, a position corresponding to a first signal may refer to a position corresponding to a signal that is applied in the first axis direction among driving signals. Also, a position corresponding to a second signal may refer to a position corresponding to a signal that is applied in the second axis direction orthogonal to the first axis among signals for controlling the driving unit 1101. Also, an acquisition signal value may be a signal including the light-receiving information obtained by the light-receiving unit 123. However, the present invention is not limited thereto, and the information regarding returning light may be included in the acquisition signal value.

In detail, the first axis direction may refer to the x-axis in the Cartesian coordinate system, and the second axis direction may refer to the y-axis in the Cartesian coordinate system. However, the present invention is not limited thereto, and any coordinate system for emitting light to an object O using a scanning pattern may be included, such as the polar coordinate system. For convenience of description, the following description assumes that the first signal is applied in the first axis direction corresponding to the x-axis in the Cartesian coordinate system and the second signal is applied to the second axis direction corresponding to the y-axis in the Cartesian coordinate system. Accordingly, the position corresponding to the first signal may refer to an x-axis coordinate value of the image obtained by the controller 130, and the position corresponding to the second signal may refer to a y-axis coordinate value of the image obtained by the controller 130. Here, the position corresponding to the first signal and the position corresponding to the second signal may indicate coordinate values varying over time.

Also, as described above, the first axis direction and the second axis direction may be the same as the first axis direction and the second axis direction when the scanning unit 1100 is driven in the scanning module 110. The image obtained by the controller 130 may include a plurality of pixels. Therefore, the position corresponding to the first signal and the position corresponding to the second signal, that is, the x-axis coordinate value and the y-axis coordinate value of the image obtained by the controller 130 may indicate position information of the plurality of pixels of the image obtained by the controller 130.

According to an embodiment, the position corresponding to the driving signal input through the controller 130 in order to drive the driving unit 1101 may be predetermined. For example, the controller 130 may apply the driving signal to the driving unit 1101 every predetermined period. In this case, the controller 130 may obtain the position corresponding to the first signal every predetermined period. Here, the predetermined period may be a frame rate (FR) which is used for the image generating device to obtain an image. In this case, the position corresponding to the first signal may be represented as first-first to first-$n^{th}$ positions corresponding to n time points corresponding to the predetermined period. Here, the n time points corresponding to the predetermined period may be n time points that are evenly distributed within a predetermined period. However, the present invention is not limited thereto, and a plurality of time points which are predetermined within a predetermined period may be the n time points. Also, the position corresponding to the second signal may be represented as second-first to second-$n^{th}$ positions corresponding to n time points corresponding to the predetermined period.

Also, when the driving signal is input to the driving unit 1101, the driving unit 1101 may input the scanning driving signal to the scanning unit 1100, and the scanning unit 1100 may emit light to the object O according to the scanning unit output signal when the scanning unit 1100 is driven by the scanning unit driving signal. In this case, light that is emitted to the object O according to the scanning unit output signal and that returns from the object O may be obtained through the light-receiving unit 123 in the form of the light-receiving information. As shown in FIG. 52, the light-receiving information obtained by the light-receiving unit 123 may be obtained by the controller 130 as the acquisition signal value. That is, as the light-receiving information is sequentially obtained by the light-receiving unit 123 for a predetermined period, the controller 130 may obtain first to $n^{th}$ acquisition values as the acquisition signal value. For convenience of description, a format in which the position corresponding to the first signal, the position corresponding to the second signal, and the acquisition signal values are obtained by the controller 130 will be expressed below as a dataset.

Therefore, the controller 130 may obtain position information of a pixel that is determined according to a position corresponding to a first signal corresponding to an x-axis coordinate value of an image and a position corresponding to a second signal corresponding to a y-axis coordinate value of the image and may provide an image by using information obtained by making the sequentially obtained acquisition signal values correspond to the position information of the plurality of pixels, that is, by using the dataset.

7.1.1 Scheme in which Controller 130 Obtains Phase-Delayed Image or Phase-Calibrated Image When the scanning module 110 scans the object O, the driving signal, the scanning unit driving signal, and the scanning unit output signal may have different phases. For convenience of description, the phases of the driving signal, the scanning unit driving signal, and the scanning unit output signal being different will be expressed below as the phases being delayed.

According to an embodiment, the phase being delayed may mean that the position corresponding to the first signal or the position corresponding to the second signal at a predetermined time point within a predetermined period is different from a position at which the scanning unit output signal passes through the object O at the corresponding time point. In detail, the scanning unit 1100 may receive the scanning unit driving signal and may emit light to the object O according to the scanning unit output signal, which is a signal output when the scanning unit 1100 is driven.

In this case, when position information corresponding to the scanning unit output signal can be obtained, the controller 130 may provide an image such that an acquisition signal value corresponds to the pixel position of the image indicating a position corresponding to the scanning unit output signal. In this case, the image provided by the controller 130 may be an image with no phase delay.

However, when the image is provided from the controller 130, the first signal and the second signal of the driving signal may be used to specify the pixel position information in the image. In this case, when the driving signal and the scanning unit output signal are delayed in phase and thus become different from each other, an image obtained by the controller 130 using the position corresponding to the first signal, the position corresponding to the second signal, and the acquisition signal values may be a phase-delayed image.

Therefore, when the phase adjustment is performed such that the phase of the driving signal corresponds to the phase of the scanning unit output signal at a predetermined level or more, the controller 130 may obtain an image with no phase delay. Here, when the phase adjustment is performed such that the phase of the driving signal and the phase of the scanning unit output signal match at a predetermined level or more, the phase of the driving signal may be adjusted using the input unit 140 of the controller 130. Also, when the phase adjustment is performed such that the phase of the driving signal and the phase of the scanning unit output signal correspond to each other at a predetermined level or more, the controller 130 may automatically adjust the phase of the driving signal using the algorithm. For convenience of description, the phase adjustment being performed such that the phase of the driving signal and the phase of the scanning unit output signal correspond to each other at a predetermined level or more will be expressed below as phase calibration.

The table (a) of FIG. 53 shows a dataset of acquirable information when there is no phase delay. The table (b) of FIG. 53 shows a dataset of acquirable information when there is some phase delay.

According to an embodiment, referring to the table (a) shown in FIG. 53, when the phase of the driving signal and the phase of the scanning unit output signal are not different, a plurality of acquisition signal values obtained at a pixel position specified through the position corresponding to the first signal and the position corresponding to the second signal may correspond to one another. For example, referring to the table shown in FIG. 53, among the dataset values, a value X1 obtained at the position corresponding to the first signal and a value Y1 obtained at the position corresponding to the second signal may indicate one pixel position in an image which is expected to be obtained. Thus, an acquisition signal value I1 may be obtained at the pixel position represented by X1 and Y1.

Also, the position corresponding to the first signal and the position corresponding to the second signal may appear repeatedly within a predetermined period. Thus, the specified pixel position may appear repeatedly through the position corresponding to the first signal and the position corresponding to the second signal. Referring to the table (a) shown in FIG. 53, among the dataset values, X1 obtained at the position corresponding to the first signal may be obtained at the position corresponding to the first signal again after a predetermined time point. Also, Y1 obtained at the position corresponding to the second signal at the same time point as the time point when X1 is obtained may be obtained at the position corresponding to the second signal again after a predetermined time point. In this case, since the same acquisition signal value I1 is obtained at the pixel position corresponding to X1 and Y1 at different time points, there may be no phase delay between the driving signal and the scanning unit output signal.

According to another embodiment, referring to the table (b) shown in FIG. 53, when the phase of the driving signal and the phase of the scanning unit output signal are different, a plurality of acquisition signal values obtained at a pixel position specified through the position corresponding to the first signal and the position corresponding to the second signal may not correspond to one another. For example, referring to the table (b) shown in FIG. 53, among the dataset values, a value X3 obtained at the position corresponding to the first signal and a value Y1 obtained at the position corresponding to the second signal may indicate one pixel position in an image which is expected to be obtained. Accordingly, an acquisition signal value I1 may be obtained at the pixel position represented by X3 and Y1.

Also, the position corresponding to the first signal and the position corresponding to the second signal may appear repeatedly within a predetermined period. Thus, the specified pixel position may appear repeatedly through the position corresponding to the first signal and the position corresponding to the second signal. Referring to the table (b) shown i FIG. 53, among the dataset values, X1 obtained at the position corresponding to the first signal may be obtained at the position corresponding to the first signal again after a predetermined time point. Also, Y1 obtained at the position corresponding to the second signal at the same time point as the time point when X1 is obtained may be obtained at the position corresponding to the second signal again after a predetermined time point. In this case, since values I2 and I3 are obtained at the pixel position corresponding to X1 and Y1 at different time points, there may be a phase delay between the driving signal and the scanning unit output signal.

According to another embodiment, referring to FIGS. 52, 53A, and 53B, in order to calibrate a phase delay between the driving signal and the scanning unit output signal, n position values obtained at the position corresponding to the first signal or the position corresponding to the second signal among the dataset may be obtained at another position according to a delayed phase. For example, when there is a phase delay in the first signal of the driving signal, a value obtained at a first-first position may be obtained at a first-$n^{th}$ position, and a value obtained at a first-$n^{th}$ position may be obtained at a first-(n−1)th position. In detail, referring to FIGS. 53A and 53B, when the phase of the first signal is delayed, the phase component of the first signal may be adjusted such that X1 obtained at a first-second position can be obtained at the first-first position. Thus, in the dataset obtained by the controller 130, the controller 130 may obtain the position corresponding to the first signal as phase-adjusted values. Also, when there is a phase delay at the position corresponding to the second signal of the driving signal, a value obtained at a second-first position may be obtained at a second-$n^{th}$ position, and a value obtained at a second-$n^{th}$ position may be obtained at a second-(n−1)th position. In detail, referring to FIGS. 53A and 53B, when the phase of the second signal is delayed, the phase component of the second signal may be adjusted such that Y1 obtained at a second-second position can be obtained at the second-first position. Thus, in the dataset obtained by the controller 130, the controller 130 may obtain the position corresponding to the second signal as phase-adjusted values. However, the present invention is not limited thereto, and when there is a phase delay between the positions corresponding to the first signal and the second signal of the driving signal, the values obtained at the position corresponding to the first signal and the position corresponding to the second signal may be obtained at another position according to a delayed phase.

According to another embodiment, in order to calibrate the phase delay between the driving signal and the scanning unit output signal, n values obtained in an acquisition signal value due to the light-receiving information may be obtained at the position of another obtained value according to a delayed phase. For example, the value obtained at the first obtained value position may be obtained at the obtained value position, and the value obtained at the $n^{th}$ obtained value position may be obtained at the (n−1)th obtained value position. In detail, referring to the tables (a) and (b) shown in FIG. 53, when there is no phase delay, the value I1 obtained at a pixel position specified through X1 and Y1 may be obtained at the pixel position specified through X1 and Y1 when there is a phase delay. That is, as shown in the table (b) of FIG. 53, the controller 130 may adjust sequentially obtained acquisition signal values such that I1 obtained for the first obtained value can be obtained at the second obtained value.

Accordingly, the controller 130 may obtain a phase-calibrated image using the position corresponding to the first signal, the position corresponding to the second signal, or the acquisition signal value of which a phase is calibrated.

An algorithm for obtaining a phase delay using a standard deviation of an obtained image in order for the controller 130 to obtain the degree to which a phase is delayed will be described below.

7.2 Acquisition of Phase Delay Value Using Standard Deviation

In order to obtain the degree to which a phase delay is present between the driving signal and the scanning unit output signal, the acquisition signal value obtained by the controller 130 may be used. For example, in order to obtain the degree to which the phase delay is present between the driving signal and the scanning unit output signal, the controller 130 may obtain a phase delay value using a difference between an acquisition signal value predicted to be obtained in the same pixel of the image obtained by the controller 130 and an acquisition signal value including a standard deviation obtained at an actually predicted time.

Also, the controller 130 may obtain the phase delay degree using the difference between the obtained signal value predicted to be obtained in the same pixel and the acquisition signal value including the standard deviation. It will be appreciated that the method of finding the difference between the acquisition signal values is not limited thereto. In addition to finding the standard deviation between the acquisition signal values, the phase delay value may be obtained using an average and a variance between the obtained signal values and the absolute value of the difference between the acquisition signal values. However, for convenience of description, the following description assumes that the standard deviation is used to obtain a phase delay value.

7.2.1 Acquisition of Standard Deviation Using Prediction Time Point

Figure 54:
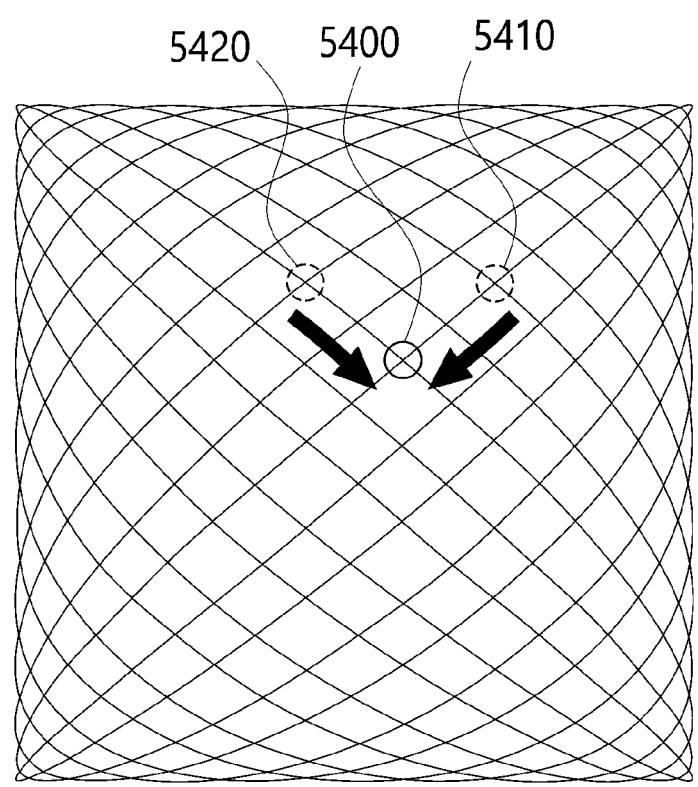
FIG. 54 is a diagram for describing a method of finding a difference between signal values obtained at prediction times along a light pattern according to an embodiment.

FIG. 54 is a diagram showing a pixel 5400 having an acquisition signal value expected at a prediction time point when a phase is delayed (hereinafter referred to as an expected pixel corresponding to the prediction time point) and a pixel having an acquisition signal value obtained at an actual prediction time point (hereinafter referred to as an actual pixel according to the prediction time point) along a path of light emitted from the scanning module 110.

According to an embodiment, referring to FIG. 54, when a scanning pattern including a Lissajous pattern is formed according to the first signal or the second signal of the driving signal, the expected pixel 5400 corresponding to the prediction time point may refer to a pixel when different time points are present along the light path but are represented as the same pixel position. In this case, a direction in which light is traveling at different time points when the light passes through the expected pixel 5400 corresponding to the prediction time point along the light path may include a first scanning direction and a second scanning direction. A time point predicted when the light passes through the expected pixel 5400 corresponding to the prediction time point in the first scanning direction may be a first prediction time point, and a time point predicted when the light passes through the expected pixel 5400 corresponding to the prediction time point in the second scanning direction may be a second prediction time point. In detail, when the scanning unit output signal has a delayed phase compared to the driving signal, a signal value 5410 obtained according to the first prediction time point and a signal value 5420 obtained according to the second prediction time point may not be a signal value corresponding to the expected pixel 5400 corresponding to the prediction time point.

Figure 55:
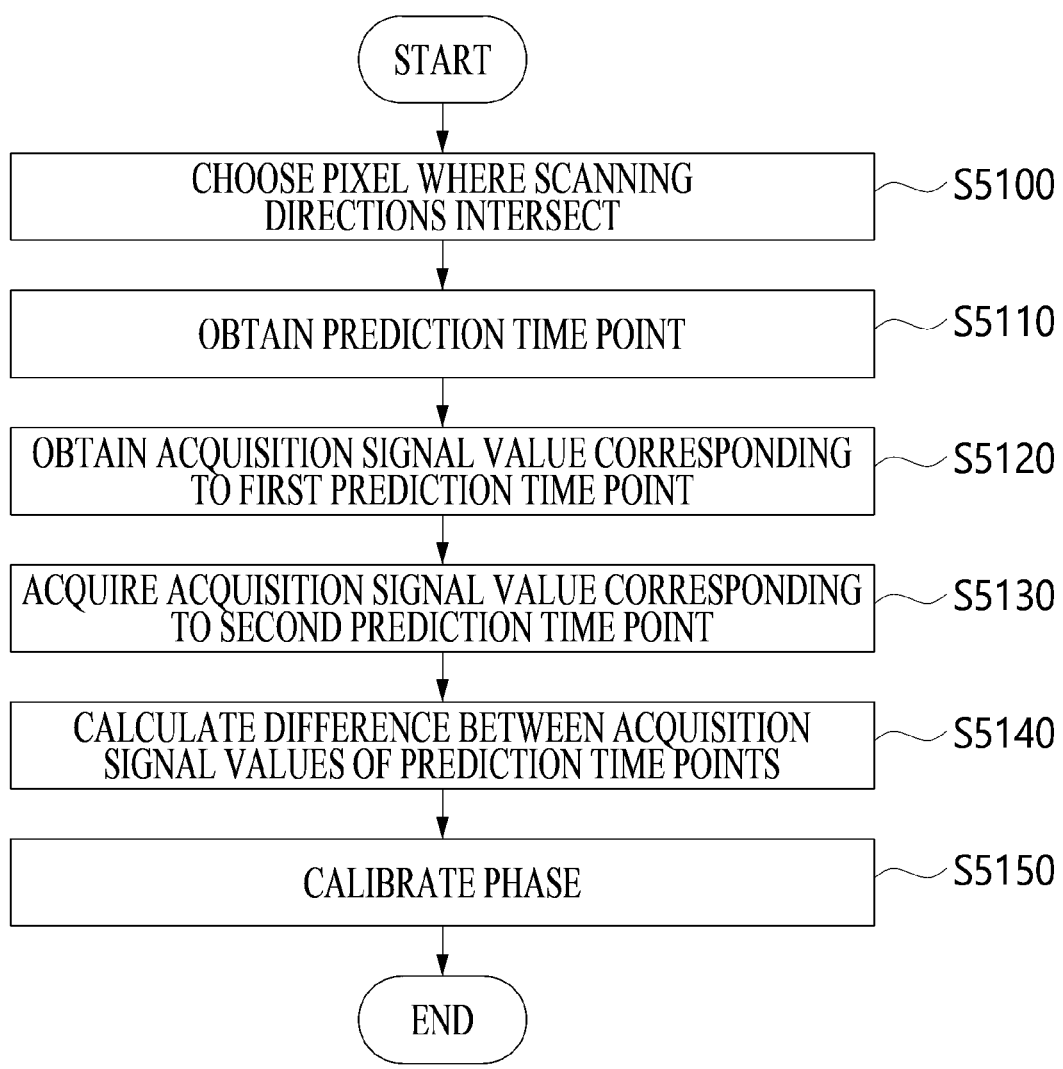
FIG. 55 is a flowchart for describing that a phase is corrected using a difference between values obtained at prediction times along a light pattern according to an embodiment.

FIG. 55 is a flowchart showing a process of performing phase calibration using a difference between signal values obtained at prediction time points. In detail, the phase calibration may include choosing a pixel positioned where scanning directions intersect, obtaining a prediction time point, obtaining an acquisition signal value 5410 corresponding to a first prediction time point, obtaining an acquisition signal value 5420 corresponding to a second prediction time point, calculating a difference between the acquisition signal values corresponding to the prediction time points, and performing phase calibration.

Referring to FIG. 55, the choosing of a pixel positioned where scanning directions intersect (S5100) may include choosing an expected pixel corresponding to a prediction time point when a first scanning direction and a second scanning direction meet each other. In detail, there may be different scanning directions with respect to a path of light passing through one pixel. Accordingly, in the case of a time point passing through the expected pixel 5400 corresponding to the prediction time point when the first scanning direction and the second scanning direction meet each other in one scanning pattern, a time point passing through the expected pixel corresponding to the prediction time point in the first scanning direction may be different from a time point passing though the expected pixel corresponding to the prediction time point in the second scanning direction. Therefore, when an intersection between the first scanning direction and the second scanning direction along the light path is selected, one pixel position may be represented at different prediction time points of the driving signal. Accordingly, when the driving signal and the scanning unit output signal have different phases, different obtained signal values corresponding to the scanning unit output signal may represent different values. Thus, any pixel corresponding to the first scanning direction and the second scanning direction may be chosen from the driving signal.

Also, referring to FIG. 55, the obtaining of a prediction time point (S5110) may include obtaining, from a driving signal, a first time point expected to pass through the expected pixel corresponding to the prediction time point in the first scanning direction and a second time point expected to pass through the expected pixel corresponding to the prediction time point in the second scanning direction. In detail, since a phase delay may occur between the driving signal and the scanning unit output signal, acquisition signal values obtained at the first time point and the second time point may differ when the light is emitted to the object O according to the scanning unit output signal. Accordingly, after a prediction time point predicted to pass through the expected pixel corresponding to the prediction time point according to the driving signal is obtained, a standard deviation between acquisition signal values obtained according to the scanning unit output signal may be found. Accordingly, the first time point or the second time point, which is a prediction time point predicted to pass through the expected pixel corresponding to the prediction time point chosen from the driving signal, may be obtained.

Also, referring to FIG. 55, the obtaining of an acquisition signal value corresponding to a first prediction time point (S5120) and the obtaining of an acquisition signal value corresponding to a second prediction time point (S5130) may include obtaining acquisition signal values corresponding to the first prediction time point and the second prediction time point corresponding to the scanning unit output signal when the controller 130 emits light to the object O according to the scanning unit output signal and obtains an acquisition signal value using returning light. In detail, since the phase of the driving signal and the phase of the scanning unit output signal may be different from each other, one signal value may need to be obtained from the expected pixel corresponding to the prediction time point according to the driving signal. However, the signal values corresponding to the first prediction time point and the second prediction time point in the scanning unit output signal may be different from each other. Accordingly, a phase delay value may be obtained using an acquisition signal value corresponding to the first prediction time point acquirable according to the first prediction time point and an acquisition signal value corresponding to the second prediction time point acquirable according to the second prediction time point in the scanning unit output. However, FIG. 55 sequentially shows obtaining an acquisition signal value corresponding to the first prediction time point and obtaining an acquisition signal value corresponding to the second prediction time point. However, the present invention is not limited thereto, and the obtaining of the acquisition signal value corresponding to the second prediction time point may precede the obtaining of the acquisition signal value corresponding to the first prediction time point. Accordingly, a first time point or a second time point predicted as representing the expected pixel corresponding to the prediction time point may be present in the driving signal, and a signal value obtained at the first time point or the second time point corresponding to the scanning unit output signal may be obtained.

Also, referring to FIG. 55, the calculating of the difference between the acquisition signal values at the prediction time points (S5140) may include calculating the standard deviation between the acquisition signal value corresponding to the first prediction time point and the acquisition signal value corresponding to the second prediction time point. In detail, when a phase delay occurs between the driving signal and the scanning unit output signal, a signal that would have been obtained from the expected pixel corresponding to the prediction time point corresponding to the driving signal may be different from the acquisition signal value corresponding to the first prediction time point or the acquisition signal value corresponding to the second prediction time point. However, when the acquisition signal value corresponding to the first prediction time point and the acquisition signal value corresponding to the second prediction time point match each other at a predetermined level or more, the acquisition signal value corresponding to the first prediction time point and the acquisition signal value corresponding to the second prediction time may indicate the same pixel in the image obtained by the controller 130 or may indicate pixels adjacent to the expected pixel corresponding to the prediction time point. Accordingly, when the acquisition signal value corresponding to the first prediction time point and the acquisition signal value corresponding to the second prediction time point match at a predetermined level or higher, the standard deviation between the obtained signal values may be small. Accordingly, when the standard deviation is small, the phase delay value between the driving signal and the scanning unit output signal may be small. Alternatively, when the acquisition signal value corresponding to the first prediction time point and the acquisition signal value corresponding to the second prediction time point match are different from each other, the acquisition signal values may indicate pixels that are not adjacent to the expected pixel corresponding to the prediction time point. Accordingly, when the acquisition signal value corresponding to the first prediction time point and the acquisition signal value corresponding to the second prediction time point are different, the standard deviation between the obtained signal values may be large. Accordingly, when the standard deviation is large, the phase delay value between the driving signal and the scanning unit output signal may be large. However, the present invention is not limited thereto, and the phase delay value between the driving signal and the scanning unit output signal may not be large even when the standard deviation is large. Accordingly, the expected pixel corresponding to the prediction time point may not be one pixel, and one or more pixels may be chosen as the expected pixels corresponding to the prediction time points. In this case, the degree to which the phase is delayed may be obtained using all standard deviations between the acquisition signal values which are obtained through a phase-delayed signal in the expected pixels corresponding to the prediction time points.

Also, referring to FIG. 55, the phase calibration (S5150) may include changing a value obtained at the position corresponding to the first signal or the position corresponding to the second signal or changing the position corresponding to the first signal, the position corresponding to the second signal, or the acquisition signal value using a phase value in which a value obtained by calculating the standard deviation corresponding to the prediction time point while changing the acquisition signal value is less than or equal to a predetermined level. In detail, by changing the phase of the driving signal, the value obtained at the position corresponding to the first signal or the position corresponding to the second signal may be changed. Thus, the expected pixel corresponding to the prediction time point may be chosen again, and the standard deviation value may be calculated. In this case, by changing the phase of the driving signal to a phase value with the smallest standard deviation, the position corresponding to the first signal or the position corresponding to the second signal may be changed, and the controller 130 may obtain a phase-calibrated image.

7.2.2 Acquisition of Standard Deviation Between Acquisition Signal Values Obtained in Same Pixel of Image Obtained by Controller 130

The controller 130 may obtain an acquisition signal value for the time predetermined for a pixel of an image obtained by the controller 130. Accordingly, the controller 130 may find a standard deviation between acquisition signal values obtained at a pixel position for a predetermined time and may obtain an image obtained by changing the phase of the driving signal to a phase corresponding to when the value of the standard deviation obtained by changing the phase of the driving signal is less than or equal to a predetermined level.

Figure 56:
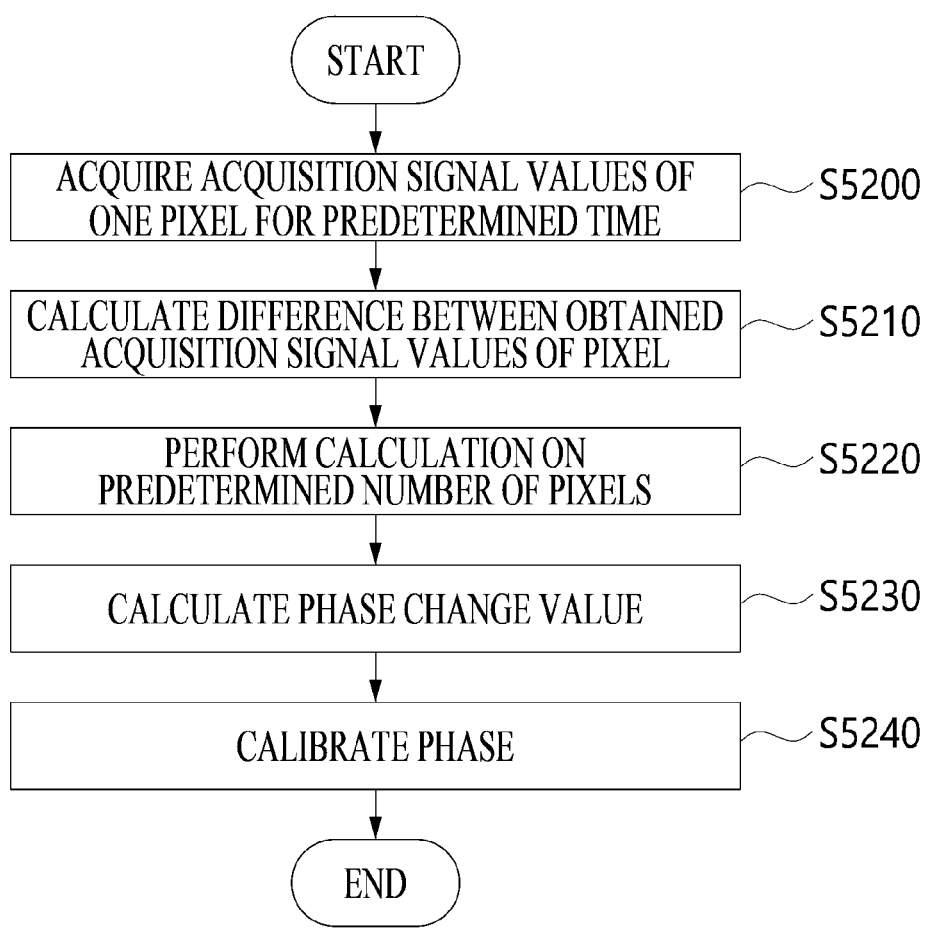
FIG. 56 is a flowchart for describing that a phase is corrected using a value acquired for a pixel of an image obtained by a control module according to an embodiment.

FIG. 56 is a flowchart showing a process of performing phase calibration using a standard deviation between acquisition signal values obtained at a pixel of an image obtained by the controller 130. In detail, the phase calibration may include obtaining acquisition signal values of one pixel for a predetermined time, calculating a difference between the obtained acquisition signal values of the pixel, performing a calculation on a predetermined number of pixels, calculating a phase change value, and calibrating a phase. For example, the obtaining of acquisition signal values of one pixel for a predetermined time may include obtaining light intensity obtained at one pixel included in an image.

Referring to FIG. 56, the obtaining of acquisition signal values of one pixel for a predetermined time (S5200) may include obtaining an acquisition signal value acquirable from the light-receiving information at the position of the pixel which can be obtained on the basis of the position corresponding to the first signal and the position corresponding to the second signal. Here, the position corresponding to the first signal may refer to an x-axis coordinate in pixel information of the entire image obtained by the controller 130, and the position corresponding to the second signal may refer to a y-axis coordinate in pixel information of the entire image obtained by the controller 130. Accordingly, an x-axis coordinate and a y-axis coordinate determined in the Cartesian coordinate system may represent one piece of position information. Accordingly, one pixel position may be determined on the basis of the position corresponding to the first signal and the position corresponding to the second signal. However, position information of a pixel based on the positions corresponding to the first signal and the second signal of the driving signal may be obtained at least once for a predetermined time. In detail, when the position corresponding to the first signal and the position corresponding to the second signal are chosen, the position information of one pixel may be obtained. In this case, an acquisition signal value may be obtained for the position information of one pixel. Also, since at least one acquisition signal value may be obtained for the position information of one pixel for a predetermined time, the controller 130 may obtain at least one acquisition signal value for a predetermined time.

Here, the predetermined time may be the time taken for the position corresponding to the first signal to become the first-first position again and for the position corresponding to the second signal to become the second-first position again. However, the present invention is not limited thereto, and the predetermined time may be the time taken for the position corresponding to the first signal and the position corresponding to the second signal to be repeated several times and may include any time.

Also, the obtained acquisition signal value may refer to the intensity of light returning from an object.

Also, referring to FIG. 56, the calculating of the difference between the acquisition signal values of the obtained pixel (S5210) may include calculating a difference between one or more acquisition signal values obtained by the controller 130. In detail, the controller 130 may calculate the difference between the one or more acquisition signal values obtained at one pixel position based on the position corresponding to the first signal and the position corresponding to the second signal for a predetermined time. Here, the difference between the acquisition signal values may be a difference value including a standard deviation, a variance, or the like. However, for convenience of description, the following description assumes that the difference refers to a standard deviation between the acquisition signal values obtained by the controller 130.

Also, referring to FIG. 56, the performing of calculation on a predetermined number of pixels (S5220) may include causing the controller 130 to calculate a standard deviation between acquisition signal values obtained at a predetermined number of pixel positions or a plurality of randomly determined pixel positions, in addition to the calculating of the standard deviation between one or more acquisition signal values obtained at one pixel position. Here, a predetermined number or more of pixels which perform calculation may be one pixel position of the image obtained by the controller 130. However, the present invention is not limited thereto, and the pixels may include all pixels of the image obtained by the controller 130. Also, the predetermined number or more of pixels may include one or more pixel positions.

According to an embodiment, the performing of calculation on a predetermined number of pixels (S5220) may include causing the controller 130 to obtain one piece of standard deviation information using the acquisition signal values calculated at the pixel positions as well as calculating a standard deviation between the acquisition signal values obtained at each of the pixel positions. For example, standard deviation information for all the pixels may be obtained using the standard deviation calculated at one pixel position. In detail, the controller 130 obtaining one piece of standard deviation information may find the sum of the standard deviations obtained at each of the pixel positions used for the calculation. However, the present invention is not limited thereto, and the controller 130 may perform various calculations including an average, a product, a variance, and a standard deviation of the standard deviations obtained at each of the pixel positions. For convenience of description, the following description assumes that the acquisition of one piece of standard deviation information refers to the calculation of the sum of the standard deviations obtained at each of the pixel positions.

Also, referring to FIG. 56, the calculating of the phase change value (S5230) may include causing the controller 130 to change the position corresponding to the first signal, the position corresponding to the second signal, or the acquisition signal value and to obtain one piece of standard deviation information. In detail, the position corresponding to the first signal or the position corresponding to the second signal which is obtained by changing the phase of the driving signal may be different from position information of a pixel represented by the position corresponding to the first signal or the position corresponding to the second signal before the phase of the driving signal is changed. Thus, since the order of the obtained signal values obtained by the controller 130 may not change, an acquisition signal value obtained for the position information of the pixel represented by positions corresponding to a first signal and a second signal included in a driving signal with a changed phase may be different from an acquisition signal value before the phase is changed. Accordingly, the standard deviation of the acquisition signal value obtained at a pixel position based on the position corresponding to the first signal and the position corresponding to the second signal for a predetermined value may be different from the standard deviation at the pixel position before the phase of the driving signal is changed. Accordingly, one piece of standard deviation information in a predetermined number of pixels may vary depending on the change in phase of the driving signal. When the phase of the driving signal continues to be changed, one or more pieces of standard deviation information may be obtained.

According to an embodiment, when there is no phase delay between the driving signal and the scanning unit output signal, the standard deviation at the pixel position based on the position corresponding to the first driving signal and the position corresponding to the second driving signal may have a value close to zero. In detail, the standard deviation between acquisition signal values obtained in one pixel being equal to zero may mean that there is no difference between the obtained acquisition signal values. This may represent that the driving signal and the scanning unit output signal between which there is no phase delay indicate the same position. Thus, when the standard deviation information using acquisition signal values obtained at a predetermined number of pixel positions is close to zero, this may mean that there is little phase delay between the driving signal and the scanning unit output signal.

Accordingly, among the standard deviation information of phase-changed driving signals, the phase of the driving signal exhibiting the smallest standard deviation information may be determined as a phase to be changed by the controller 130. However, the present invention is not limited thereto, and the controller 130 may change the phase into the phase of a driving signal indicating standard deviation information at a predetermined level or less among standard deviation information of the phase-changed driving signals. However, for convenience of description, the following description assumes that the phase of a driving signal with the smallest standard deviation information is to be changed by the controller 130.

Also, referring to FIG. 56, the phase calibration (S5240) may include changing the phase of a driving signal into the phase of a driving signal exhibiting the smallest standard deviation information. In detail, the phase calibration may be performed by changing a value obtained at the position corresponding to the first signal or the second signal of the driving signal or by changing the acquisition signal value. Here, the phase of the driving signal with the smallest standard deviation information may include the phases of the first signal and the second signal included in the driving signal. Accordingly, the controller 130 may change the position corresponding to the first signal according to the phase of the first signal with the smallest standard deviation information and may change the position corresponding to the second signal according to the phase of the second signal with the smallest standard deviation information. For convenience of description, the following description assumes that the changing according to the phase with the smallest standard deviation information refers to the phase calibration of the driving signal.

7.2.3 Search for Phase Calibration Value Using Trajectory Tracking Method

Figure 57:
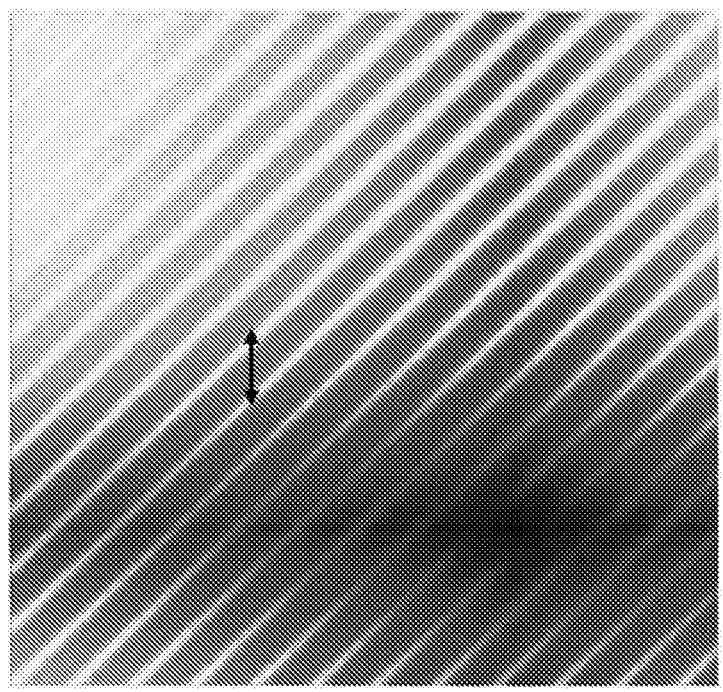
FIG. 57 is a diagram showing standard deviation information corresponding to a phase change according to an embodiment.

FIG. 57 is a diagram showing standard deviation information corresponding to the change of the phase, wherein an x-axis indicates a phase corresponding to a first signal and a y-axis indicates a phase corresponding to a second signal. In detail, in FIG. 57, a bright part may indicate that the standard deviation information has a large value, and a dark part may indicate that the standard deviation information has a small value. Accordingly, in order to calibrate the phases of the first signal and the second signal of the driving signal, the phase corresponding to the first signal and the phase corresponding to the second signal may be obtained in the darkest part indicating that the standard deviation information is smallest.

Figure 58:
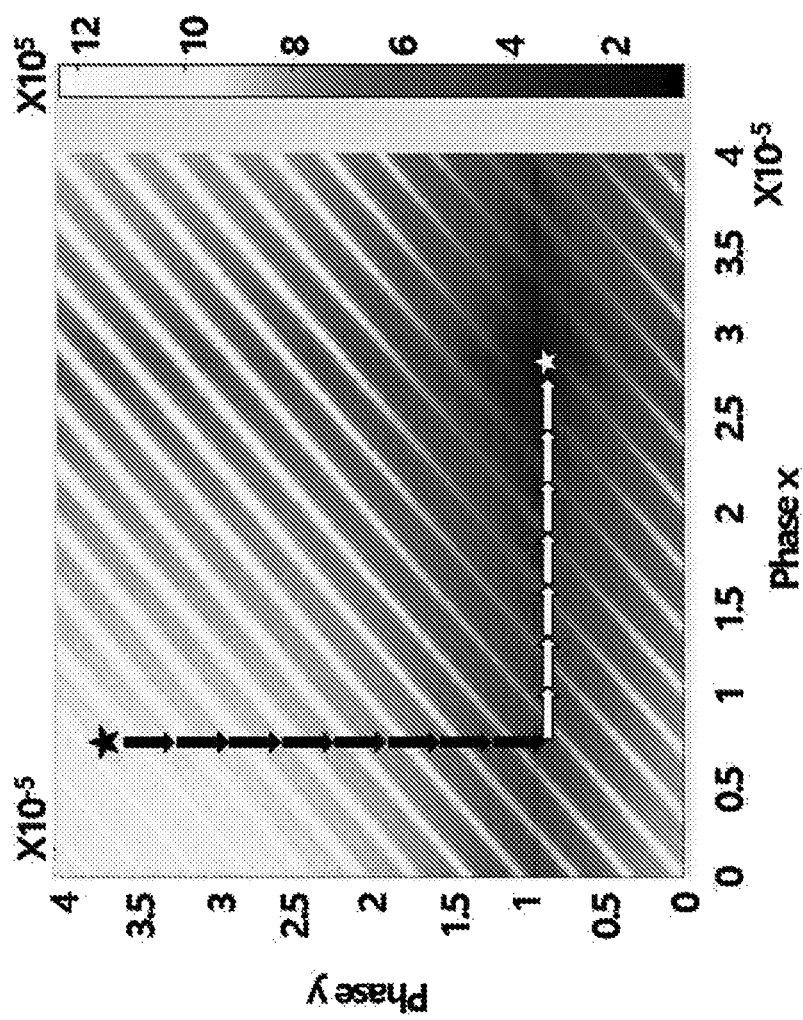
FIG. 58 is a diagram for describing a method of finding a value of minimizing standard deviation information along a trajectory according to an embodiment.

Also, FIG. 58 is a diagram showing standard deviation information according to the change in phase and a path for changing the phase corresponding to the first signal and the phase corresponding to the second signal, wherein an x-axis indicates the phase corresponding to the first signal and a y-axis indicates the phase corresponding to the second signal. In detail, in FIG. 58, a bright part may indicate that the standard deviation information has a large value, and a dark part may indicate that the standard deviation information has a small value. Accordingly, in order to calibrate the phases of the first signal and the second signal of the driving signal, the phase corresponding to the first signal and the phase corresponding to the second signal may be obtained in the darkest part indicating that the standard deviation information is smallest.

According to an embodiment, referring to FIG. 58, the standard deviation information corresponding to the first signal and the second signal of which phases are not calibrated may be standard deviation information at a position where a black star is present. Also, a white star may indicate a value with the smallest standard deviation information. In this case, the controller 130 may change the phase of the first signal and the phase of the second signal in the black star into the phase of the first signal and the phase of the second signal in the white star while changing the phase corresponding to the first signal or the phase corresponding to the second signal by a predetermined phase change period. Here, the controller 130 may change the phase of the first signal and the phase of the second signal in the black star into the phase of the first signal and the phase of the second signal in the white star by a predetermined phase change period along a trajectory of an arrow shown in FIG. 58. This may be expressed as the trajectory tracking method.

However, a trajectory for discovering the phase of the first signal and the phase of the second signal having the smallest standard deviation information according to the trajectory tracking method is not limited to the trajectory of the arrow shown in FIG. 58. The trajectory may be changed by a predetermined phase change period in a direction of the phase corresponding to the second signal and then changed by a predetermined phase change period in a direction of the phase corresponding to the first signal, or the phase of the first signal or the second signal may be alternately changed by a predetermined phase change period in the direction of the phase corresponding to the first signal and in the direction of the phase corresponding to the second signal.

In detail, the trajectory tracking method may be an algorithm for discovering the phases of the first signal and the second signal with the smallest standard deviation information while changing the phase of the first signal or the phase of the second signal by a predetermined phase change period. The algorithm for discovering the phases of the first signal and the second signal with the smallest standard deviation information according to the predetermined phase change period will be described below.

7.2.4 Search for Phase Calibration Value Using Range Limiting Method

Figure 59:
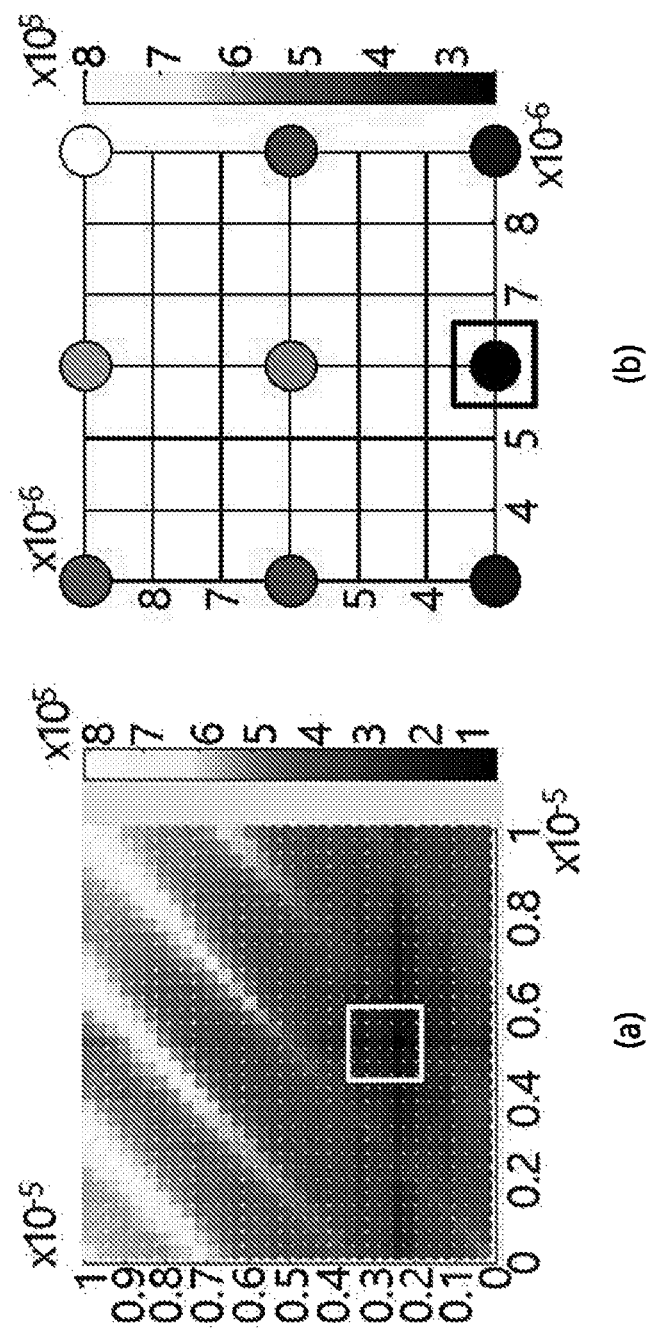
FIG. 59 is a diagram for describing a method of finding a value of minimizing standard deviation information within a limited range according to an embodiment.

FIG. 59A is a diagram showing standard deviation information according to the change in phase of the first signal and the second signal and showing that the phase variations of the first signal and the second signal are small, wherein an x-axis indicates the phase corresponding to the first signal and a y-axis indicates the phase corresponding to the second signal. In detail, as shown in the image (a) of FIG. 59, a bright part may indicate that the standard deviation information has a large value, and a dark part may indicate that the standard deviation information has a small value. Also, the image (b) of FIG. 59 is a diagram showing standard deviation information according to the change in phase of the first signal and the second signal and showing that the phase variation of the first signal or the second signal changes is large, wherein an x-axis indicates the phase corresponding to the first signal and a y-axis indicates the phase corresponding to the second signal. In detail, as shown in the image (b) of FIG. 59, a bright part may indicate that the standard deviation information has a large value, and a dark part may indicate that the standard deviation information has a small value. Accordingly, in order to calibrate the phases of the first signal and the second signal of the driving signal, the phase corresponding to the first signal and the phase corresponding to the second signal may be obtained in the darkest part indicating that the standard deviation information is smallest.

For convenience of description, a process of setting a predetermined range at the phase of the first signal and the phase of the second signal according to the smallest standard deviation when the phase variation of the first signal or the second signal is large, setting the phase variation of the first signal or the second signal to be small within the corresponding range, and discovering the phase of the first signal and the phase of the second signal indicating the smallest standard deviation information will be expressed below as a range limitation method.

According to an embodiment, referring to the image (a) of FIG. 59, when the phase variations of the first signal and the second signal are small, the amount of standard deviation information to be obtained by the controller 130 may be large. When the amount of standard deviation information to be obtained by the controller 130 is large, the controller 130 may require more time to obtain the standard deviation information. Accordingly, in order for the controller 130 to spend less time in obtaining the standard deviation information, the phase variation degrees of the first signal and the second signal may be increased. In this case, according to the standard deviation information obtained by the controller 130, the controller 130 may change the phases of the first signal and the second signal. However, the phase of the first signal and the phase of the second signal according to the smallest standard deviation information when the phase variations of the first signal and the second signal are large may be different from the phase of the first signal and the phase of the second signal according to the smallest standard deviation information when the phase variations of the first signal and the second signal are small. In detail, when the phase variations of the first signal and the second signal are large, the controller 130 cannot obtain the standard deviation information for the phase of the first signal and the phase of the second signal corresponding to the smallest standard deviation information when the phase variations of the first signal and the second signal are small. Accordingly, when a predetermined range is set after the phase variations of the first signal and the second signal are increased, the phase of the first signal and the phase of the second signal exhibiting the smallest standard deviation information when the phase variations of the first signal and the second signal are small may not be included in the corresponding range.

Accordingly, in order for the controller 130 to reduce the spent time and obtain the phase of the first signal and the phase of the second signal exhibiting the smallest standard deviation information when the phase variations of the first signal and the second signal are small, the controller 130 may obtain the phase of the first signal and the phase of the second signal exhibiting the smallest standard deviation information using the trajectory tracking method and may obtain the phase of the first signal and the phase of the second signal exhibiting the smallest standard deviation information in the range obtained according to the trajectory tracking method by using the range limitation method.

8 Phase Calibration Using Predetermined Phase Change Period

In order for the controller 130 to obtain the phase of the first signal and the phase of the second signal with the smallest standard deviation information using the aforementioned trajectory tracking method, the controller 130 may discover the phase of the first signal and the phase of the second signal with the smallest standard deviation information using a predetermined phase change period.

Figure 60:
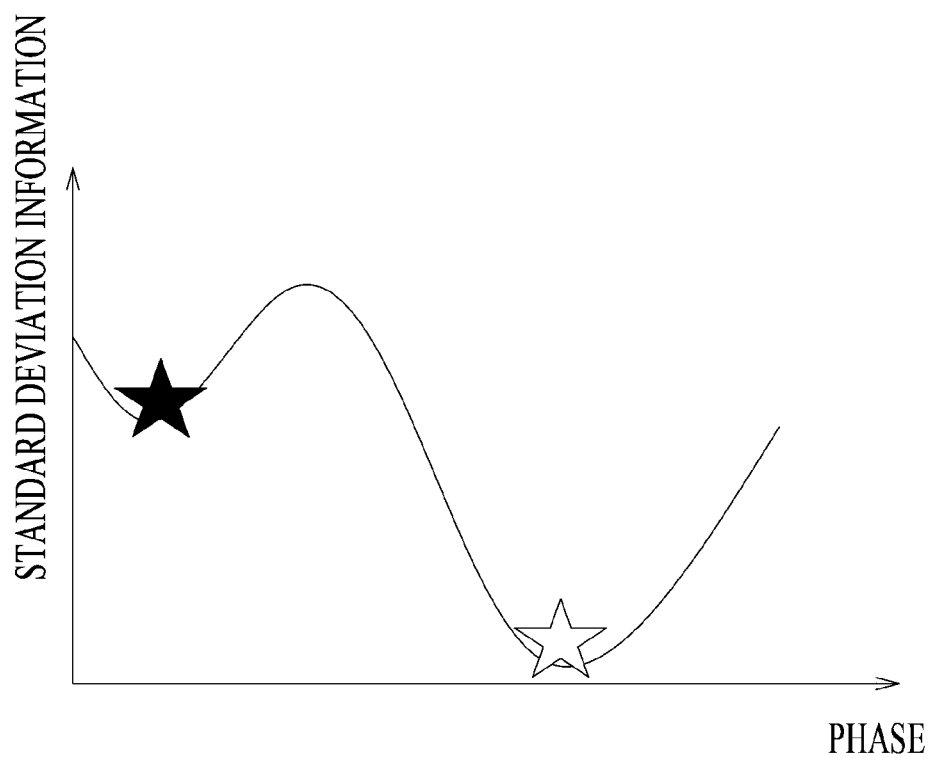
FIG. 60 is a diagram for describing a local minimal value when a minimal value of standard deviation information is found using a trajectory according to an embodiment.

FIG. 60 is a diagram showing the phase of the first signal or the second signal with the smallest deviation information discovered using the trajectory tracking method and a phase with the smallest standard deviation information in the entire phase range of the first signal or the second signal, wherein an x-axis indicates one of the phase of the first signal or the phase of the second signal, and a y-axis indicates the standard deviation information. In detail, in FIG. 60, a black star may be the phase of the first signal or the second signal with the smallest standard deviation information which is discovered using the trajectory tracking method, and a white star may be a phase with the smallest standard deviation information in the entire phase range of the first signal or the second signal.

According to an embodiment, in FIG. 60, the position of the black star and the position of the white star may be different. For example, a phase delay may be present between the driving signal and the scanning unit output signal when the scanning module 110 is driven (hereinafter referred to as an initial delayed phase). In this case, the trajectory tracking method is used to discover the phase of the first signal or the second signal with the smallest standard deviation information at the initial delayed phase according to a predetermined phase change period. Accordingly, when the discovery is performed by changing a phase by the predetermined phase change period, the phase of the first signal or the second signal may be a phase represented by the position of the black star. However, when the difference between the phase represented by the position of the black star and the phase represented by the position of the white star is not equal to the predetermined phase change period, the discovered phase with the smallest standard deviation information may be the phases of the first signal and the second signal represented by the position of the black star. Accordingly, no calibration may be made with the phase for the controller 130 generating a high-resolution image having a calibrated phase which has been described with reference to the image shown in (b) of FIG. 39, i.e., the phase represented by the position of the white star when the standard deviation information is smallest in the entire phase range. For convenience of description, the following description assumes that a phase corresponding to a local minimum is obtained when the controller 130 obtains a phase other than a phase corresponding to the smallest standard deviation information in the entire phase range as a phase for calibrating the phase of the driving signal.

According to another embodiment, after the phase is discovered using the trajectory tracking method, the phase corresponding to the local minimum may be obtained using the range limitation method even when the controller 130 obtains a phase at which the information of the standard deviation is minimized. In detail, the phase of the first signal or the phase of the second signal with the smallest standard deviation information may be obtained using the trajectory tracking method, and the phase of the first signal or the phase of the second signal with the smallest standard deviation information may be obtained using the range limitation method within a range predetermined from the phase of the first signal or the phase of the second signal obtained according to the trajectory tracking method. However, when the range limitation method is used in a predetermined range, the phase of the first signal or the phase of the second signal with the smallest standard deviation information in the entire phase range may not be present in the predetermined range on the basis of the phase of the first signal or the second signal obtained according to the trajectory tracking method. Accordingly, even when the phase of the first signal or the second signal with the smallest standard deviation information is discovered using the range limitation method after the discovery is made according to the trajectory tracking method, the phase corresponding to the local minimum may be obtained.

A predetermined phase change period in the trajectory tracking method and a predetermined change range in the range limitation method for discovering the phase of the first signal or the second signal with the smallest standard deviation information in the entire phase range will be described below.

8.1 Predetermined Phase Change Period Acquisition Method

As described above with reference to FIG. 57, a bright part and a dark part indicating the degree of the standard deviation information (hereinafter referred to as light and shade) may be repeated in a certain pattern. Accordingly, in order to obtain the phase of the first signal or the second signal with the smallest standard deviation information in the entire phase range using the trajectory tracking method, a period in which light and shade is repeated in a certain pattern may be necessary.

Figure 61:
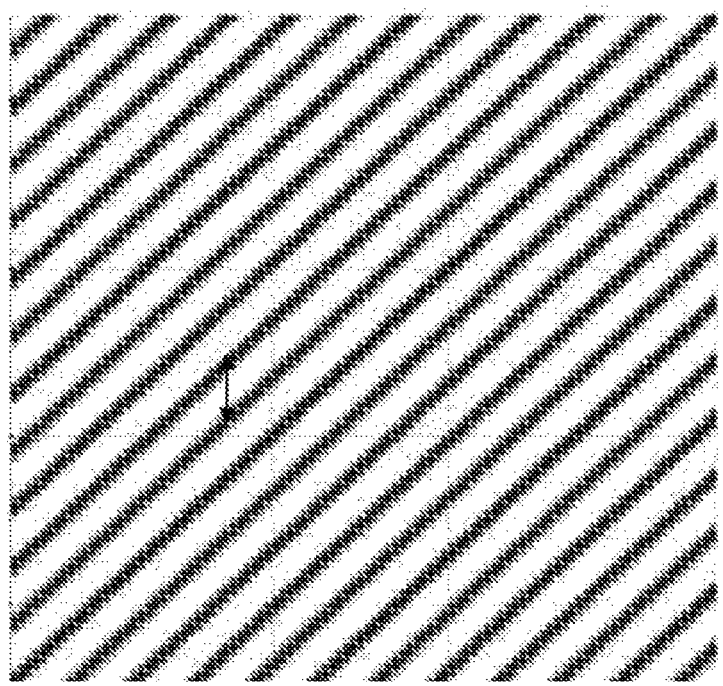
FIG. 61 is a diagram for describing a change in a fill factor (FF) along with a phase change according to an embodiment.

FIG. 61 is a diagram showing a fill factor (FF) of an image obtained by the controller 130 along with the change in phase, wherein an x-axis indicates a phase corresponding to a first signal and a y-axis indicates a phase corresponding to a second signal. Here, the FF may indicate the ratio of pixels based on the position corresponding to the first signal and the position corresponding to the second signal to all pixels of an image to be generated by the controller 130 when the scanning module 110 emits light toward the object O. However, the present invention is not limited thereto, and the FF may indicate the ratio of the area occupied by a path in which light has passed according to the scanning pattern to the area where the scanning is performed when the scanning module 110 is scanning the object O. In detail, in FIG. 61, a bright part may indicate a part having a high FF, and a dark part may indicate a part having a low FF. For convenience of description, the bright part and the dark part will be expressed as light and shade.

According to an embodiment, the light-and-shade pattern of FIG. 57 and the light-and-shade pattern of FIG. 61 may be the same. In detail, a period in which the bright part indicated by the black arrow is repeated in FIG. 57 may be the same as a period in which the bright part indicated by the black arrow is repeated. Accordingly, the period in which light and shade is repeated in a certain pattern in FIG. 57 may be calculated using the period of a pattern in which light and shade is repeated in FIG. 61.

According to an embodiment, in order to calculate a pattern in which an FF is repeated according to FIG. 61, information of the driving signal generated by the controller 130 may be necessary. Here, the controller 130 may use an alternating current signal as the driving signal. Accordingly, since the waveform of the alternating current signal is repeated in a certain period, the controller 130 may obtain a pattern in which light and shade is repeated in one axis direction in FIG. 61 by calculating a period in which an alternating current signal of the first signal or the second signal of the driving signal is repeated.

$$Y = A\sin\left(2\pi f_y \left(t + \frac{\phi_y}{2\pi f_y}\right)\right) \quad \text{[Formula 5]}$$

The waveform of the alternating current signal in which the second signal of the driving signal is generated may be expressed as Formula 5 above. Here, Y may indicate the position corresponding to the second signal, and A may indicate the amplitude of the second signal. Also, $f_y$ may be the frequency component of the second signal, and $\phi_y$ may be the phase component of the second signal. Also, like the second signal, the first signal may also be expressed using Formula 5 above, and the frequency component and the phase component for expressing the position of the first signal may be expressed as the frequency component and the phase component corresponding to the x-axis direction.

Here, when the phase component of the first signal $\phi_x$ is determined, the same position may be repeated for the second signal according to the phase component of the second signal. For example, when the phase component of the first signal is zero, the phase component of the second signal $\phi_y$ may be repeated every $$\frac{\pi}{n_x}.$$

Here, $n_x$ may be a component obtained by dividing the frequency component of the first signal by the greatest common divisor (hereinafter, referred to as GCD) obtained using the frequency component of the first signal and the frequency component of the second signal. Likewise, $n_y$ may be a component obtained by dividing the frequency component of the second signal by the GCD, and $n_x$ and $n_y$ may be coprime integers which have no divisors except one.

In the case of the second signal, the position corresponding to the second signal may be repeated whenever $\phi_y$ is $$\frac{\pi}{n_x},$$

and thus the position corresponding to the second signal may repeatedly appear whenever $$\frac{\phi_y}{2\pi f_y}$$

is $$\frac{1}{2n_x n_y}.$$

Even in the case of the first signal, the position corresponding to the first signal may appear repeatedly whenever $\phi_x$ is $$\frac{\pi}{n_y},$$

and thus the first signal may appear repeatedly whenever $$\frac{\phi_x}{2\pi f_x}$$

is $$\frac{1}{2n_x n_y}.$$

In this case, the position corresponding to the second signal may be repeated according to $$\frac{1}{2n_x n_y}$$

only when the GCD is 1. Thus, when the GCD is not 1, the phase may be repeated by $$\frac{1}{2n_x n_y GCD}$$

in order to repeat the position corresponding to the first signal or the second signal. Here, $$\frac{1}{2n_x n_y GCD}$$

is $$\frac{GCD}{2 f_x f_y},$$

and thus the position of the first signal or the second signal may appear repeatedly when a period in which the phase component of the first signal or the second signal changes is $$\frac{GCD}{2f_x f_y}.$$

Therefore, when the predetermined phase change period is $$\frac{GCD}{2f_x f_y},$$

the FF corresponding to FIG. 61 may appear repeatedly. However, the present invention is not limited thereto, and the FF may appear repeatedly even when the predetermined phase change period is an integer multiple of $$\frac{GCD}{2f_x f_y}.$$

8.1.1 Discovery of Phase Calibration Value Using Predetermined Phase Change Period A phase may be calibrated by obtaining the phase of the first signal or the second signal with the smallest standard deviation information using the above-described predetermined phase change period. In detail, the trajectory tracking method may be used on the basis of the predetermined phase change period. Also, even when the range limitation method is used on the basis of the phase obtained by the controller 130 using the trajectory tracking method, the predetermined phase change period may be used.

8.1.1.1 Trajectory Tracking Method Using Predetermined Phase Change Period

Figure 62:
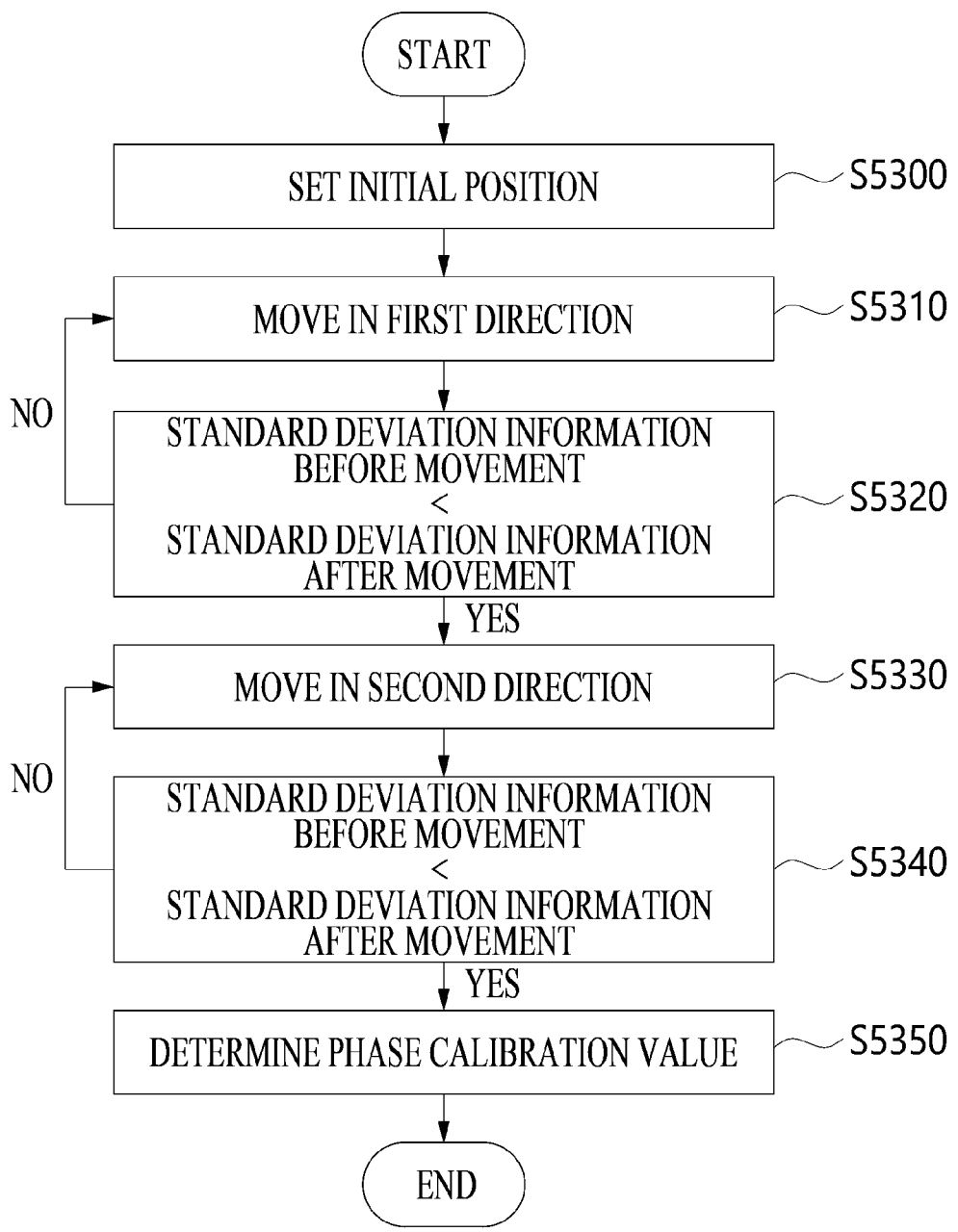
FIG. 62 is a flowchart showing that discovery is performed along a trajectory to discover a phase in which standard deviation information is smallest according to an embodiment.

FIG. 62 is a flowchart showing a process of discovering the phase of the first signal or the second signal having the smallest standard deviation information when the trajectory tracking method is performed based on the predetermined phase change period. In detail, like the above-described trajectory tracking method, the phase of the first signal or the second signal having the smallest standard deviation information may be discovered in the phase direction for the first signal or the second signal on the basis of the predetermined phase change period.

Referring to FIG. 62, the setting of the initial position (S5300) may include setting the phase of the first signal or the second signal at an initial stage when the phase of the first signal or the second signal with the smallest standard deviation information is discovered using the trajectory tracking method. In detail, the controller 130 may obtain the position corresponding to the first signal or the position corresponding to the second signal by changing the phase component of the first signal or the second signal to a phase perpendicular to the phase component of the first signal or the second signal of the driving signal which is input to drive the driving unit 1101. Here, an angle at which phase components are perpendicular to each other may refer to 90 degrees or an angle close to 90 degrees which may be regarded as an angle at which the phase components are substantially perpendicular to each other. However, the initial phase may be set to have a phase difference substantially close to 45 degrees depending on a direction in which the phase is discovered. However, the present invention is not limited thereto, and the initial phase may be set in the entire phase range. For example, when a signal having a resonant frequency is input to an object, the phase of a signal output according to the signal input to the object may be delayed by 90 degrees from the phase of the signal having the resonant frequency. Accordingly, when the first signal or the second signal having the resonant frequency of the scanning unit 1100 is input to the scanning unit 1100, the phase of the output signal of the scanning unit may be changed to an angle close to 90 degrees compared to the first signal or the second signal of the driving signal input from the controller 130. Accordingly, the initial phase of the first signal or the second signal at which the discovery is started may be set to 90 degrees or an angle close to 90 degrees. Thus, when the initial position for the discovery is set to 90 degrees or an angle close to 90 degrees, the controller 130 can reduce the time required for the trajectory tracking method to discover a phase delay between the driving signal and the scanning unit output signal.

Also, referring to FIG. 62, the shift in the first direction (S5310) may include obtaining standard deviation information having the phase of the first signal or the second signal changed by the controller 130 according to the predetermined phase change period in the phase direction corresponding to the first signal or the phase direction corresponding to the second signal. Here, referring back to FIG. 58, the first direction may be an x-axis indicating the phase of the first signal or an y-axis indicating the phase of the second signal. Likewise, the second direction may be an x-axis indicating the phase of the first signal or a y-axis indicating the phase of the second signal. For convenience of description, the following description assumes that the first direction is an x-axis direction indicating the phase of the first signal and the second direction is a y-axis direction indicating the phase of the second signal. Also, the controller 130 may change the phase of the driving signal in the first direction or in the second direction by a predetermined phase change period, and the change may be expressed as a shift. For example, a phase before the controller 130 changes the phase of the driving signal in the first direction by the predetermined phase change period may be expressed as a pre-shift phase, and a phase after the controller 130 changes the phase of the driving signal by the predetermined phase change period may be expressed as a post-shift phase. Accordingly, the controller 130 may obtain standard deviation information using the phase after the shift in the first direction. In this case, the phase may not change in the second direction but may be changed to the post-shift phase in the first direction.

Also, referring to FIG. 62, the comparing of pre-shift standard deviation information to post-shift standard deviation information (S5320) includes causing the controller 130 to compare standard deviation information corresponding to the pre-shift phase to standard deviation information corresponding to the post-shift phase during the shift in the first direction. For example, when the standard deviation information corresponding to the phase before the shift in the first direction is larger than the standard deviation information corresponding to the phase after the shift in the first direction, the controller 130 may obtain the phase after the shift in the first direction as the current phase and then may change the current phase in the first direction by the predetermined phase change period. Also, when the standard deviation information corresponding to the phase before the shift in the first direction is smaller than the standard deviation information corresponding to the phase after the shift in the first direction, the controller 130 may obtain the phase before the shift in the first direction as the current phase and then may change the current phase in the second direction by the predetermined phase change period.

Also, referring to FIG. 62, the shift in the second direction (S5330) may include causing the controller 130 to obtain a phase with the smallest standard deviation information in the first direction and shift the phase in the second signal. In detail, when the controller 130 performs comparison on the standard deviation information corresponding to the phase shift in the first direction and obtains the phase of the first signal with the minimal standard deviation information, the phase of the second direction may be changed in the second direction by the predetermined phase change period such that the standard deviation information corresponding to the phase of the second signal in the second direction is minimal. Accordingly, the phase in the first direction may not be changed, and only the phase in the second direction may be changed by the predetermined phase change period. The controller 130 may obtain the standard deviation information using the phase after the shift in the second direction.

Also, referring to FIG. 62, the comparing of pre-shift standard deviation information to post-shift standard deviation information (S5340) includes causing the controller 130 to compare standard deviation information corresponding to the pre-shift phase to standard deviation information corresponding to the post-shift phase during the shift in the second direction. For example, when the standard deviation information corresponding to the phase before the shift in the second direction is larger than the standard deviation information corresponding to the phase after the shift in the second direction, the controller 130 may obtain the phase after the shift in the second direction as the current phase and then may change the current phase in the second direction by the predetermined phase change period. Also, when the standard deviation information corresponding to the phase before the shift in the second direction is smaller than the standard deviation information corresponding to the phase after the shift in the second direction, the controller 130 may obtain the phase before the shift in the second direction as the current phase.

Also, referring to FIG. 62, the determining of the phase calibration value (S5350) may include calibrating the phase of the driving signal using the phase of the first signal obtained by the controller 130 through the shift in the first direction and calibrating the phase of the driving signal using the phase of the second signal obtained by the controller 130 through the shift in the second direction. In detail, the standard deviation information corresponding to the phase of the first signal after the final shift in the first direction and the phase of the second signal after the final shift in the second direction may indicate a value with the smallest standard deviation information in the entire phase range. Accordingly, the phase of the first signal and the phase of the second signal which are obtained by the controller 130 may indicate the degree to which the phase of the scanning unit output signal is delayed from the phase of the driving signal. Accordingly, the phase of the driving signal may be calibrated using the phase of the first signal and the phase of the second signal which are obtained by the controller 130, and the controller 130 may obtain or provide an image using the acquisition signal values and the positions corresponding to the first signal and the second signal of the driving signal.

According to an embodiment, the method of discovering the phase with the smallest standard deviation information as shown in FIG. 62 may be equal to the discovery direction shown in FIG. 58. In FIG. 62, when a direction in which the phase of the driving signal is moved for the first time, i.e., the first direction, is a y-axis, the controller 130 may discover a phase according to a movement path from the black star, which is an initial setting phase, to the white star in order to discover a value with the smallest standard deviation, as shown in FIG. 58.

Figure 63:
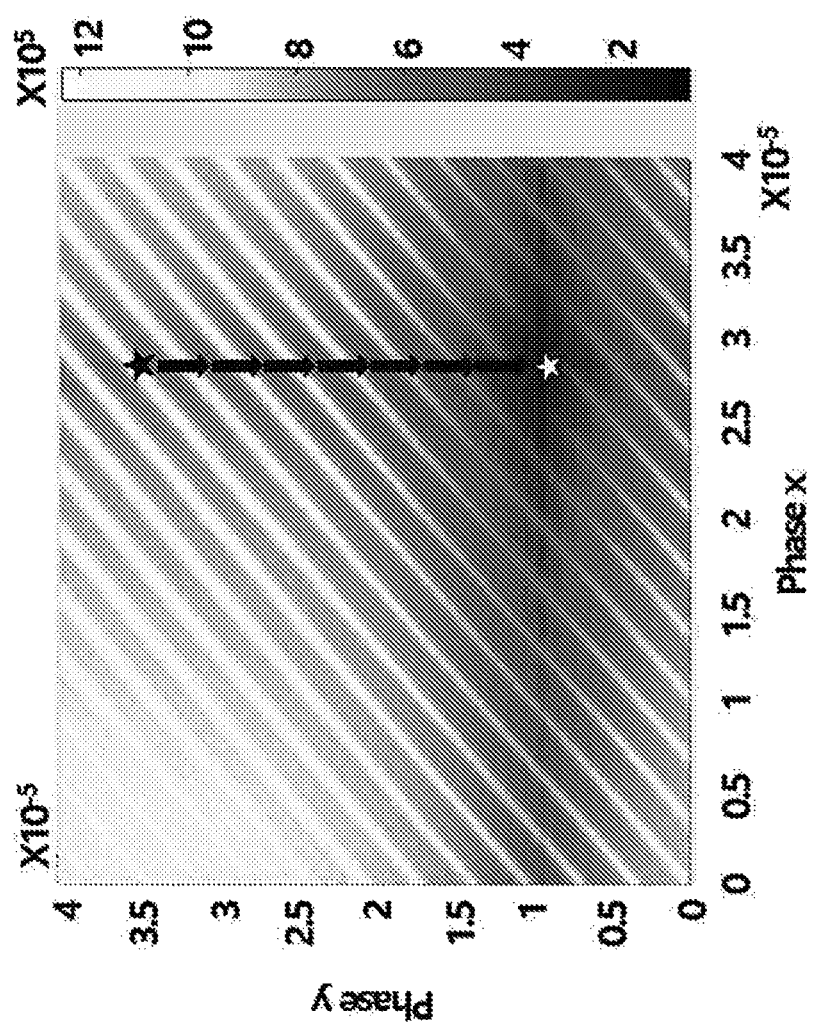
FIG. 63 is a diagram for describing a method of finding a phase of minimizing standard deviation information along a trajectory according to an embodiment.
Figure 64:
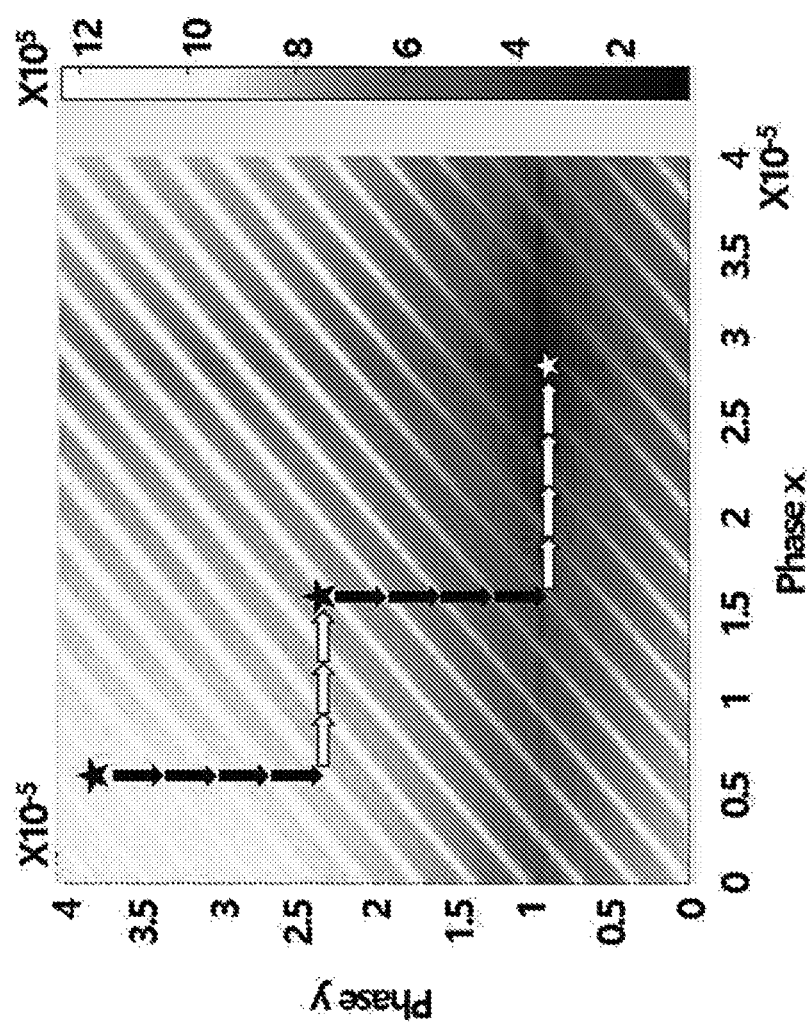
FIG. 64 is a diagram for describing a method of finding a phase of minimizing standard deviation information along a trajectory according to an embodiment.

FIGS. 63 and 64 are diagrams showing a path for discovering the phase of the first signal or the second signal with the smallest standard deviation information using the trajectory tracking method. In FIGS. 63 and 64, an x-axis may indicate the phase corresponding to the first signal, and a y-axis may indicate the phase corresponding to the second signal.

According to an embodiment, a path for the controller 130 to discover the phase of the first signal or the second signal with the smallest standard deviation information using the predetermined phase change period is not limited to the path shown in FIG. 58 and may be the path shown in FIG. 63. For example, when the initial phase at which the discovery is started is the same as at least one of the phases of the first signal and the second signal having the smallest standard deviation information, the controller 130 may discover a phase with the smallest standard deviation information in only one direction.

According to another embodiment, a path for the controller 130 to discover the phase of the first signal or the second signal with the smallest standard deviation information using the predetermined phase change period is not limited to that shown in FIG. 58 and may be the path shown in FIG. 64. In detail, as shown in FIG. 58, the phase of the driving signal with the smallest standard deviation information may be discovered in one direction first, and then the phase of the driving signal with the smallest standard deviation information may be discovered in another direction. However, as shown in FIG. 64, the discovery is performed in one direction, in another direction at the phase in which the standard deviation information is not smallest, and then in the one direction again. However, the present invention is not limited thereto, and the controller 130 may perform the discovery alternately in the first direction and in the second direction. When a value with the smallest standard deviation information is discovered in one direction, the shift direction may no longer be changed.

According to another embodiment, the controller 130 may discover the phase of the first signal or the second signal with the smallest standard deviation in a diagonal direction between the first direction and the second direction. In detail, as shown in FIG. 57, since light and shade, which indicates the degree of the standard deviation information, is repeated in a certain pattern, the standard deviation information is repeated in the first direction or in the second direction. Furthermore, light and shade, which indicates standard deviation information, is repeated in a certain pattern in a diagonal direction between the first direction and the second direction. Accordingly, the controller 130 may discover a phase with the smallest standard deviation information in the diagonal direction between the first direction and the second direction. In this case, when the discovery is performed in the diagonal direction between the first direction and the second direction, the discovery may be performed in the diagonal direction between the first direction and the second direction by changing the phase by the half of the aforementioned predetermined phase change period. However, the present invention is not limited thereto. When the discovery is performed in a direction in which both of the phase in the first direction and the phase in the second direction are increased or decreased, the discovery may be performed with any phase change value regardless of the predetermined phase change period. In this case, the controller 130 may obtain a phase with the minimum standard deviation information according to the discovery in the diagonal direction. Also, the controller 130 may additionally discover the phase of the driving signal with the smallest standard deviation information in the first direction or in the second direction at the phase with the smallest standard deviation information discovered in the diagonal direction.

8.1.1.2 Phase Discovery Using Range Limitation Method after Trajectory Tracking Method When the controller 130 obtains the phase of the driving signal with the smallest standard deviation information by the trajectory tracking method, the obtained phase of the driving signal may be the phase corresponding to the local minimum. Accordingly, the controller 130 may obtain the phase with the smallest standard deviation information in the entire phase range by using a predetermined phase variation for the phase of the driving signal discovered by the trajectory tracking method.

Figure 65:
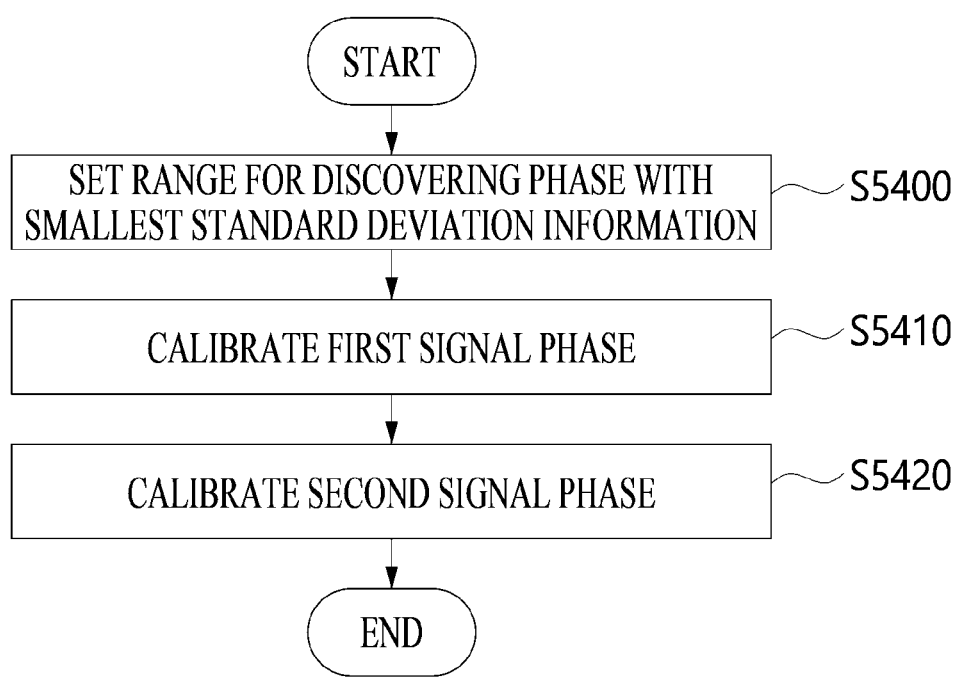
FIG. 65 is a flowchart for describing a method of discovering a phase in which standard deviation information is smallest within a limited range after discovery is made along a trajectory according to an embodiment.

FIG. 65 is a flowchart showing a process of obtaining a phase corresponding to the trajectory tracking method through a predetermined phase change period, discovering a phase with the smallest standard deviation information in the entire phase range using the range limitation method, and calibrating the phase of the first signal or the second signal to the corresponding phase in order for the controller 130 to perform phase calibration.

Referring to FIG. 65, the setting of a range for discovering the phase with the smallest standard deviation information may include causing the controller 130 to set the phase obtained by the controller 130 using the trajectory tracking method as the center of the set range and to obtain the phase having the smallest standard deviation information in the entire phase range. In detail, since the discovery is performed while the phase of the driving signal is changed by the predetermined phase change period through the trajectory tracking method, the phase with the smallest standard deviation information in the entire phase range may be positioned at a distance less than the predetermined phase change period from the phase obtained by the controller 130 using the trajectory tracking method. Accordingly, the phase obtained by the controller 130 through the trajectory tracking method may be set as a center point, the range of the phase corresponding to the first signal may be set to be the predetermined phase change period from the center point, and the range of the phase corresponding to the second signal may also be set to be the predetermined phase change period from the center point. Accordingly, the controller 130 may obtain the phase with the smallest standard deviation information in the entire phase range by using the range limitation method within a certain range that is set from the center point.

However, the present invention is not limited thereto, and the controller 130 may set an arbitrary range on the basis of the phase obtained by the controller 130 using the trajectory tracking method. Here, a phase which is a reference for setting the range may be the center point within the set range and may be positioned within the boundary of the set range. Also, the arbitrary range may be set using the predetermined phase change period or may be set using an arbitrary phase interval instead of the predetermined phase change period. However, in order to reduce the time required for the controller 130 to discover the phase with the smallest standard deviation information, the arbitrary range set for the range limiting method may be a phase interval smaller than the predetermined phase change period.

Also, referring to FIG. 65, the calibrating of the phase of the first signal (S5410) and the calibrating of the phase of the second signal (S5420) may include calibrating the phase of the first signal or the second signal on the basis of the phase obtained by the controller 130 when the range for discovering the phase with the smallest standard deviation information is set. In detail, the phase obtained by the controller 130 when the range for discovering the phase with the smallest standard deviation information is set may be a delayed phase between the phase of the driving signal and the phase of the scanning unit output signal. Accordingly, the phase of the first signal and the second signal of the driving signal may be calibrated with the delayed phase.

8.1.1.3 Phase Discovery Using Predetermined Unit after Trajectory Tracking Method As described above, when the controller 130 obtains the phase of the driving signal with the smallest standard deviation information by using the trajectory tracking method, the obtained phase of the driving signal may be the phase corresponding to the local minimum. Accordingly, the controller 130 may obtain the phase with the smallest standard deviation information in the entire phase range using a unit smaller than the predetermined phase change period on the basis of the phase of the driving signal discovered by the trajectory tracking method.

In detail, when the delayed phase of the driving signal is discovered using the trajectory tracking method by the predetermined phase change period, the obtained phase may be the phase corresponding to the local minimum of the standard deviation information. The local minimum may be obtained when the phase with the smallest standard deviation information in the entire phase range is present in a range smaller than the predetermined phase change period from the phase discovered using the trajectory tracking method.

Accordingly, in order for the controller 130 to obtain the phase with the smallest standard deviation information in the entire phase range, a predetermined unit, which is a unit smaller than the predetermined phase change period, may be used.

Figure 66:
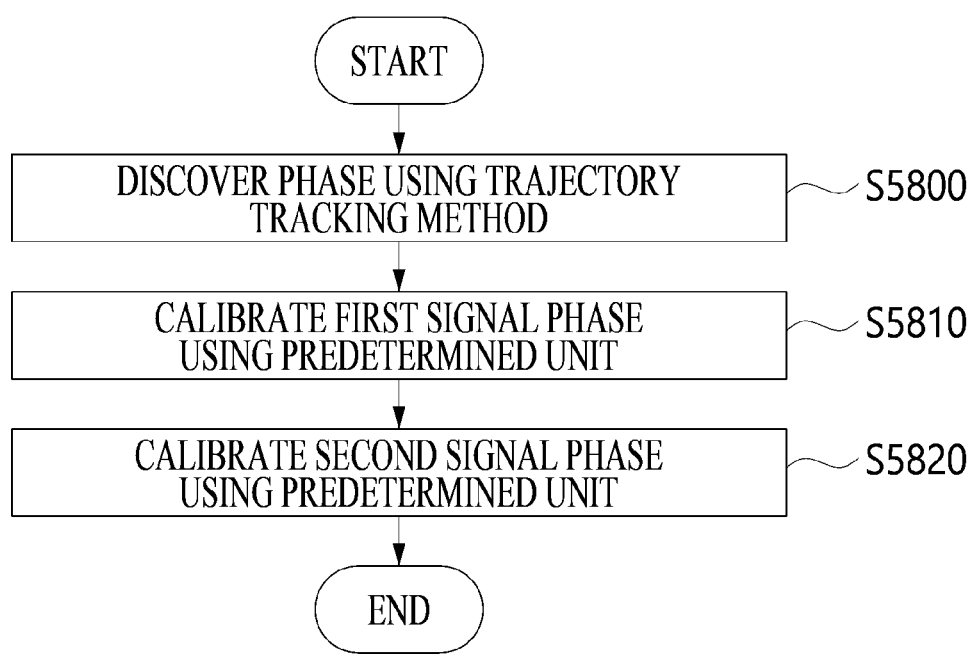
FIG. 66 is a flowchart for describing a method of discovering a phase in which standard deviation information is smallest within a shortened phase discovery unit after phase discovery is made along a trajectory in order to perform a phase calibration according to an embodiment.

FIG. 66 is a flowchart showing a process of discovering a phase using the trajectory tracking method and then obtaining the phase with the minimal standard deviation information in the entire phase range using a unit smaller than the phase change period used in the trajectory tracking method.

Referring to FIG. 66, the discovering of a phase using the trajectory tracking method (S5800) may include discovering the phase with the smallest standard deviation information corresponding to the trajectory tracking method by using the aforementioned predetermined phase change period. In detail, the phase may be discovered in the first direction and the second direction by the predetermined phase change period, and the phase discovery may be performed in a diagonal direction between the first direction and the second direction, rather than in the first direction and the second direction. For convenience of description, the following description assumes that when the phase is discovered using the trajectory tracking method, the phase discovery is performed in the first direction and the second direction.

Referring to FIG. 66, the calibrating of the phase of the first signal using the predetermined unit (S5810) and the calibrating of the phase of the second signal using the predetermined unit (S5820) may include discovering the phase with the minimal standard deviation information using the predetermined unit and calibrating the phase of the first signal and the phase of the second signal using the corresponding phase. Here, the predetermined unit may be a phase change value having a smaller value than the predetermined phase change period. In detail, the phase obtained by the controller 130 when the phase discovery is performed using the trajectory tracking method (S5800) may be a local minimum, not the phase with the minimal standard deviation information in the entire phase range. Accordingly, by decreasing a phase variation in the phase obtained using the trajectory tracking method, the phase with the minimal standard deviation information in the entire phase range may be discovered.

In detail, when the discovery has been performed in any one of the first direction and the second direction in order to obtain the phase in the trajectory tracking method, the discovery may be re-performed using the predetermined unit in the other direction, which is different from the one of the first direction and the second direction, i.e., the final direction in which the discovery has been performed to obtain the phase. For example, when the direction in which the discovery has been finally performed to obtain the phase in the trajectory tracking method is the first direction, the discovery may be performed in the second direction using a predetermined unit in which a phase variation is reduced.

In this case, when the phase with the smallest standard deviation information is discovered in the corresponding direction after the discovery is performed using the predetermined unit in a direction different from the final discovery direction of the trajectory tracking method, the phase with the standard deviation information may be discovered in a direction different from the direction in which the discovery is performed using the predetermined unit for the first time. For example, when the direction in which the discovery is performed using the predetermined unit for the first time is the second direction, the phase with the minimal standard deviation information may be discovered in the first direction on the basis of the phase of the second signal corresponding to the second direction with the minimal standard deviation information.

When the controller 130 discovers and obtains, using the predetermined unit, the phase of the first signal corresponding to the first direction and the phase of the second signal corresponding to the second direction with the minimal standard deviation information in the entire phase range, the phases of the first signal and the second signal of the driving signal may be calibrated with the obtained phase.

8.2 Increase in FF Through Change of Driving Signal Input to Driving Unit 1101

In order for the quality of an image obtained by the controller 130 to be determined as good, there may need to be no phase delay between the driving signal and the scanning unit output signal, or the controller 130 may need to calibrate the phase of the driving signal by the delayed phase when the image is obtained. In this case, the quality of the image may be expressed as "good." Also, as another cause, when the scanning module 110 emits light to the object O, the ratio of the area occupied by the scanning pattern to the area to which the light is emitted or the ratio of a pixel position where an acquisition signal value is present in an image obtained by the controller 130 to all pixels of the obtained image may be high. In this case, the quality of the image may be expressed as "good." Here, the ratio of the area occupied by the scanning pattern to the area to which the light is emitted or the ratio of a pixel position where an acquisition signal value is present to all the pixels of the image obtained by the controller 130 may be expressed as an PP. Also, the scanning pattern in the area to which the light is emitted may include a Lissajous pattern.

According to an embodiment, the phase delay between the driving signal and the scanning unit output signal may not be large or may be reduced by calibrating the phase of the driving signal. In this case, as the ratio of the area occupied by the scanning pattern to the area to which light is emitted increases, the ratio of the pixel position where the acquisition signal value is present to all the pixels of the image obtained by the controller 130 may increase. However, the present invention is not limited thereto. Even when the phase delay between the driving signal and the scanning unit output signal is small or the difference between the calibrated phase of the driving signal and the phase of the scanning unit output signal is great, the FF may be high.

A method of increasing the FF of the image obtained by the controller 130 by changing the phase of the driving signal will be described below.

8.2.1 Relationship Between FF and Predetermined Phase Change Period

Figure 67:
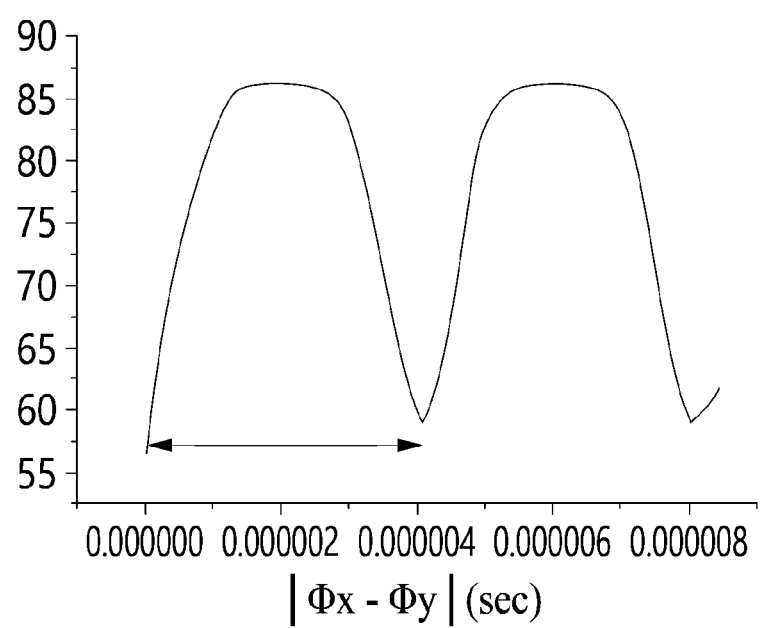
FIG. 67 is a diagram for describing a change in an FF along with a phase difference between driving signals according to an embodiment.
Figure 68:
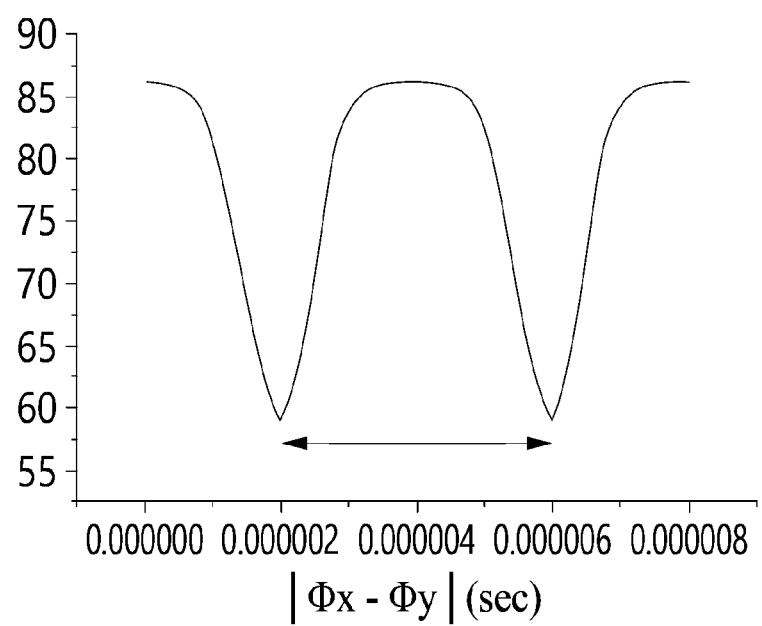
FIG. 68 is a diagram for describing a change in an FF along with a phase difference between driving signals according to an embodiment.

FIGS. 67 and 68 are diagrams showing the change in FF value due to the difference in phase between the first signal and the second signal, wherein an x-axis indicates a time unit indicating the phases of the first signal and the second signal among signals for generating the scanning pattern, including the driving signal, the scanning unit driving signal, and the scanning unit output signal, and a y-axis indicates FF in units of %.

In detail, FIG. 67 is a diagram showing the change in FF due to the difference between the phase of the first signal and the phase of the second signal when values obtained by dividing the frequency component of the first signal and the frequency component of the second signal by the greatest common divisor of the frequency components of the first signal and the second signal (hereinafter referred to as a unit frequency of the first signal and a unit frequency of the second signal) are all odd numbers.

Also, FIG. 68 is a diagram showing the change in FF due to the difference between the phase of the first signal and the phase of the second signal when only one of the unit frequency of the first signal and the unit frequency of the second signal is an even number.

According to an embodiment, the FF may be repeated depending on the difference between the phase of the first signal and the phase of the second signal. The intervals indicated by the black arrows shown in FIGS. 67 and 68 indicate predetermined phase change periods. In detail, a period in which a value for maximizing the FF due to the difference between the phase of the first signal and the phase of the second signal is repeated is as follows.

$$|\phi_x - \phi_y| = \tfrac{1}{2}\text{Dip} + N*\text{Dip} = A \qquad \text{[Formula 6]}$$

$$|\phi_x - \phi_y| = 0 + N*\text{Dip} = A \qquad \text{[Formula 7]}$$

Here, Formula 6 above indicates a period in which the difference between the phase of the first signal and the phase of the second signal where the FF is maximized (hereinafter referred to as the phase difference) is repeated when the unit frequency of the first signal and the unit frequency of the second signal are all odd numbers. In detail, Dip may indicate a predetermined phase change period, and N may indicate an integer including a natural number. Also, A may indicate a period in which a phase difference for maximizing the FF of the image obtained by the controller 130 is repeated.

Also, Formula 7 indicates a period in which a phase difference for maximizing the FF is repeated when only one of the unit frequency of the first signal and the unit frequency of the second signal is an even number. In detail, Dip may indicate a predetermined phase change period, and N may indicate an integer including a natural number. Also, A may indicate a period in which a phase difference for maximizing the FF of the image obtained by the controller 130 is repeated.

Figure 69:
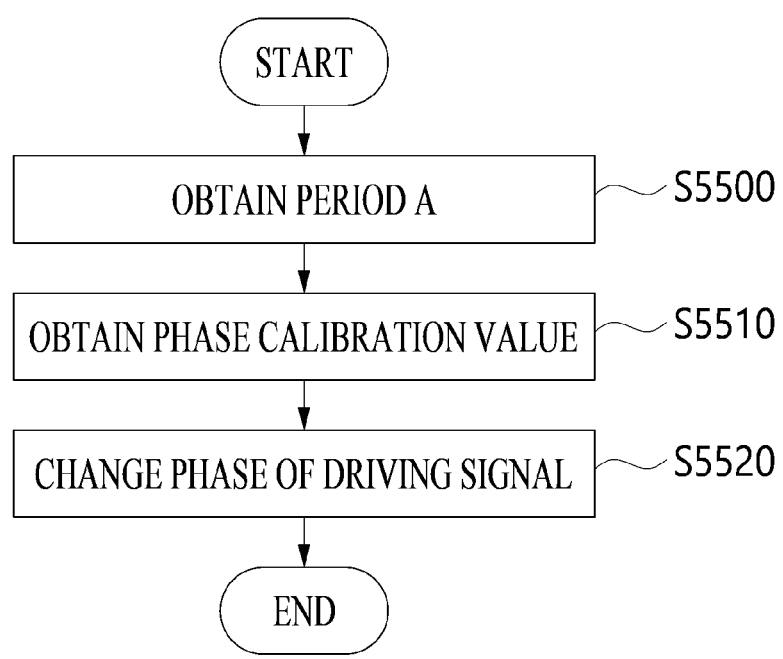
FIG. 69 is a flowchart for describing that an image having a high FF is obtained by adjusting the phase of a driving signal according to an embodiment.

FIG. 69 is a flowchart showing a process of adjusting the phase of the driving signal and increasing the FF of the image obtained by the controller 130.

Referring to FIG. 69, the obtaining of period A (S5500) may include causing the controller 130 to obtain the period of the phase difference in which a high FF is repeated on the basis of the frequency component of the driving signal. In detail, in Formula 6 or Formula 7, Dip may indicate a predetermined phase change period and thus may be obtained by the frequency component of the first signal and the frequency component of the second signal. Here, when the driving signal is input to the driving unit 1101, the frequency components of the first signal and the second signal may not change. Thus, a period A in which a phase difference for maximizing the FF of the image obtained by the controller 130 is repeated may be set when the driving signal is input to the driving unit 1101, and period A may be obtained by the controller 130.

Also, referring to FIG. 69, the obtaining of the phase calibration value (S5510) includes causing the controller 130 to obtain a delayed phase value between the phase of the driving signal and the phase of the scanning unit output signal. In detail, when the controller 130 obtains the delayed phase value, the aforementioned standard deviation or the predetermined phase change period may be used. However, the present invention is not limited thereto, and even when the delayed phase value between the phase of the driving signal and the phase of the scanning unit output signal is obtained by a method other than the above-described method, the controller 130 may obtain the delayed phase value.

Also, referring to FIG. 69, the changing of the phase of the driving signal (S5520) may include changing the phase of the driving signal using the phase of at least one of the obtained period A, a value obtained by delaying the phase of the first signal, a value obtained by delaying the phase of the second signal, and the driving signal. For convenience of description, the following description assumes that the phase of the second signal is changed. In detail, when a phase delay is present between the phase of the driving signal and the phase of the scanning unit output signal, the scanning unit output signal may be obtained by adding the delayed phase to the phase of the driving signal. Also, since the period for maximizing the value of the FF in the scanning unit output signal is also A, the difference between the phases of the first signal and the second signal of the scanning unit output signal may be a. Accordingly, the phase of the second signal of the scanning unit output signal and the phase of the first signal of the scanning unit output signal may have a difference of a. Here, the phase of the first signal of the scanning unit output signal may be a value obtained by adding the degree to which the phase of the first signal is delayed to the phase of the first signal of the driving signal, and the phase of the second signal of the scanning unit output signal may be a value obtained by adding the degree to which the phase of the second signal is delayed to the phase of the second signal of the driving signal. Accordingly, the following formula may be obtained.

$$\phi_y = \phi_x + \phi_{ex} - \phi_{ey} \mp A \qquad \text{[Formula 8]}$$

Referring to Formula 8 above, the phase of the second signal of the driving signal to be changed, i.e., $\phi_y$, may have a phase difference of a from the phase of the first signal of the scanning unit output signal, which is a value obtained by adding the delayed phase of the first signal of the driving signal to the phase of the first signal of the driving signal, minus the delayed phase of the second signal of the driving signal. Accordingly, when the phase of the first signal of the driving signal is not changed and the phase of the second signal of the driving signal is changed according to Formula 4, the controller 130 may obtain an image having a high FF.

9 Acquisition of Image with FF Increased Using Plurality of Driving Signals

In the case of a device for emitting light to an object O using a scanning pattern including a Lissajous pattern, a spiral pattern, and a raster pattern and for obtaining and generating an image, the ratio of the area occupied by the scanning pattern to the area to which the light is emitted or the ratio of the pixel position where an acquisition signal value is present to all pixels of an image obtained by the controller 130, i.e., an FF, is not 100%, and thus the quality or resolution of the image may be low.

Figure 70:
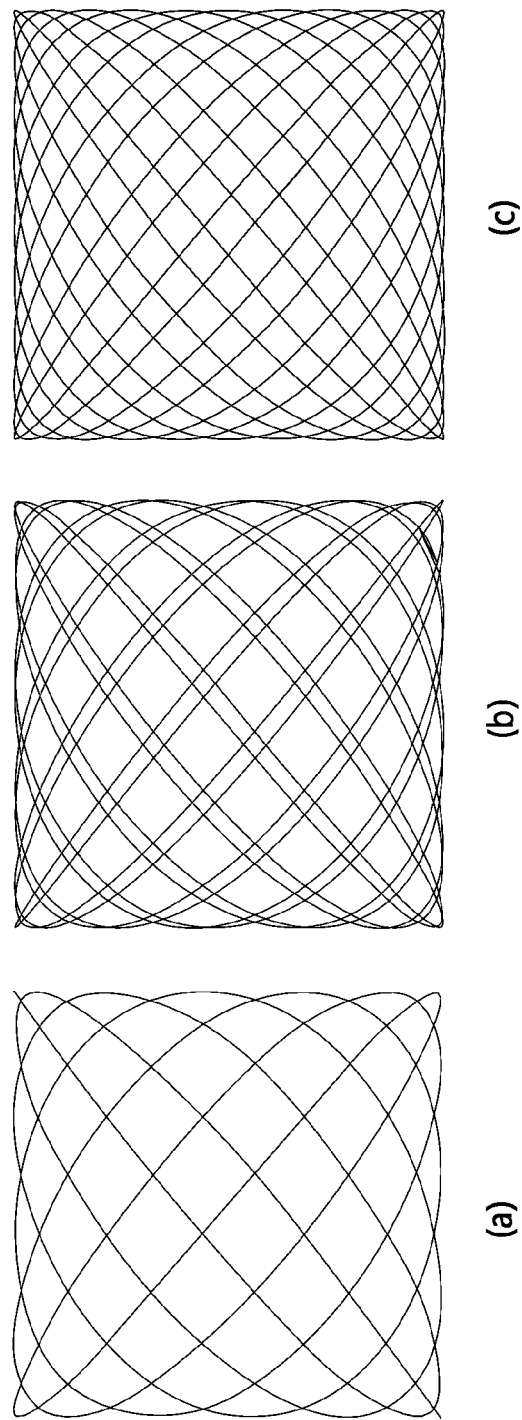
FIG. 70 is a diagram for describing that a light path is changed by changing the phase of a driving signal according to an embodiment.

FIG. 70 is a diagram showing that a path of emitted light varies when a phase is changed.

Also, referring to FIG. 70, a path in which light is emitted may vary when the phase component of the driving signal for generating a Lissajous pattern is changed. Accordingly, when at least one of the phases of the first signal and the second signal of the driving signal is changed, a scanning pattern having a high FF as shown in the image (b) or (c) of FIG. 70 may be provided instead of a scanning pattern having a low FF as shown in the image (a) of FIG. 70. However, the phase having a high FF as shown in the image (b) or (c) of FIG. 70 may not fill all the pixels of the image. Accordingly, by overlapping acquisition signal values obtained at the pixel position of the image obtained by controller 130 by changing the phase, the controller 130 may obtain an image having an FF which is close to 100%.

Figure 71:
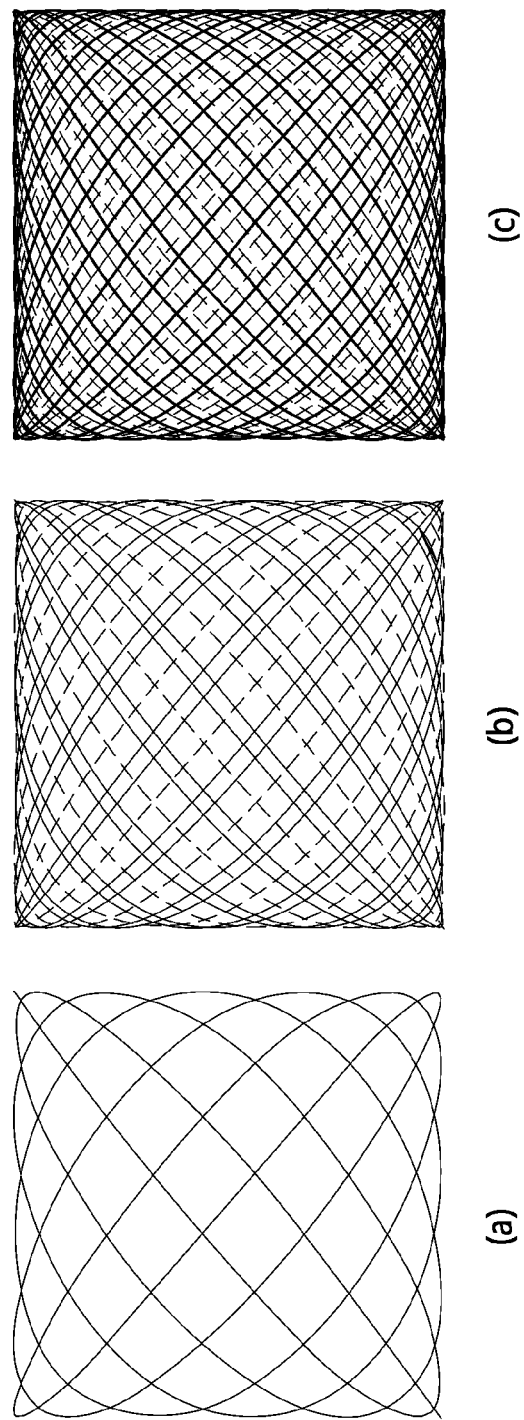
FIG. 71 is a diagram for describing that a position where a light pattern passes is overlapping while the phase of a driving signal is being changed according to an embodiment.

FIG. 71 is a diagram showing that the phase of the driving signal is changed and that a position through which the scanning pattern has passed overlaps. In detail, the image (a) of FIG. 71 shows a path of light when the phase component of the driving signal is not changed. The path of light of the image (a) shown in FIG. 71 does not pass through many pixels in the entire area where the scanning is performed, which may mean that the FF is small. The image (b) shown in FIG. 71 is a diagram showing that a scanning pattern in which the driving signal is changed by a phase that is predetermined for the phase component when the phase component of the driving signal is not changed is overlapped with a scanning pattern in which the phase component of the driving signal is not changed. The scanning pattern in which the phase component of the driving signal is changed is shown by dashed lines. The image (c) shown in FIG. 71 is a diagram showing that an additionally generated scanning pattern is further overlapped with the overlapped scanning pattern shown in the image (b) of FIG. 71 by further changing the phase component of the driving signal by a predetermined phase after changing the phase component by a predetermined phase. The additionally generated scanning pattern is shown by thick lines. However, the thickness of the line of the path through which the scanning pattern passes is for distinguishing various scanning patterns and may not occupy the pixel area on the image as much as the area occupied by the thickness of the line.

According to an embodiment, as shown in FIG. 71, the phase component of the driving signal may be changed by a predetermined phase. At this point, acquisition signal values obtained at each pixel position of the image may be overlapped with each other. Here, a predetermined phase at which the number of overlaps of signal values and the phase component of the driving signal are changed may be obtained using the aforementioned predetermined phase change period for calibrating the phase.

Figure 72:
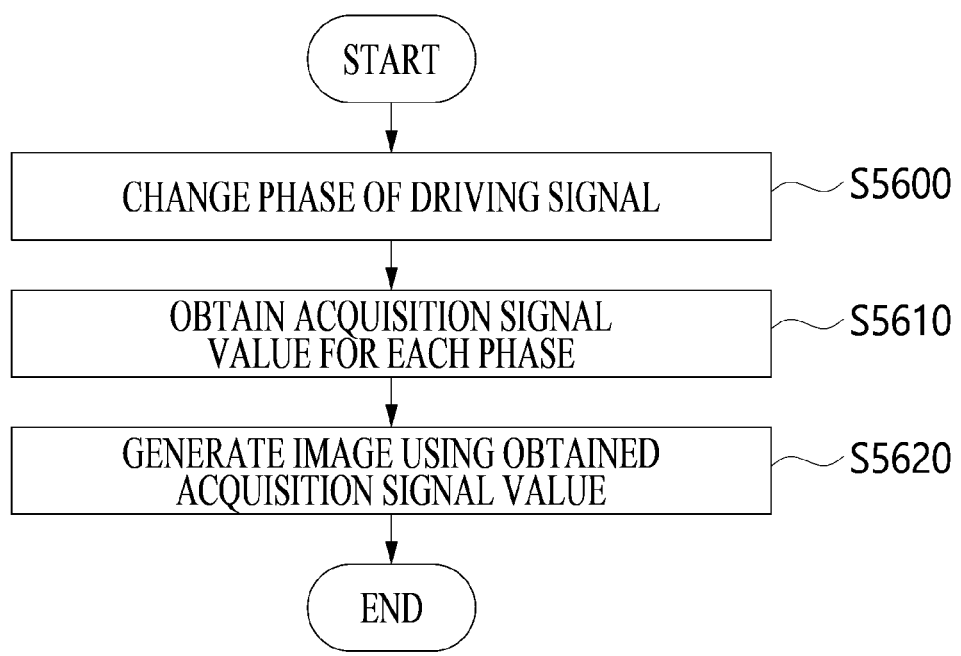
FIG. 72 is a flowchart for describing that one image is generated using obtained values while the phase of a driving signal is being changed according to an embodiment.

FIG. 72 is a flowchart showing a process of generating one image using an acquisition signal value obtained by the controller 130 while changing the phase component of the driving signal.

Referring to FIG. 72, the changing of the phase of the driving signal (S5600) includes changing the phase of the driving signal using a predetermined phase in order for the FF of the image obtained by the controller 130 to be 100%. In detail, in order for the controller 130 to obtain an image having an FF of 100%, the degree to which the position of the scanning pattern corresponding to the change of the phase of the driving signal is moved may need to be smaller than one pixel of the image obtained by the controller 130. Here, the position of the scanning pattern may refer to a position that is indicated by a driving signal in the image obtained by the controller 130 at a certain time.

$$\phi_x - \phi_y = 2\text{dip} \quad \text{[Formula 9]}$$

Formula 9 is a formula that represents a period in which a position where the scanning pattern appears is repeated by using the difference between the phases of the first signal and the second signal of the driving signal. Referring to Formula 6 and Formula 7, when the difference between the phase of the first signal of the driving signal and the phase of the second signal of the driving signal is two times a predetermined phase change period (hereinafter referred to as dip) as shown in Formula 9, the position indicated by the scanning pattern corresponding to the driving signal may be repeated irrespective of whether the unit frequency of the first signal or the unit frequency of the second signal is an odd number or an even number.

Also, when it is assumed that a is a value obtained by dividing dip, which is the position indicated by the first signal or the second signal being repeated according to the phase of the first signal or the second signal, by a certain interval (hereinafter referred to as n), the phase of the first signal or the second signal may be changed by a. In this case, when the phase of the first signal or the second signal is changed by a n times, the controller 130 may obtain the same position as the position corresponding to the unchanged phase of the first signal or the second signal. Accordingly, when the phase of the driving signal is changed by a until the position corresponding to the driving signal is repeated once according to the change in phase of the driving signal, the time required for the controller 130 to obtain an image having an FF of 100% may be reduced, and also the controller 130 may obtain a high-resolution image having an FF of 100%.

Here, the number of times the phase is changed in order to obtain an acquisition signal value such that the FF becomes 100%, i.e., n, may be obtained using the number of pixels of the image obtained by the controller 130 in the first direction or the second direction and the frequency component of the first signal or the second signal. For convenience of description, the following description assumes that the phase component of the first signal is changed.

$$X = A \sin(2\pi f_x(t+\phi_x)) \quad \text{[Formula 10]}$$

Formula 10 is a formula indicating the position corresponding to the first signal of the driving signal. In detail, Formula 10 may show the waveform of alternating current in which the first signal of the driving signal is generated. Here, X may indicate the position corresponding to the first signal, and A may indicate the amplitude of the first signal. Also, $f_x$ may be the frequency component of the first signal, and $\phi_x$ may be the phase component of the first signal. Also, t may indicate time, and the position corresponding to the first signal may be changed over time. For convenience of description, the following description assumes that amplitude A of the first signal has a size of 1, which is a default amplitude, and the phase component of the first signal, i.e., $\phi_x$, has a size of zero.

$$0 \leq \frac{X+1}{2} * p \leq 1 \quad \text{[Formula 11]}$$

Formula 11 is a formula in which the position corresponding to the first signal is expressed as the pixel position of the image obtained by the controller 130. Here, referring to Formula 10, X may indicate the position corresponding to the first signal, and the total number of pixels obtained by the controller 130 in the first axis direction may be p.

According to an embodiment, in Formula 10, the position corresponding to the first signal, i.e., X may range from −1 to 1 because a sine waveform is applied to the position. In this case, referring to Formula 11, the range of the position corresponding to the first signal may be set to correspond to the pixel position of the image obtained by the controller 130. In detail, since the position corresponding to the first signal, i.e., X, may range from −1 to 1, the controller 130 may obtain the pixel position in the first axis direction (hereinafter referred to as the pixel position corresponding to the first signal) of the image obtained by the controller 130 along with the change in X over time by using the number of pixels, i.e., P.

Here, since the phase of the driving signal is changed, the pixel position corresponding to the first signal changed according to a value a at which the phase of the driving signal is changed may need to be smaller than the size of one pixel in order for the controller 130 to obtain an image having an FF of 100%. For example, when the value of a is larger than the size of one pixel, the pixel position corresponding to the first signal may be changed with the change in phase by a. In this case, the pixel position corresponding to the first signal may not be changed from the pixel position corresponding to the first signal before the phase is changed to an adjacent pixel. The pixel position corresponding to the first signal obtained by the controller 130 may not be obtained as much as all pixels P in the first axis direction of the obtained image. Accordingly, a value at which the pixel position corresponding to the first signal is changed according to a at which the phase component of the first signal is changed may be smaller than the size of one pixel. However, the present invention is not limited thereto, and the value at which the pixel position corresponding to the first signal is changed may be greater than one pixel, but the object O may be scanned multiple times.

$$\left| \left( \frac{\sin(2\pi f_x t) + 1}{2} - \frac{\sin(2\pi f_x (t+a)) + 1}{2} \right) * p \right| \leq 1 \quad \text{[Formula 12]}$$

$$\left| (\sin(2\pi f_x t) - \sin(2\pi f_x (t+a))) \right| \leq \frac{2}{p} \quad \text{[Formula 13]}$$

Formula 12 is a formula indicating that the distance between the pixel position corresponding to the first signal before the phase is changed and the pixel position corresponding to the first signal after the phase is changed is smaller than the size of one pixel.

Formula 13 summarizes a formula indicating the distance between the pixel position corresponding to the first signal before the phase of Formula 12 is changed and the pixel position corresponding to the first signal after the phase is changed.

In detail, referring to Formula 12, since a value indicated by the pixel position of the first signal after the phase is changed is greater than a value indicated by the pixel position of the first signal before the phase is changed, an absolute value may be used to represent the distance.

Also, referring to Formula 13, a formula expressing the distance shown in Formula 12 may be summarized, and thus a difference between trigonometric functions related to time and phase may be expressed using a range that uses the number of pixels of the entire image, i.e., p.

$$a = \frac{1}{2\pi f_x}\sin^{-1}\left(\frac{2}{p}\right)$$ [Formula 14]

$$n = \frac{GCD * \pi}{f_y * \sin^{-1}\left(\frac{2}{p}\right)}$$ [Formula 15]

Formula 14 is a formula indicating a value a obtained by the controller 130 according to the pixel positions corresponding to the first signal before and after the phase is changed with reference to Formula 13.

Formula 15 is a formula indicating a value n, which is the number of times the phase is repeated, using the obtained value a.

In detail, referring to Formula 13 and Formula 14, in order to minimize a function shown on the left side of Formula 13, the value of the entire function at the initial time, i.e., when t=0, may be minimized. Accordingly, the value of the phase to be changed, i.e., a, may be expressed as.

$$\sin(2\pi f_x(a)) \le \frac{2}{\text{pixel}}$$

Accordingly, the maximum value of the phase a to be changed such that the FF becomes 100% may be the value of a shown in Formula 14, but the present invention is not limited thereto. The maximum value of the phase a may be smaller than or greater than a. In this case, the degree to which the pixel position corresponding to the first signal is changed may be less than the size of one pixel.

Also, referring to Formula 14, the period in which the position indicated by the first signal or the second signal is repeated, i.e., dip, may be divided by a according to the phase of the first signal or the second signal. Accordingly, the number of times the phase is repeated and changed, i.e., n, may be calculated, and this may be a value shown in Formula 15. In this case, n may be the number of times the phase at which the FF is 100% is repeated and changed. However, the present invention is not limited thereto, and this number may be smaller or larger than n shown in Formula 15. Here, n is the number of times the phase at which the FF of the image obtained by the controller 130 is 100% is repeated and changed. Even when the phase is repeated and changed a number of times smaller than n, the FF of the image obtained by the controller 130 may be 100%.

Also, referring to FIG. 72, the acquisition of the acquisition signal value corresponding to each phase (S5610) may include causing the controller 130 to obtain the acquisition signal value whenever the phase of the driving signal is changed by a while the phase of the driving signal is repeated and changed by the controller 130 by a n times. In detail, when the phase of the driving signal is changed by a, the acquisition signal value obtained by the controller 130 may be stored at another pixel position, and thus the acquisition signal values may be obtained at all the pixel positions of the image obtained by the controller 130.

According to an embodiment, along with the change in the period of the driving signal by a, the acquisition signal value obtained by the controller 130 for the last time may be obtained for pixel position information when at least one acquisition signal value is obtained at one pixel position obtained using the driving signal. However, the present invention is not limited thereto, and the acquisition signal value may be obtained at the pixel position by using the average of the plurality of acquisition signal values.

Also, referring to FIG. 72, the generating of an image using an obtained acquisition signal value (S5620) may include causing the controller 130 to obtain an acquisition signal value and a pixel position corresponding to the driving signal and to generate and provide one image. In detail, when the controller 130 obtains the image without using the plurality of acquisition signal values while changing the phase of the driving signal, the FF of the entire image may not be high. Here, when the controller 130 obtains one image by using the plurality of acquisition signal values while changing the phase of the driving signal, the image obtained by the controller 130 may be an image having an FF of 100%.

However, the present invention is not limited to the acquisition of the image having an FF of 100% by the controller 130, and a predetermined FF may be set such that the image obtained by the controller 130 has an FF greater than the predetermined FF.

Figure 73:
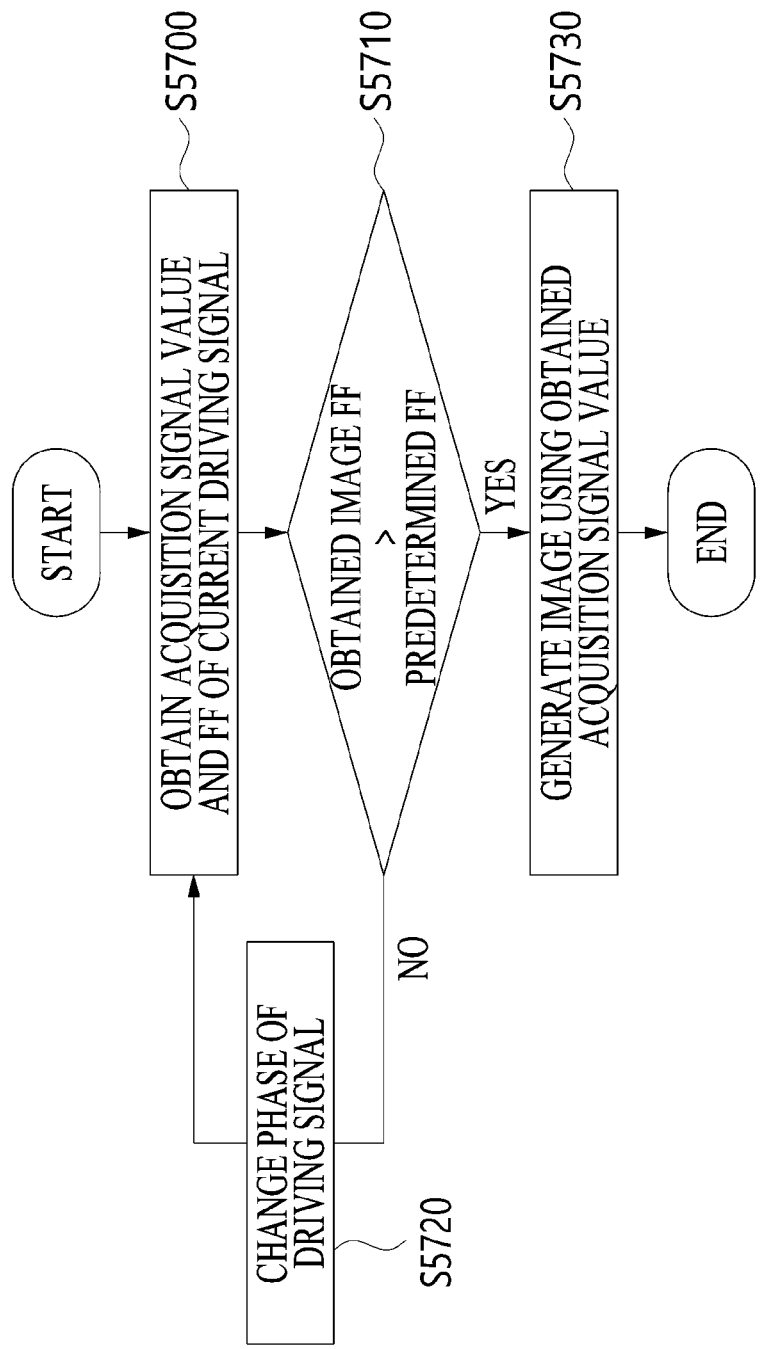
FIG. 73 is a flowchart for describing that one image is generated using obtained values while the phase of a driving signal is being changed to have a predetermined FF according to an embodiment.

FIG. 73 is a flowchart showing a process of obtaining an image by the controller 130 by using an obtained acquisition signal value while changing the phase of the driving signal such that the image obtained by the controller 130 has a predetermined FF.

Referring to FIG. 73, the obtaining of an acquisition signal value and an FF of the current driving signal (S5700) may include causing the controller 130 to obtain an FF using the driving signal and obtain an acquisition signal value corresponding to light emitted to and returned from an object O. In detail, the controller 130 may input the driving signal to the driving unit 1101, emit light to the object O, and obtain an acquisition signal value using light-receiving information regarding the light returning from the object O. Also, a pixel for which the acquisition signal value is obtained among pixels of an image acquirable by the controller 130 may be changed depending on the driving signal. Thus, when the controller 130 generates the driving signal, an FF may be obtained. Also, when the controller 130 redundantly obtains the acquisition signal value because the phase is already changed, the controller 130 may obtain the FF using a pixel of an image to be obtained and a pixel for which an acquisition signal is obtained.

Also, referring to FIG. 73, the comparing of an FF of an obtained image to a predetermined FF (S5710) may include causing the controller 130 to change the phase of the driving signal when the FF of the current image obtained by the controller 130 is lower than the predetermined FF and causing the controller 130 to generate an image using the currently obtained acquisition signal value when the FF of the obtained image is higher than the predetermined FF. In detail, the predetermined FF may be an FF that is determined to provide an image such that the image provided by the controller 130 is a high-resolution image. Also, when the FF of the obtained image is compared to the predetermined FF, the controller 130 may compare an FF obtained due to the overlap of acquisition signal values obtained while changing the phase of the driving signal to the aforementioned predetermined FF and change the phase of the driving signal again when the FF obtained when the acquisition signal values overlap is smaller than the predetermined FF. Also, when the FF due to the overlap of the acquisition signal values is greater than the predetermined FF, the controller 130 may generate an image using the acquisition signal values that are redundantly obtained. Here, the acquisition signal value being redundantly obtained may mean that the acquisition signal values obtained by the controller 130 when the phase of the driving signal is changed overlap.

Also, referring to FIG. 73, the changing of the phase of the driving signal (S5720) may include changing the phase of the driving signal to a predetermined change. Here, the predetermined phase may be an arbitrary phase but may not include a predetermined phase change value at which the phase of the first signal of the driving signal or the position indicated by the second signal may be the same along with the change in phase. In detail, when the phase of the driving signal is changed by the aforementioned predetermined phase change period dip, the same position may be indicated even though the phase component of the driving signal is changed. Thus, the predetermined phase change value to be changed may not include the predetermined phase change period dip.

Also, referring to FIG. 73, the generating of an image using an obtained acquisition signal value (S5730) may include causing the controller 130 to generate and provide an image using the current acquisition signal values obtained by the controller 130. In detail, the controller 130 may obtain one image using a signal that includes a driving signal and an acquisition signal value obtained by the controller 130 or a value obtained by overlapping acquisition signal values obtained while the phase of the driving signal is being changed and that may indicate the position of the pixel. Here, the obtained image may be an image having an FF greater than or equal to a predetermined FF, and thus an image generated and provided by the controller 130 may be a high-resolution image.

Figure 37:
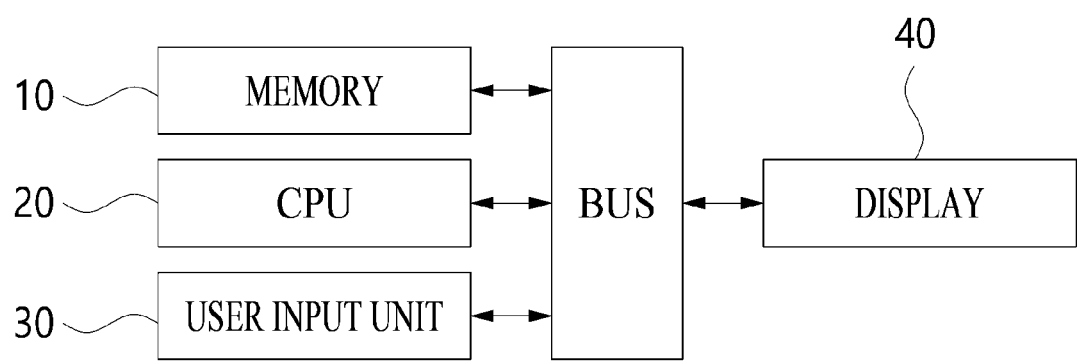
FIG. 37 is a diagram for exemplarily describing a computer system in which embodiments described herein may be implemented.

FIG. 37 is a diagram for exemplarily describing a computer system in which embodiments described herein may be implemented.

Referring to FIG. 37, the computer system may include a memory 10, a CPU 20, and a system bus BUS configured to connect the CPU 20 to various components of the computer system.

The CPU 20 may include one or more processors and may be any commercially available processor.

The memory may include a read-only memory (ROM) configured to store a basic input/output system including startup routines for a random access memory (RAM) and the computer system.

Also, the computer system may include a permanent storage memory (not shown) connected to the system bus BUS, for example, hard drives, floppy drives, CD ROM drives, magnetic tape drives, flash memory devices, digital video disks, and the like.

Also, the computer system may include one or more computer-readable medium disks (not shown) that store data, data structures, and computer-executable instructions.

The method according to an embodiment may be implemented as program instructions executable by a variety of computer means and may be recorded on a computer-readable medium. The computer-readable medium may include, alone or in combination, program instructions, data files, data structures, and the like. The program instructions recorded on the medium may be designed and configured specifically for an embodiment or may be publicly known and available to those who are skilled in the field of computer software. Examples of the computer-readable medium include a magnetic medium, such as a hard disk, a floppy disk, and a magnetic tape, an optical medium, such as a compact disc read-only memory (CD-ROM), a digital versatile disc (DVD), etc., a magneto-optical medium such as a floptical disk, and a hardware device specially configured to store and perform program instructions, for example, a read-only memory (ROM), a random access memory (RAM), a flash memory, etc. Examples of the computer instructions include not only machine language code generated by a compiler, but also high-level language code executable by a computer using an interpreter or the like. The hardware device may be configured to operate as one or more software modules in order to perform operations of an embodiment, and vice versa.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

According to embodiments of the present invention, it is possible to provide a compact optical device configured to observe the inside and outside of an object in real-time.

Also, according to embodiments of the present invention, it is possible to provide a high-resolution image by correcting a phase delay occurring due to a difference between a driving signal and an output signal.

Also, according to embodiments of the present invention, it is possible to provide a structure for separating frequencies in each axis of an optical fiber, a position to which the corresponding structure is to be attached, and an angle at which the corresponding structure is to be attached.

Also, according to embodiments of the present invention, it is possible to provide a probe mounting stand for correcting the phase of an output image for the first time.

Also, according to embodiments of the present invention, it is possible to provide an output image having an aspect ratio adjusted by adjusting the voltage of a signal input to an optical fiber.

Also, according to embodiments of the present invention, it is possible to provide a high-resolution image by adjusting the phase of a signal input to an optical fiber.

Also, according to embodiments of the present invention, it is possible to provide a method of finding a phase for calibrating an output image using a predetermined phase change period.

Also, according to embodiments of the present invention, it is possible to provide a method of correcting the phase of the output image using a difference between light intensity values obtained at one pixel position.

Although the present invention has been described with reference to specific embodiments and drawings, it will be appreciated that various modifications and changes can be made from the disclosure by those skilled in the art. For example, appropriate results may be achieved although the described techniques are performed in an order different from that described above and/or although the described components such as a system, a structure, a device, or a circuit are combined in a manner different from that described above and/or replaced or supplemented by other components or their equivalents.

Therefore, other implementations, embodiments, and equivalents are within the scope of the following claims.

What is claimed is:

1. An optical device, comprising:
   an optical fiber extending in a central axis between a fixed end and a free end;
   a first actuator connected to the optical fiber at an actuator position between the fixed end and the free end, the first actuator being configured to apply a first force to the optical fiber in a first direction perpendicular to the central axis such that the free end of the optical fiber moves in the first direction in response to the first force; and
   a deformable rod spaced in parallel to the optical fiber, the deformable rod being attached to the optical fiber with at least one connector;
   wherein in response to the first force, the free end of the optical fiber is to move in a second direction perpendicular to the first direction in addition to moving in the first direction in accordance with an attachment angle of the deformable rod,
   wherein the attachment angle is an angle between the first direction and an attachment direction in a cross-section plane perpendicular to the central axis, the attachment direction being a direction from the optical fiber to the deformable rod in the cross-section plane, and
   wherein the deformable rod is attached to the optical fiber within an allowable angle range, the allowable angle range being determined to limit a movement of the free end in the second direction.

2. The optical device of claim 1,
   wherein the at least one connector is located between the actuator position and the free end of the optical fiber.

3. The optical device of claim 1,
   wherein the at least one connector comprises a first connector and the second connector.

4. The optical device of claim 3,
   wherein the first connector is connected to a first point of the deformable rod and also connected to a first rod position of the optical fiber, the first rod position being located between the actuator position and the free end of the optical fiber, and
   wherein the second connector is connected to a second point of the deformable rod and also connected to a second rod position of the optical fiber, the second rod position being located between the actuator position and the first rod position.

5. The optical device of claim 4,
   wherein the first connector and the second connector are configured to move as the optical fiber vibrates.

6. The optical device of claim 1,
   wherein the at least one connector comprises at least one of an adhesive or a silicon structure.

7. The optical device of claim 1, wherein the optical device is configured to move the free end of the optical fiber according to a Lissajous pattern.

8. The optical device of claim 1, wherein the optical fiber has a first rigidity, and the deformable rod has a second rigidity.

9. The optical device of claim 1, wherein the optical fiber has different resonant frequencies with respect to the first direction and the second direction.

10. The optical device of claim 1,
    wherein the deformable rod is shorter than the optical fiber.

11. The optical device of claim 1, further comprising: a controller configured to apply a first driving frequency to the first actuator.

* * * * *